US012624003B2

(12) United States Patent
Schkeryantz et al.

(10) Patent No.: US 12,624,003 B2
(45) Date of Patent: May 12, 2026

(54) CARBOXYLIC ACID CONTAINING INDANYL COMPOUNDS FOR THE TREATMENT OF NEURODEGENERATIVE DISEASES

(71) Applicant: Celgene Corporation, Summit, NJ (US)

(72) Inventors: Jeffrey M. Schkeryantz, Summit, NJ (US); Julie Selkirk, Summit, NJ (US); Philip Stewart Turnbull, San Diego, CA (US); Junko Tamiya, Carlsbad, CA (US); Patrick W. Papa, Carlsbad, CA (US); Jean-Francois Brazeau, San Diego, CA (US); Karin Worm, Summit, NJ (US)

(73) Assignee: Celgene Corporation, Princeton, NJ (US)

( * ) Notice: Subject to any disclaimer, the term of this patent is extended or adjusted under 35 U.S.C. 154(b) by 378 days.

(21) Appl. No.: 18/267,551

(22) PCT Filed: Dec. 22, 2021

(86) PCT No.: PCT/US2021/064881
§ 371 (c)(1),
(2) Date: Jun. 15, 2023

(87) PCT Pub. No.: WO2022/140555
PCT Pub. Date: Jun. 30, 2022

(65) Prior Publication Data

US 2024/0124394 A1 Apr. 18, 2024

Related U.S. Application Data

(60) Provisional application No. 63/130,023, filed on Dec. 23, 2020.

(51) Int. Cl.

| | |
|---|---|
| *C07D 205/12* | (2006.01) |
| *A61P 25/28* | (2006.01) |
| *C07D 205/04* | (2006.01) |
| *C07D 207/16* | (2006.01) |
| *C07D 209/52* | (2006.01) |
| *C07D 211/66* | (2006.01) |
| *C07D 211/78* | (2006.01) |
| *C07D 221/20* | (2006.01) |
| *C07D 221/22* | (2006.01) |
| *C07D 405/10* | (2006.01) |
| *C07D 413/10* | (2006.01) |

(52) U.S. Cl.
CPC ............ *C07D 205/12* (2013.01); *A61P 25/28* (2018.01); *C07D 205/04* (2013.01); *C07D 207/16* (2013.01); *C07D 209/52* (2013.01); *C07D 211/66* (2013.01); *C07D 211/78* (2013.01); *C07D 221/20* (2013.01); *C07D 221/22* (2013.01); *C07D 405/10* (2013.01); *C07D 413/10* (2013.01)

(58) Field of Classification Search
CPC ..... A61P 25/28; C07D 205/12; C07D 205/04; C07D 207/16; C07D 209/52; C07D 211/66; C07D 211/78; C07D 221/20; C07D 221/22; C07D 405/10; C07D 413/10
See application file for complete search history.

(56) References Cited

U.S. PATENT DOCUMENTS

| | | | | |
|---|---|---|---|---|
| 7,220,734 | B2 * | 5/2007 | Doherty .................. | A61P 31/04 548/251 |
| 2006/0106083 | A1 | 5/2006 | Martina et al. | |
| 2013/0018055 | A1 | 1/2013 | Aebi et al. | |
| 2017/0174670 | A1 | 6/2017 | Brownstein et al. | |
| 2017/0174672 | A1 | 6/2017 | Amberg et al. | |
| 2017/0327439 | A1 | 11/2017 | Kusumi et al. | |

FOREIGN PATENT DOCUMENTS

| | | | |
|---|---|---|---|
| JP | 2006511579 | A | 4/2006 |
| WO | 2004058149 | A2 | 7/2004 |
| WO | 2016088834 | A1 | 6/2016 |

OTHER PUBLICATIONS

Hao, Frontiers in Molecular Neuroscience, Apr. 2020, vol. 13, Article 58, 1-17. (Year: 2020).*
Lyapina, Nature Communications, Aug. 2022, vol. 1:4736, 1-14. (Year: 2022).*
Kurano, Frontiers in Aging Neuroscience, Dec. 2022, 1-17. (Year: 2022).*
International Search Report and Written Opinion for PCT/US2021/064881 dated May 4, 2022, 10 pages.
Roberts et al., "Sphingosine 1-phosphate receptor agonists: a patent review (2010-2012)," Expert Opinion on Therapeutic Patents, 2013, 23(7): 817-841.

* cited by examiner

*Primary Examiner* — D Margaret M Seaman
(74) *Attorney, Agent, or Firm* — McNeill PLLC

(57) ABSTRACT

Provided herein are compounds and compositions thereof for modulating S1P5. In some embodiments, the compounds and compositions are provided for treatment of neurological diseases.

19 Claims, No Drawings

CARBOXYLIC ACID CONTAINING INDANYL COMPOUNDS FOR THE TREATMENT OF NEURODEGENERATIVE DISEASES

CROSS-REFERENCE TO RELATED APPLICATIONS

This application is a national stage entry pursuant to 35 U.S.C. § 371 of International Application No. PCT/US2021/064881, filed Dec. 22, 2021, which claims priority to U.S. Provisional Application No. 63/130,023, filed on Dec. 23, 2020, each of which is incorporated herein by reference in its entirety for any purpose.

FIELD

The present disclosure relates generally to compounds, compositions, and methods for their preparation and use of the compounds and compositions for treating neurodegenerative diseases.

BACKGROUND

Sphingosine-1-phosphate (S1P; (2S,3R,4E)-2-amino-3-hydroxyoctadec-4-enyl-1-phosphate) is a bioactive sphingolipid that is synthesized by metabolic turnover of sphingolipids in cells and by the extracellular action of a secreted sphingosine kinase. S1P binds to and stimulates members of the endothelial cell differentiation gene family (EDG receptors), which are plasma membrane-localized G protein-coupled receptors. The five members of this family of receptors are S1P1 (EDG-1), S1P2 (EDG-5), S1P3 (EDG-3), S1P4 (EDG-6), and S1P5 (EDG-8). S1P mediates a wide variety of cellular responses including proliferation, cytoskeletal organization and migration, adherence- and tight junction assembly, and morphogenesis.

S1P5 is primarily expressed in the central nervous system. Specifically, S1P5 is highly expressed in oligodendrocytes (oligodendroglia) and oligodendrocyte progenitor cells (Jaillard, C. et al., *J. Neuroscience,* 2005, 25(6), 1459-1469; Novgorodov, A. S. et al., *FASEB J.,* 2007, 21, 1503-1514). Oligodendrocytes are glial cells that form myelin sheaths (myelin) by binding to the axons of nerve cells. Compounds that bind to S1P5 can modulate the function of S1P5 and may be useful for treating neurodegenerative diseases.

Accordingly, in one aspect, provided herein are compounds that modulate S1P5 for use in treating neurodegenerative diseases.

SUMMARY

Described herein, in certain embodiments, are compounds and compositions thereof for modulating S1P5. In various embodiments, the compounds and compositions thereof may be used for treatment of neurodegenerative diseases.

The present embodiments can be understood more fully by reference to the detailed description and examples, which are intended to exemplify non-limiting embodiments.

Exemplary embodiments include the following.

Embodiment 1. In some embodiments, provided herein are compounds of Formula (I):

(I)

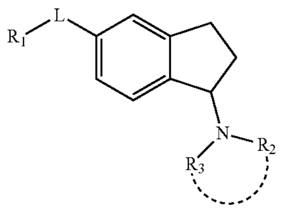

or a pharmaceutically acceptable salt thereof, wherein:

L is —C(Y)$\equiv$C(X)— or a bond;

X and Y are independently H, O, $H_2$, or absent;

$\equiv$ is a single, double, or triple bond;

$R_1$ is $C_6$-$C_{10}$ aryl, fused bicyclic 8- to 10-membered heteroaryl, or fused bicyclic 8- to 10-membered heterocyclyl, each of which is optionally substituted by 1-5 R' groups, wherein the heterocyclyl and heteroaryl contain 1-3 heteroatoms selected from nitrogen and oxygen;

each R' is independently halo, $C_1$-$C_6$ alkyl, $C_1$-$C_6$ haloalkyl, $C_1$-$C_6$ alkoxy, or $C_3$-$C_6$ cycloalkyl;

$R_2$ is H or $C_1$-$C_6$ alkyl;

$R_3$ is $—(CH_2)_x—CO_2H$ or

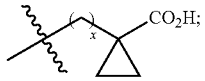

or the dashed line between $R_2$ and $R_3$ represents a ring structure where $R_2$ and $R_3$ are taken together with the nitrogen atom to which they are attached to form a 4- to 6-membered heterocyclyl substituted by 1-5 $R_4$ groups, wherein at least one $R_4$ group is $—CO_2H$ or contains a $—CO_2H$ moiety;

x is 1-5; and each $R_4$ is independently $—CO_2H$, halo, or $C_1$-$C_6$ alkyl, or two $R_4$ groups are taken together with the carbon atoms to which they are attached to form a fused, bridged, or spiro $C_3$-$C_5$ cycloalkyl optionally substituted by $—CO_2H$.

Embodiment 2. The compound of embodiment 1, or a pharmaceutically acceptable salt thereof, wherein:

L is —C(Y)$\equiv$C(X)—.

Embodiment 3. The compound of embodiment 2, or a pharmaceutically acceptable salt thereof, wherein:

L is —C≡C—, —HC═CH—, or $—CH_2CH_2—$.

Embodiment 4. The compound of embodiment 2, or a pharmaceutically acceptable salt thereof, wherein:

L is $—C(O)—CH_2—$ or $—CH_2—C(O)—$.

Embodiment 5. The compound of embodiment 1, or a pharmaceutically acceptable salt thereof, wherein:

L is a bond.

Embodiment 6. The compound of any one of embodiments 1-5, or a pharmaceutically acceptable salt thereof, wherein:

$R_1$ is phenyl, phenyl fused to a cycloalkyl, fused bicyclic 9-membered heteroaryl, or fused bicyclic 9-membered heterocyclyl, each of which is optionally substituted by 1-3 R' groups, wherein the heterocyclyl and heteroaryl contain 1-2 heteroatoms selected from nitrogen and oxygen.

Embodiment 7. The compound of any one of embodiments 1-6, or a pharmaceutically acceptable salt thereof, wherein:

each R' is independently halo, $C_1$-$C_3$ alkyl, $C_1$-$C_3$ haloalkyl, $C_1$-$C_3$ alkoxy, or $C_3$-$C_6$ cycloalkyl.

Embodiment 8. The compound of embodiment 7, or a pharmaceutically acceptable salt thereof, wherein:

each R is independently Cl, F, methyl, ethyl, isopropyl, —$CF_3$, —$OCH_3$, or cyclopropyl.

Embodiment 9. The compound of any one of embodiments 6-8, or a pharmaceutically acceptable salt thereof, wherein:

$R_1$ is

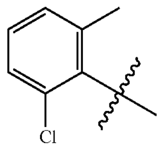 , 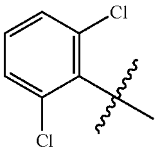 ,

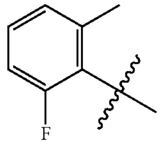 , 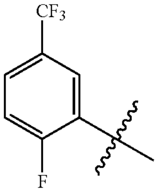 ,

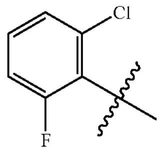 , 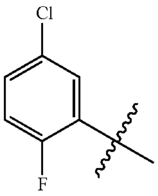 ,

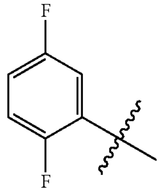 , 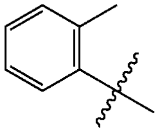 ,

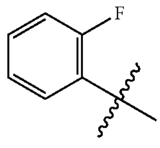 , 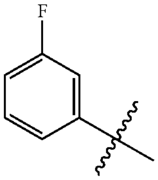 ,

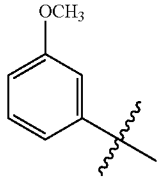 , 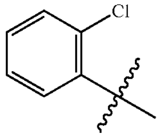 ,

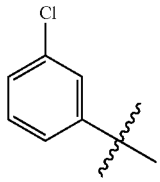 , 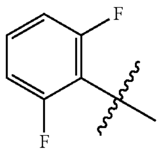 ,

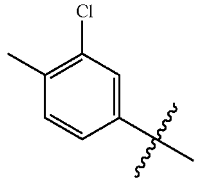 , 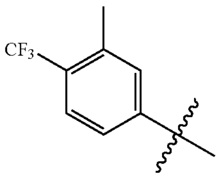 ,

-continued

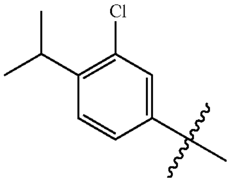 , 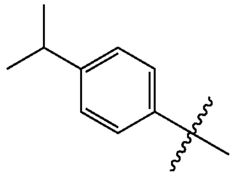 ,

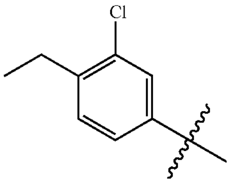 , 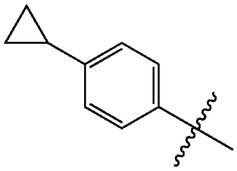 ,

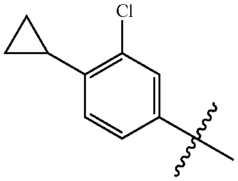 , 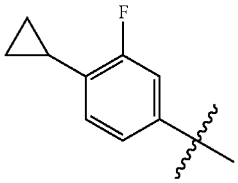 ,

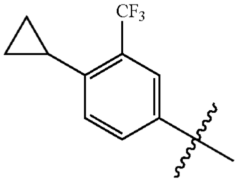 , 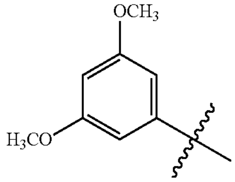 ,

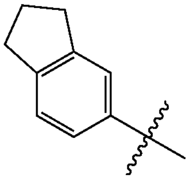 , 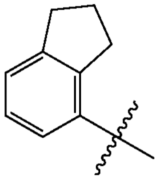 ,

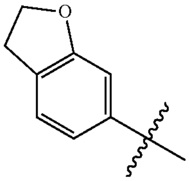 , 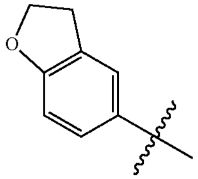 , or

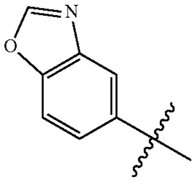 .

Embodiment 10. The compound of any one of embodiments 1-9, or a pharmaceutically acceptable salt thereof, wherein:

$R_2$ is H or $C_1$-$C_3$ alkyl;

$R_3$ is —$(CH_2)_x$—$CO_2H$ or

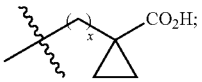

and x is 1-3.

Embodiment 11. The compound of embodiment 10, or a pharmaceutically acceptable salt thereof, wherein:

$R_2$ is H or methyl; and $R_3$ is $-CH_2CO_2H$, $-(CH_2)_2CO_2H$, $-(CH_2)_3CO_2H$, or

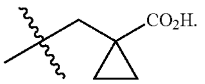 [SMILES: *CC1(C(=O)O)CC1]

Embodiment 12. The compound of embodiment 11, or a pharmaceutically acceptable salt thereof, wherein:

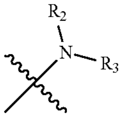

is

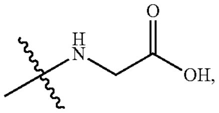

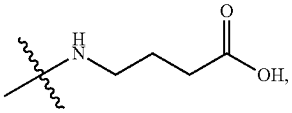

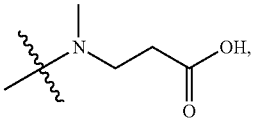

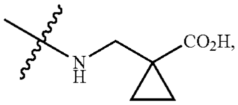

or

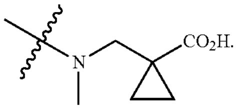

Embodiment 13. The compound of any one of embodiments 1-9, or a pharmaceutically acceptable salt thereof, wherein:

$R_2$ and $R_3$ are taken together with the nitrogen atom to which they are attached to form a 4- to 6-membered heterocyclyl substituted by 1-3 $R_4$ groups, wherein at least one $R_4$ group is $-CO_2H$ or contains a $-CO_2H$ moiety.

Embodiment 14. The compound of embodiment 13, or a pharmaceutically acceptable salt thereof, wherein:

$R_2$ and $R_3$ are taken together with the nitrogen atom to which they are attached to form azetidinyl, pyrrolidinyl, or piperidinyl, each of which is substituted by 1-3 $R_4$ groups, wherein at least one $R_4$ group is $-CO_2H$ or contains a $-CO_2H$ moiety.

Embodiment 15. The compound of any one of embodiments 1-9, 13, and 14, wherein:

each $R_4$ is independently $-CO_2H$, halo, or $C_1$-$C_3$ alkyl, or two $R_4$ groups are taken together with the carbon atoms to which they are attached to form a fused, bridged, or Spiro $C_3$-$C_5$ cycloalkyl optionally substituted by $-CO_2H$, wherein at least one $R_4$ group is $-CO_2H$ or contains a $-CO_2H$ moiety.

Embodiment 16. The compound of embodiment 15, wherein:

each $R_4$ is independently $-CO_2H$, F, or methyl, or two $R_4$ groups are taken together with the carbon atoms to which they are attached to form a fused cyclopropyl, a spiro cyclopropyl, a spiro cyclobutyl, or a bridged cyclopentyl, each of which is optionally substituted by $-CO_2H$, wherein at least one $R_4$ group is $-CO_2H$ or contains a $-CO_2H$ moiety.

Embodiment 17. The compound of any one of embodiments 1-9 and 13-16, or a pharmaceutically acceptable salt thereof, wherein:

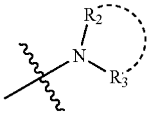

is

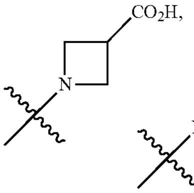

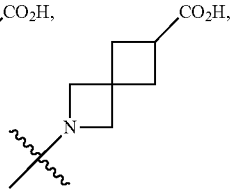

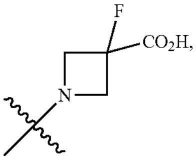

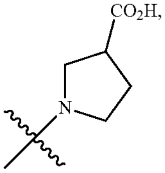

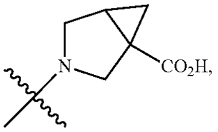

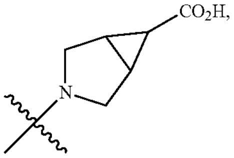

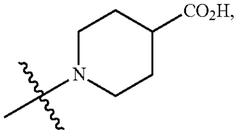

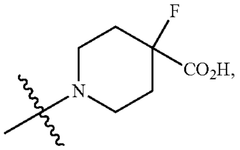

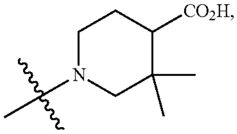

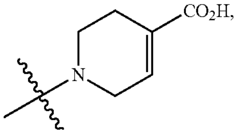

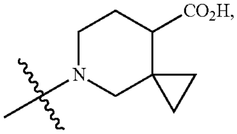

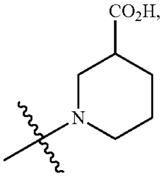

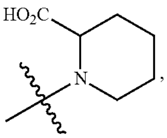

, or

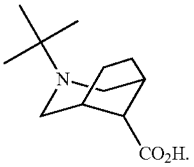

Embodiment 18. The compound of any one of embodiments 1-9 and 13-17, or a pharmaceutically acceptable salt thereof, wherein the compound is of Formula (II):

(II)

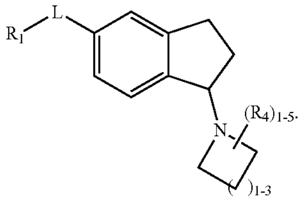

Embodiment 19. The compound of any one of embodiments 1-12, or a pharmaceutically acceptable salt thereof, wherein the compound is of Formula (IIIa) or (IIIb):

(IIIa)

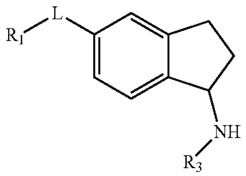

(IIIb)

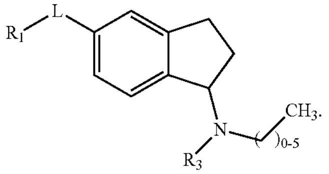

Embodiment 20. A compound selected from the compounds of Table 1 or a pharmaceutically acceptable salt thereof.

Embodiment 21. A pharmaceutical composition comprising the compound of any one of embodiments 1-20, or a pharmaceutically acceptable salt thereof, and a pharmaceutically acceptable excipient.

Embodiment 22. A method of modulating sphingosine 1-phosphate receptor 5 (S1P5) comprising contacting S1P5 with an effective amount of the compound of any one of embodiments 1-20, or a pharmaceutically acceptable salt thereof, or the pharmaceutical composition of embodiment 21.

Embodiment 23. A method of treating a neurological disease in a subject in need thereof, comprising administering to the subject an effective amount of the compound of any one of embodiments 1-20, or a pharmaceutically acceptable salt thereof, or the pharmaceutical composition of embodiment 21.

Embodiment 24. The method of embodiment 23, wherein the neurological disease is Alzheimer's disease or multiple sclerosis.

DETAILED DESCRIPTION

Definitions

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size, or thickness, are to be understood to include any integer within the recited range, unless otherwise indicated. As used herein, the terms "about" and "approximately" mean±20%, ±10%, ±5%, or ±1% of the indicated range, value, or structure, unless otherwise indicated.

An "alkyl" group is a saturated, partially saturated, or unsaturated straight chain or branched non-cyclic hydrocarbon having from 1 to 10 carbon atoms ($C_1$-$C_{10}$ alkyl), typically from 1 to 8 carbons ($C_1$-$C_8$ alkyl) or, in some embodiments, from 1 to 6 ($C_1$-$C_6$ alkyl), 1 to 3 ($C_1$-$C_3$ alkyl), or 2 to 6 ($C_2$-$C_6$ alkyl) carbon atoms. In some embodiments, the alkyl group is a saturated alkyl group. Representative saturated alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, -neopentyl, tert-pentyl, -2-methylpentyl, -3-methylpentyl, -4-methylpentyl, -2,3-dimethylbutyl and the like. In some embodiments, an alkyl group is an unsaturated alkyl group, also termed an alkenyl or alkynyl group. An "alkenyl" group is an alkyl group that contains one or more carbon-carbon double bonds. An "alkynyl" group is an alkyl group that contains one or more carbon-carbon triple bonds. Examples of unsaturated alkyl groups include, but are not limited to, vinyl, allyl, $-CH{=}CH(CH_3)$, $-CH{=}C(CH_3)_2$, $-C(CH_3){=}CH_2$, $-C(CH_3){=}CH(CH_3)$, $-C(CH_2CH_3){=}CH_2$, $-C{\equiv}CH$, $-C{\equiv}C(CH_3)$, $-C{\equiv}C(CH_2CH_3)$, $-CH_2C{\equiv}CH$, $-CH_2C{\equiv}C(CH_3)$ and $-CH_2C{\equiv}C(CH_2CH_3)$, among others. An alkyl group can be substituted or unsubstituted. When the alkyl groups described herein are said to be "substituted," they may be substituted with any substituent or substituents as those found in the exemplary compounds and embodiments disclosed herein, as well as halogen; hydroxy; alkoxy; cycloalkyloxy, aryloxy, heterocyclyloxy, heteroaryloxy, heterocycloalkyloxy, cycloalkylalkyloxy, aralkyloxy, heterocyclylalkyloxy, heteroarylalkyloxy, heterocycloalkylalkyloxy; oxo (=O); amino, alkylamino, cycloalkylamino, arylamino, heterocyclylamino, heteroarylamino, heterocycloalkylamino, cycloalkylalkylamino, aralkylamino, heterocyclylalkylamino, heteroaralkylamino, heterocycloalkylalkylamino; imino; imido; amidino; guanidino; enamino; acylamino; sulfonylamino; urea, nitrourea; oxime; hydroxylamino; alkoxyamino; aralkoxyamino; hydrazino;

hydrazido; hydrazono; azido; nitro; thio (—SH), alkylthio; =S; sulfinyl; sulfonyl; aminosulfonyl; phosphonate; phosphinyl; acyl; formyl; carboxy; ester; carbamate; amido; cyano; isocyanato; isothiocyanato; cyanato; thiocyanato; or —$B(OH)_2$. In certain embodiments, when the alkyl groups described herein are said to be "substituted," they may be substituted with any substituent or substituents as those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; $B(OH)_2$, or O(alkyl)aminocarbonyl.

A "cycloalkyl" group is a saturated, or partially saturated cyclic alkyl group of from 3 to 10 carbon atoms ($C_3$-$C_{10}$ cycloalkyl) having a single cyclic ring or multiple condensed or bridged rings that can be optionally substituted. In some embodiments, the cycloalkyl group has 3 to 8 ring carbon atoms ($C_3$-$C_8$ cycloalkyl), whereas in other embodiments the number of ring carbon atoms ranges from 3 to 5 ($C_3$-$C_5$ cycloalkyl), 3 to 6 ($C_3$-$C_6$ cycloalkyl), or 3 to 7 ($C_3$-$C_7$ cycloalkyl). In some embodiments, the cycloalkyl groups are saturated cycloalkyl groups. Such saturated cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as 1-bicyclo[1.1.1]pentyl, bicyclo[2.1.1]hexyl, bicyclo[2.2.1]heptyl, bicyclo[2.2.2]octyl, adamantyl and the like. In other embodiments, the cycloalkyl groups are unsaturated cycloalkyl groups. Examples of unsaturated cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanol and the like.

An "aryl" group is an aromatic carbocyclic group of from 6 to 14 carbon atoms ($C_6$-$C_{14}$ aryl) having a single ring (e.g., phenyl) or multiple condensed rings (e.g., naphthyl or anthryl). In some embodiments, aryl groups contain 6-14 carbons ($C_6$-$C_{14}$ aryl), and in others from 6 to 12 ($C_6$-$C_{12}$ aryl) or even 6 to 10 carbon atoms ($C_6$-$C_{10}$ aryl) in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "halogen" or "halo" is fluorine, chlorine, bromine or iodine.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. In some embodiments, the haloalkyl group has one to six carbon atoms and is substituted by one or more halo radicals ($C_1$-$C_6$ haloalkyl), or the haloalkyl group has one to three carbon atoms and is substituted by one or more halo radicals ($C_1$-$C_3$ haloalkyl). The halo radicals may be all the same or the halo radicals may be different. Unless specifically stated otherwise, a haloalkyl group is optionally substituted.

A "heteroaryl" group is an aromatic ring system having one to four heteroatoms as ring atoms in a heteroaromatic ring system, wherein the remainder of the atoms are carbon atoms. In some embodiments, heteroaryl groups contain 3 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, benzisoxazolyl (e.g., benzo[d]isoxazolyl), thiazolyl, pyrolyl, pyridazinyl, pyrimidyl, pyrazinyl, thiophenyl, benzothiophenyl, furanyl, benzofuranyl, indolyl (e.g., indolyl-2-onyl or isoindolin-1-onyl), azaindolyl (pyrrolopyridyl or 1H-pyrrolo[2,3-b]pyridyl), indazolyl, benzimidazolyl (e.g., 1H-benzo[d]imidazolyl), imidazopyridyl (e.g., azabenzimidazolyl or 1H-imidazo[4,5-b]pyridyl), pyrazolopyridyl, triazolopyridyl, benzotriazolyl (e.g., 1H-benzo[d][1,2,3]triazolyl), benzoxazolyl (e.g., benzo[d]oxazolyl), benzothiazolyl, benzothiadiazolyl, isoxazolopyridyl, thianaphthalenyl, purinyl, xanthinyl, adeninyl, guaninyl, quinolinyl, isoquinolinyl (e.g., 3,4-dihydroisoquinolin-1(2H)-onyl), tetrahydroquinolinyl, quinoxalinyl, and quinazolinyl groups. A heteroaryl group can be substituted or unsubstituted.

A "heterocyclyl" is a non-aromatic cycloalkyl in which one to four of the ring carbon atoms are independently replaced with a heteroatom selected from O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocycloalkyl group can be substituted or unsubstituted. Heterocyclyl groups encompass saturated and partially saturated ring systems. Further, the term heterocyclyl is intended to encompass any non-aromatic ring containing at least one heteroatom, which ring may be fused to an aryl or heteroaryl ring, regardless of the attachment to the remainder of the molecule. The phrase also includes bridged polycyclic ring systems containing a heteroatom. Representative examples of a heterocyclyl group include, but are not limited to, aziridinyl, azetidinyl, azepanyl, pyrrolidyl, imidazolidinyl (e.g., imidazolidin-4-onyl or imidazolidin-2,4-dionyl), pyrazolidinyl, thiazolidinyl, tetrahydrothiophenyl, tetrahydrofuranyl, piperidyl, piperazinyl (e.g., piperazin-2-onyl), morpholinyl, thiomorpholinyl, tetrahydropyranyl (e.g., tetrahydro-2H-pyranyl), tetrahydrothiopyranyl, oxathianyl, dithianyl, 1,4-dioxaspiro[4.5]decanyl, homopiperazinyl, quinuclidyl, or tetrahydropyrimidin-2(1H)-one. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

An "alkoxy" group is —O-(alkyl), wherein alkyl is defined above.

A "carboxy" group is a radical of the formula: —C(O)OH.

When the groups described herein, with the exception of alkyl group, are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy;

nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; oxygen (=O); $B(OH)_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidyl, benzimidazolyl, benzothiophenyl, or benzofuranyl) aryloxy; aralkyloxy; heterocyclyloxy; and heterocyclyl alkoxy.

Embodiments of the disclosure are meant to encompass pharmaceutically acceptable salts, tautomers, isotopologues, and stereoisomers of the compounds provided herein, such as the compounds of Formula (I).

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds of formula (I) include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methyl-glucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, maleic, phosphoric, sulfuric, and methanesulfonic acids. Examples of specific salts thus include hydrochloride, formic, and mesylate salts. Others are well-known in the art, see for example, *Remington's Pharmaceutical Sciences,* $18^{th}$ eds., Mack Publishing, Easton PA (1990) or *Remington: The Science and Practice of Pharmacy,* $19^{th}$ eds., Mack Publishing, Easton PA (1995).

As used herein and unless otherwise indicated, the term "stereoisomer" or "stereoisomerically pure" means one stereoisomer of a particular compound that is substantially free of other stereoisomers of that compound. For example, a stereoisomerically pure compound having one chiral center will be substantially free of the opposite enantiomer of the compound. A stereoisomerically pure compound having two chiral centers will be substantially free of other diastereomers of the compound. A typical stereoisomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The compounds disclosed herein can have chiral centers and can occur as racemates, individual enantiomers or diastereomers, and mixtures thereof. All such isomeric forms are included within the embodiments disclosed herein, including mixtures thereof.

The use of stereoisomerically pure forms of the compounds disclosed herein, as well as the use of mixtures of those forms, are encompassed by the embodiments disclosed herein. For example, mixtures comprising equal or unequal amounts of the enantiomers of a particular compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. *L., Stereochemistry of Carbon Compounds* (McGraw-Hill, N Y, 1962); Wilen, S. H., *Tables of Resolving Agents and Optical Resolutions* p. 268 (E. L. Eliel, Ed., Univ. of Notre Dame Press, Notre Dame, IN, 1972); Todd, M., *Separation Of Enantiomers: Synthetic Methods* (Wiley-VCH Verlag GmbH & Co. KGaA, Weinheim, Germany, 2014); Toda, F., *Enantiomer Separation: Fundamentals and Practical Methods* (Springer Science & Business Media, 2007); Subramanian, G. *Chiral Separation Techniques: A Practical Approach* (John Wiley & Sons, 2008); Ahuj a, S., *Chiral Separation Methods for Pharmaceutical and Biotechnological Products* (John Wiley & Sons, 2011).

It should also be noted the compounds disclosed herein can include E and Z isomers, or a mixture thereof, and cis and trans isomers or a mixture thereof. In certain embodiments, the compounds are isolated as either the E or Z isomer. In other embodiments, the compounds are a mixture of the E and Z isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

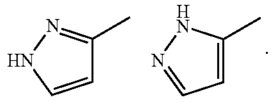

As readily understood by one skilled in the art, a wide variety of functional groups and other structures may exhibit tautomerism and all tautomers of compounds of Formula (I) are within the scope of the present disclosure.

It should also be noted the compounds disclosed herein can contain unnatural proportions of atomic isotopes at one or more of the atoms. For example, the compounds may be radiolabeled with radioactive isotopes, such as for example tritium (H), iodine-125 ($^{125}I$), sulfur-35 ($^{35}S$), or carbon-14 ($^{14}C$), or may be isotopically enriched, such as with deuterium ($^{2}H$), carbon-13 ($^{13}C$), or nitrogen-15 ($^{15}N$). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer therapeutic agents, research reagents, e.g., binding assay reagents, and diagnostic agents, e.g., in vivo imaging agents. All isotopic variations of the compounds as described herein, whether radioactive or not, are intended to be encompassed within the scope of the embodiments provided herein. In some embodiments, there are provided isotopologues of the compounds disclosed herein, for example, the isotopologues are deuterium, carbon-13, and/or nitrogen-15 enriched compounds. As used herein, "deuterated", means a compound wherein at least one hydrogen (H) has been replaced by deuterium (indicated by D or $^2$H), that is, the compound is enriched in deuterium in at least one position.

It is understood that, independently of stereoisomerical or isotopic composition, each compound disclosed herein can be provided in the form of any of the pharmaceutically acceptable salts discussed herein. Equally, it is understood that the isotopic composition may vary independently from the stereoisomerical composition of each compound referred to herein. Further, the isotopic composition, while being restricted to those elements present in the respective compound or salt thereof disclosed herein, may otherwise vary independently from the selection of the pharmaceutically acceptable salt of the respective compound.

It should be noted that if there is a discrepancy between a depicted structure and a name for that structure, the depicted structure is to be accorded more weight.

"Treating" as used herein, means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself. In one embodiment, the disorder is a neurodegenerative disease, as described herein, or a symptom thereof.

"Preventing" as used herein, means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition. In one embodiment, the disorder is a neurodegenerative disease, as described herein, or symptoms thereof.

The term "effective amount" in connection with a compound disclosed herein means an amount capable of treating or preventing a disorder, disease or condition, or symptoms thereof, disclosed herein.

The term "subject" or "patient" as used herein include an animal, including, but not limited to, an animal such a cow, monkey, horse, sheep, pig, chicken, turkey, quail, cat, dog, mouse, rat, rabbit or guinea pig, in one embodiment a mammal, in another embodiment a human. In one embodiment, a subject is a human having or at risk for having an S1P5 mediated disease, or a symptom thereof.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Compounds

In one aspect, provided herein is a compound of Formula (I):

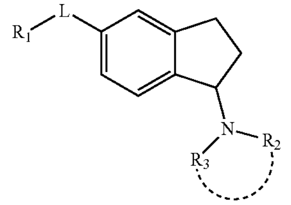

(I)

or a pharmaceutically acceptable salt thereof, wherein:

L is —C(Y)≡C(X)— or a bond;

X and Y are independently H, O, $H_2$, or absent;

≡ is a single, double, or triple bond;

$R_1$ is $C_6$-$C_{10}$ aryl, fused bicyclic 8- to 10-membered heteroaryl, or fused bicyclic 8- to 10-membered heterocyclyl, each of which is optionally substituted by 1-5 R' groups, wherein the heterocyclyl and heteroaryl contain 1-3 heteroatoms selected from nitrogen and oxygen;

each R' is independently halo, $C_1$-$C_6$ alkyl, $C_1$-$C_6$ haloalkyl, $C_1$-$C_6$ alkoxy, or $C_3$-$C_6$ cycloalkyl;

$R_2$ is H or $C_1$-$C_6$ alkyl;

$R_3$ is —$(CH_2)_x$—$CO_2H$ or

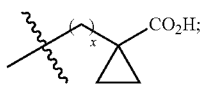

or the dashed line between $R_2$ and $R_3$ represents a ring structure where $R_2$ and $R_3$ are taken together with the nitrogen atom to which they are attached to form a 4- to 6-membered heterocyclyl substituted by 1-5 $R_4$ groups, wherein at least one $R_4$ group is —$CO_2H$ or contains a —$CO_2H$ moiety;

x is 1-5; and each $R_4$ is independently —$CO_2H$, halo, or $C_1$-$C_6$ alkyl, or two $R_4$ groups are taken together with the carbon atoms to which they are attached to form a fused, bridged, or spiro $C_3$-$C_5$ cycloalkyl optionally substituted by —$CO_2H$.

In some embodiments, L is a bond.

In some embodiments, L is —C(Y)≡C(X)—. In some embodiments, Y is H, O, $H_2$, or absent. In some embodiments, X is H, O, $H_2$, or absent. In some embodiments, ≡ is a single bond. In some embodiments, ≡ is a double bond. In some embodiments, ≡ is a triple bond. In some embodiments, Y and X are both absent, ≡ is a triple bond, and L is —C≡C—. In some embodiments, Y and X are both H, ≡ is a double bond, and L is —HC═CH—. In some embodiments, Y and X are both $H_2$, ≡ is a single bond, and L is —$CH_2CH_2$—. In some embodiments, L is —C≡C—, —HC═CH—, or —$CH_2CH_2$—. In some embodiments, Y is O, X is $H_2$, ≡ is a single bond, and L is —C(O)—$CH_2$—. In some embodiments, X is $H_2$, Y is O, ≡ is a single bond, and L is —$CH_2$—C(O)—. In some embodiments, L is —C(O)—$CH_2$— or —$CH_2$—C(O)—. In some embodiments, L is —C≡C—, —HC═CH—, —$CH_2CH_2$—, —C(O)—$CH_2$—, or —$CH_2$—C(O)—. In some embodiments, L is —C≡C—. In some embodiments, L is —HC═CH—. In some embodiments, L is —$CH_2CH_2$—. In some embodiments, L is —C(O)—$CH_2$—. In some embodiments, L is —$CH_2$—C(O)—.

In some embodiments, $R_1$ is $C_6$-$C_{10}$ aryl, fused bicyclic 8- to 10-membered heteroaryl, or fused bicyclic 8- to 10-membered heterocyclyl, each of which is optionally substituted by 1-5 R' groups, wherein the heterocyclyl and heteroaryl contain 1-3 heteroatoms selected from nitrogen and oxygen. In some embodiments, $R_1$ is $C_6$-$C_{10}$ aryl optionally substituted by 1-3 R' groups. In some embodiments, $R_1$ is fused bicyclic 8- to 10-membered heteroaryl containing 1-3 heteroatoms selected from nitrogen and oxygen and optionally substituted by 1-5 R' groups. In some embodiments, $R_1$ is fused bicyclic 8- to 10-membered heterocyclyl containing 1-3 heteroatoms selected from nitrogen and oxygen and optionally substituted by 1-5 R' groups. In some embodiments, $R_1$ is unsubstituted. In other embodiments, $R_1$ is substituted by 1-5 R' groups. In some variations, $R_1$ is substituted by 1-3 R' groups. In some variations, $R_1$ is substituted by R' group. In some variations, $R_1$ is substituted by 2 R' groups. In some embodiments, $R_1$ is connected to substituent L through an aryl moiety, such as through a phenyl group.

In some embodiments, $R_1$ is phenyl, phenyl fused to a cycloalkyl, fused bicyclic 9-membered heteroaryl, or fused bicyclic 9-membered heterocyclyl, each of which is optionally substituted by 1-3 R' groups, wherein the heterocyclyl and heteroaryl contain 1-2 heteroatoms selected from nitrogen and oxygen.

In some embodiments, $R_1$ is phenyl optionally substituted by 1-3 R' groups. In some embodiments, $R_1$ is phenyl fused to a cycloalkyl, such as cyclopropyl, cyclobutyl, cyclopentyl, or cyclohexyl, optionally substituted by 1-3 R' groups. In some embodiments, $R_1$ is phenyl fused to a cyclohexyl.

In some embodiments, $R_1$ is fused bicyclic 9-membered heteroaryl containing 1-2 heteroatoms selected from nitrogen and oxygen and optionally substituted by 1-3 R' groups. In some embodiments, $R_1$ is fused bicyclic 9-membered heteroaryl containing one nitrogen atom and one oxygen atom and optionally substituted by 1-3 R' groups. In some embodiments, $R_1$ is fused bicyclic 9-membered heteroaryl containing two nitrogen atoms and optionally substituted by 1-3 R' groups. In some embodiments, $R_1$ is fused bicyclic 9-membered heteroaryl containing one nitrogen atom and optionally substituted by 1-3 R' groups.

In some embodiments, $R_1$ is fused bicyclic 9-membered heterocyclyl containing 1-2 heteroatoms selected from nitrogen and oxygen and optionally substituted by 1-3 R' groups. In some embodiments, $R_1$ is fused bicyclic 9-membered heterocyclyl containing one oxygen atom and optionally substituted by 1-3 R' groups. In some embodiments, $R_1$ is fused bicyclic 9-membered heterocyclyl containing one nitrogen atom and optionally substituted by 1-3 R' groups. In some embodiments, $R_1$ is fused bicyclic 9-membered heterocyclyl containing one nitrogen atom and one oxygen atom and optionally substituted by 1-3 R' groups.

In some embodiments, each R' is independently halo, $C_1$-$C_6$ alkyl, $C_1$-$C_6$ haloalkyl, $C_1$-$C_6$ alkoxy, or $C_3$-$C_6$ cycloalkyl. In some embodiments, each R' is independently halo, $C_1$-$C_3$ alkyl, $C_1$-$C_3$ haloalkyl, $C_1$-$C_3$ alkoxy, or $C_3$-$C_6$ cycloalkyl. In some embodiments, each R is independently Cl, F, methyl, ethyl, isopropyl, —$CF_3$, —$OCH_3$, or cyclopropyl.

In some embodiments, R' is halo. In some embodiments, R' is F, Cl, or Br. In some embodiments, R' is F. In some embodiments, R' is Cl.

In some embodiments, R is $C_1$-$C_6$ alkyl. In some embodiments, R' is $C_1$-$C_3$ alkyl. In some embodiments, R is methyl, ethyl, n-propyl, or isopropyl. In some embodiments, R is methyl. In some embodiments, R' is ethyl. In some embodiments, R' is isopropyl.

In some embodiments, R is $C_1$-$C_6$ haloalkyl. In some embodiments, R is $C_1$-$C_6$ haloalkyl containing 1-13 halogen atoms. In some embodiments, R is $C_1$-$C_3$ haloalkyl. In some embodiments, R is $C_1$-$C_3$ haloalkyl containing 1-7 halogen atoms. In some embodiments, R is —$CF_3$, —$CHF_2$, —$CH_2F$, —$CCl_3$, —$CHCl_2$, —$CH_2Cl$, —$CF_2Cl$, —$CFCl_2$, —$CH_2CF_3$, —$CH_2CHF_2$, or —$CH_2CCl_3$. In some embodiments, R is —$CF_3$.

In some embodiments, R is $C_1$-$C_6$ alkoxy. In some embodiments, R is $C_1$-$C_3$ alkoxy. In some embodiments, R is —$OCH_3$, —$OCH_2CH_3$, or —$OCH(CH_3)_2$. In some embodiments, R is —$OCH_3$.

In some embodiments, R' is $C_3$-$C_6$ cycloalkyl. In some embodiments, R is $C_3$-$C_5$ cycloalkyl. In some embodiments, R' is cyclopropyl, cyclobutyl, cyclopentyl, or cyclohexyl. In some embodiments, R is cyclopropyl.

In some embodiments, $R_1$ is

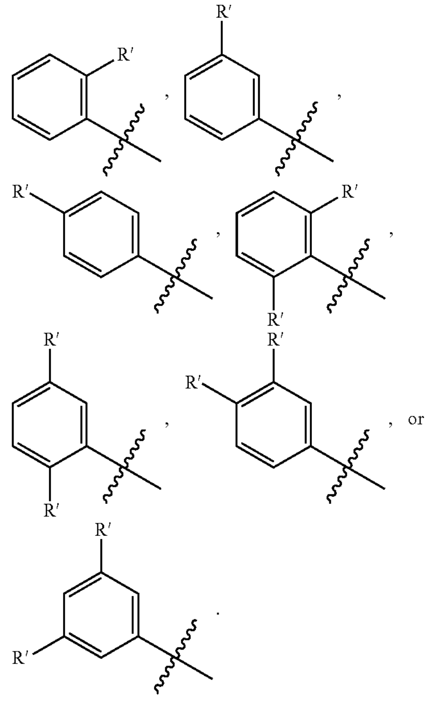

In some embodiments, $R_1$ is

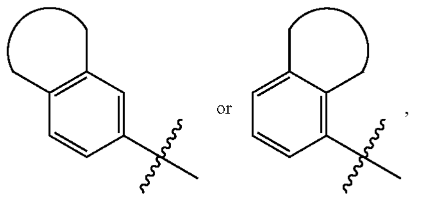

wherein the fused cyclic ring structure is $C_3$-$C_6$ cycloalkyl, 4- to 6-membered heterocyclyl, or 4- to 6-membered heteroaryl.

In some embodiments, $R_1$ is

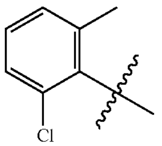,
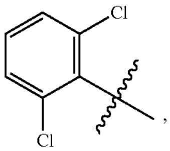,
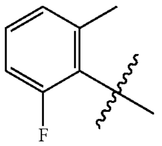,
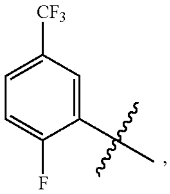,
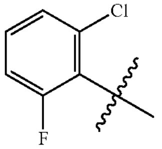,
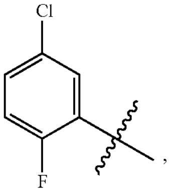,
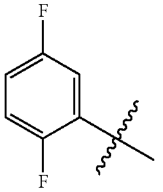,
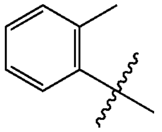,
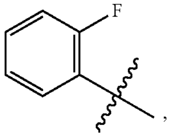,
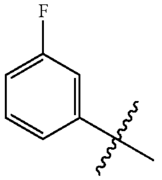,
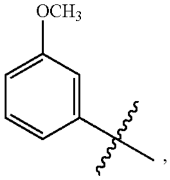,
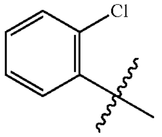,
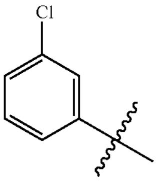,
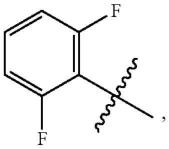,
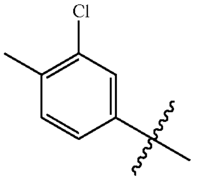,
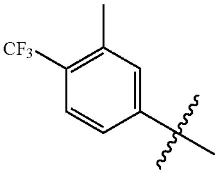,
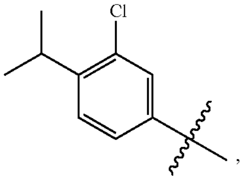,
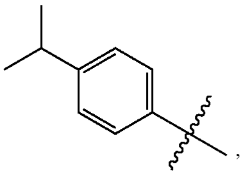,
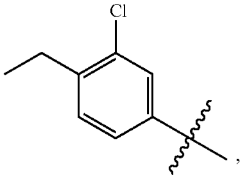,
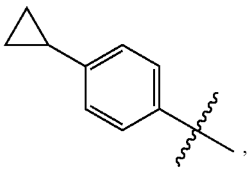, -continued

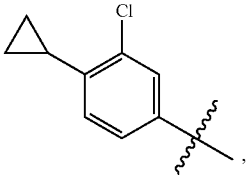,
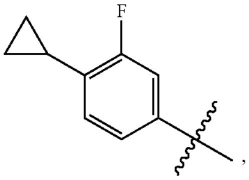,
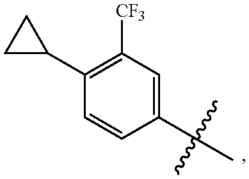,
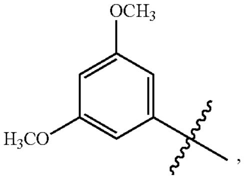,
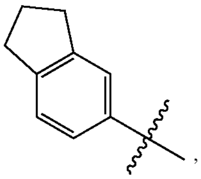,
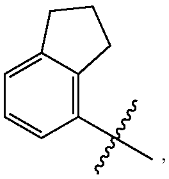,
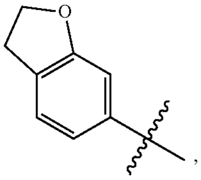,
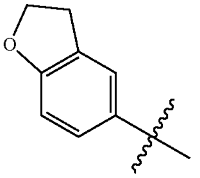, or
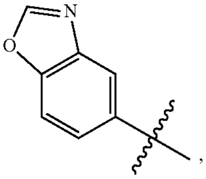, In some embodiments, $R_2$ is H or $C_1$-$C_6$ alkyl. In some embodiments, $R_2$ is H. In some embodiments, $R_2$ is $C_1$-$C_6$ alkyl. In some embodiments, $R_2$ is $C_1$-$C_3$ alkyl. In some embodiments, $R_2$ is methyl, ethyl, n-propyl, or isopropyl. In some embodiments, $R_2$ is methyl.

In some embodiments, $R_3$ is $-(CH_2)_x-CO_2H$ or

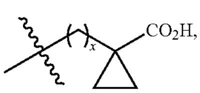

wherein x is 1-5. In some embodiments, $R_3$ is $-(CH_2)_x-CO_2H$, wherein x is 1-5. In some embodiments, $R_3$ is $-(CH_2)_x-CO_2H$, wherein x is 1-3. In some embodiments, $R_3$ is $-CH_2CO_2H$, $-(CH_2)_2CO_2H$, or $-(CH_2)_3CO_2H$. In some embodiments, $R_3$ is $-CH_2CO_2H$. In some embodiments, $R_3$ is $-(CH_2)_2CO_2H$. In some embodiments, $R_3$ is $-(CH_2)_3CO_2H$. In some embodiments, $R_3$ is

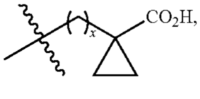

wherein x is 1-5. In some embodiments, $R_3$ is

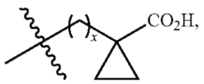

wherein x is 1-3. In some embodiments, $R_3$ is

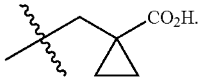

In some embodiments, $R_2$ is H or $C_1$-$C_3$ alkyl; $R_3$ is $-(CH_2)_x-CO_2H$ or

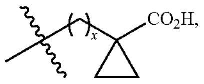

and x is 1-3. In some embodiments, $R_2$ is H or methyl; and $R_3$ is $-CH_2CO_2H$, $-(CH_2)_2CO_2H$, $-(CH_2)_3CO_2H$, or

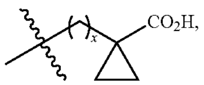

In some embodiments,

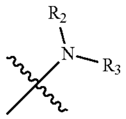

is

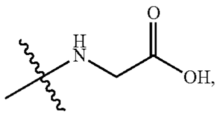

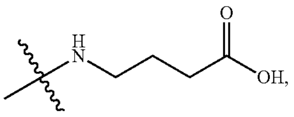

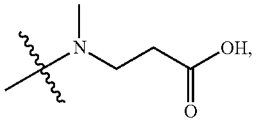

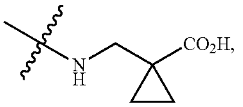

or

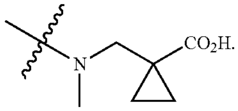

In some embodiments,

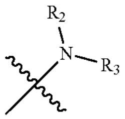

is

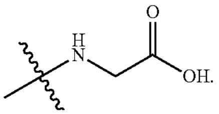

In some embodiments,

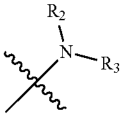

is

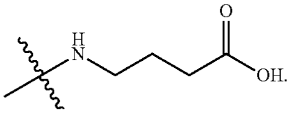

In some embodiments,

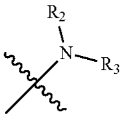

is

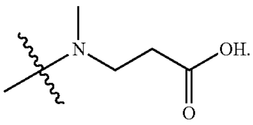

In some embodiments,

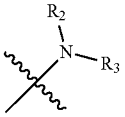

is

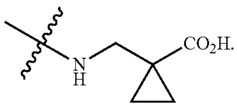

In some embodiments,

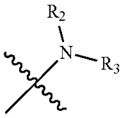

is

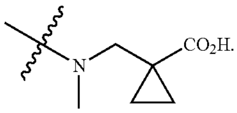

In some embodiments, x is 1-5. In some embodiments, x is 1-3. In some embodiments, x is 1. In some embodiments, x is 2. In some embodiments, x is 3. In some embodiments, x is 4. In some embodiments, x is 5.

In some embodiments, $R_2$ and $R_3$ are taken together with the nitrogen atom to which they are attached to form a 4- to 6-membered heterocyclyl substituted by 1-5 $R_4$ groups, wherein at least one $R_4$ group is $-CO_2H$ or contains a $-CO_2H$ moiety. In some embodiments, $R_2$ and $R_3$ are taken together with the nitrogen atom to which they are attached to form a 4- to 6-membered heterocyclyl substituted by 1-5 $R_4$ groups, wherein at least one $R_4$ group is $-CO_2H$. In some embodiments, $R_2$ and $R_3$ are taken together with the nitrogen atom to which they are attached to form a 4- to 6-membered heterocyclyl substituted by 1-5 $R_4$ groups, wherein at least one $R_4$ group contains a $-CO_2H$ moiety. In some embodiments, $R_2$ and $R_3$ are taken together with the nitrogen atom to which they are attached to form a 4- to 6-membered heterocyclyl that does not contain any additional heteroatoms, wherein the heterocyclyl is substituted by 1-5 $R_4$ groups, and wherein at least one $R_4$ group is $-CO_2H$ or contains a $-CO_2H$ moiety. In some embodiments, $R_2$ and $R_3$ are taken together with the nitrogen atom to which they are attached to form a 4-membered heterocyclyl substituted by 1-5 $R_4$ groups, wherein at least one $R_4$ group is —$CO_2H$ or contains a —$CO_2H$ moiety. In some embodiments, $R_2$ and $R_3$ are taken together with the nitrogen atom to which they are attached to form a 5-membered heterocyclyl substituted by 1-5 $R_4$ groups, wherein at least one $R_4$ group is —$CO_2H$ or contains a —$CO_2H$ moiety. In some embodiments, $R_2$ and $R_3$ are taken together with the nitrogen atom to which they are attached to form a 6-membered heterocyclyl substituted by 1-5 $R_4$ groups, wherein at least one $R_4$ group is —$CO_2H$ or contains a —$CO_2H$ moiety.

In some embodiments, $R_2$ and $R_3$ are taken together with the nitrogen atom to which they are attached to form azetidinyl, pyrrolidinyl, or piperidinyl, each of which is substituted by 1-3 $R_4$ groups, wherein at least one $R_4$ group is —$CO_2H$ or contains a —$CO_2H$ moiety. In some embodiments, $R_2$ and $R_3$ are taken together with the nitrogen atom to which they are attached to form azetidinyl, pyrrolidinyl, or piperidinyl, each of which is substituted by 1-3 $R_4$ groups, wherein at least one $R_4$ group is —$CO_2H$. In some embodiments, $R_2$ and $R_3$ are taken together with the nitrogen atom to which they are attached to form azetidinyl, pyrrolidinyl, or piperidinyl, each of which is substituted by 1-3 $R_4$ groups, wherein at least one $R_4$ group contains a —$CO_2H$ moiety.

In some embodiments, $R_2$ and $R_3$ are taken together with the nitrogen atom to which they are attached to form azetidinyl substituted by 1-3 $R_4$ groups, wherein at least one $R_4$ group is —$CO_2H$ or contains a —$CO_2H$ moiety. In some embodiments, $R_2$ and $R_3$ are taken together with the nitrogen atom to which they are attached to form pyrrolidinyl substituted by 1-3 $R_4$ groups, wherein at least one $R_4$ group is —$CO_2H$ or contains a —$CO_2H$ moiety. In some embodiments, $R_2$ and $R_3$ are taken together with the nitrogen atom to which they are attached to form piperidinyl substituted by 1-3 $R_4$ groups, wherein at least one $R_4$ group is —$CO_2H$ or contains a —$CO_2H$ moiety.

In any of the embodiments or variations of Formula (I) described herein, at least one $R_4$ group is —$CO_2H$ or contains a —$CO_2H$ moiety.

In some embodiments, each $R_4$ is independently —$CO_2H$, halo, or $C_1$-$C_6$ alkyl. In some embodiments, each $R_4$ is independently —$CO_2H$, halo, or $C_1$-$C_3$ alkyl. In some embodiments, $R_4$ is —$CO_2H$. In some embodiments, $R_4$ is halo. In some embodiments, $R_4$ is fluoro, chloro, or bromo. In some embodiments, $R_4$ is fluoro. In some embodiments, $R_4$ is $C_1$-$C_6$ alkyl. In some embodiments, $R_4$ is $C_1$-$C_3$ alkyl. In some embodiments, $R_4$ is methyl, ethyl, n-propyl, or isopropyl. In some embodiments, $R_4$ is methyl. In some embodiments, each $R_4$ is independently —$CO_2H$, F, or methyl.

In some embodiments, two $R_4$ groups are taken together with the carbon atoms to which they are attached to form a fused, bridged, or spiro $C_3$-$C_5$ cycloalkyl optionally substituted by —$CO_2H$. In some embodiments, two $R_4$ groups are taken together with the carbon atoms to which they are attached to form a fused $C_3$-$C_5$ cycloalkyl optionally substituted by —$CO_2H$. In some embodiments, two $R_4$ groups are taken together with the carbon atoms to which they are attached to form a bridged $C_3$-$C_5$ cycloalkyl optionally substituted by —$CO_2H$. In some embodiments, two $R_4$ groups are taken together with the carbon atoms to which they are attached to form a spiro $C_3$-$C_5$ cycloalkyl optionally substituted by —$CO_2H$. In some embodiments, two $R_4$ groups are taken together with the carbon atoms to which they are attached to form a fused, bridged, or spiro $C_3$-$C_5$ cycloalkyl that is not substituted. In some embodiments, two $R_4$ groups are taken together with the carbon atoms to which they are attached to form a fused, bridged, or spiro $C_3$-$C_5$ cycloalkyl that is substituted by —$CO_2H$.

In some embodiments, two $R_4$ groups are taken together with the carbon atoms to which they are attached to form a fused cyclopropyl, a spiro cyclopropyl, a spiro cyclobutyl, or a bridged cyclopentyl, each of which is optionally substituted by —$CO_2H$. In some embodiments, two $R_4$ groups are taken together with the carbon atoms to which they are attached to form a fused cyclopropyl optionally substituted by —$CO_2H$. In some embodiments, two $R_4$ groups are taken together with the carbon atoms to which they are attached to form a spiro cyclopropyl optionally substituted by —$CO_2H$. In some embodiments, two $R_4$ groups are taken together with the carbon atoms to which they are attached to form a spiro cyclobutyl optionally substituted by —$CO_2H$. In some embodiments, two $R_4$ groups are taken together with the carbon atoms to which they are attached to form a bridged cyclopentyl optionally substituted by —$CO_2H$.

In some embodiments,

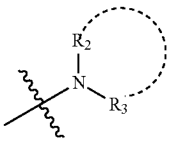

is

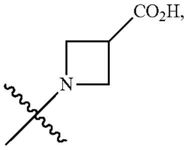, 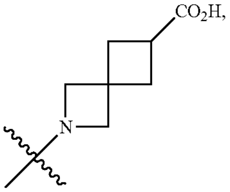, 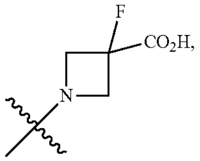, 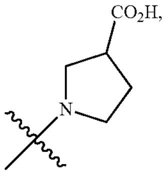, 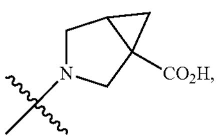, 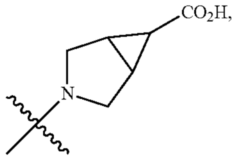, 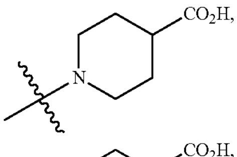, 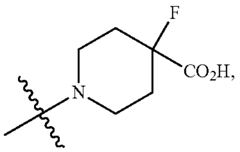, 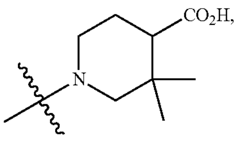, 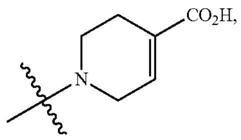

-continued

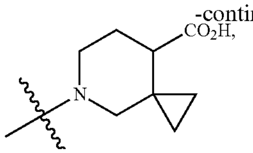

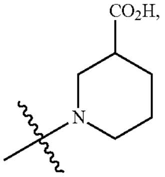

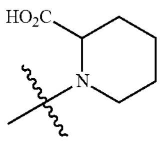

, or

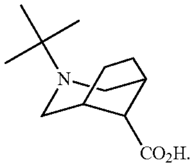

In some embodiments, the compound of Formula (I) is a compound of Formula (IA):

(IA)

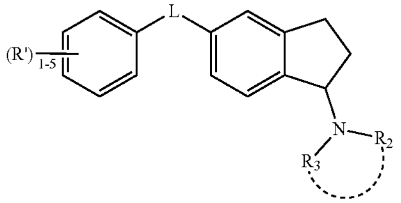

wherein R', $R_2$, $R_3$, and L are as described for Formula (I).

In some embodiments, the compound of Formula (I) is a compound of Formula (II):

(II)

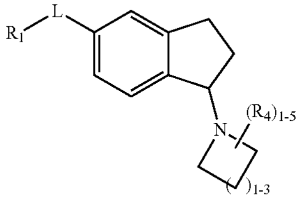

wherein L, $R_1$, and $R_4$ are as described for Formula (I).

In some embodiments, the compound of Formula (I) is a compound of Formula (III):

(III)

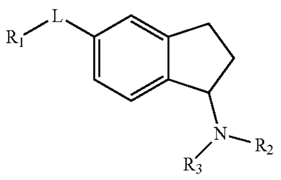

wherein $R_2$ is H or $C_1$-$C_6$ alkyl; $R_3$ is $-(CH_2)_x-CO_2H$ or

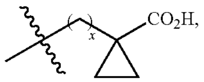

wherein x is 1-5; and L and $R_1$ are as described for Formula (I).

In some embodiments, the compound of Formula (I) is a compound of Formula (IIIa) or (IIIb):

(IIIa)

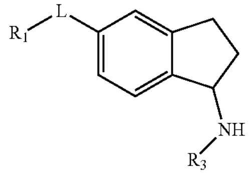

(IIIb)

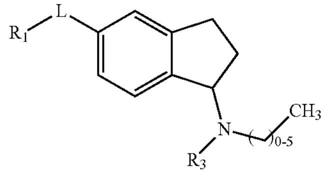

wherein L, $R_1$, and $R_3$ are as described for Formula (I).

In some embodiments, the compound of Formula (I) is a compound of Formula (IVa), (IVb), (IVc), (IVd), (IVe), or (IVf):

(IVa)

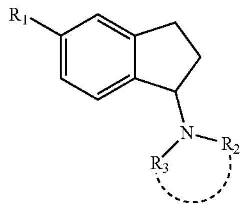

(IVb)

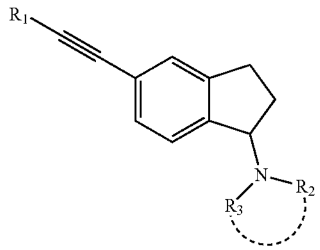

(IVc)

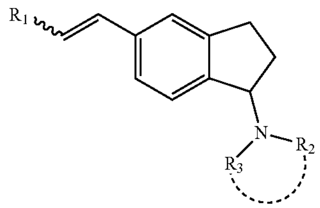

(IVd)

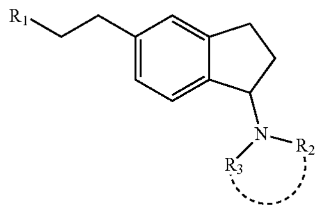

-continued (IVe)

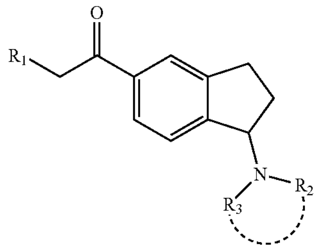

(IVf)

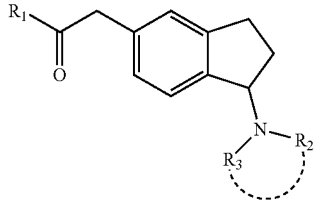

wherein $R_1$, $R_2$, and $R_3$ are as described for Formula (I), and ∿∿ indicates either cis or trans orientation.

In some embodiments, the compound of Formula (I) is a compound of Formula (Va), (Vb), (Vc), (Vd), (Ve), or (Vf):

(Va)

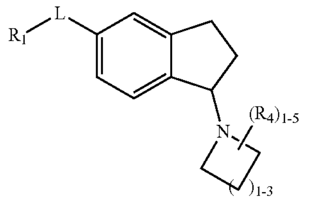

(Vb)

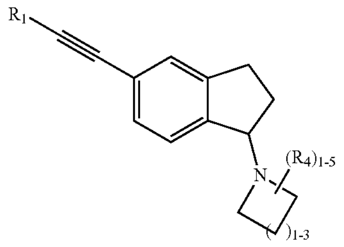

(Vc)

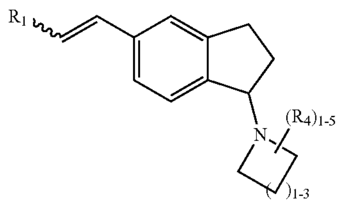

(Vd)

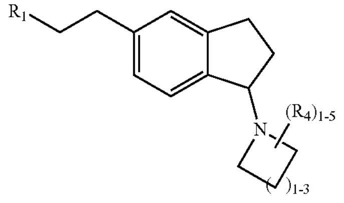

-continued (Ve)

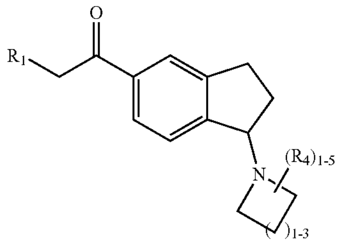

(Vf)

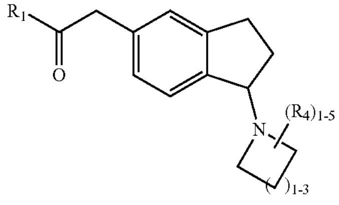

wherein $R_1$ and $R_4$ are as described for Formula (I), and ∿∿ indicates either cis or trans orientation.

In some embodiments, the compound of Formula (I) is a compound of Formula (VIa), (VIb), (VIc), (VId), (VIe), or (VIf):

(VIa)

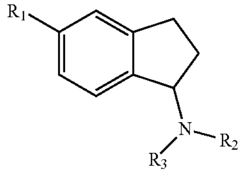

(VIb)

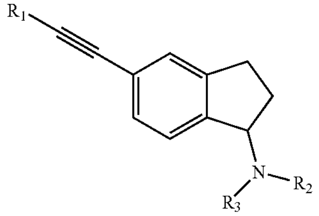

(VIc)

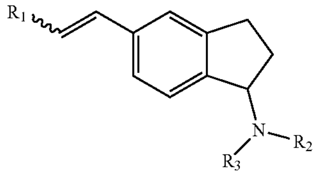

(VId)

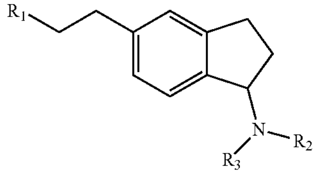

-continued (VIe)

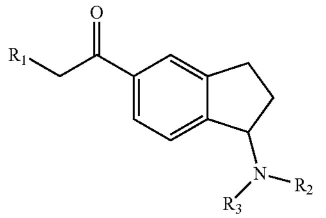

(VIf)

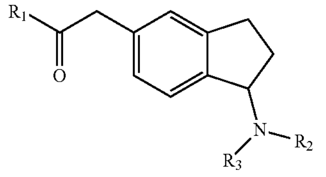

wherein $R_1$ is as described for Formula (I); $R_2$ is H or $C_1$-$C_6$ alkyl; $R_3$ is $-(CH_2)_x-CO_2H$ or

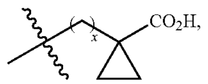

wherein x is 1-5; and ∿ indicates either cis or trans orientation.

In the descriptions herein, it is understood that every description, variation, embodiment, or aspect of a moiety may be combined with every description, variation, embodiment, or aspect of other moieties the same as if each and every combination of descriptions is specifically and individually listed. For example, every description, variation, embodiment, or aspect provided herein with respect to L of Formula (I) may be combined with every description, variation, embodiment, or aspect of X, Y, $\equiv$, $R_1$, R', $R_2$, $R_3$, $R_4$, and x the same as if each and every combination were specifically and individually listed. It is also understood that all descriptions, variations, embodiments, or aspects of Formula (I), where applicable, apply equally to other formulae detailed herein, and are equally described, the same as if each and every description, variation, embodiment, or aspect were separately and individually listed for all formulae. For example, all descriptions, variations, embodiments, or aspects of Formula (I), where applicable, apply equally to any of the formulae as detailed herein, such as Formulae (IA), (II), (III), (IIIa), (IIIb), (IVa), (IVb), (IVc), (IVd), (IVe), (IVf), (Va), (Vb), (Vc), (Vd), (Ve), (Vf), (VIa), (VIb), (VIc), (VId), (VIe), and (VIf), are equally described, the same as if each and every description, variation, embodiment, or aspect were separately and individually listed for all formulae.

In some embodiments, provided is a compound selected from the compounds in Table 1 or a pharmaceutically acceptable salt thereof. Although certain compounds described in the present disclosure, including in Table 1, are presented as specific stereoisomers and/or in a non-stereochemical form, it is understood that any or all stereochemical forms, including any enantiomeric or diastereomeric forms, and any tautomers or other forms of any of the compounds of the present disclosure, including in Table 1, are herein described.

TABLE 1

| Compound No. | Structure | Name |
|---|---|---|
| 1 | 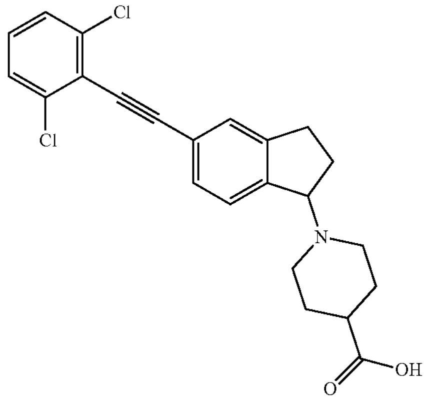 [SMILES: O=C(O)C1CCN(C2CCc3cc(C#Cc4c(Cl)cccc4Cl)ccc32)CC1] | 1-(5-((2,6-dichlorophenyl)ethynyl)-2,3-dihydro-1H-inden-1-yl)piperidine-4-carboxylic acid |

TABLE 1-continued

| Compound No. | Structure | Name |
|---|---|---|
| 2 | 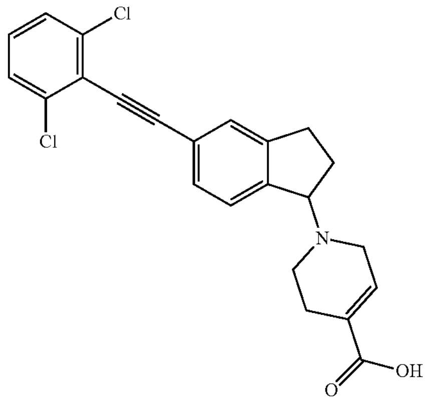 [SMILES: O=C(O)C1=CCN(C2CCc3cc(C#Cc4c(Cl)cccc4Cl)ccc32)CC1] | 1-(5-((2,6-dichlorophenyl)ethynyl)-2,3-dihydro-1H-inden-1-yl)-1,2,3,6-tetrahydropyridine-4-carboxylic acid |
| 3a | 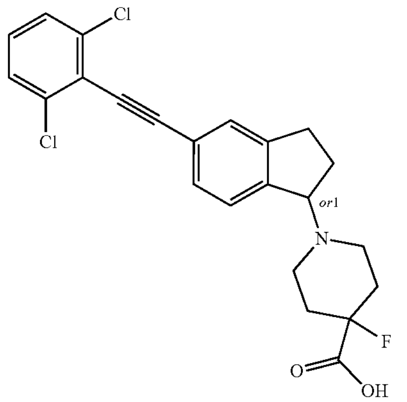 [SMILES: O=C(O)C1(F)CCN(C2CCc3cc(C#Cc4c(Cl)cccc4Cl)ccc32)CC1] | 1-(5-((2,6-dichlorophenyl)ethynyl)-2,3-dihydro-1H-inden-1-yl)-4-fluoropiperidine-4-carboxylic acid Enantiomer 1 |
| 3b | 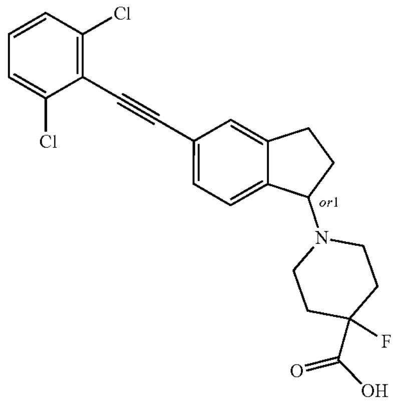 [SMILES: O=C(O)C1(F)CCN(C2CCc3cc(C#Cc4c(Cl)cccc4Cl)ccc32)CC1] | 1-(5-((2,6-dichlorophenyl)ethynyl)-2,3-dihydro-1H-inden-1-yl)-4-fluoropiperidine-4-carboxylic acid Enantiomer 2 |
| 4a | 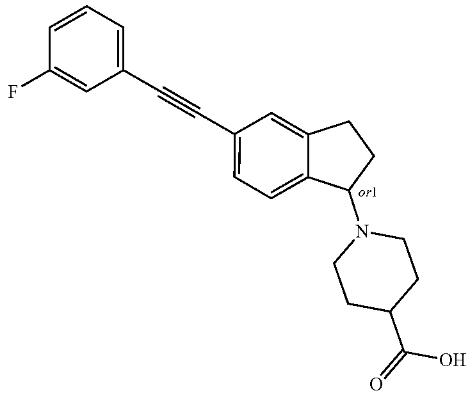 [SMILES: O=C(O)C1CCN(C2CCc3cc(C#Cc4cccc(F)c4)ccc32)CC1] | 1-(5-((3-fluorophenyl)ethynyl)-2,3-dihydro-1H-inden-1-yl)piperidine-4-carboxylic acid Enantiomer 1 |

TABLE 1-continued

| Compound No. | Structure | Name |
| --- | --- | --- |
| 4b | 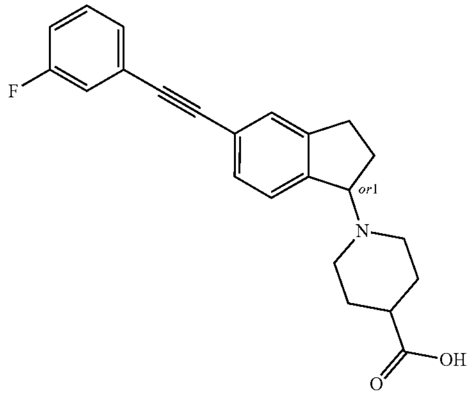 [SMILES: O=C(O)C1CCN(C2CCc3cc(C#Cc4cccc(F)c4)ccc32)CC1] | 1-(5-((3-fluorophenyl)ethynyl)-2,3-dihydro-1H-inden-1-yl)piperidine-4-carboxylic acid Enantiomer 2 |
| 5 | 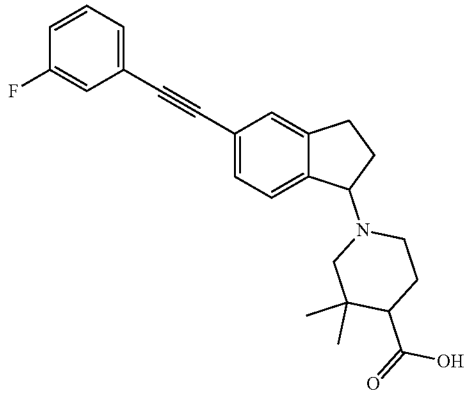 [SMILES: CC1(C)CN(C2CCc3cc(C#Cc4cccc(F)c4)ccc32)CCC1C(=O)O] | 1-(5-((3-fluorophenyl)ethynyl)-2,3-dihydro-1H-inden-1-yl)-3,3-dimethylpiperidine-4-carboxylic acid |
| 6a | 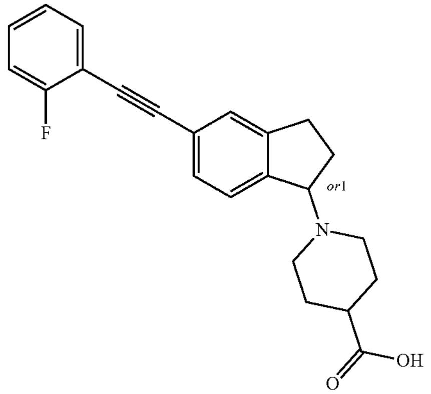 [SMILES: O=C(O)C1CCN(C2CCc3cc(C#Cc4ccccc4F)ccc32)CC1] | 1-(5-((2-fluorophenyl)ethynyl)-2,3-dihydro-1H-inden-1-yl)piperidine-4-carboxylic acid Enantiomer 1 |
| 6b | 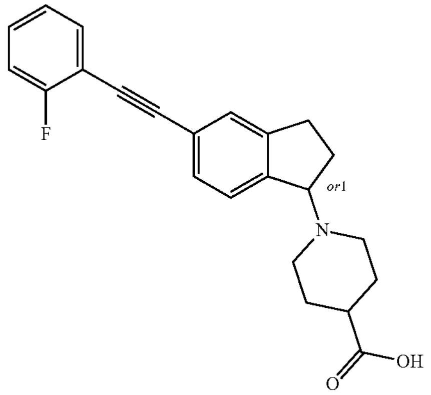 [SMILES: O=C(O)C1CCN(C2CCc3cc(C#Cc4ccccc4F)ccc32)CC1] | 1-(5-((2-fluorophenyl)ethynyl)-2,3-dihydro-1H-inden-1-yl)piperidine-4-carboxylic acid Enantiomer 2 |

TABLE 1-continued

| Compound No. | Structure | Name |
|---|---|---|
| 7a | 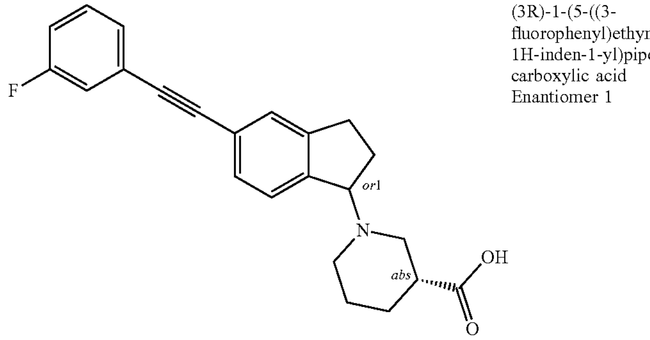 | (3R)-1-(5-((3-fluorophenyl)ethynyl)-2,3-dihydro-1H-inden-1-yl)piperidine-3-carboxylic acid Enantiomer 1 |
| 7b | 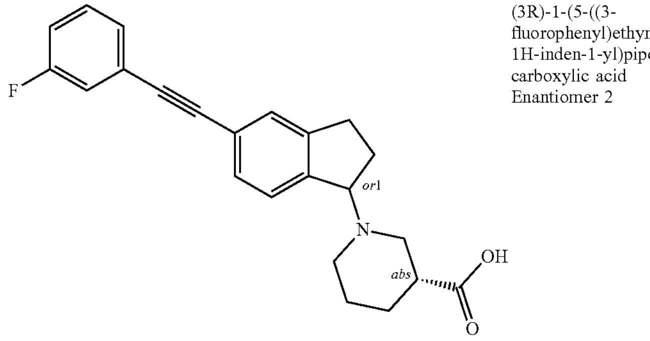 | (3R)-1-(5-((3-fluorophenyl)ethynyl)-2,3-dihydro-1H-inden-1-yl)piperidine-3-carboxylic acid Enantiomer 2 |
| 8a | 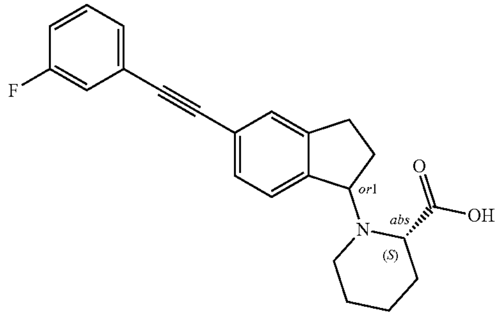 | (2S)-1-(5-((3-fluorophenyl)ethynyl)-2,3-dihydro-1H-inden-1-yl)piperidine-2-carboxylic acid Enantiomer 1 |
| 8b | 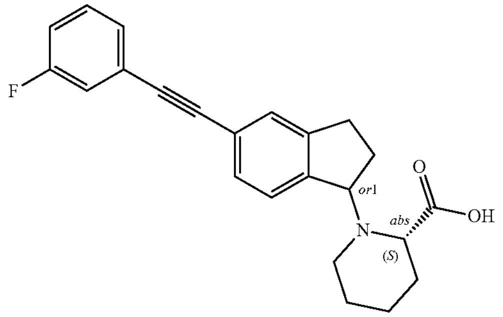 | (2S)-1-(5-((3-fluorophenyl)ethynyl)-2,3-dihydro-1H-inden-1-yl)piperidine-2-carboxylic acid Enantiomer 2 |

TABLE 1-continued

| Compound No. | Structure | Name |
| --- | --- | --- |
| 9a | 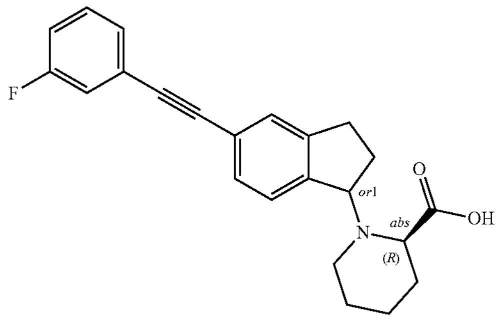 | (2R)-1-(5-((3-fluorophenyl)ethynyl)-2,3-dihydro-1H-inden-1-yl)piperidine-2-carboxylic acid Enantiomer 1 |
| 9b | 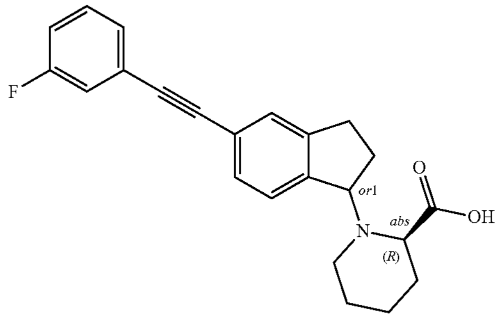 | (2R)-1-(5-((3-fluorophenyl)ethynyl)-2,3-dihydro-1H-inden-1-yl)piperidine-2-carboxylic acid Enantiomer 2 |
| 10 | 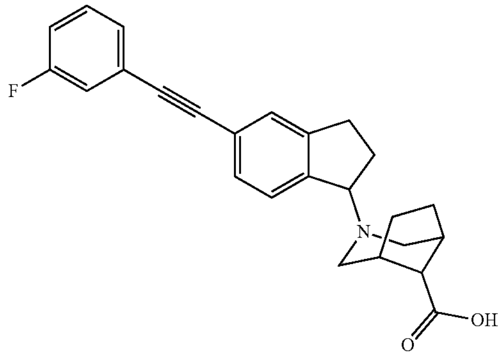 [SMILES: O=C(O)C1C2CCC1CN(C1CCc3cc(C#Cc4cccc(F)c4)ccc31)C2] | (1R,5S,8s)-3-(5-((3-fluorophenyl)ethynyl)-2,3-dihydro-1H-inden-1-yl)-3-azabicyclo[3.2.1]octane-8-carboxylic acid |
| 11 | 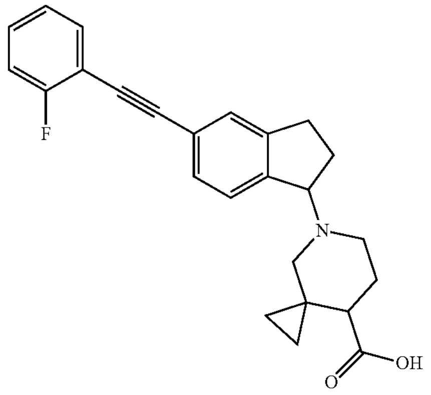 [SMILES: O=C(O)C1CCN(C2CCc3cc(C#Cc4ccccc4F)ccc32)CC12CC2] | 5-(5-((2-fluorophenyl)ethynyl)-2,3-dihydro-1H-inden-1-yl)-5-azaspiro[2.5]octane-8-carboxylic acid |

TABLE 1-continued

| Compound No. | Structure | Name |
|---|---|---|
| 12 | 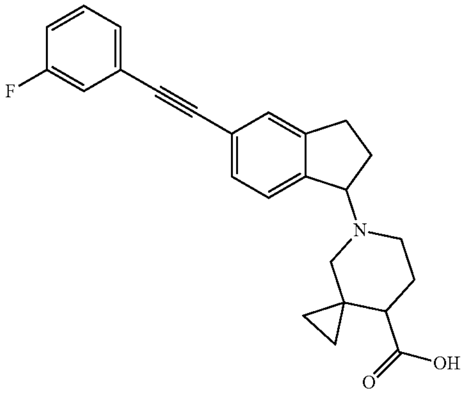 [SMILES: O=C(O)C1CCN(C2CCc3cc(C#Cc4cccc(F)c4)ccc32)CC12CC2] | 5-(5-((2-fluorophenyl)ethynyl)-2,3-dihydro-1H-inden-1-yl)-5-azaspiro[2.5]octane-8-carboxylic acid |
| 13a | 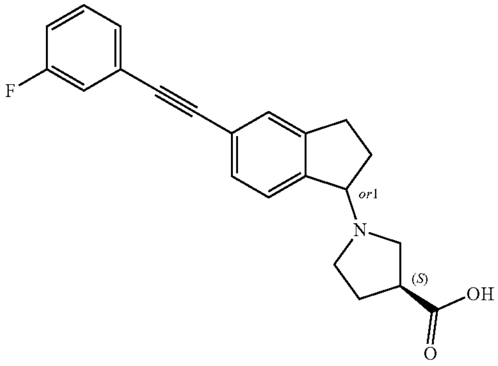 | (3S)-1-(5-((3-fluorophenyl)ethynyl)-2,3-dihydro-1H-inden-1-yl)pyrrolidine-3-carboxylic acid<br>Enantiomer 1 |
| 13b | 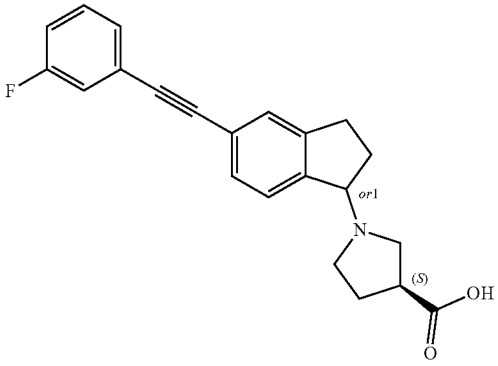 | (3S)-1-(5-((3-fluorophenyl)ethynyl)-2,3-dihydro-1H-inden-1-yl)pyrrolidine-3-carboxylic acid<br>Enantiomer 2 |
| 14a | 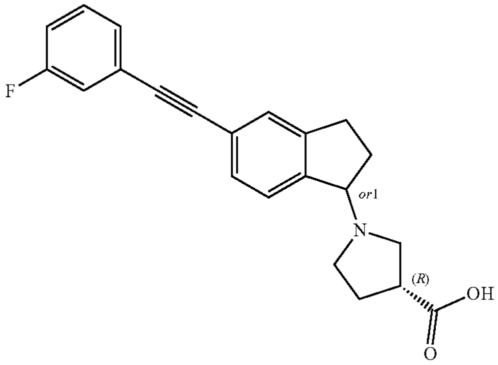 | (3R)-1-(5-((3-fluorophenyl)ethynyl)-2,3-dihydro-1H-inden-1-yl)pyrrolidine-3-carboxylic acid<br>Enantiomer 1 |

TABLE 1-continued

| Compound No. | Structure | Name |
|---|---|---|
| 14b | 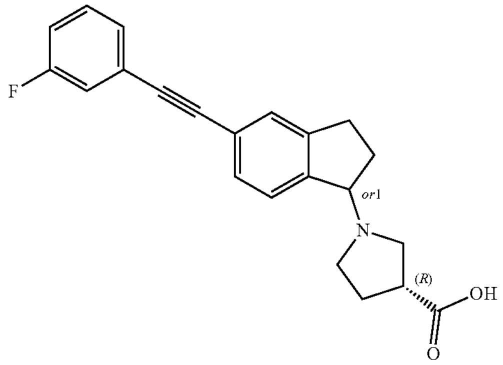 | (3R)-1-(5-((3-fluorophenyl)ethynyl)-2,3-dihydro-1H-inden-1-yl)pyrrolidine-3-carboxylic acid Enantiomer 2 |
| 15 | 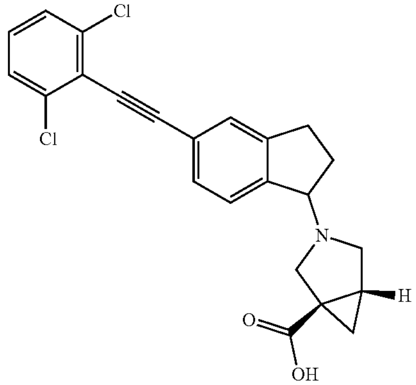 [SMILES: O=C(O)[C@]12C[C@H]1CN(C1CCc3cc(C#Cc4c(Cl)cccc4Cl)ccc31)C2] | (1R,5R)-3-(5-((2,6-dichlorophenyl)ethynyl)-2,3-dihydro-1H-inden-1-yl)-3-azabicyclo[3.1.0]hexane-1-carboxylic acid |
| 16 | 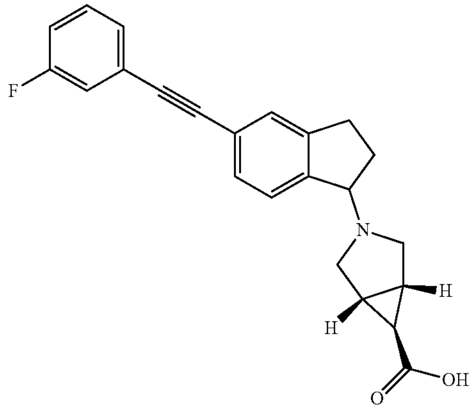 [SMILES: O=C(O)[C@H]1[C@@H]2CN(C3CCc4cc(C#Cc5cccc(F)c5)ccc43)C[C@@H]21] | (1R,5S,6r)-3-(5-((3-fluorophenyl)ethynyl)-2,3-dihydro-1H-inden-1-yl)-3-azabicyclo[3.1.0]hexane-6-carboxylic acid |
| 17 | 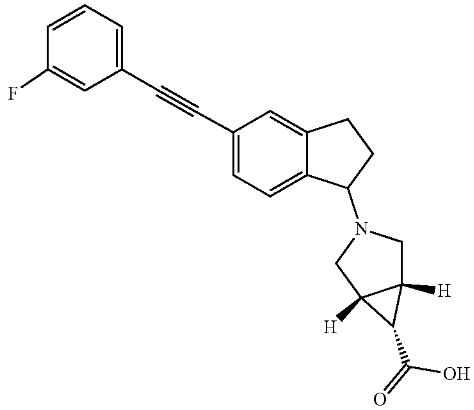 [SMILES: O=C(O)[C@@H]1[C@@H]2CN(C3CCc4cc(C#Cc5cccc(F)c5)ccc43)C[C@@H]21] | (1R,5S,6s)-3-(5-((3-fluorophenyl)ethynyl)-2,3-dihydro-1H-inden-1-yl)-3-azabicyclo[3.1.0]hexane-6-carboxylic acid |

TABLE 1-continued
| Compound No. | Structure | Name |
| --- | --- | --- |
| 18 | 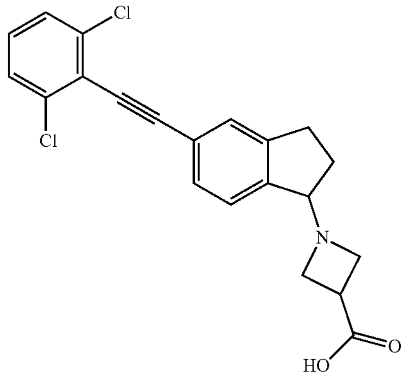 [SMILES: O=C(O)C1CN(C2CCc3cc(C#Cc4c(Cl)cccc4Cl)ccc32)C1] | 1-(5-((2,6-dichlorophenyl)ethynyl)-2,3-dihydro-1H-inden-1-yl)azetidine-3-carboxylic acid |
| 19 | 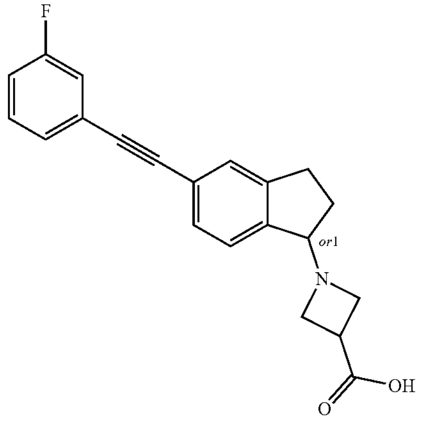 [SMILES: O=C(O)C1CN(C2CCc3cc(C#Cc4cccc(F)c4)ccc32)C1] | 1-(5-((3-fluorophenyl)ethynyl)-2,3-dihydro-1H-inden-1-yl)azetidine-3-carboxylic acid |
| 20 | 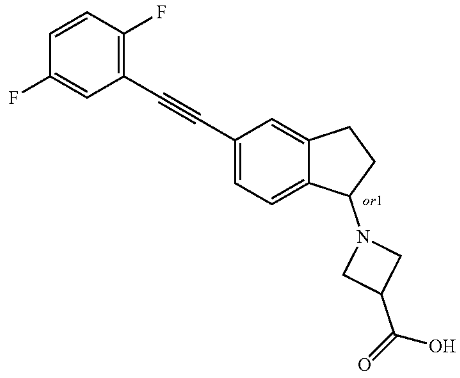 [SMILES: O=C(O)C1CN(C2CCc3cc(C#Cc4cc(F)ccc4F)ccc32)C1] | (S)-1-(5-((2,5-difluorophenyl)ethynyl)-2,3-dihydro-1H-inden-1-yl)azetidine-3-carboxylic acid |
| 21 | 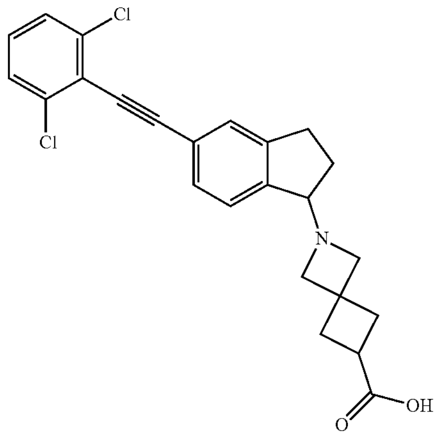 [SMILES: O=C(O)C1CC2(C1)CN(C1CCc3cc(C#Cc4c(Cl)cccc4Cl)ccc31)C2] | 2-(5-((2,6-dichlorophenyl)ethynyl)-2,3-dihydro-1H-inden-1-yl)-2-azaspiro[3.3]heptane-6-carboxylic acid |

TABLE 1-continued
| Compound No. | Structure | Name |
|---|---|---|
| 22a | 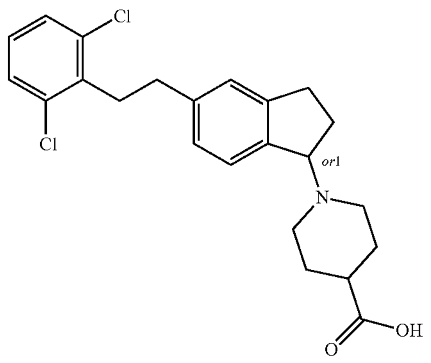 | 1-(5-(2,6-dichlorophenethyl)-2,3-dihydro-1H-inden-1-yl)piperidine-4-carboxylic acid Enantiomer 1 |
| 22b | 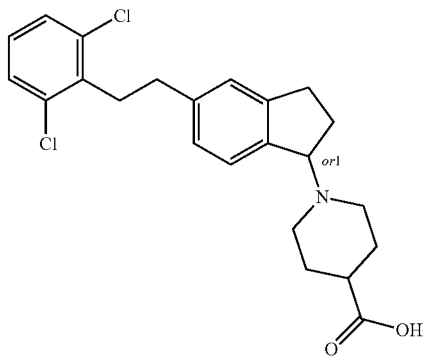 [SMILES: O=C(O)C1CCN(C2CCc3cc(CCc4c(Cl)cccc4Cl)ccc32)CC1] | 1-(5-(2,6-dichlorophenethyl)-2,3-dihydro-1H-inden-1-yl)piperidine-4-carboxylic acid Enantiomer 2 |
| 23 | 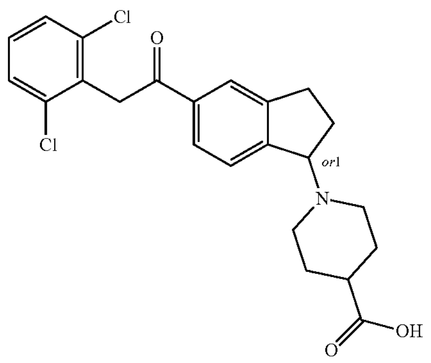 [SMILES: O=C(Cc1c(Cl)cccc1Cl)c1ccc2c(c1)CCC2N1CCC(C(=O)O)CC1] | (R)-1-(5-(2-(2,6-dichlorophenyl)acetyl)-2,3-dihydro-1H-inden-1-yl)piperidine-4-carboxylic acid |
| 24 | 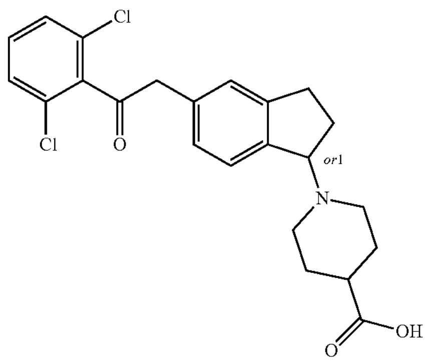 [SMILES: O=C(Cc1ccc2c(c1)CCC2N1CCC(C(=O)O)CC1)c1c(Cl)cccc1Cl] | (R)-1-(5-(2-(2,6-dichlorophenyl)-2-oxoethyl)-2,3-dihydro-1H-inden-1-yl)piperidine-4-carboxylic acid |

TABLE 1-continued
| Compound No. | Structure | Name |
| --- | --- | --- |
| 25a | 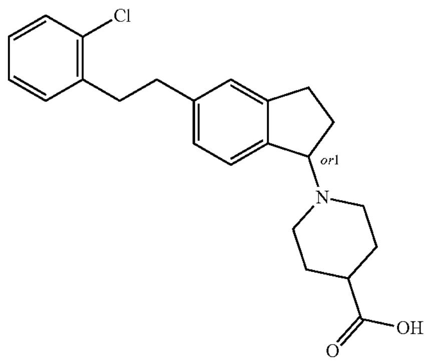 [SMILES: O=C(O)C1CCN(C2CCc3cc(CCc4ccccc4Cl)ccc32)CC1] | 1-(5-(2-chlorophenethyl)-2,3-dihydro-1H-inden-1-yl)piperidine-4-carboxylic acid Enantiomer 1 |
| 25b | 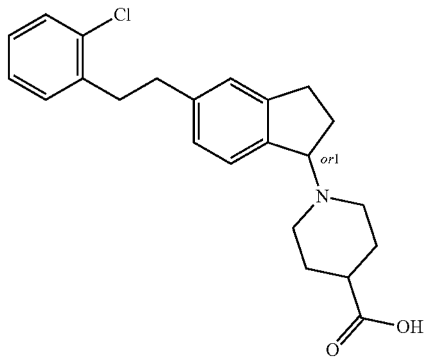 [SMILES: O=C(O)C1CCN(C2CCc3cc(CCc4ccccc4Cl)ccc32)CC1] | 1-(5-(2-chlorophenethyl)-2,3-dihydro-1H-inden-1-yl)piperidine-4-carboxylic acid Enantiomer 2 |
| 26a | 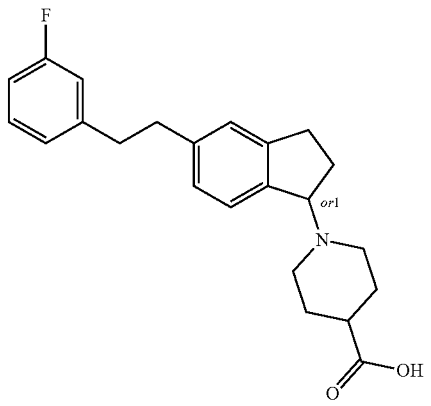 [SMILES: O=C(O)C1CCN(C2CCc3cc(CCc4cccc(F)c4)ccc32)CC1] | 1-(5-(3-fluorophenethyl)-2,3-dihydro-1H-inden-1-yl)piperidine-4-carboxylic acid Enantiomer 1 |
| 26b | 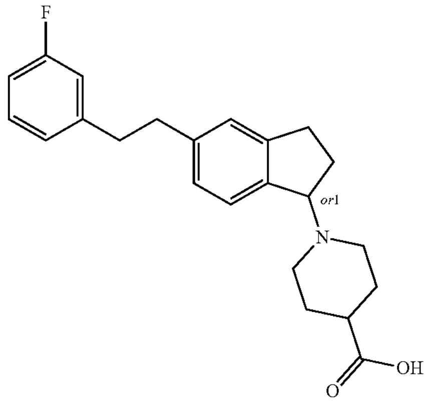 [SMILES: O=C(O)C1CCN(C2CCc3cc(CCc4cccc(F)c4)ccc32)CC1] | 1-(5-(3-fluorophenethyl)-2,3-dihydro-1H-inden-1-yl)piperidine-4-carboxylic acid Enantiomer 2 |

TABLE 1-continued

| Compound No. | Structure | Name |
| --- | --- | --- |
| 27a | 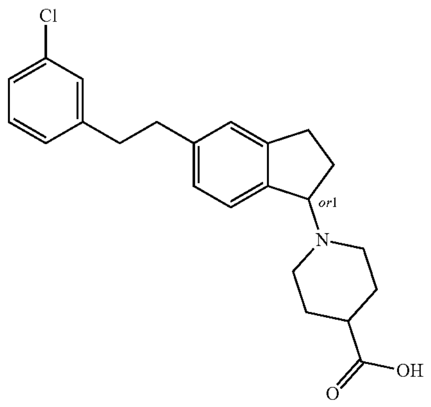 | 1-(5-(3-chlorophenethyl)-2,3-dihydro-1H-inden-1-yl)piperidine-4-carboxylic acid Enantiomer 1 |
| 27b | 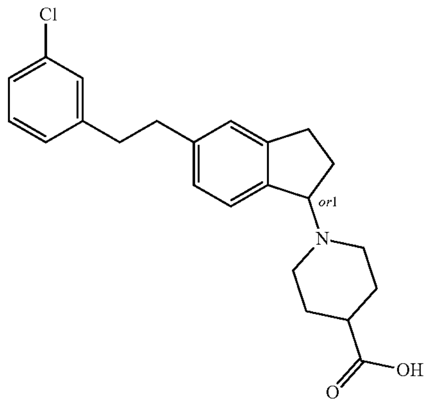 [SMILES: O=C(O)C1CCN(C2CCc3cc(CCc4cccc(Cl)c4)ccc32)CC1] | 1-(5-(3-chlorophenethyl)-2,3-dihydro-1H-inden-1-yl)piperidine-4-carboxylic acid Enantiomer 2 |
| 28a | 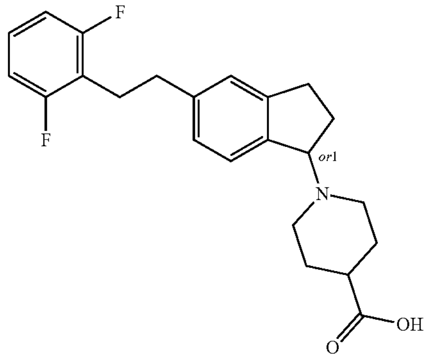 [SMILES: O=C(O)C1CCN(C2CCc3cc(CCc4c(F)cccc4F)ccc32)CC1] | 1-(5-(2,6-difluorophenethyl)-2,3-dihydro-1H-inden-1-yl)piperidine-4-carboxylic acid Enantiomer 1 |
| 28b | 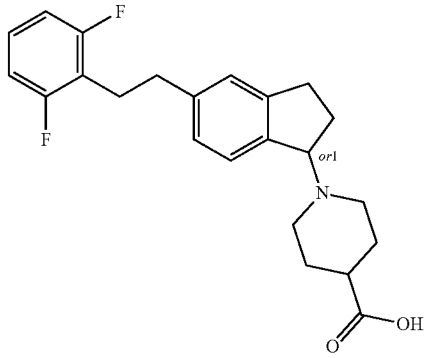 [SMILES: O=C(O)C1CCN(C2CCc3cc(CCc4c(F)cccc4F)ccc32)CC1] | 1-(5-(2,6-difluorophenethyl)-2,3-dihydro-1H-inden-1-yl)piperidine-4-carboxylic acid Enantiomer 2 |

TABLE 1-continued

| Compound No. | Structure | Name |
|---|---|---|
| 29 | 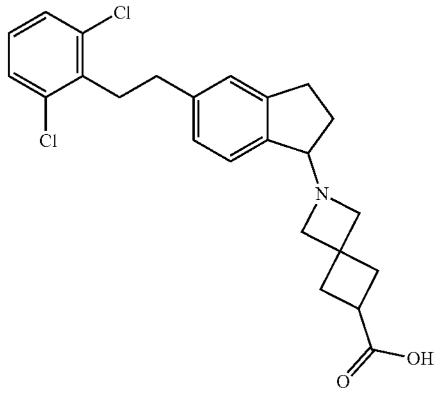 [SMILES: O=C(O)C1CC2(C1)CN(C1CCc3cc(CCc4c(Cl)cccc4Cl)ccc31)C2] | 2-(5-(2,6-dichlorophenethyl)-2,3-dihydro-1H-inden-1-yl)-2-azaspiro[3.3]heptane-6-carboxylic acid |
| 30a | 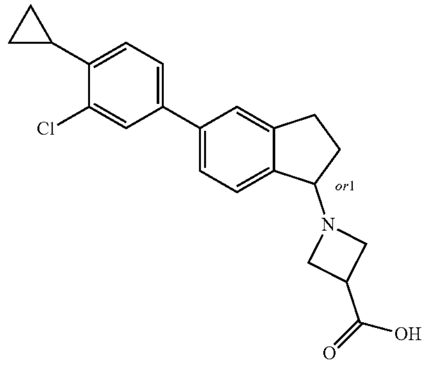 [SMILES: O=C(O)C1CN(C2CCc3cc(-c4ccc(C5CC5)c(Cl)c4)ccc32)C1] | (R)-1-(5-(3-chloro-4-cyclopropylphenyl)-2,3-dihydro-1H-inden-1-yl)azetidine-3-carboxylic acid Enantiomer 1 |
| 30b | 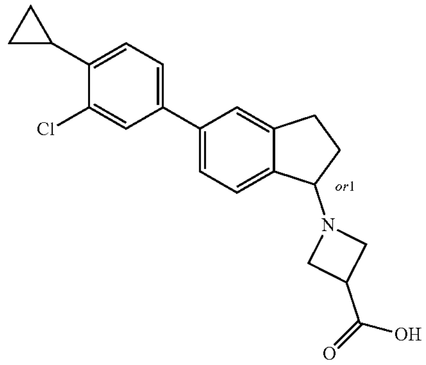 | (S)-1-(5-(3-chloro-4-cyclopropylphenyl)-2,3-dihydro-1H-inden-1-yl)azetidine-3-carboxylic acid Enantiomer 2 |
| 31a | 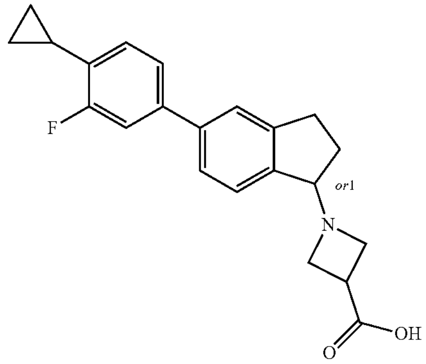 [SMILES: O=C(O)C1CN(C2CCc3cc(-c4ccc(C5CC5)c(F)c4)ccc32)C1] | (R)-1-(5-(4-cyclopropyl-3-fluorophenyl)-2,3-dihydro-1H-inden-1-yl)azetidine-3-carboxylic acid Enantiomer 1 |

TABLE 1-continued

| Compound No. | Structure | Name |
| --- | --- | --- |
| 31b | 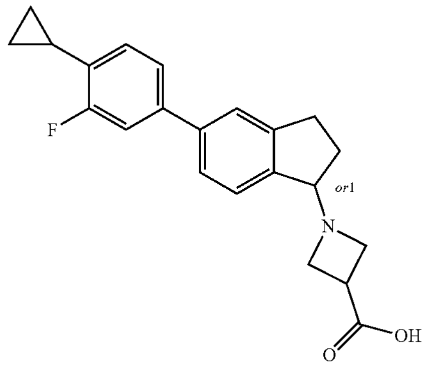 [SMILES: O=C(O)C1CN(C2CCc3cc(-c4ccc(C5CC5)c(F)c4)ccc32)C1] | (S)-1-(5-(4-cyclopropyl-3-fluorophenyl)-2,3-dihydro-1H-inden-1-yl)azetidine-3-carboxylic acid Enantiomer 2 |
| 32a | 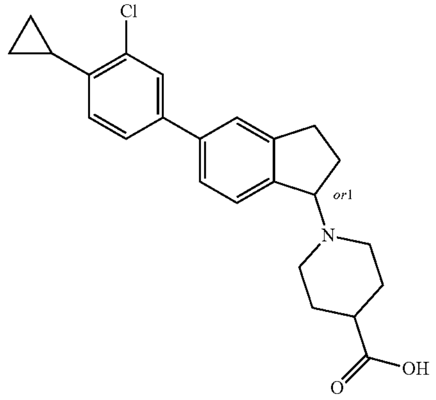 [SMILES: O=C(O)C1CCN(C2CCc3cc(-c4ccc(C5CC5)c(Cl)c4)ccc32)CC1] | 1-(5-(3-chloro-4-cyclopropylphenyl)-2,3-dihydro-1H-inden-1-yl)piperidine-4-carboxylic acid Enantiomer 1 |
| 32b | 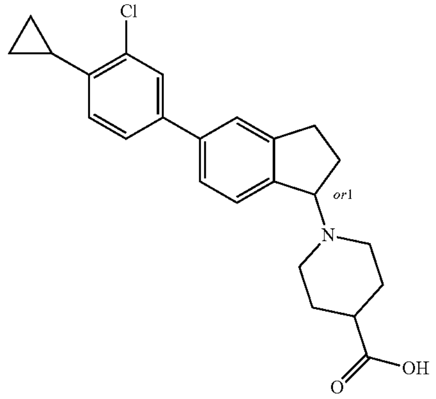 [SMILES: O=C(O)C1CCN(C2CCc3cc(-c4ccc(C5CC5)c(Cl)c4)ccc32)CC1] | 1-(5-(3-chloro-4-cyclopropylphenyl)-2,3-dihydro-1H-inden-1-yl)piperidine-4-carboxylic acid Enantiomer 2 |
| 33 | 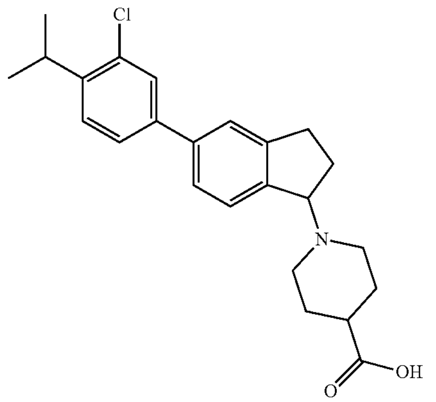 [SMILES: CC(C)c1ccc(-c2ccc3c(c2)CCC3N2CCC(C(=O)O)CC2)cc1Cl] | 1-(5-(3-chloro-4-isopropylphenyl)-2,3-dihydro-1H-inden-1-yl)piperidine-4-carboxylic acid |

TABLE 1-continued

| Compound No. | Structure | Name |
| --- | --- | --- |
| 34a | 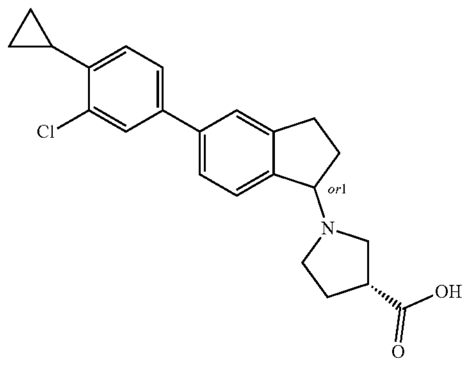 [SMILES: O=C(O)[C@@H]1CCN(C2CCc3cc(-c4ccc(C5CC5)c(Cl)c4)ccc32)C1] | (3R)-1-(5-(3-chloro-4-cyclopropylphenyl)-2,3-dihydro-1H-inden-1-yl)pyrrolidine-3-carboxylic acid Enantiomer 1 |
| 34b | 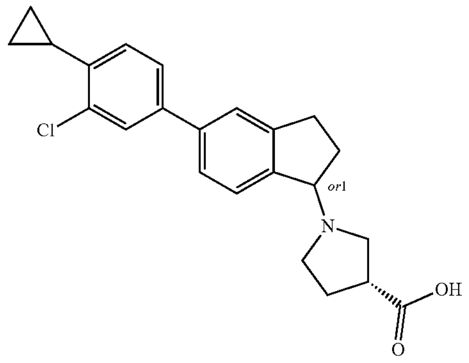 [SMILES: O=C(O)[C@@H]1CCN(C2CCc3cc(-c4ccc(C5CC5)c(Cl)c4)ccc32)C1] | (3R)-1-(5-(3-chloro-4-cyclopropylphenyl)-2,3-dihydro-1H-inden-1-yl)pyrrolidine-3-carboxylic acid Enantiomer 2 |
| 35a | 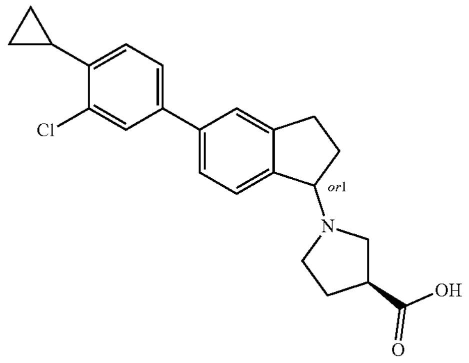 [SMILES: O=C(O)[C@H]1CCN(C2CCc3cc(-c4ccc(C5CC5)c(Cl)c4)ccc32)C1] | (3S)-1-(5-(3-chloro-4-cyclopropylphenyl)-2,3-dihydro-1H-inden-1-yl)pyrrolidine-3-carboxylic acid Enantiomer 1 |
| 35b | 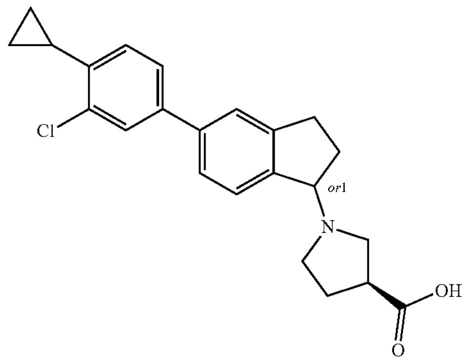 [SMILES: O=C(O)[C@H]1CCN(C2CCc3cc(-c4ccc(C5CC5)c(Cl)c4)ccc32)C1] | (3S)-1-(5-(3-chloro-4-cyclopropylphenyl)-2,3-dihydro-1H-inden-1-yl)pyrrolidine-3-carboxylic acid Enantiomer 2 |

TABLE 1-continued

| Compound No. | Structure | Name |
| --- | --- | --- |
| 36a | 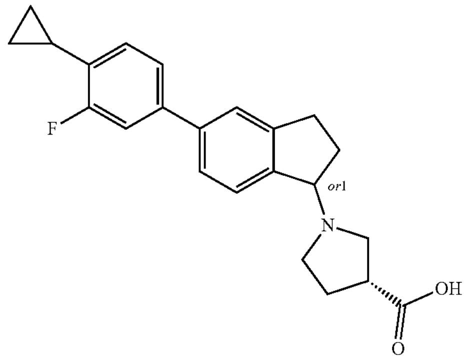 [SMILES: O=C(O)[C@@H]1CCN(C2CCc3cc(-c4ccc(C5CC5)c(F)c4)ccc32)C1] | (3R)-1-(5-(4-cyclopropyl-3-fluorophenyl)-2,3-dihydro-1H-inden-1-yl)pyrrolidine-3-carboxylic acid<br>Enantiomer 1 |
| 36b | 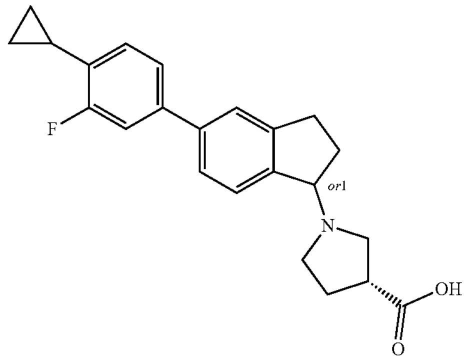 [SMILES: O=C(O)[C@@H]1CCN(C2CCc3cc(-c4ccc(C5CC5)c(F)c4)ccc32)C1] | (3R)-1-(5-(4-cyclopropyl-3-fluorophenyl)-2,3-dihydro-1H-inden-1-yl)pyrrolidine-3-carboxylic acid<br>Enantiomer 2 |
| 37a | 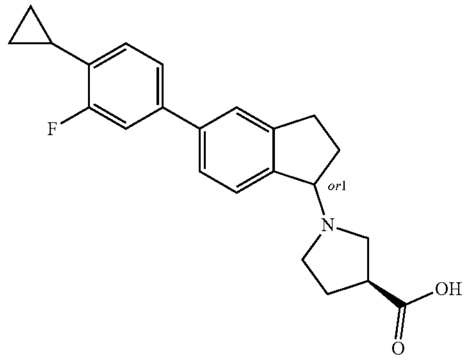 [SMILES: O=C(O)[C@H]1CCN(C2CCc3cc(-c4ccc(C5CC5)c(F)c4)ccc32)C1] | (3S)-1-(5-(4-cyclopropyl-3-fluorophenyl)-2,3-dihydro-1H-inden-1-yl)pyrrolidine-3-carboxylic acid<br>Enantiomer 1 |
| 37b | 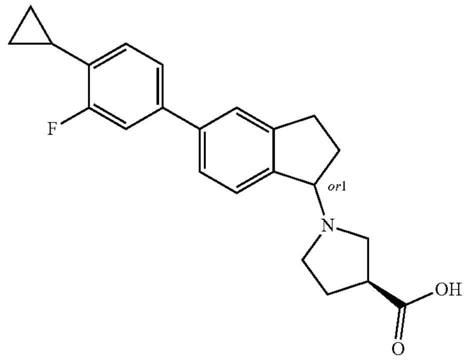 [SMILES: O=C(O)[C@H]1CCN(C2CCc3cc(-c4ccc(C5CC5)c(F)c4)ccc32)C1] | (3S)-1-(5-(4-cyclopropyl-3-fluorophenyl)-2,3-dihydro-1H-inden-1-yl)pyrrolidine-3-carboxylic acid<br>Enantiomer 2 |

TABLE 1-continued
| Compound No. | Structure | Name |
| --- | --- | --- |
| 38 | 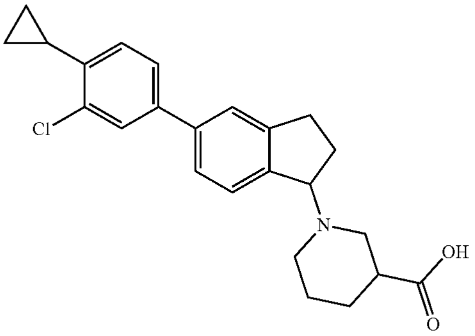 [SMILES: O=C(O)C1CCCN(C2CCc3cc(-c4ccc(C5CC5)c(Cl)c4)ccc32)C1] | 1-(5-(3-chloro-4-cyclopropylphenyl)-2,3-dihydro-1H-inden-1-yl)piperidine-3-carboxylic acid |
| 39 | 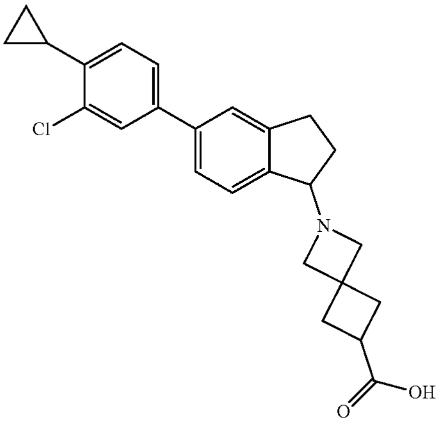 [SMILES: O=C(O)C1CC2(C1)CN(C1CCc3cc(-c4ccc(C5CC5)c(Cl)c4)ccc31)C2] | 2-(5-(3-chloro-4-cyclopropylphenyl)-2,3-dihydro-1H-inden-1-yl)-2-azaspiro[3.3]heptane-6-carboxylic acid |
| 40 | 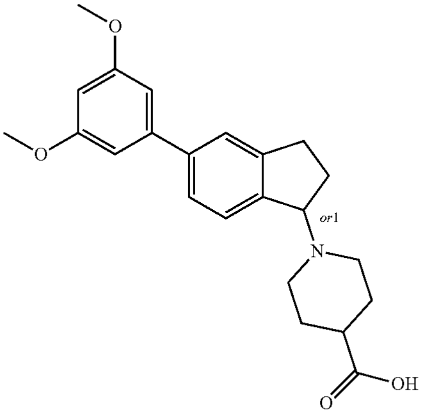 [SMILES: COc1cc(OC)cc(-c2ccc3c(c2)CCC3N2CCC(C(=O)O)CC2)c1] | (S)-1-(5-(3,5-dimethoxyphenyl)-2,3-dihydro-1H-inden-1-yl)piperidine-4-carboxylic acid |
| 41 | 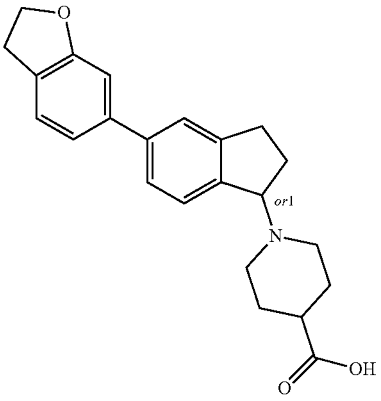 [SMILES: O=C(O)C1CCN(C2CCc3cc(-c4ccc5c(c4)OCC5)ccc32)CC1] | (S)-1-(5-(2,3-dihydrobenzofuran-6-yl)-2,3-dihydro-1H-inden-1-yl)piperidine-4-carboxylic acid |

TABLE 1-continued
| Compound No. | Structure | Name |
| --- | --- | --- |
| 42 | 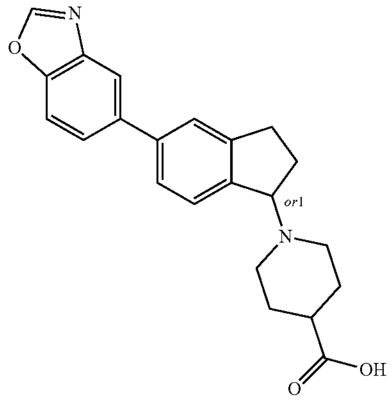 [SMILES: O=C(O)C1CCN(C2CCc3cc(-c4ccc5ocnc5c4)ccc32)CC1] | (S)-1-(5-(benzo[d]oxazol-5-yl)-2,3-dihydro-1H-inden-1-yl)piperidine-4-carboxylic acid |
| 43 | 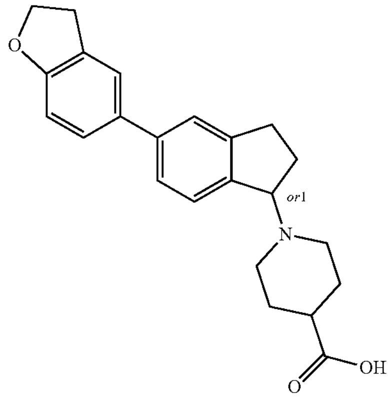 [SMILES: O=C(O)C1CCN(C2CCc3cc(-c4ccc5c(c4)CCO5)ccc32)CC1] | (S)-1-(5-(2,3-dihydrobenzofuran-5-yl)-2,3-dihydro-1H-inden-1-yl)piperidine-4-carboxylic acid |
| 44 | 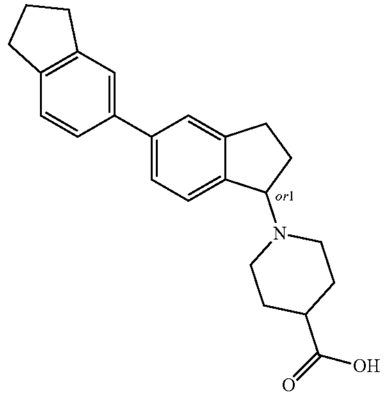 [SMILES: O=C(O)C1CCN(C2CCc3cc(-c4ccc5c(c4)CCC5)ccc32)CC1] | (S)-1-(2,2',3,3'-tetrahydro-1H,1'H-[5,5'-biinden]-1-yl)piperidine-4-carboxylic acid |
| 45 | 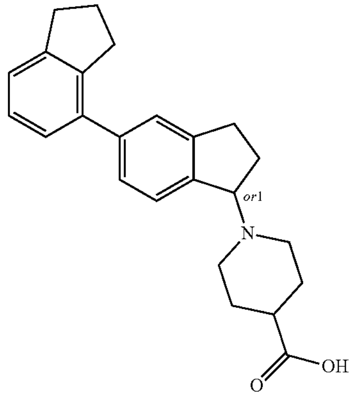 [SMILES: O=C(O)C1CCN(C2CCc3cc(-c4cccc5c4CCC5)ccc32)CC1] | (S)-1-(2,2',3,3'-tetrahydro-1H,1'H-[4,5'-biinden]-1'-yl)piperidine-4-carboxylic acid |

"or1" indicates that the absolute stereochemistry was not determined.

or a pharmaceutically acceptable salt thereof.

It is understood that in the present description, combinations of substituents and/or variables of the depicted formulae are permissible only if such contributions result in stable compounds.

Furthermore, all compounds of Formula (I) that exist in free base or acid form can be converted to their pharmaceutically acceptable salts by treatment with the appropriate inorganic or organic base or acid by methods known to one skilled in the art. Salts of the compounds of Formula (I) can be converted to their free base or acid form by standard techniques.

Methods of Synthesis

The compounds described herein can be made using conventional organic syntheses and commercially available starting materials, or the methods provided herein. By way of example and not limitation, compounds of Formula (I) can be prepared as outlined in Scheme 1, as well as in the examples set forth herein. It should be noted that one skilled in the art would know how to modify the procedures set forth in the illustrative schemes and examples to arrive at the desired products.

Scheme 1.
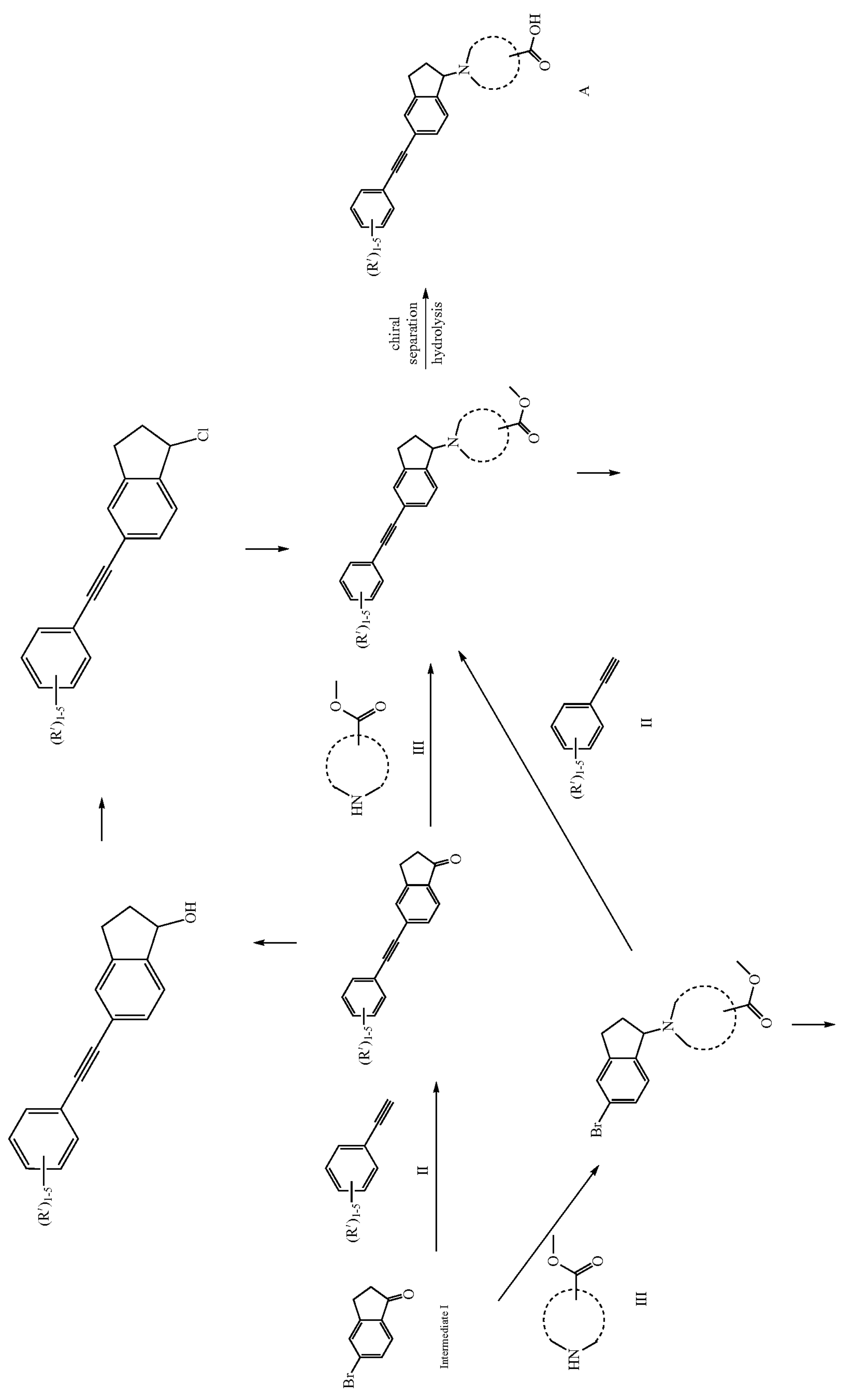

-continued
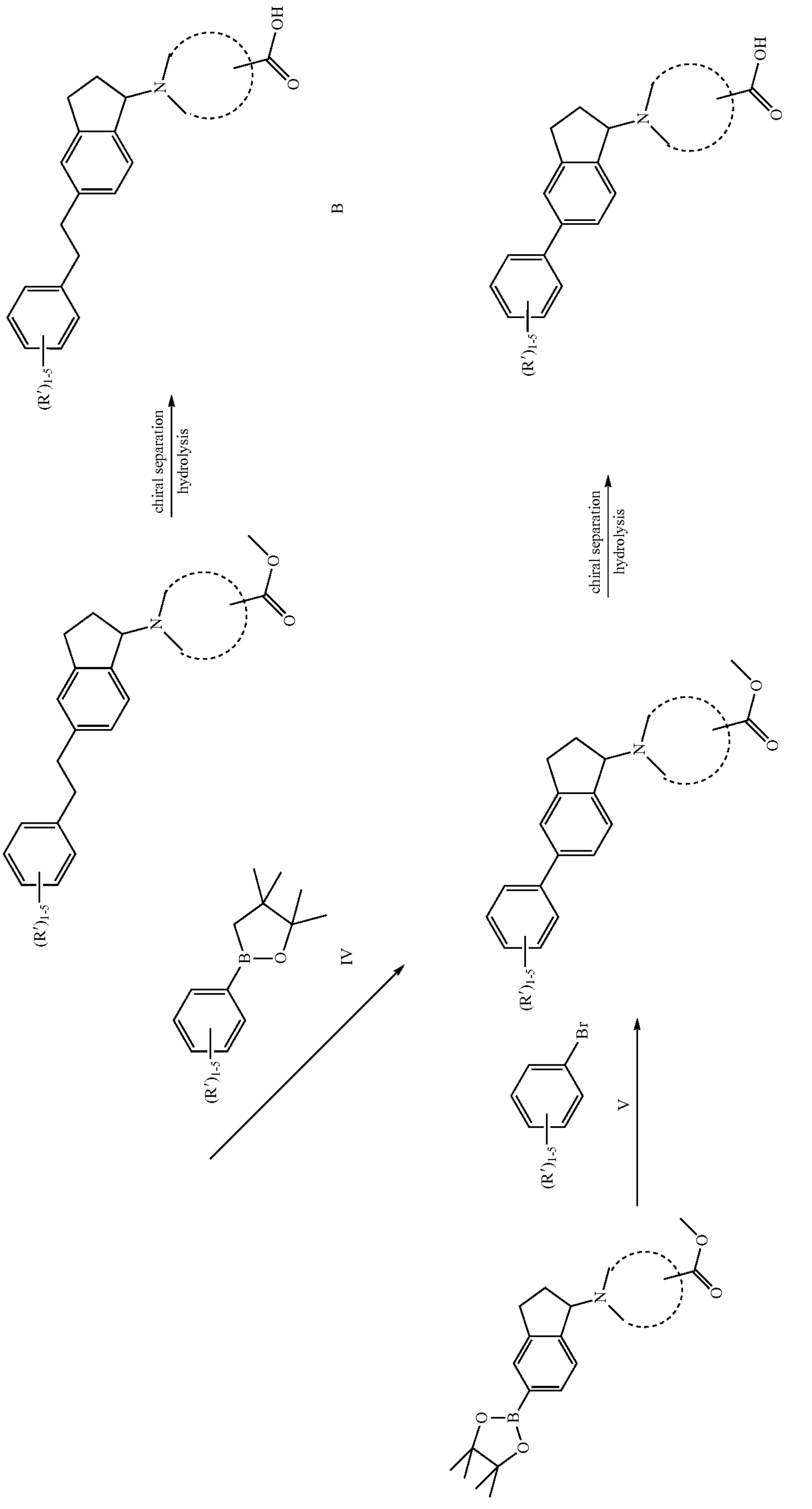
B
C

As outlined in Scheme 1, compounds of general formula A can be synthesized from 5-bromo-2,3-dihydro-1H-inden-1-one (Intermediate I compounds) via Sonogashira coupling with alkyne II, followed by reductive amination with aminoacid ester III and subsequent hydrolysis. Alternatively, the ketone intermediate can be reduced to an alcohol, converted to a chloride, and subsequently reacted with aminoacid ester III and hydrolyzed to yield compounds of general formula A.

Compounds of general formula B can be obtained through Pd-catalyzed reduction of compounds of general formula A, as shown in Scheme 1.

Biaryl compounds of general formula C can be synthesized from Intermediate I compounds by reductive amination, followed by Suzuki coupling with boronate IV and subsequent hydrolysis, as outlined in Scheme 1. Alternatively, following reductive amination, the bromide intermediate can be converted to a boronate, coupled with aryl bromide V and hydrolyzed to provide compounds of general formula C.

Methods of Use

Embodiments of the present disclosure provide a method for modulating sphingosine 1-phosphate receptor 5 (S1P5) in a subject in need thereof, the method comprising administering to the subject an effective amount of a compound of Formula (I). Modulation (e.g., inhibition or activation) of S1P5 can be assessed and demonstrated by a wide variety of ways known in the art. Kits and commercially available assays can be utilized for determining whether and to what degree S1P5 has been modulated (e.g., inhibited or activated).

In one aspect, provided herein is a method of modulating S1P5 comprising contacting S1P5 with an effective amount of a compound of Formula (I) or any embodiment or variation thereof. In some embodiments, the compound of Formula (I) inhibits S1P5. In other embodiments, the compound of Formula (I) activates S1P5. In some embodiments, the compound of Formula (I) is an agonist of S1P5. In some embodiments, the compound of Formula (I) is an antagonist of S1P5.

In some embodiments, a compound of Formula (I) modulates the activity of S1P5 by about 1%, 5%, 10%, 15%, 20%, 25%, 30%, 35%, 40%, 45%, 50%, 55%, 60%, 65%, 70%, 75%, 80%, 85%, 90%, 95%, or 100%. In some embodiments, a compound of formula (I) modulates the activity of S1P5 by about 1-100%, 5-100%, 10-100%, 15-100%, 20-100%, 25-100%, 30-100%, 35-100%, 40-100%, 45-100%, 50-100%, 55-100%, 60-100%, 65-100%, 70-100%, 75-100%, 80-100%, 85-100%, 90-100%, 95-100%, 5-95%, 5-90%, 5-85%, 5-80%, 5-75%, 5-70%, 5-65%, 5-60%, 5-55%, 5-50%, 5-45%, 5-40%, 5-35%, 5-30%, 5-25%, 5-20%, 5-15%, 5-10%, 10-90%, 20-80%, 30-70%, or 40-60%.

In another aspect, provided herein is a method for treating a neurological disease in a subject in need thereof, comprising administering to the subject an effective amount of a compound of Formula (I). In some embodiments, provided herein is a method for preventing a neurological disease in a subject in need thereof, comprising administering to the subject an effective amount of a compound of Formula (I). Non-limiting examples of a neurological disease include Alzheimer's disease, multiple sclerosis (MS), amyotrophic lateral schlerosis (ALS), Bell's Palsy, ataxia, cerebral aneurysm, epilepsy, seizures, acute spinal cord injury, Guillain-Barre syndrome, meningitis, Niemann Pick disease, and Parkinson's disease. In some embodiments, the neurological disease is Alzheimer's disease or multiple sclerosis. In some embodiments, the neurological disease is Alzheimer's disease. In some embodiments, the neurological disease is multiple sclerosis.

In some embodiments, administering a compound of Formula (I) to a subject that is predisposed to a neurological disease prevents the subject from developing any symptoms of the neurological disease. In some embodiments, administering a compound of Formula (I) to a subject that is does not yet display symptoms of a neurological disease prevents the subject from developing any symptoms of the neurological disease. In some embodiments, administering a compound of Formula (I) to a subject in need thereof diminishes the extent of the neurological disease in the subject. In some embodiments, administering a compound of Formula (I) to a subject in need thereof stabilizes the neurological disease (prevents or delays the worsening of the neurological disease). In some embodiments, administering a compound of Formula (I) to a subject in need thereof delays the occurrence or recurrence of the neurological disease. In some embodiments, administering a compound of Formula (I) to a subject in need thereof slows the progression of the neurological disease. In some embodiments, administering a compound of Formula (I) to a subject in need thereof provides a partial remission of the neurological disease. In some embodiments, administering a compound of Formula (I) to a subject in need thereof provides a total remission of the neurological disease. In some embodiments, administering a compound of Formula (I) to a subject in need thereof decreases the dose of one or more other medications required to treat the neurological disease. In some embodiments, administering a compound of Formula (I) to a subject in need thereof enhances the effect of another medication used to treat the neurological disease. In some embodiments, administering a compound of Formula (I) to a subject in need thereof delays the progression of the neurological disease. In some embodiments, administering a compound of Formula (I) to a subject in need thereof increases the quality of life of the subject having a neurological disease. In some embodiments, administering a compound of Formula (I) to a subject in need thereof prolongs survival of a subject having a neurological disease.

In one aspect, provided herein is method of preventing a subject that is predisposed to a neurological disease from developing any symptoms of the neurological disease, the method comprising administering a compound of Formula (I) to the subject. In some embodiments, provided herein is a method of preventing a subject that does not yet display symptoms of a neurological disease from developing any symptoms of the neurological disease, the method comprising administering a compound of Formula (I) to the subject.

In some aspects, provided herein is a method of diminishing the extent of a neurological disease in a subject, the method comprising administering a compound of Formula (I) to the subject. In some embodiments, provided herein is a method of stabilizing a neurological disease in a subject, the method comprising administering a compound of Formula (I) to the subject. In some embodiments, the method prevents the worsening of the neurological disease. In some embodiments, the method delays the worsening of the neurological disease.

In another aspect, provided herein is a method of delaying the occurrence or recurrence of a neurological disease in a subject, the method comprising administering a compound of Formula (I) to the subject.

In some embodiments, provided herein is a method of slowing the progression of a neurological disease in a subject, the method comprising administering a compound of Formula (I) to the subject. In some embodiments, the method provides a partial remission of the neurological disease. In some embodiments, the method provides a total remission of the neurological disease.

In further aspects, provided herein is a method of decreasing the dose of one or more other medications required to treat a neurological disease in a subject, the method comprising administering a compound of Formula (I) to the subject. In some embodiments, provided herein is a method of enhancing the effect of another medication used to treat a neurological disease in a subject, the method comprising administering a compound of Formula (I) to the subject.

Also provided here is a method of delaying the progression of a neurological disease in a subject, the method comprising administering a compound of Formula (I) to the subject. In some embodiments, the method increases the quality of life of the subject having a neurological disease. In some embodiments, the method prolongs survival of the subject having a neurological disease.

In another aspect, provided herein is a method for treating neurological symptoms caused by a disease in a subject in need thereof, comprising administering to the subject an effective amount of a compound of Formula (I). In some embodiments, provided herein is a method for preventing neurological symptoms caused by a disease in a subject in need thereof, comprising administering to the subject an effective amount of a compound of Formula (I). In some embodiments, administering a compound of Formula (I) to a subject that is predisposed to a disease which causes neurological symptoms prevents the subject from developing any neurological symptoms. In some embodiments, administering a compound of Formula (I) to a subject that is does not yet display neurological symptoms of a disease which causes neurological symptoms prevents the subject from developing any neurological symptoms. In some embodiments, administering a compound of Formula (I) to a subject in need thereof diminishes the extent of the neurological symptoms caused by the disease in the subject. In some embodiments, administering a compound of Formula (I) to a subject in need thereof stabilizes the neurological symptoms of the disease (prevents or delays the worsening of the neurological symptoms). In some embodiments, administering a compound of Formula (I) to a subject in need thereof delays the occurrence or recurrence of the neurological symptoms caused by the disease. In some embodiments, administering a compound of Formula (I) to a subject in need thereof slows the progression of the neurological symptoms caused by the disease. In some embodiments, administering a compound of Formula (I) to a subject in need thereof provides a partial remission of the disease which causes neurological symptoms. In some embodiments, administering a compound of Formula (I) to a subject in need thereof provides a total remission of the disease which causes neurological symptoms. In some embodiments, administering a compound of Formula (I) to a subject in need thereof decreases the dose of one or more other medications required to treat the disease which causes neurological symptoms. In some embodiments, administering a compound of Formula (I) to a subject in need thereof enhances the effect of another medication used to treat the neurological symptoms of the disease. In some embodiments, administering a compound of Formula (I) to a subject in need thereof delays the progression of the disease which causes neurological symptoms. In some embodiments, administering a compound of Formula (I) to a subject in need thereof increases the quality of life of the subject having a disease which causes neurological symptoms. In some embodiments, administering a compound of Formula (I) to a subject in need thereof prolongs survival of a subject having a disease which causes neurological symptoms. In some embodiments, the disease is Niemann-Pick disease.

In some embodiments, compounds of Formula (I) are useful for treating a disorder selected from Alzheimer's disease, arthritis, rheumatoid arthritis, osteoarthritis, juvenile chronic arthritis, Lyme arthritis, psoriatic arthritis, reactive arthritis, and septic arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection (including but not limited to bone marrow and solid organ rejection), acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein *purpurea*, microscopic vasculitis of the kidneys, chronic active hepatitis, uveitis, septic shock, toxic shock syndrome, sepsis syndrome, cachexia, infectious diseases, parasitic diseases, acute transverse myelitis, Huntington's chorea, Parkinson's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia areata, seronegative arthopathy, arthropathy, Reiter's disease, psoriatic arthropathy, ulcerative colitic arthropathy, enteropathic synovitis, chlamydia, yersinia and salmonella associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinemia), dilated cardiomyopathy, infertility, female infertility, ovarian failure, premature ovarian failure, fibrotic lung disease, chronic wound healing, cryptogenic fibrosing alveolitis, post-inflammatory interstitial lung disease, fibrosis, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polytnyositis associated lung disease, Sjogren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis *nigricans*, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjogren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and ThI Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma), and hematopoietic malignancies (leukemia and lymphoma), Abetalipoprotemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti cd3 therapy, antiphospholipid syndrome, anti-receptor hypersensitivity reactions, aordic and peripheral aneuryisms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, Burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chromic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetes, diabetes mellitus, diabetic ateriosclerotic disease, Diffuse Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, Epstein Barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallerrorden-Spatz disease, Hashimoto's thyroiditis, hay fever, heart transplant rejection, hemachromatosis, hemodialysis, hemolytic uremic syndrome/thrombolytic thrombocytopenic purpura, hemorrhage, hepatitis (A), His bundle arrythmias, HIV infection/HIV neuropathy, Hodgkin's disease, hyperkinetic movement disorders, hypersensitity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia, ischemia-reperfusion injury, ischemic stroke, juvenile rheumatoid arthritis, juvenile spinal muscular atrophy, Kaposi's sarcoma, kidney transplant rejection, legionella, leishmaniasis, leprosy, lesions of the corticospinal system, lipedema, liver transplant rejection, lymphedema, malaria, malignant Lymphoma, malignant histiocytosis, malignant melanoma, meningitis, meningococcemia, metabolic/idiopathic, migraine headache, mitochondrial multisystem disorder, mixed connective tissue disease, monoclonal gammopathy, multiple myeloma, multiple systems degenerations (Mencel Dejerine-Thomas Shi-Drager and Machado-Joseph), myasthenia gravis, *Mycobacterium avium intracellulare, Mycobacterium tuberculosis*, myelodyplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-hodgkins lymphoma, occlusion of the abdominal aorta and its branches, occulsive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherlosclerotic disease, peripheral vascular disorders, peritonitis, pernicious anemia, *Pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, Progressive supranucleo Palsy, primary pulmonary hypertension, radiation therapy, Raynaud's phenomenon and disease, Raynaud's disease, Refsum's disease, regular narrow QRS tachycardia, renovascular hypertension, reperfusion injury, restrictive cardiomyopathy, sarcomas, scleroderma, senile chorea, Senile Dementia of Lewy body type, seronegative arthropathies, shock, sickle cell anemia, skin allograft rejection, skin changes syndrome, small bowel transplant rejection, solid tumors, specific arrythmias, spinal ataxia, spinocerebellar degenerations, streptococcal myositis, structural lesions of the cerebellum, subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, acute pain, age-associated memory impairment (AAMI), anxiety attention deficit disorder, attention deficit disorder in general, attention deficit hyperactivity disorder (ADHD), bipolar disorder, cancer pain, central neuropathic pain syndromes, central post-stroke pain, chemotherapy-induced neuropathy, cognitive deficits and dysfunction in psychiatric disorders, cognitive deficits associated with aging and neurodegeneration, cognitive deficits associated with diabetes, cognitive deficits of schizophrenia, complex regional pain syndrome, declines in cognitive function in Alzheimer's and associated dementias, deficits in attention, dementia, dementia associated with Down's syndrome, dementia associated with Lewy bodies, depression in Cushing's syndrome, diminished CNS function associated with traumatic brain injury, diseases with deficits of memory, dizziness, drug abuse, epilepsy, HIV sensory neuropathy, Huntingdon's disease, hyperalgesia including neuropathic pain, inflammation and inflammatory disorders, inflammatory hyperalgesia, inflammatory pain, insulin resistance syndrome, jet lag, lack of circulation, learning, major depressive disorder, medullary thyroid carcinoma, Meniere's disease, metabolic syndrome, mild cognitive impairment, mood alteration, motion sickness, multiple sclerosis pain, narcolepsy, need for new blood vessel growth associated with vascularization of skin grafts and lack of circulation, need for new blood vessel growth associated with wound healing, neuropathic pain, neuropathy, neuropathy secondary to tumor infiltration, non-inflammatory pain, obesity, obsessive compulsive disorder, painful diabetic neuropathy, panic disorder, Parkinson disease pain, pathological sleepiness, phantom limb pain, Pick's Disease, polycystic ovary syndrome, post traumatic stress disorder, post-herpetic neuralgia, post-mastectomy pain, post-surgical pain, psychotic depression, schizoaffective disorder, seizures, senile dementia, sepsis syndrome, sleep disorders, smoking cessation, spinal cord injury pain, steroid-induced acute psychosis, sub-categories of neuropathic pain including peripheral neuropathic pain syndromes, substance abuse including alcohol abuse, Syndrome X, Tourette's syndrome, treatment resistant depression, trigeminal neuralgia, type II diabetes, vertigo, and vestibular disorders.

Pharmaceutical Compositions and Routes of Administration

The compounds provided herein can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions.

The compounds disclosed herein can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the compounds of Formula (I) in the pharmaceutical composition may be at a level that will exercise the desired effect; for example, about 0.005 mg/kg of a subject's body weight to about 10 mg/kg of a subject's body weight in unit dosage for both oral and parenteral administration.

The dose of a compound of Formula (I) to be administered to a subject is rather widely variable and can be subject to the judgment of a health-care practitioner. In general, the compounds disclosed herein can be administered one to four times a day in a dose of about 0.001 mg/kg of a subject's body weight to about 10 mg/kg of a subject's body weight, but the above dosage may be properly varied depending on the age, body weight and medical condition of the subject and the type of administration. In one embodiment, the dose is about 0.001 mg/kg of a subject's body weight to about 5 mg/kg of a subject's body weight, about 0.01 mg/kg of a subject's body weight to about 5 mg/kg of a subject's body weight, about 0.05 mg/kg of a subject's body weight to about 1 mg/kg of a subject's body weight, about 0.1 mg/kg of a subject's body weight to about 0.75 mg/kg of a subject's body weight or about 0.25 mg/kg of a subject's body weight to about 0.5 mg/kg of a subject's body weight. In one embodiment, one dose is given per day. In any given case, the amount of the compound of Formula (I) administered will depend on such factors as the solubility of the active component, the formulation used and the route of administration.

In some embodiments, a compound of Formula (I) is administered to a subject at a dose of about 0.01 mg/day to about 750 mg/day, about 0.1 mg/day to about 375 mg/day, about 0.1 mg/day to about 150 mg/day, about 0.1 mg/day to about 75 mg/day, about 0.1 mg/day to about 50 mg/day, about 0.1 mg/day to about 25 mg/day, or about 0.1 mg/day to about 10 mg/day.

In another embodiment, provided herein are unit dosage formulations that comprise between about 0.1 mg and 500 mg, about 1 mg and 250 mg, about 1 mg and about 100 mg, about 1 mg and about 50 mg, about 1 mg and about 25 mg, or between about 1 mg and about 10 mg of a compound of Formula (I).

In a particular embodiment, provided herein are unit dosage formulations comprising about 0.1 mg or 100 mg of a compound of Formula (I).

In another embodiment, provided herein are unit dosage formulations that comprise 0.5 mg, 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a compound of Formula (I).

A compound of Formula (I) can be administered once, twice, three, four or more times daily. In a particular embodiment, closes of 100 mg or less are administered as a once daily dose and doses of more than 100 mg are administered twice daily in an amount equal to one half of the total daily dose.

A compound of Formula (I) can be administered orally for reasons of convenience. In one embodiment, when administered orally, a compound of Formula (I) is administered with a meal and water. In another embodiment, the compound of Formula (I) is dispersed in water or juice (e.g., apple juice or orange juice) or any other liquid and administered orally as a solution or a suspension.

The compounds disclosed herein can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a compound of Formula (I) without an additional carrier, excipient or vehicle.

In another embodiment, provided herein are compositions comprising an effective amount of a compound of Formula (I) and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a compound of Formula (I) with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the dye. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a compound of Formula (I) as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the compound of Formula (I) can be delayed or prolonged by proper formulation. For example, a slowly soluble pellet of the compound of Formula (I) can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the compound of Formula (I) in oily or emulsified vehicles that allow it to disperse slowly in the serum.

EXAMPLES

The following Examples are presented by way of illustration, not limitation. Compounds are named using the automatic name generating tool provided in ChemBiodraw Ultra (Cambridgesoft), which generates systematic names for chemical structures, with support for the Cahn-Ingold-Prelog rules for stereochemistry. One skilled in the art can modify the procedures set forth in the illustrative examples to arrive at the desired products.

Salts of the compounds described herein can be prepared by standard methods, such as inclusion of an acid (for example TFA, formic acid, or HCl) in the mobile phases during chromatography purification, or stirring of the products after chromatography purification, with a solution of an acid (for example, aqueous HCl).

As used in certain of the chemical structures provided in the following Examples, designation of a particular atom with "or1" indicates that the absolute stereochemistry of the indicated atom was not determined.

The following abbreviations may be relevant for the application.

Abbreviations

ACN or MeCN: acetonitrile
AcOK: potassium acetate
aq.: aqueous
d: day(s)
DCM: dichloromethane
DEA: diethanolamine
DIPA: diisopropylamine
DME: dimethoxyethane
DMF: dimethylformamide
DMSO: dimethyl sulfoxide
EA or EtOAc: ethyl acetate
EDTA: ethylenediaminetetraacetic acid
e.e.: enantiomeric excess
equiv.: equivalents
ESI: electrospray ionization
h: hour(s)

HEPES: (4-(2-hydroxyethyl)-1-piperazineethanesulfonic acid)

Hex: hexanes

IPA: isopropyl alcohol

LCMS: liquid chromatography mass spectrometry

MeOH: methanol

2-Me-THF: 2-methyltetrahydrofuran

Pd(Amphos)$Cl_2$: bis(di-tert-butyl(4-dimethylaminophenyl)phosphine)dichloropalladium(II)

Pd(dppf)$Cl_2$: [1,1'-bis(diphenylphosphino)ferrocene]palladium(II) dichloride $PdCl_2$(dppf)$CH_2Cl_2$ or Pd(dppf)$Cl_2$·DCM: [1,1'-bis(diphenylphosphino)ferrocene]

dichloropalladium(II), complex with dichloromethane

Pd(DTBPF)$Cl_2$: [1,1'-bis(di-tert-butylphosphino)ferrocene]dichloropalladium(II)

PE: petroleum ether

Prep-HPLC: preparative high-performance liquid chromatography

Prep-TLC: preparative thin layer chromatography rpm: revolutions per minute

RT: retention time sat.: saturated

SFC: supercritical-fluid chromatography

TBSOTf: tert-butyldimethylsilyl triflate

TEA: triethylamine

TFA: trifluoroacetic acid

TfOH: triflic acid

THF: tetrahydrofuran

SYNTHETIC EXAMPLES

Example S1. 1-(5-((2,6-dichlorophenyl)ethynyl)-2,3-dihydro-1H-inden-1-yl)piperidine-4-carboxylic acid (1)

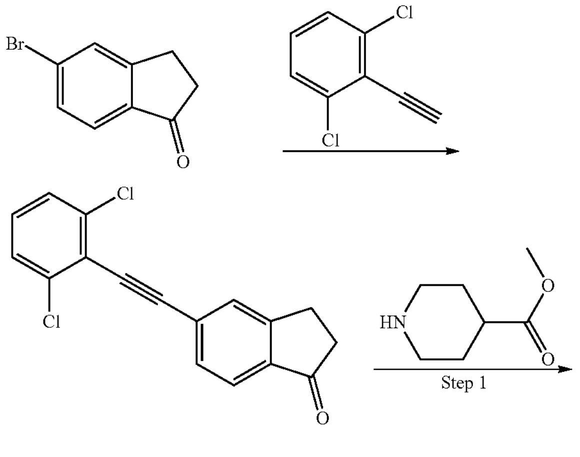

-continued

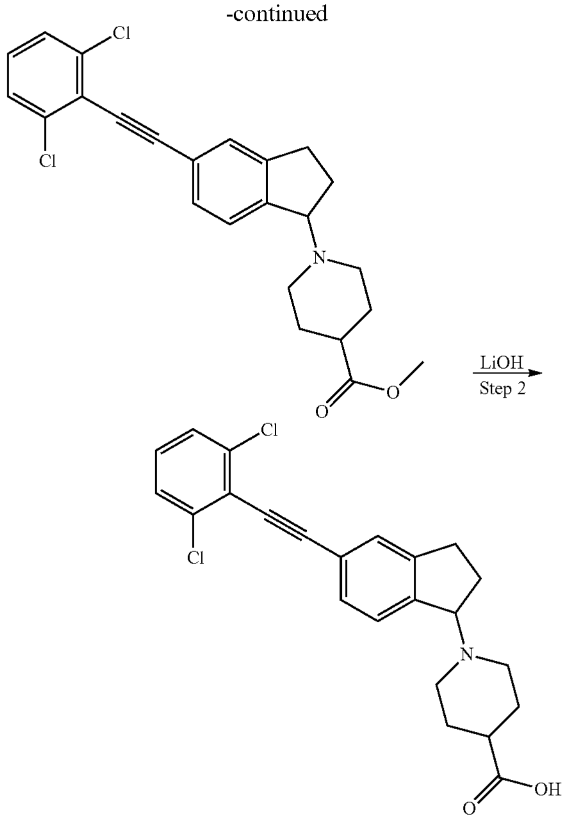

Synthesis of 5-((2,6-dichlorophenyl)ethynyl)-2,3-dihydro-1H-inden-1-one

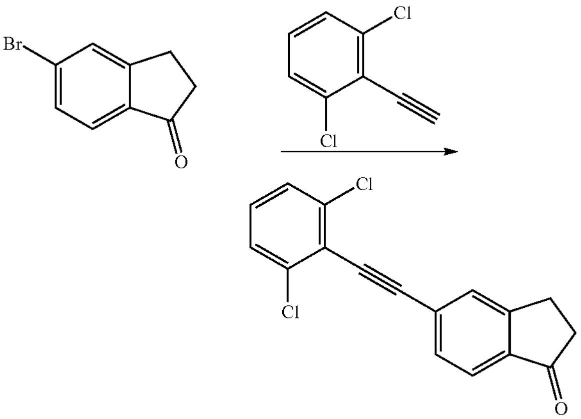

A solution of 5-bromo-2,3-dihydro-1H-inden-1-one (1. g, 4.74 mmol), 1,3-dichloro-2-ethynyl-benzene (0.81 g, 4.74 mmol), Pd(Amphos)$Cl_2$ (0. g, 0 mmol) and CuI (0. g, 0 mmol) in DIPA (10. mL, 70.86 mmol) was placed in a 100 mL round-bottom flask. The resulting solution was stirred at 60° C. for 15 h under $N_2$ atmosphere. LCMS showed the reaction was complete. The resulting solution was diluted with 20 mL of water, then extracted with ethyl acetate (3×20 mL). The combined organic layers were washed with sodium carbonate and brine, dried over $Na_2SO_4$ and concentrated under reduced pressure. The residue was purified by flash chromatography on silica gel (EA/PE=50%) to give the desired product 5-((2,6-dichlorophenyl)ethynyl)-2,3-dihydro-1H-inden-1-one (900 mg, 63%) as a solid. LCMS (ESI, m/z): 302 $[M+H]^+$.

Synthesis of methyl 1-(5-((2,6-dichlorophenyl)ethynyl)-2,3-dihydro-1H-inden-1-yl)piperidine-4-carboxylate

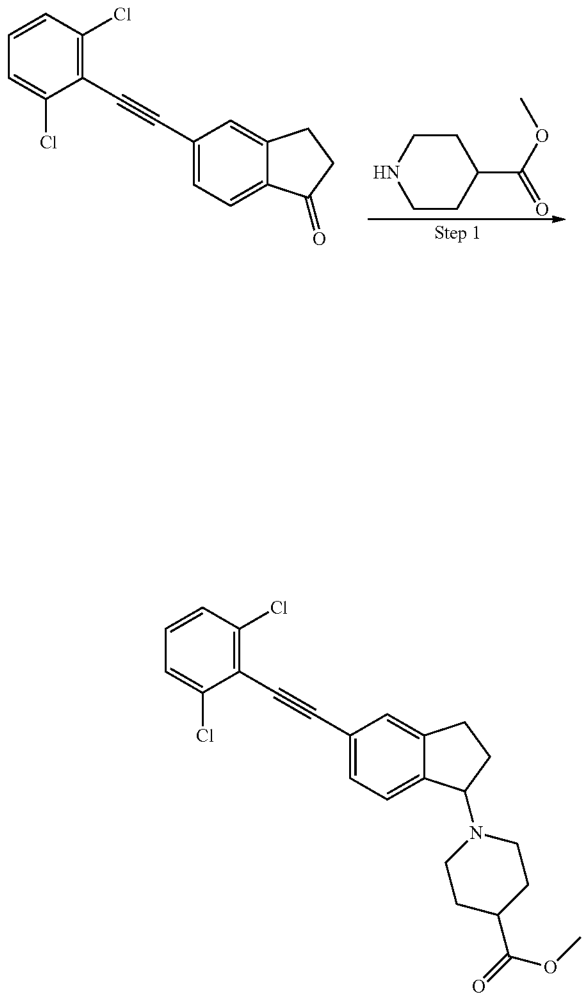

To a solution of $NaBH_3CN$ (83 mg, 1.330 mmol, 4.00 equiv.) in methanol (2.0 mL) was added $ZnCl_2$ (2M in 2-Me-THF, 0.33 mL, 0.660 mmol, 2.00 equiv.). The resulting solution was stirred at room temperature for 5-10 min. Then 5-((2,6-dichlorophenyl)ethynyl)-2,3-dihydro-1H-inden-1-one (100 mg, 0.330 mmol, 1.00 equiv.) and methyl piperidine-4-carboxylate (95 mg, 0.660 mmol, 2.00 equiv.) were added. The resulting mixture was stirred at 60° C. for 16 h under nitrogen atmosphere. LCMS showed the reaction was complete. The reaction mixture was concentrated under reduced pressure. The residue was purified by Prep-TLC with ethyl acetate/petroleum ether (1:3) to give methyl 1-(5-((2,6-dichlorophenyl)ethynyl)-2,3-dihydro-1H-inden-1-yl)piperidine-4-carboxylate (90 mg, 63%) as a solid. LCMS (ESI, m/z): 428 $[M+H]^+$.

Synthesis of 1-(5-((2,6-dichlorophenyl)ethynyl)-2,3-dihydro-1H-inden-1-yl)piperidine-4-carboxylic acid

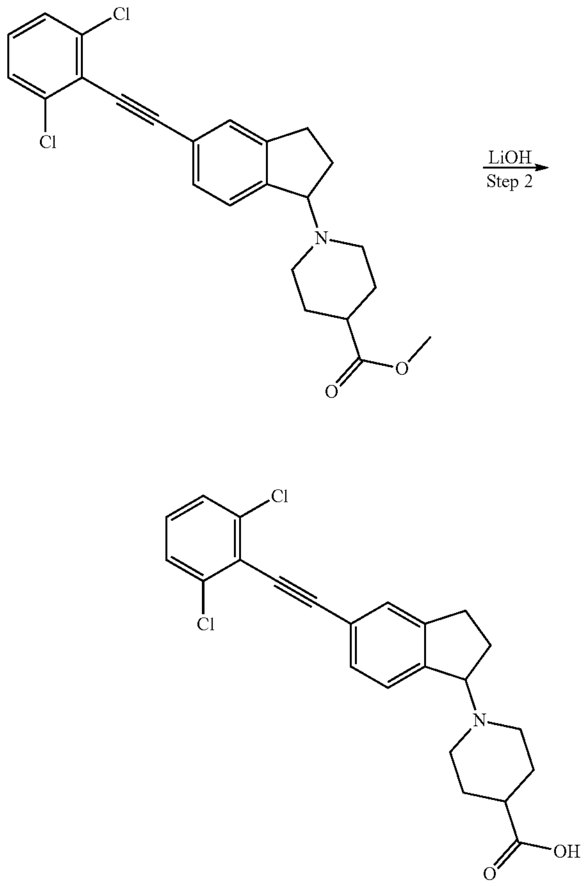 [SMILES: COC(=O)C1CCN(C2CCc3cc(C#Cc4c(Cl)cccc4Cl)ccc32)CC1 ; "LiOH" ; O=C(O)C1CCN(C2CCc3cc(C#Cc4c(Cl)cccc4Cl)ccc32)CC1]

A solution of methyl 1-(5-((2,6-dichlorophenyl)ethynyl)-2,3-dihydro-1H-inden-1-yl)piperidine-4-carboxylate (90 mg, 0.210 mmol, 1.00 equiv.) and $LiOH \cdot H_2O$ (26 mg, 0.630 mmol, 3.00 equiv.) in THF (1.0 mL) and water (1.0 mL) was stirred at room temperature for 2 h. LCMS showed the reaction was complete. The solution was adjusted to pH 4-5 with 1N HCl, and then concentrated under vacuum. The residue was purified by Prep-HPLC (Column: Sunfire prep C18 column, 30*150 mm, 5 μm; Mobile Phase A: water (0.05% HCl), Mobile Phase B: ACN; Flow rate: 60 mL/min; Gradient: 15% B to 35% B in 7 min, hold at 35% B for 3 min; 210/254 nm; RT: 9.68 min) to afford 1-(5-((2,6-dichlorophenyl)ethynyl)-2,3-dihydro-1H-inden-1-yl)piperidine-4-carboxylic acid (1, 48.7 mg, 56%) as a HCl salt.

$^1H$ NMR (300 MHz, Methanol-$d_4$) δ 7.69 (d, J=8.1 Hz, 1H), 7.64 (s, 1H), 7.60-7.56 (m, 1H), 7.50 (d, J=1.2 Hz, 1H), 7.47 (s, 1H), 7.38-7.32 (m, 1H), 5.03-4.99 (m, 1H), 3.60-3.53 (m, 1H), 3.39-3.35 (m, 1H), 3.27-3.18 (m, 2H), 3.12-3.04 (m, 2H), 2.63-2.54 (m, 3H), 2.29-2.21 (m, 2H), 2.00-1.85 (m, 2H).

LCMS (ESI, m/z): 414 $[M+H]^+$. Analytic Conditions: Shim-pack XR-ODS, 3.0*50 mm, 2.2 μm; Mobile Phase A: Water/0.05% TFA, Mobile Phase B: Acetonitrile/0.05% TFA; Flow rate: 1.20 mL/min; Gradient: 5% B to 100% B in 1.1 min, hold at 100% B for 0.55 min, 100% B to 5% B in 0.05 min; 254 nm; RT: 1.219 min.

Example S2. 1-(5-((2,6-dichlorophenyl)ethynyl)-2,3-dihydro-1H-inden-1-yl)-1,2,3,6-tetrahydropyridine-4-carboxylic acid (2)

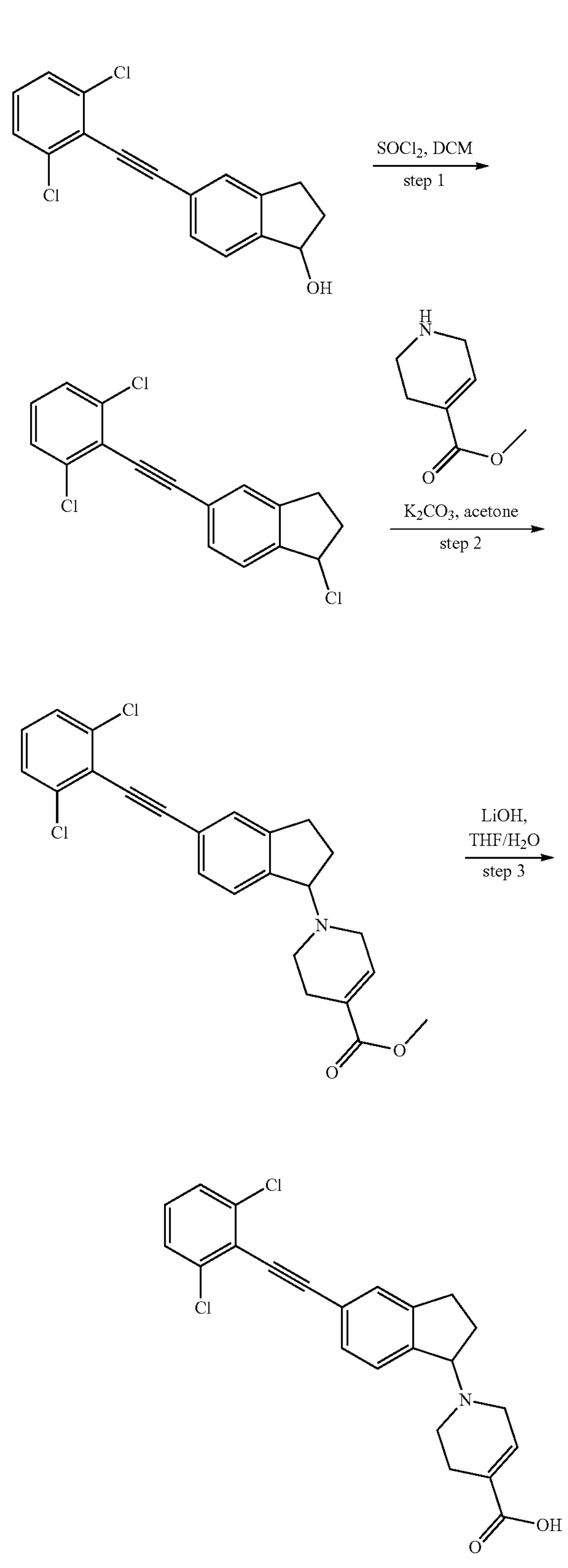

Synthesis of 1-chloro-5-((2,6-dichlorophenyl)ethynyl)-2,3-dihydro-1H-indene

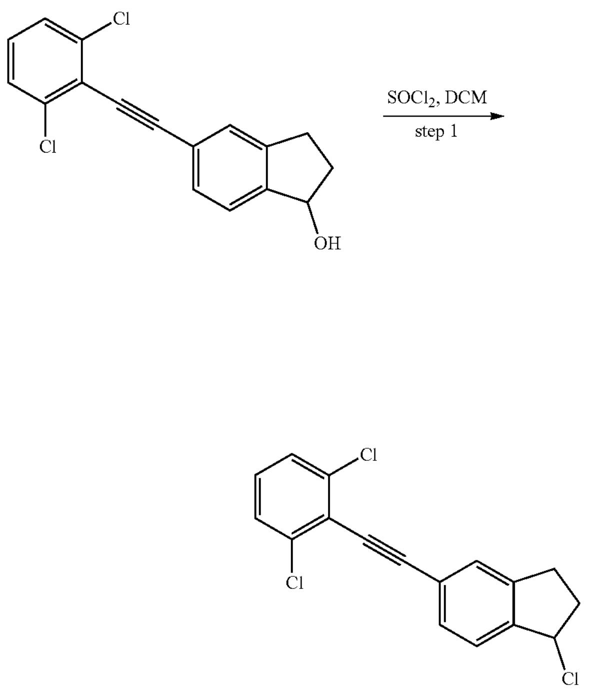

To a stirred solution of 5-((2,6-dichlorophenyl)ethynyl)-2,3-dihydro-1H-inden-1-ol (100 mg, 0.330 mmol, 1.00 equiv.) in 1,4-dioxane (5.0 mL) was added $SOCl_2$ (392 mg, 3.298 mmol, 10.0 equiv.) dropwise at 0° C. The resulting mixture was stirred at room temperature for 6 h. TLC showed that the reaction was complete. The reaction mixture was concentrated under reduced pressure to obtain 1-chloro-5-((2,6-dichlorophenyl)ethynyl)-2,3-dihydro-1H-indene (120 mg, 94%) as an oil. LCMS (ESI, m/z): 285 $[M+H]^+$ (de-Cl fragment).

Synthesis of methyl 1-(5-((2,6-dichlorophenyl)ethynyl)-2,3-dihydro-1H-inden-1-yl)-1,2,3,6-tetrahydropyridine-4-carboxylate

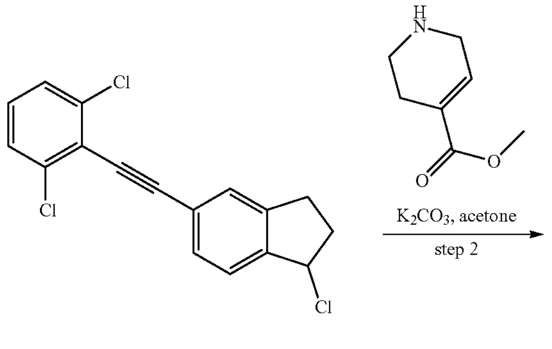

-continued

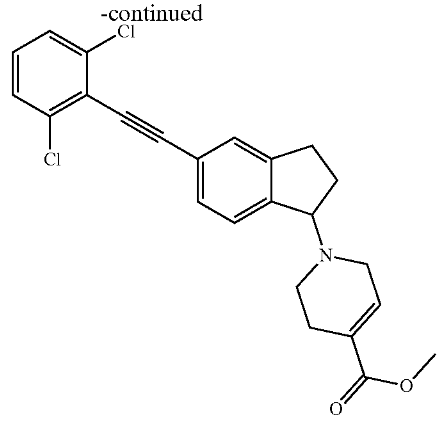

To a stirred solution of 1-chloro-5-((2,6-dichlorophenyl) ethynyl)-2,3-dihydro-1H-indene (120 mg, 0.373 mmol, 1.00 equiv.) in acetone (5.0 mL) were added methyl 1,2,3,6-tetrahydropyridine-4-carboxylate (105 mg, 0.746 mmol, 2.00 equiv.) and $K_2CO_3$ (396 mg, 1.866 mmol, 5.00 equiv.). The resulting mixture was stirred at 80° C. for 12 h. LCMS showed that the reaction was complete. The reaction mixture was purified by Flash column chromatography (eluted with PE/EtOAc, 4/1) to afford methyl 1-(5-((2,6-dichlorophenyl) ethynyl)-2,3-dihydro-1H-inden-1-yl)-1,2,3,6-tetrahydro-pyridine-4-carboxylate (60 mg, 38%) as a semi-solid. LCMS (ESI, m/z): 426 $[M+H]^+$.

Synthesis of 1-(5-((2,6-dichlorophenyl)ethynyl)-2,3-dihydro-1H-inden-1-yl)-1,2,3,6-tetrahydro-pyridine-4-carboxylic acid

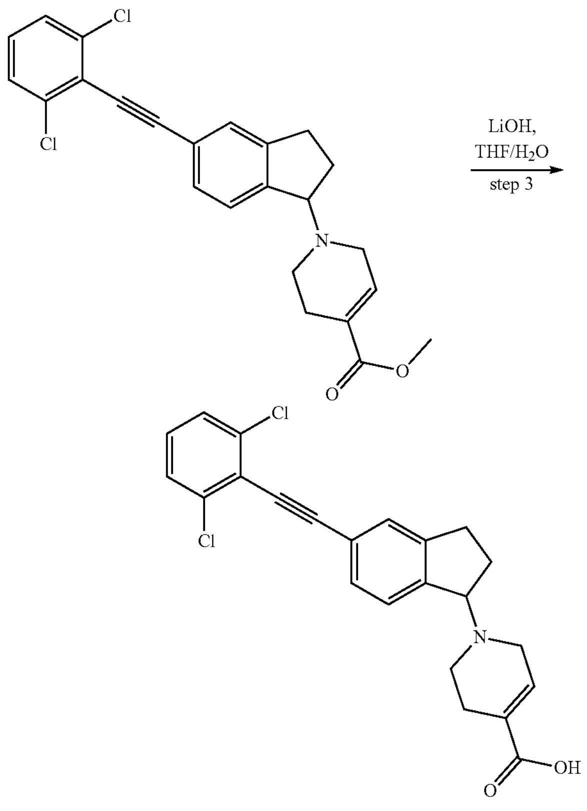

To a stirred solution of methyl 1-(5-((2,6-dichlorophenyl) ethynyl)-2,3-dihydro-1H-inden-1-yl)-1,2,3,6-tetrahydro-pyridine-4-carboxylate (55 mg, 0.129 mmol, 1.00 equiv.) in water (1.5 mL)/THF (1.5 mL) was added $LiOH \cdot H_2O$ (16 mg, 0.387 mmol, 3.00 equiv.). The resulting mixture was stirred at room temperature for 12 h. LCMS showed that the reaction was complete. The reaction mixture was acidified to pH 4-5 by adding 1N HCl, and then was concentrated under reduced pressure. The residue was purified by preparative HPLC (Column: Xselect CSH OBD Column 30*150 mm 5 μm; Mobile Phase A: water (0.05% HCl), Mobile Phase B: ACN; Flow rate: 60 mL/min; Gradient: 18% B to 48% B in 7 min; 254/210 nm; RT: 6.55 min) to afford 1-(5-((2,6-dichlorophenyl)ethynyl)-2,3-dihydro-1H-inden-1-yl)-1,2,3,6-tetrahydropyridine-4-carboxylic acid (2, 16.4 mg, 31%) as a solid.

$^1H$ NMR (400 MHz, Methanol-$d_4$) δ 7.70-7.67 (m, 2H), 7.61 (dd, J=7.6, 1.2 Hz, 1H), 7.51-7.49 (m, 2H), 7.37 (dd, J=8.8, 7.6 Hz, 1H), 6.90-6.88 (m, 1H), 5.15 (dd, J=8.4, 2.8 Hz, 1H), 3.99 (dd, J=18.0, 3.2 Hz, 1H), 3.79 (dd, J=18.0, 3.2 Hz, 1H), 3.51-3.40 (m, 2H), 3.29-3.23 (m, 1H), 3.13-3.08 (m, 1H), 2.79-2.69 (m, 2H), 2.67-2.53 (m, 2H).

LCMS (ESI, m/z): 412 $[M+H]^+$. Analytic Conditions: Column: Shim-pack XR-ODS Column 3*50 mm, 2.2 m; Mobile Phase A: water/0.05% TFA, Mobile Phase B: acetonitrile/0.05% TFA; Flow rate: 1.20 mL/min; Gradient: 5% B to 95% B in 2.0 min, hold at 95% for 0.7 min, 95% B to 5% B in 0.05 min; 254 nm; RT: 1.683 min.

Example S3. 1-(5-((2,6-dichlorophenyl)ethynyl)-2,3-dihydro-1H-inden-1-yl)-4-fluoropiperidine-4-carboxylic acid (3a and 3b)

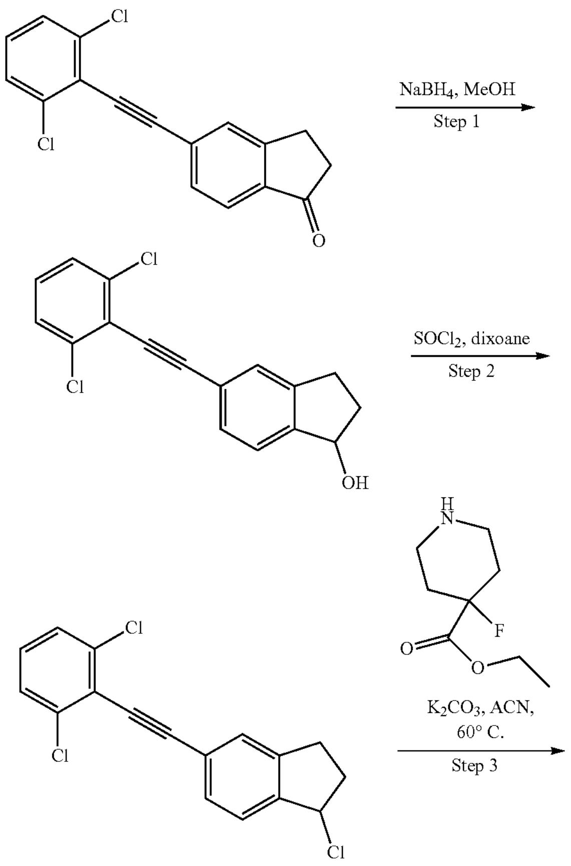

-continued

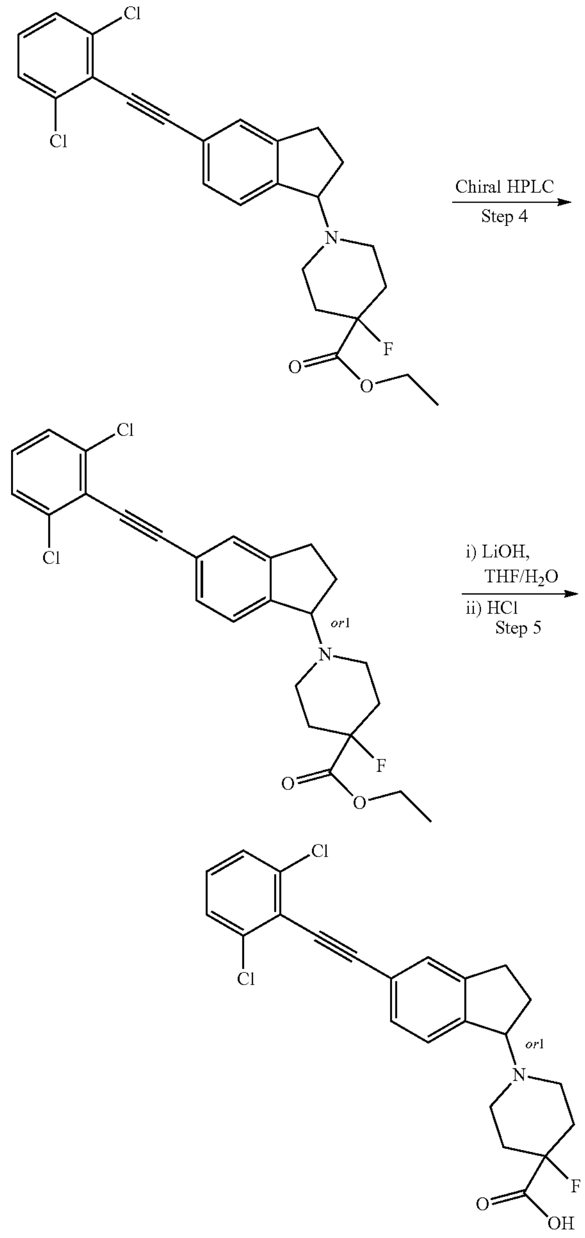

Synthesis of 5-((2,6-dichlorophenyl)ethynyl)-2,3-dihydro-1H-inden-1-ol

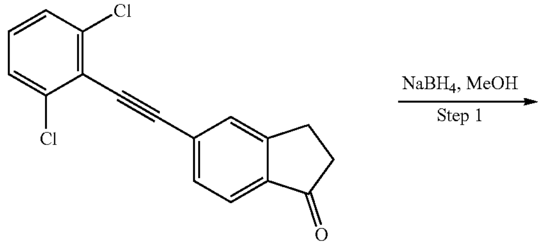

-continued

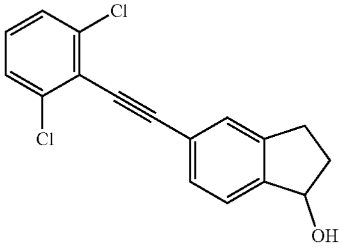

To a stirred solution of 5-((2,6-dichlorophenyl)ethynyl)-2,3-dihydro-1H-inden-1-one (1.2 g, 3.980 mmol, 1.00 equiv) in methanol (25.0 mL) was added $NaBH_4$ (151 mg, 3.980 mmol, 1.00 equiv). The resulting mixture was stirred at room temperature for 45 min. LCMS showed the reaction was complete. The mixture was concentrated to under reduced pressure. The crude was purified by flash chromatography on silica gel with PE: EA (6:1) to afford 5-((2,6-dichlorophenyl)ethynyl)-2,3-dihydro-1H-inden-1-ol (870 mg, 72%) as a solid. LCMS (ESI, m/z): 303 $[M+H]^+$.

Synthesis of 1-chloro-5-((2,6-dichlorophenyl)ethynyl)-2,3-dihydro-1H-indene

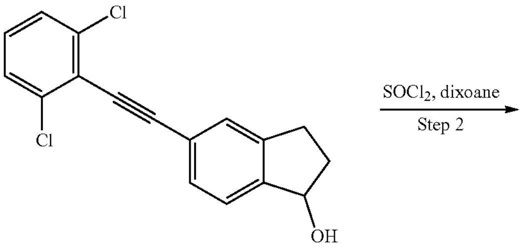

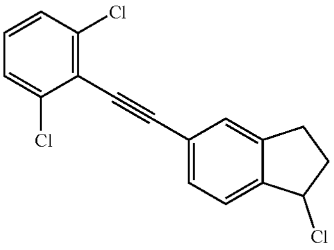

To a stirred solution of 5-((2,6-dichlorophenyl)ethynyl)-2,3-dihydro-1H-inden-1-ol (300 mg, 0.990 mmol, 1.00 equiv) in 1,4-dioxane (5.0 mL) was added $SOCl_2$ (1.4 mL, 19.980 mmol, 20.00 equiv). The resulting mixture was stirred at room temperature overnight. The crude was concentrated to dryness under reduced pressure to afford 1-chloro-5-((2,6-dichlorophenyl)-ethynyl)-2,3-dihydro-1H-indene (250 mg, 79%) as an oil. LCMS (ESI, m/z): 321 $[M+H]^+$.

Synthesis of ethyl 1-(5-((2,6-dichlorophenyl)ethynyl)-2,3-dihydro-1H-inden-1-yl)-4-fluoro-piperidine-4-carboxylate

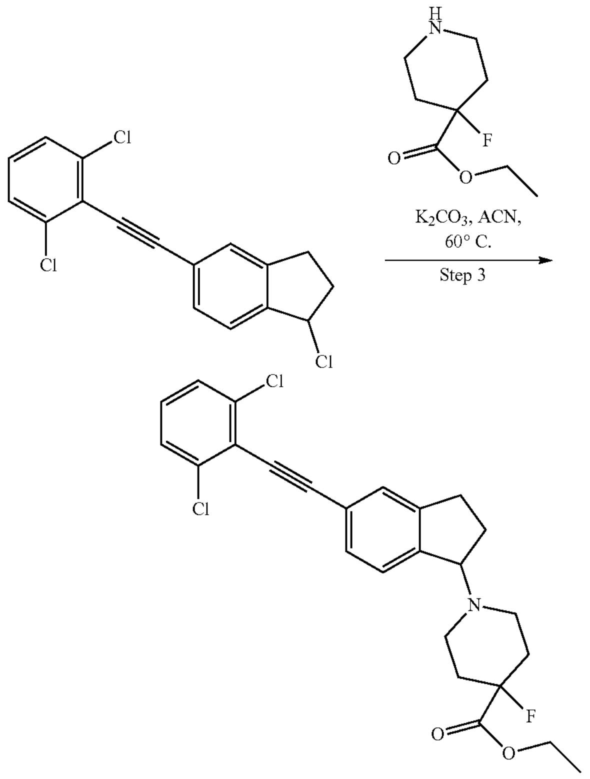

To a stirred solution of 1-chloro-5-((2,6-dichlorophenyl)ethynyl)-2,3-dihydro-1H-indene (250 mg, 0.780 mmol, 1.00 equiv) in MeCN (5.0 mL) was added ethyl 4-fluoropiperidine-4-carboxylate (273 mg, 1.560 mmol, 2.00 equiv) and $K_2CO_3$ (249 mg, 2.340, mmol, 3.00 equiv). The resulting mixture was stirred at 60° C. for 48 h. LCMS showed the reaction was complete. The reaction mixture was concentrated under reduced pressure. The crude was purified by prep-TLC (PE/EA=1/1) to afford ethyl 1-(5-((2,6-dichlorophenyl)ethynyl)-2,3-dihydro-1H-inden-1-yl)-4-fluoropiperidine-4-carboxylate (220 mg, 61%). LCMS (ESI, m/z): 460 $[M+H]^+$.

Chiral Separation.

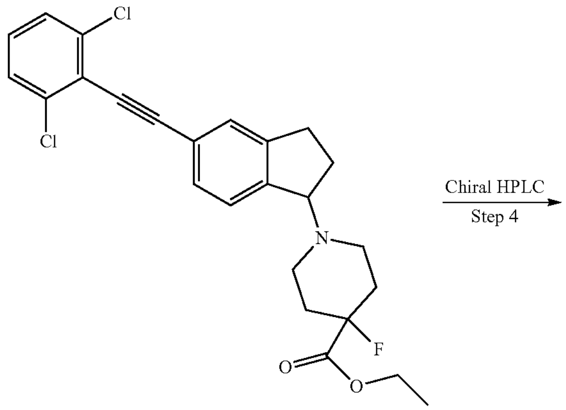

-continued

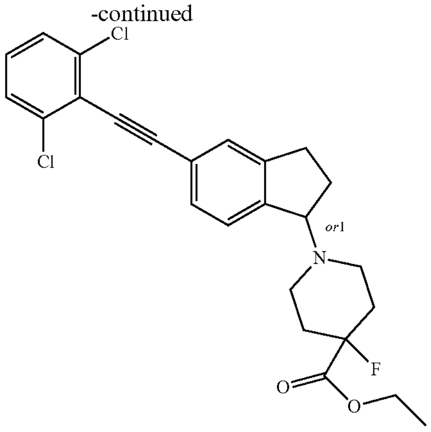

The mixture of the isomers (220 mg, 0.478 mmol) was separated by Chiral HPLC (Column: CHIRALPAK IE, 2*25 cm, 5 μm; Mobile Phase A: Hex (8 mmol/L $NH_3$·MeOH)-HPLC, Mobile Phase B: EtOH-HPLC; Flow rate: 20 mL/min; Gradient: 20% B to 20% B in 9 min; 220/254 nm; RT1: 5.88 min (chiral separation 1), RT2: 6.811 min (chiral separation 2); Injection Volume: 0.5 mL; Number Of Runs: 15) to afford the desired isomers of ethyl 1-(5-((2,6-dichlorophenyl)ethynyl)-2,3-dihydro-1H-inden-1-yl)-4-fluoropiperidine-4-carboxylate (100 mg each, 45%, 99.5% ee) as solids. LCMS (ESI, m/z): 460 $[M+H]^+$.

Synthesis of 1-(5-((2,6-dichlorophenyl)ethynyl)-2,3-dihydro-1H-inden-1-yl)-4-fluoropiperidine-4-carboxylic acid from chiral separation 1 and 2

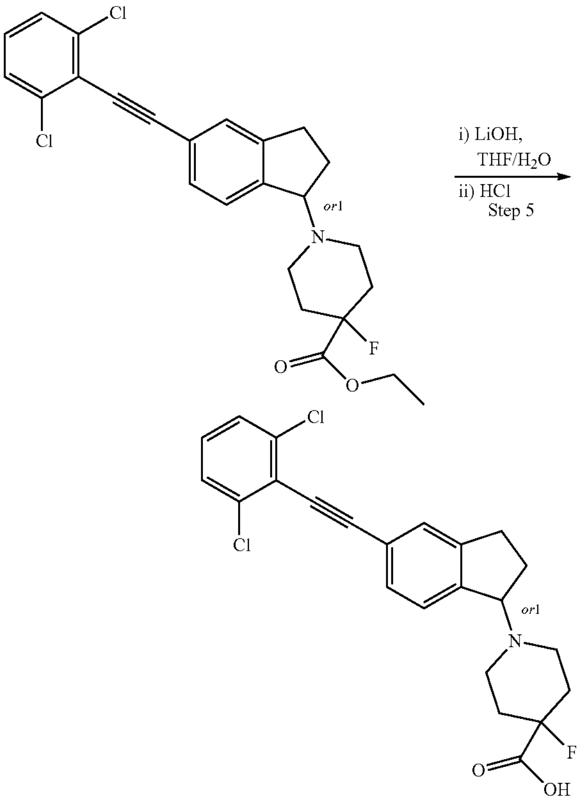

To a stirred solution of ethyl 1-(5-((2,6-dichlorophenyl)ethynyl)-2,3-dihydro-1H-inden-1-yl)-4-fluoropiperidine-4-carboxylate (100 mg, 0.220 mmol, 1.00 equiv) in THF (1.0 mL) and Water (1.0 mL) was added LiOH (16 mg, 0.660 mmol, 3.00 equiv). The resulting mixture was stirred at room temperature for 1 h. LCMS showed the reaction was complete. The reaction mixture was acidified to pH 3-4 with 1N HCl and then was concentrated under reduced pressure. The residue was purified by prep-HPLC (Column: XSelect CSH Prep C18 OBD Column, 5 μm, 19*150 mm; Mobile Phase A: Water (0.05% HCl), Mobile Phase B: ACN; Flow rate: 25 mL/min; Gradient: 30% B to 50% B in 7 min; 254/210 nm; RT1: 5.98 min) to afford 1-(5-((2,6-dichlorophenyl)ethynyl)-2,3-dihydro-1H-inden-1-yl)-4-fluoropiperidine-4-carboxylic acid (3a, 31.0 mg, 33%, 99.6% ee) and (3b, 17.6 mg, 19%, 99.2% ee) in HCl salt form as a solid.

$^1$H NMR (400 MHz, Methanol-$d_4$) δ 7.76 (d, J=8.0 Hz, 1H), 7.66 (s, 1H), 7.61 (dd, J=8.0, 1.6 Hz, 1H), 7.50 (d, J=8.0 Hz, 2H), 7.36 (dd, J=8.8, 7.6 Hz, 1H), 5.08 (dd, J=7.6, 3.2 Hz, 1H), 3.62-3.53 (m, 1H), 3.42-3.35 (m, 2H), 3.33-3.22 (m, 2H), 3.16-3.05 (m, 1H), 2.69-2.27 (m, 6H).

$^{19}$F NMR (376 MHz, Methanol-$d_4$) δ −168.85.

LCMS (ESI, m/z): 432 $[M+H]^+$. Analytic Conditions: column: Shim-pack XR-ODS Column 3.0*50 mm, 2.2 μm; mobile Phase A: water/0.05% TFA, mobile Phase B: acetonitrile/0.05% TFA; flow rate: 1.20 mL/min; gradient: 5% B to 95% B in 2.0 min, hold at 95% for 0.7 min, 95% B to 5% B in 0.05 min; 254 nm; RT: 1.745 min.

Example S4. 1-(5-((3-fluorophenyl)ethynyl)-2,3-dihydro-1H-inden-1-yl)piperidine-4-carboxylic acid (4a and 4b)

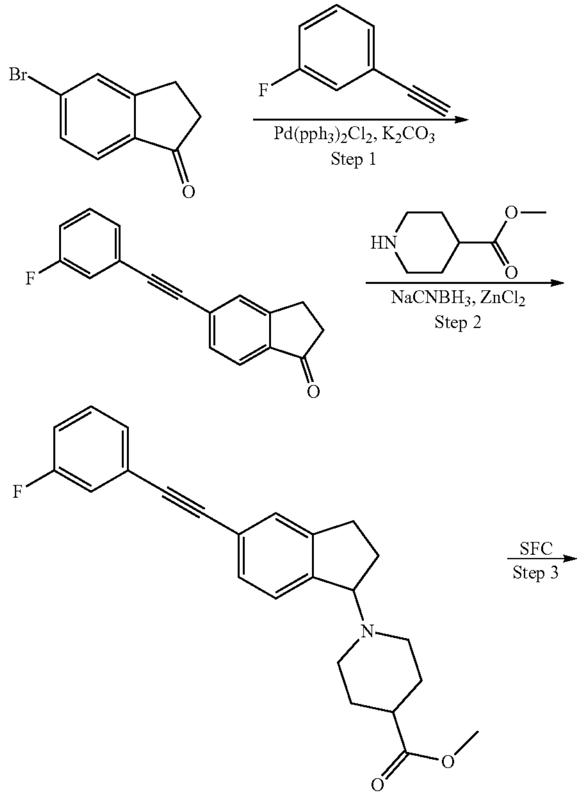

-continued

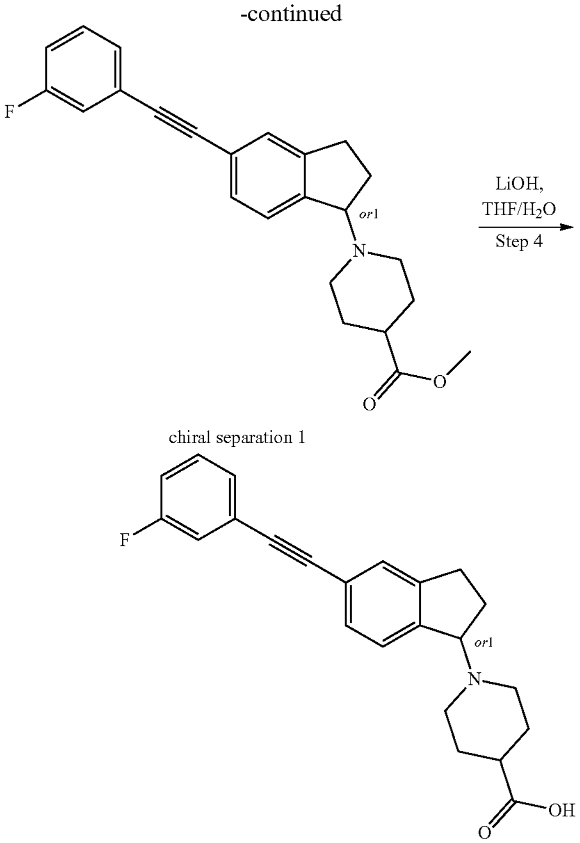

Synthesis of 5-((3-fluorophenyl)ethynyl)-2,3-dihydro-1H-inden-1-one

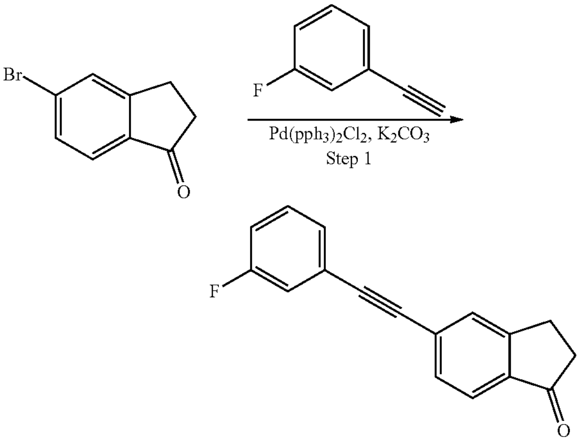

A mixture of 5-bromo-2,3-dihydro-1H-inden-1-one (4.50 g, 0.0213 mol, 1.00 equiv), 1-ethynyl-3-fluoro-benzene (2.56 g, 0.0213 mol, 1.00 equiv), $Pd(PPh_3)_2Cl_2$ (1.50 g, 2.13 mmol, 0.10 equiv), $K_2CO_3$ (8.85 g, 0.064 mol, 3.00 equiv) and CuI (0.40 g, 2.13 mmol, 0.10 equiv) in DMF (40 mL) was stirred at 80° C. for 12 h under nitrogen atmosphere. LCMS showed the reaction was complete. The reaction mixture was diluted with water (150 mL) and extracted with DCM (3*150 mL). The combined organic layers were dried over anhydrous $Na_2SO_4$ and concentrated under reduced pressure. The crude product was purified by flash chromatography on silica gel (PE:EA=3:1) to give 5-((3-fluorophenyl)ethynyl)-2,3-dihydro-1H-inden-1-one (3.0 g, 54%) as a solid. LCMS (ESI, m/z): 251 $[M+H]^+$.

Synthesis of methyl 1-(5-((3-fluorophenyl)ethynyl)-2,3-dihydro-1H-inden-1-yl)piperidine-4-carboxylate

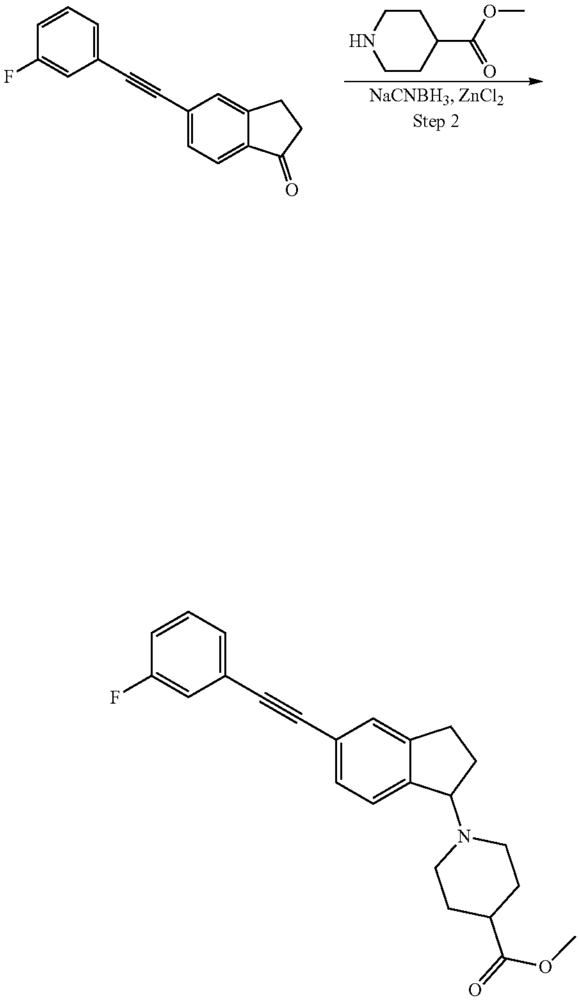

A mixture of 5-((3-fluorophenyl)ethynyl)-2,3-dihydro-1H-inden-1-one (3.0 g, 0.012 mol, 1.00 equiv), methyl piperidine-4-carboxylate (3.45 g, 0.024 mol, 2.00 equiv), $ZnCl_2$ (1.9M in 2-Me THF, 12.0 mL, 0.024 mol, 2.00 equiv), $NaBH_3CN$ (2.26 g, 0.036 mol, 3.00 equiv) in methanol (50 mL) was stirred at 60° C. for 12 h. LCMS showed the reaction was complete. The mixture was quenched with sat. aq. $NH_4Cl$ (50 mL) and extracted with DCM (3*80 mL). The combined organic layers were dried over anhydrous $Na_2SO_4$ and concentrated under reduced pressure. The crude product was purified by flash chromatography on silica gel (DCM:MeOH=10:1) to give methyl 1-(5-((3-fluorophenyl)ethynyl)-2,3-dihydro-1H-inden-1-yl)piperidine-4-carboxylate (3.0 g, 67%) as an oil. LCMS (ESI, m/z): 378 $[M+H]^+$.

Chiral Separation of methyl 1-(5-((3-fluorophenyl)ethynyl)-2,3-dihydro-1H-inden-1-yl)-piperidine-4-carboxylate

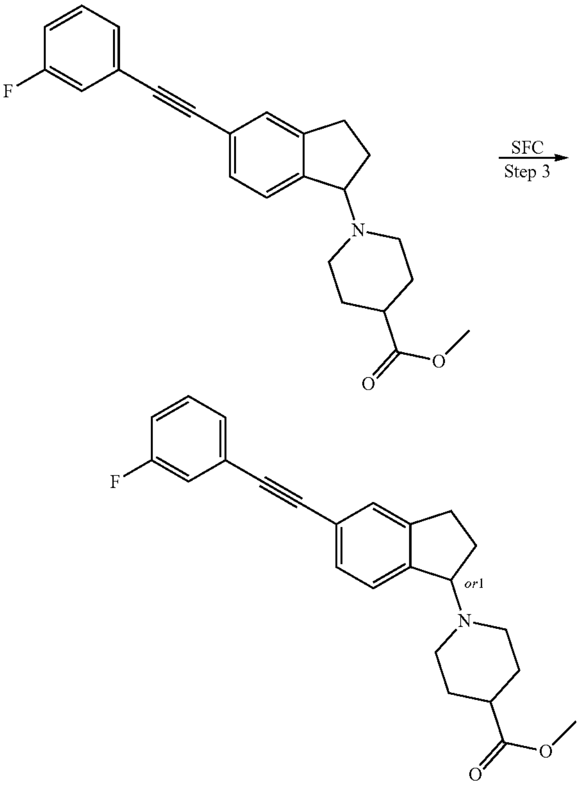

chiral separation 1

The racemate (3.0 g) was separated by SFC (Column: CHIRAL ART Amylose-C NEO, 3*25 cm, 5 μm; Mobile Phase A: $CO_2$, Mobile Phase B: EtOH:ACN=1:1 (2 mM $NH_3$-MeOH); Flow rate: 60 mL/min; Gradient: 60% B; 220 nm; RT1: 3.37 min; RT2: 6.56 min; Injection Volume: 4 mL) to give the chiral separation 1 isomer (800 mg, 27%, 100% e.e.) and separation 2 (700 mg, 23.6%, 99.9% ee) as solids. LCMS (ESI, m/z): 378$[M+H]^+$.

Synthesis of 1-(5-((3-fluorophenyl)ethynyl)-2,3-dihydro-1H-inden-1-yl)piperidine-4-carboxylic acid from chiral separation 1

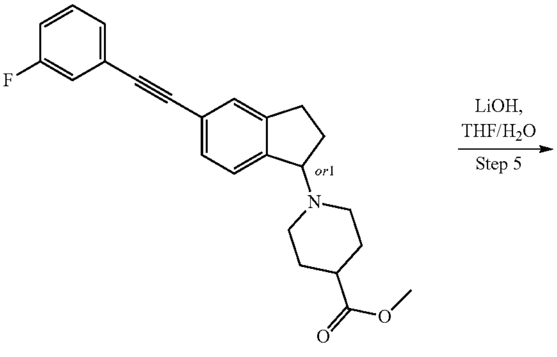

-continued

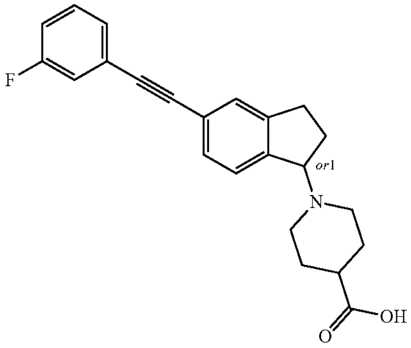

A mixture of methyl 1-(5-((3-fluorophenyl)ethynyl)-2,3-dihydro-1H-inden-1-yl)piperidine-4-carboxylate (700 mg, 1.855 mmol, 1.00 equiv) and LiOH (220 mg, 9.273 mmol, 5.00 equiv) in THF (5 mL) and water (5 mL) was stirred at room temperature for 1 h. LCMS showed the reaction was complete. The reaction mixture was acidified to pH 3-4 with 2N HCl, and concentrated under reduced pressure. The residue was purified by flash column chromatography on C18 silica (eluted with water (0.05% HCl):ACN=2:1)) to afford 1-(5-((3-fluoro-phenyl)ethynyl)-2,3-dihydro-1H-inden-1-yl)piperidine-4-carboxylic acid (4a, 511 mg, 76%) as a solid.

$^1$H NMR (400 MHz, DMSO-$d_6$) δ 12.53 (s, 1H), 11.40 (s, 1H), 8.10-7.83 (m, 1H), 7.57 (s, 1H), 7.50 (t, J=8.0 Hz, 2H), 7.46-7.40 (m, 2H), 7.35-7.27 (m, 1H), 4.98 (d, J=3.2 Hz, 1H), 3.42-3.98 (m, 2H), 3.27-2.77 (m, 5H), 2.60-2.52 (m, 1H), 2.48-2.32 (m, 1H), 2.27-2.09 (m, 1H), 2.05-1.82 (m, 3H).

$^{19}$F NMR (400 MHz, DMSO-$d_6$) δ −112.401.

LCMS (ESI, m/z): 364 $[M+H]^+$. Analytic Conditions: Column: Shim-pack XR-ODS 50*3.0 mm 2.2 μm; Mobile Phase A: Water/0.05% TFA, Mobile Phase B: Acetonitrile/0.05% TFA; Flow rate: 1.20 mL/min; Gradient: 5% B to 100% B in 2.0 min, hold at 100% B for 0.7 min; 254 nm; RT: 1.597 min.

Synthesis of 1-(5-((3-fluorophenyl)ethynyl)-2,3-dihydro-1H-inden-1-yl)piperidine-4-carboxylic acid from chiral separation 2

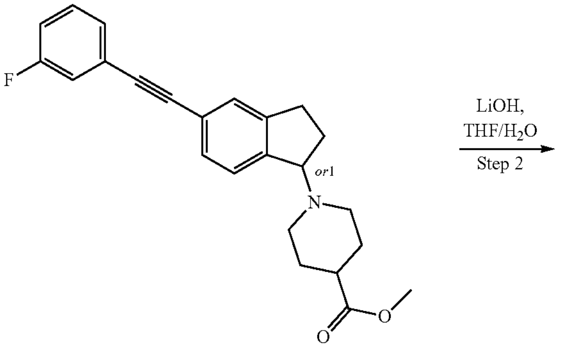

chiral separation 2

-continued

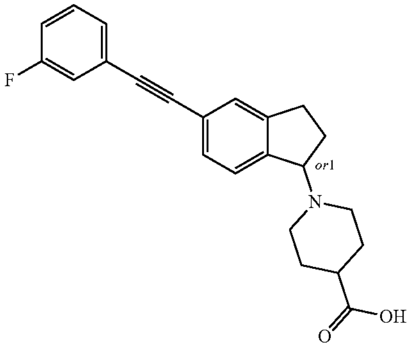

A mixture of methyl 1-(5-((3-fluorophenyl)ethynyl)-2,3-dihydro-1H-inden-1-yl)-piperidine-4-carboxylate (800 mg, 2.116 mmol, 1.00 equiv) and LiOH (250 mg, 10.582 mmol, 5.00 equiv) in THF (5 mL) and water (5 mL) was stirred at room temperature for 1 h. LCMS showed the reaction was complete. The reaction mixture was acidified to pH 3-4 with 2N HCl, and concentrated under reduced pressure. The residue was purified by flash column chromatography on C18 silica (eluted with water (0.05% HCl):ACN=2:1)) to afford 1-(5-((3-fluorophenyl)ethynyl)-2,3-dihydro-1H-inden-1-yl)piperidine-4-carboxylic acid (4b, 689.5 mg, 89%) as a solid.

$^1$H NMR (400 MHz, DMSO-$d_6$) δ 12.51 (s, 1H), 11.30 (s, 1H), 8.00-7.89 (m, 1H), 7.60-7.37 (m, 5H), 7.30 (t, J=8.4 Hz, 1H), 4.97 (d, J=8.0 Hz, 1H), 3.48-3.28 (m, 2H), 3.25-2.78 (m, 5H), 2.59-2.46 (m, 1H), 2.41-2.35 (m, 1H), 2.21-1.75 (m, 4H).

$^{19}$F NMR (400 MHz, DMSO-$d_6$) δ −112.391.

LCMS (ESI, m/z): 364 $[M+H]^+$. Analytic Conditions: Column: Shim-pack XR-ODS 50*3.0 mm 2.2 m; Mobile Phase A: Water/0.05% TFA, Mobile Phase B: Acetonitrile/0.05% TFA; Flow rate: 1.20 mL/min; Gradient: 5% B to 100% B in 2.0 min, hold at 100% B for 0.7 min; 254 nm; RT: 1.598 min.

Example S5. 1-(5-((3-fluorophenyl)ethynyl)-2,3-dihydro-1H-inden-1-yl)-3,3-dimethylpiperidine-4-carboxylic acid (5)

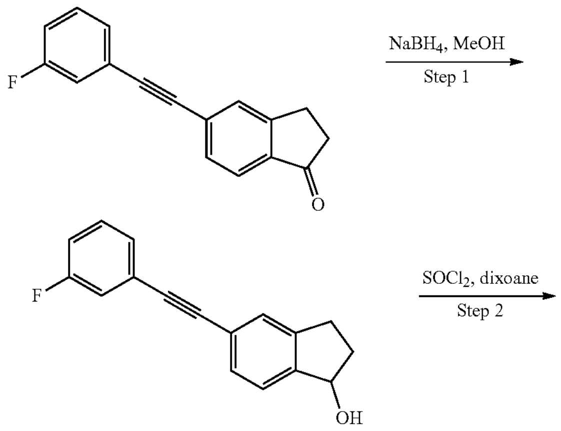

-continued

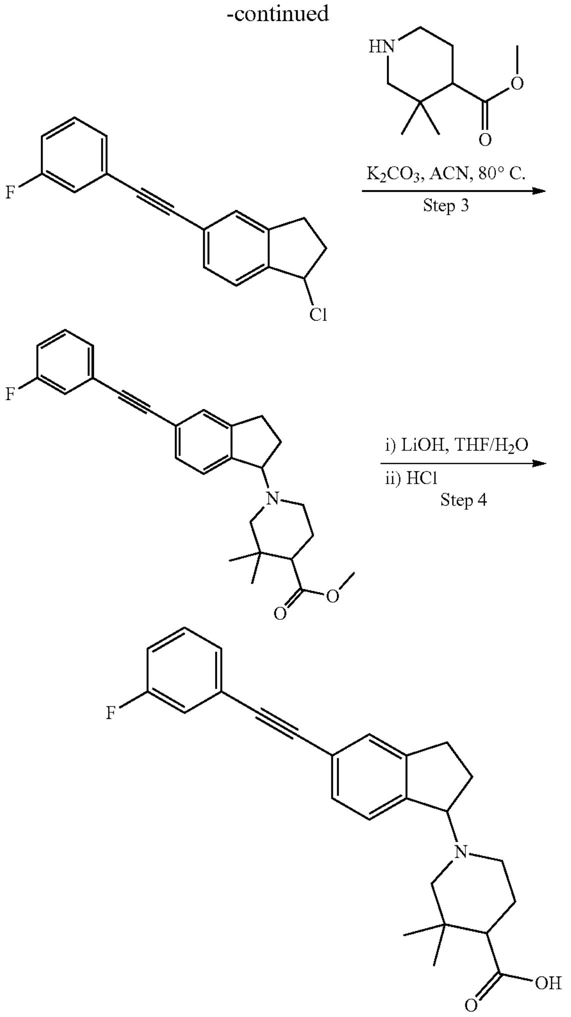

Synthesis of 5-((3-fluorophenyl)ethynyl)-2,3-dihydro-1H-inden-1-ol

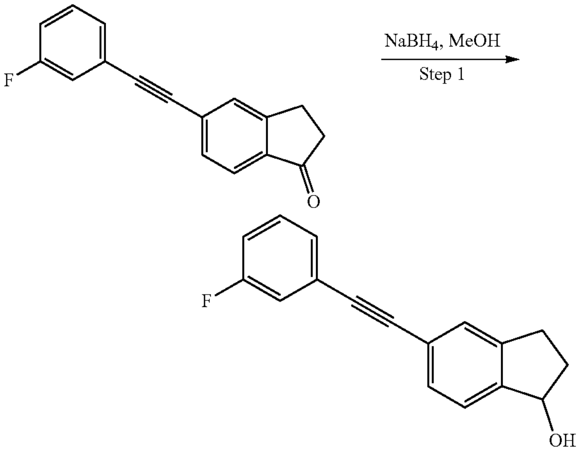

To a solution of 5-((3-fluorophenyl)ethynyl)-2,3-dihydro-1H-inden-1-one (3.1 g, 12.4 mmol, 1.00 equiv.) and methanol (30.0 mL) was added $NaBH_4$ (470 mg, 12.4 mmol, 1.00 equiv) in portions at 0° C. The reaction mixture was stirred at room temperature for 15 min. TLC showed the reaction was complete. The reaction mixture was concentrated under reduced pressure. The residue was purified by flash chromatography on silica gel with ethyl acetate/petroleum ether (1:7) to afford 5-((3-fluorophenyl)ethynyl)-2,3-dihydro-1H-inden-1-ol (2.2 g, 69.6%) as a solid. LCMS (ESI, m/z): 253 $[M+H]^+$.

Synthesis of 1-chloro-5-((3-fluorophenyl)ethynyl)-2,3-dihydro-1H-indene

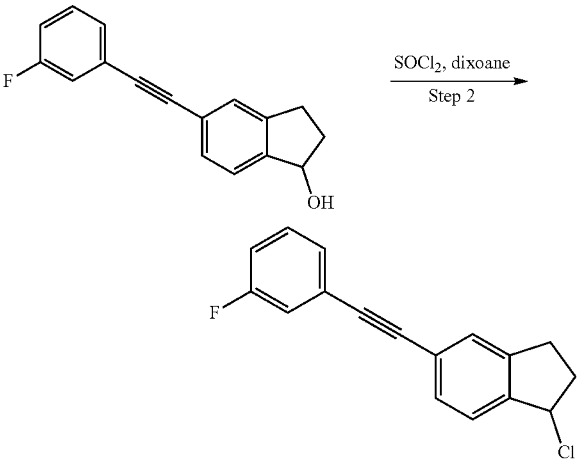

To a solution of 5-((3-fluorophenyl)ethynyl)-2,3-dihydro-1H-inden-1-ol (600 mg, 2.38 mmol, 1.00 equiv) in 1,4-dioxane (5.0 mL) was added $SOCl_2$ (2.0 mL) dropwise at 0° C. The resulting solution was stirred at room temperature for 2 h. TLC showed the reaction was complete. The resulting solution was concentrated under reduced pressure to afford crude product 1-chloro-5-((3-fluorophenyl)ethynyl)-2,3-dihydro-1H-indene as an oil, which was directly used in the next step without further purification. LCMS (ESI, m/z): 271 $[M+H]^+$.

Synthesis of methyl 1-(5-((3-fluorophenyl)ethynyl)-2,3-dihydro-1H-inden-1-yl)-3,3-dimethyl-piperidine-4-carboxylate

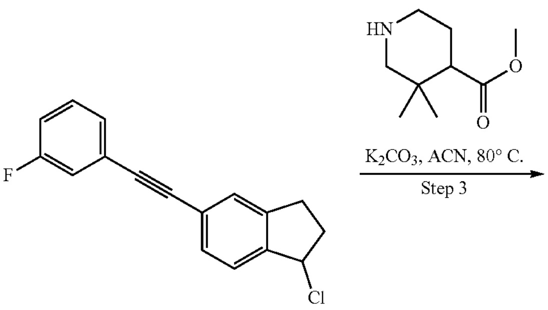

-continued

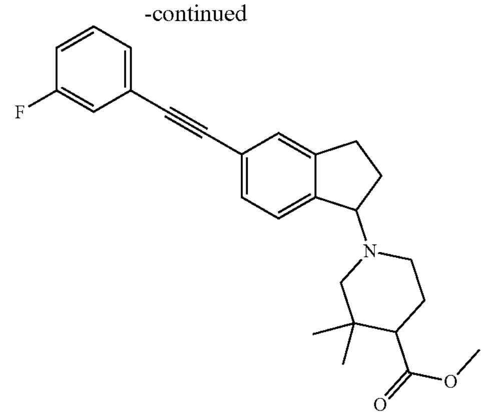

To a solution of 1-chloro-5-((3-fluorophenyl)ethynyl)-2,3-dihydro-1H-indene (400 mg, 1.48 mmol, 2.00 equiv.), methyl 3,3-dimethylpiperidine-4-carboxylate (126 mg, 0.740 mmol, 1.00 equiv.) in MeCN (8.0 mL) was added $K_2CO_3$ (306 mg, 2.22 mmol, 3.00 equiv) at room temperature. The resulting solution was stirred at 80° C. for 14 h. LCMS showed the reaction was complete. The reaction mixture was filtered and concentrated under reduced pressure. The residue was purified by flash chromatography on silica gel (PE/EA=10/1) to give methyl 1-(5-((3-fluorophenyl)ethynyl)-2,3-dihydro-1H-inden-1-yl)-3,3-dimethylpiperidine-4-carboxylate (100 mg, 31.0%) as a semi-solid. LCMS (ESI, m/z): 406 $[M+H]^+$.

Synthesis of 1-(5-((3-fluorophenyl)ethynyl)-2,3-dihydro-1H-inden-1-yl)-3,3-dimethylpiperidine-4-carboxylic acid

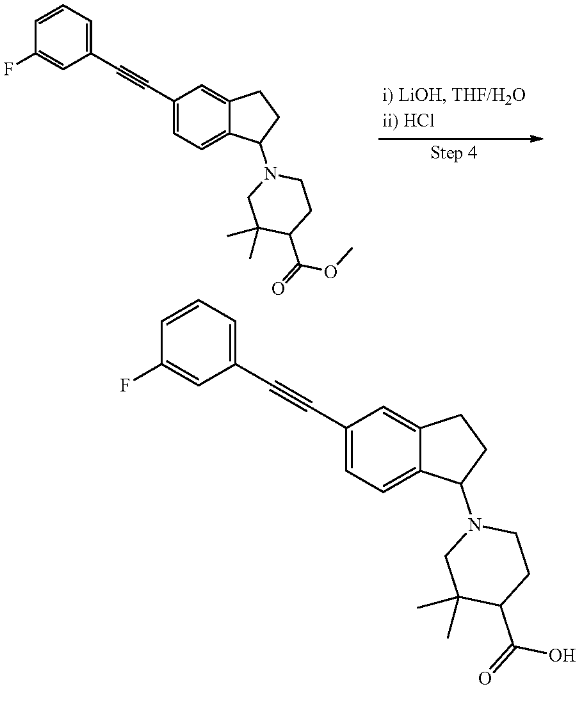

A mixture of methyl 1-(5-((3-fluorophenyl)ethynyl)-2,3-dihydro-1H-inden-1-yl)-3,3-dimethylpiperidine-4-carboxylate (100 mg, 0.250 mmol, 1.00 equiv) and $LiOH{\cdot}H_2O$ (62 mg, 1.48 mmol, 5.00 equiv) in THF (1.0 mL) and water (1.0 mL) was stirred at 80° C. for 3 days. LCMS showed the reaction was complete. The resulting mixture was adjusted to pH 5-6 with 2N HCl and concentrated under reduced pressure. The residue was purified by preparative HPLC (Column: XBridge Shield RP18 OBD Column, 30*150 mm, 5 μm; Mobile Phase A: water (10 mmol/L $NH_4HCO_3$+0.1% $NH_3{\cdot}H_2O$), Mobile Phase B: ACN; Flow rate: 60 mL/min; Gradient: 27% B to 49% B in 7 min; 254/220 nm; RT: 6.67 min) to afford 1-(5-((3-fluorophenyl)ethynyl)-2,3-dihydro-1H-inden-1-yl)-3,3-dimethylpiperidine-4-carboxylic acid (5, 36.1 mg, 37.0%) as a solid.

$^1$H NMR (300 MHz, Methanol-$d_4$) δ 7.45-7.33 (m, 5H), 7.26 (d, J=9.3 Hz, 1H), 7.14 (t, J=8.4 Hz, 1H), 4.57-4.52 (m, 1H), 3.05-2.85 (m, 4H), 2.65-2.48 (m, 1H), 2.40-1.87 (m, 5H), 1.85-1.73 (m, 1H), 1.14-1.01 (m, 6H).

$^{19}$F NMR (282 MHz, Methanol-$d_4$) δ −114.99.

LCMS (ESI, m/z): 392 $[M+H]^+$. Analytic Conditions: Shim-pack XR-ODS C18, 3.0*50 mm, 2.2 m; Mobile Phase A: Water/0.05% TFA, Mobile Phase B: ACN Acetonitrile/0.05% TFA; Flow rate: 1.50 mL/min; Gradient: 5% B to 95% B in 2.0 min, hold at 95% B for 0.7 min, 95% B to 2% B in 0.2 min; 254 nm; RT: 1.646 min.

Example S6. 1-(5-((2-fluorophenyl)ethynyl)-2,3-dihydro-1H-inden-1-yl)piperidine-4-carboxylic acid (6a and 6b)

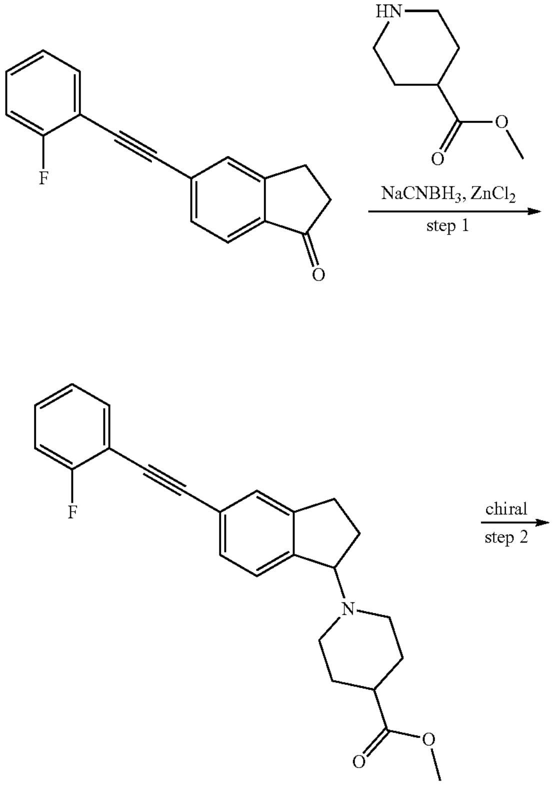

-continued

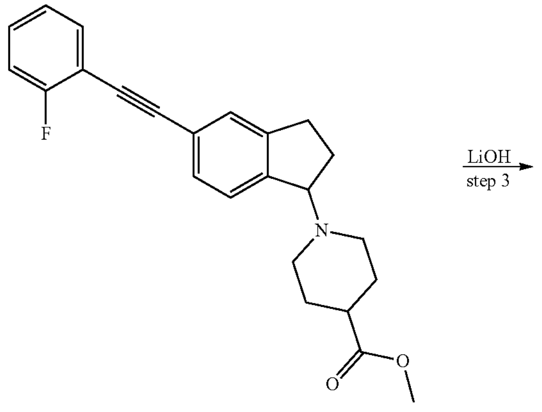

chiral separation1

-continued

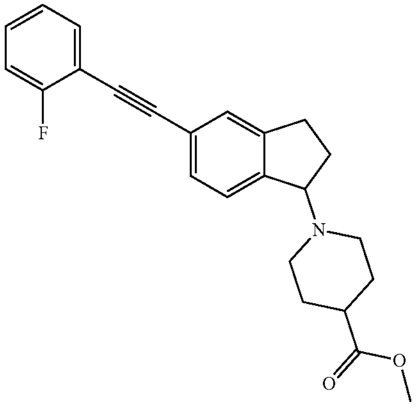

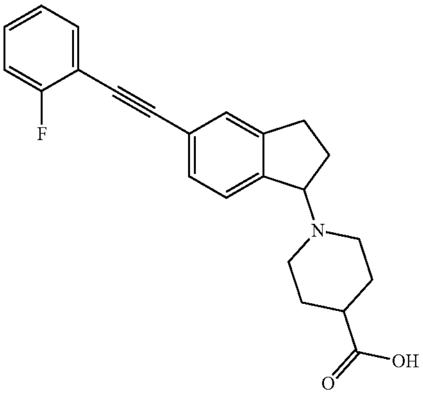

chiral separation1

Synthesis of methyl 1-(5-((2-fluorophenyl)ethynyl)-2,3-dihydro-1H-inden-1-yl)piperidine-4-carboxylate

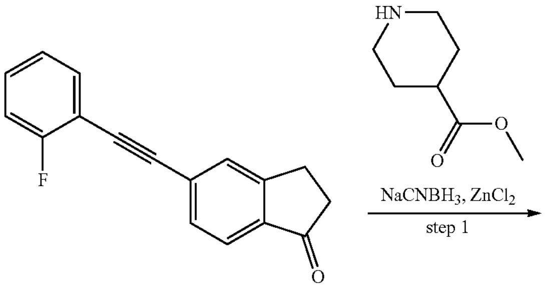

To a stirred solution of $NaCNBH_3$ (301 mg, 1.60 mmol, 4.0 equiv.) in methanol (5 mL) were added 5-((2-fluorophenyl)ethynyl)-2,3-dihydro-1H-inden-1-one (300 mg, 0.400 mmol, 1.0 equiv.), methyl piperidine-4-carboxylate (342 mg, 0.800 mmol, 2.0 equiv.) and $ZnCl_2$ (2M in THF, 0.8 mL, 1.60 mmol, 4.0 equiv.). The resulting solution was stirred at 60° C. for 72 h. LCMS showed the reaction was complete. The reaction mixture was filtered and the filtrate was concentrated under reduced pressure. The residue was purified by flash column chromatography on silica gel (eluted with MeOH/DCM, 1/15) to give methyl 1-(5-((2-fluorophenyl)ethynyl)-2,3-dihydro-1H-inden-1-yl)piperidine-4-carboxylate (277 mg, 55.7%) as a solid. LCMS (ESI, m/z): 378[M+H]$^+$.

Chiral Separation of methyl 1-(5-((2-fluorophenyl)ethynyl)-2,3-dihydro-1H-inden-1-yl)piperidine-4-carboxylate

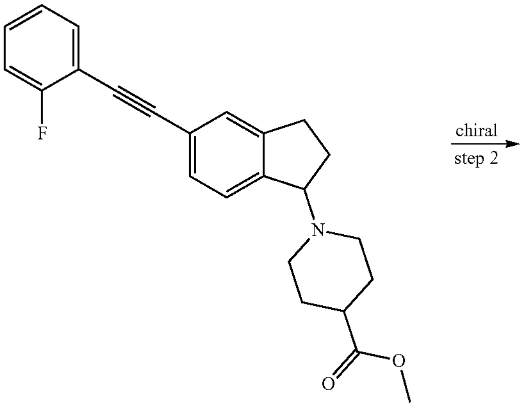

-continued

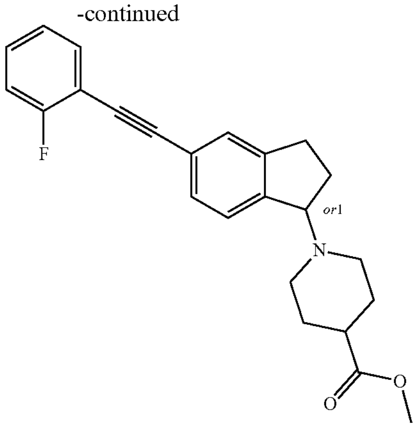

chiral separationl

The racemate was separated by SFC (Column: CHIRALPAK IG, 2*25 cm, 5 μm; Mobile Phase A: Hex (8 mmol/L $NH_3$-MeOH)-HPLC, Mobile Phase B: EtOH-HPLC; Flow rate: 20 mL/min; Gradient: 30% B to 30% B in 24 min; 220/254 nm; RT1:11.666 min; RT2: 18.917 min) to afford the enantiomers as solids.

Synthesis of 1-(5-((2-fluorophenyl)ethynyl)-2,3-dihydro-1H-inden-1-yl)piperidine-4-carboxylic acid

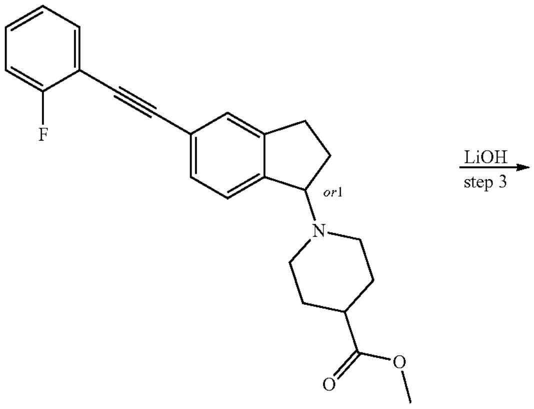

chiral separationl

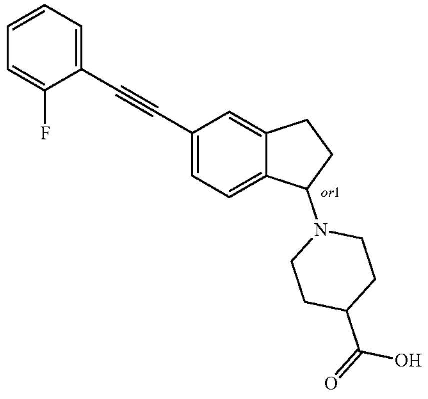

chiral separationl

To a solution of methyl 1-(5-((2-fluorophenyl)ethynyl)-2,3-dihydro-1H-inden-1-yl)piperidine-4-carboxylate (chiral separation 1; 92.0 mg, 0.240 mmol, 1.0 equiv.) in THF (3 mL) and water (3 mL) was added LiOH (17 mg, 0.730 mmol, 3.0 equiv.). The resulting solution was stirred at room temperature for 30 min. LCMS showed the reaction was complete. The reaction mixture was acidified to pH 3-4 with 1N HCl, and then was concentrated under reduced pressure. The residue was purified by Prep HPLC (Column: XSelect CSH Prep C18 OBD Column, 19*250 mm, 5 μm; Mobile Phase A: Water (0.05% HCl), Mobile Phase B: ACN; Flow rate: 25 mL/min; Gradient: 20% B to 45% B in 7 min; 210/254 nm; RT: 6.27 min) to afford 1-(5-((2-fluorophenyl)ethynyl)-2,3-dihydro-1H-inden-1-yl)piperidine-4-carboxylic acid (6a, 26.7 mg, 30.1%) as a solid.

$^1$H NMR (400 MHz, DMSO-$d_6$) δ 12.53 (s, 1H), 10.21 (s, 1H), 7.85-7.73 (m, 1H), 7.68-7.45 (m, 4H), 7.41-7.25 (m, 2H), 5.01-4.98 (m, 1H), 3.50-3.39 (m, 1H), 3.23-2.74 (m, 5H), 2.61-2.54 (m, 1H), 2.47-2.30 (m, 2H), 2.15-1.88 (m, 3H), 1.85-1.71 (m, 1H).

LCMS (ESI, m/z): 364 $[M+H]^+$. Analytic Conditions: Shim-pack XR-ODS, 3.0*50 mm, 2.2 μm; Mobile Phase A: Water/0.05% TFA, Mobile Phase B: Acetonitrile/0.05% TFA; Flow rate: 1.50 mL/min; Gradient: 5% B to 95% B in 3.0 min, hold at 95% B for 0.7 min, 95% B to 5% B in 0.2 min; 254 nm; RT: 1.536 min.

Synthesis of 1-(5-((2-fluorophenyl)ethynyl)-2,3-dihydro-1H-inden-1-yl)piperidine-4-carboxylic acid from chiral separation 2

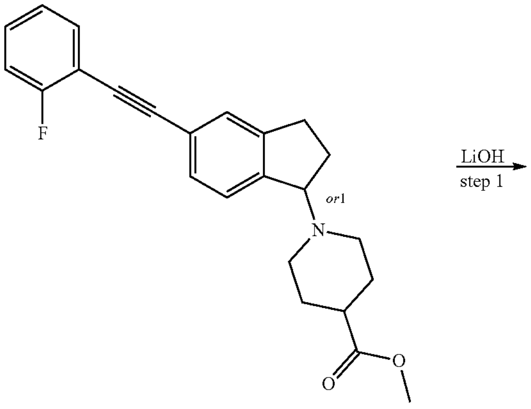

chiral separation 2

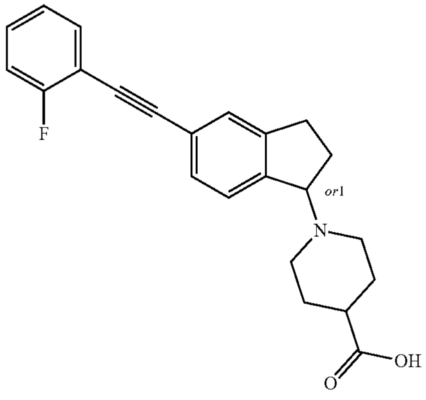

chiral separation 2

To a solution of 1-(5-((2-fluorophenyl)ethynyl)-2,3-dihydro-1H-inden-1-yl)piperidine-4-carboxylate (chiral separation 2; 86.0 mg, 0.240 mmol, 1.00 equiv.) in THF (3 mL) and water (3 mL) was added LiOH (16.0 mg, 0.730 mmol, 2.00 equiv.). The resulting solution was stirred at room temperature for 30 min. LCMS showed the reaction was complete. The reaction mixture was acidified to pH 3-4 with 1N HCl, and then was concentrated under reduced pressure. The residue was purified by Prep HPLC (Column: XSelect CSH Prep C18 OBD Column, 19*250 mm, 5 μm; Mobile Phase A: Water (0.05% HCl), Mobile Phase B: ACN; Flow rate: 25 mL/min; Gradient: 20% B to 45% B in 7 min; 210/254 nm; RT: 6.27 min) to afford 1-(5-((2-fluorophenyl)ethynyl)-2,3-dihydro-1H-inden-1-yl)piperidine-4-carboxylic acid (6b, 33.0 mg, 30.1%) as a solid.

$^1$H NMR (400 MHz, DMSO-$d_6$) δ 12.52 (s, 1H), 10.66 (s, 1H), 7.89 (dd, J=8.0 Hz, 1H), 7.67-7.48 (m, 4H), 7.40-7.28 (m, 2H), 5.00-4.97 (m, 1H), 3.44-3.41 (m, 1H), 3.15-3.09 (m, 2H), 3.03-2.86 (m, 3H), 2.62-2.55 (m, 1H), 2.49-2.29 (m, 2H), 2.14-1.94 (m, 3H), 1.92-1.84 (m, 1H).

LCMS (ESI, m/z): 364[M+H]$^+$. Analytic Conditions: Shim-pack XR-ODS C18, 3.0*50 mm, 2.2 μm; Mobile Phase A: water/0.05% TFA, Mobile Phase B: ACN/0.05% TFA; Flow rate: 1.20 mL/min; Gradient: 5% B to 95% B in 2.0 min, hold at 95% B for 0.7 min, 95% B to 5% B in 0.2 min; 254 nm; RT: 1.529 min.

Example S7. (3R)-1-(5-((3-fluorophenyl)ethynyl)-2,3-dihydro-1H-inden-1-yl)piperidine-3-carboxylic acid (7a and 7b)

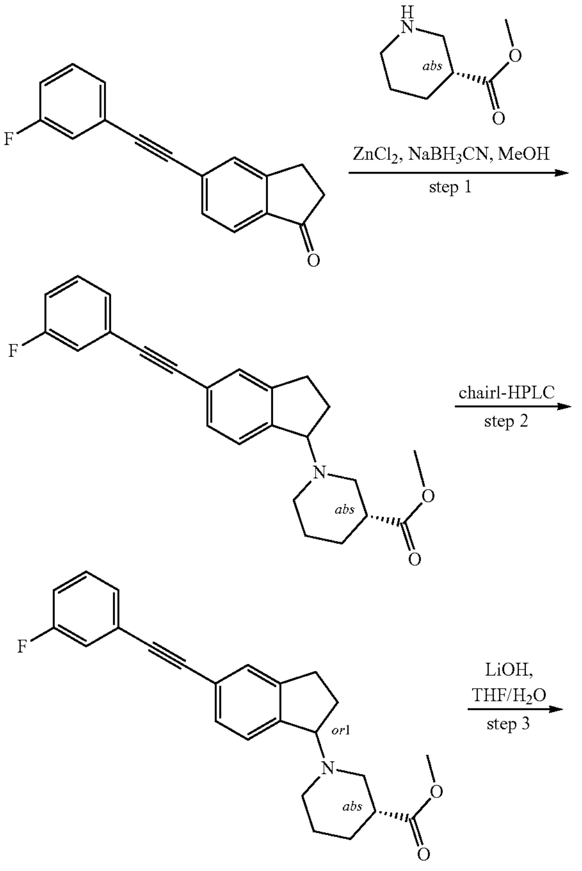

chiral separation 1

-continued

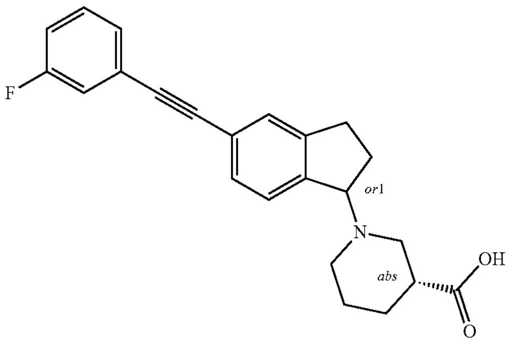

chiral separation 1

Synthesis of methyl (3R)-1-(5-((3-fluorophenyl)ethynyl)-2,3-dihydro-1H-inden-1-yl)-piperidine-3-carboxylate

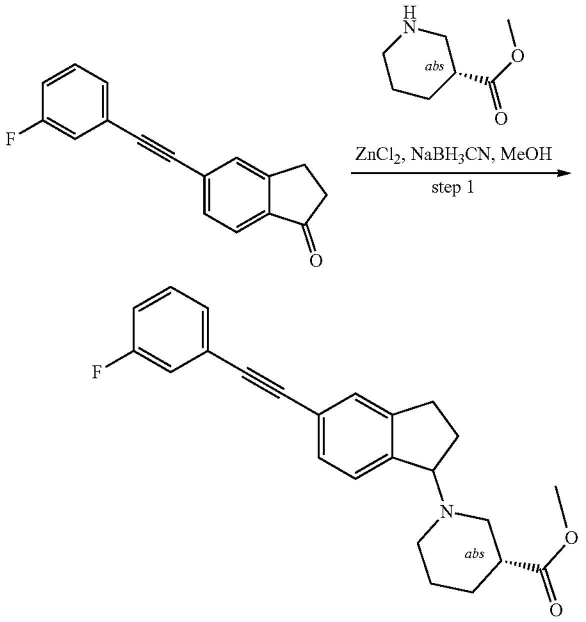

A solution of 5-((3-fluorophenyl)ethynyl)-2,3-dihydro-1H-inden-1-one (500 mg, 2.00 mmol, 1.00 equiv.), methyl (R)-piperidine-3-carboxylate (286 mg, 2.00 mmol, 1.00 equiv.), $ZnCl_2$ (2M in THF, 2.0 mL, 4.00 mmol, 2.00 equiv.) and $NaBH_3CN$ (502 mg, 8.00 mmol, 4.00 equiv.) in methanol (5.0 mL) was stirred at 60° C. for 15 h under $N_2$ atmosphere. LCMS showed the reaction was complete. The resulting solution was diluted with 10 ml of water and extracted with ethyl acetate (3*10 mL). The combined organic layers were washed with brine, and dried over anhydrous $Na_2SO_4$ and concentrated under reduced pressure. The residue was purified by flash chromatography on silica gel (PE/EA=10%) to give methyl (3R)-1-(5-((3-fluoro-phenyl)ethynyl)-2,3-dihydro-1H-inden-1-yl)-piperidine-3-carboxylate (200 mg, 26%) as an oil. LCMS (ESI, m/z): 378 [M+H]$^+$.

Chiral Separation of (3R)-1-(5-((3-fluorophenyl) ethynyl)-2,3-dihydro-1H-inden-1-yl)-piperidine-3-carboxylate

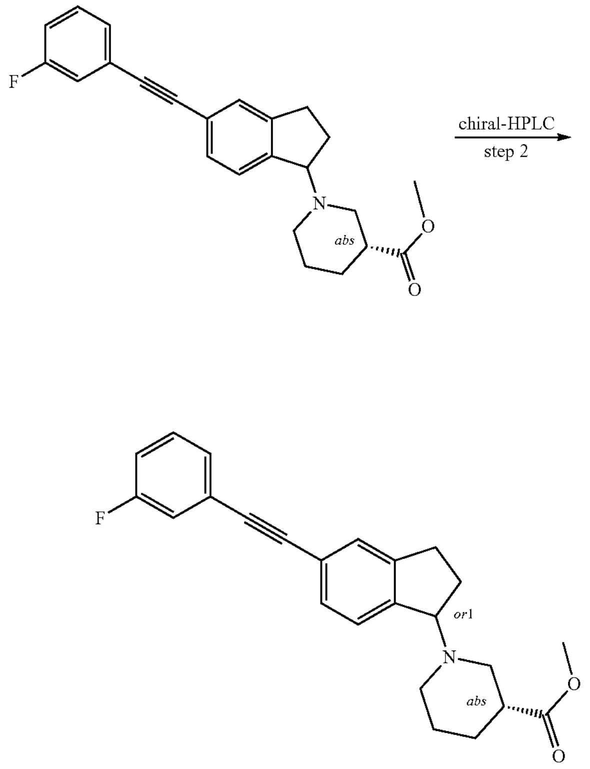

chiral separation 1

The racemate (200 mg) was separated by chiral-HPLC (Column: CHIRALPAK IG, 2*25 cm, 5 μm; Mobile Phase A: Hex (8 mmol/L $NH_3$-MeOH, Mobile Phase B: IPA; Flow rate: 20 mL/min; Gradient: 20% B to 20% B in 8.5 min; 220/254 nm; RT1: 5.278 min; RT2: 6.92 min) to afford the chiral separation 1 isomer (80 mg, 99% e.e.) as an oil.

Synthesis of (3R)-1-(5-((3-fluorophenyl)ethynyl)-2,3-dihydro-1H-inden-1-yl)piperidine-3-carboxylic acid from chiral separation 1

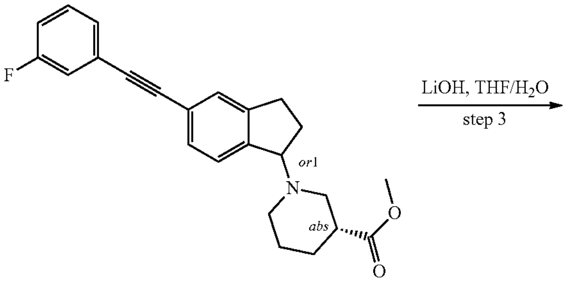

chiral separation 1

-continued

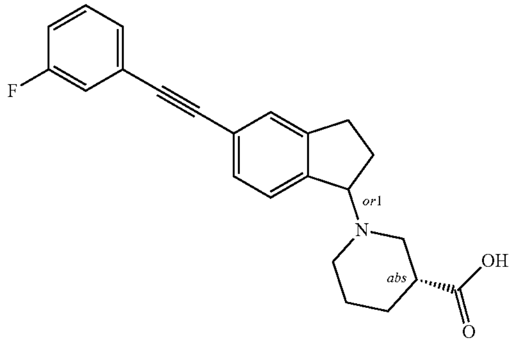

chiral separation 1

A solution of methyl (3R)-1-(5-((3-fluorophenyl)ethynyl)-2,3-dihydro-1H-inden-1-yl)-piperidine-3-carboxylate isomer 1 (80 mg, 0.210 mmol, 1.00 equiv.) and LiOH (15 mg, 0.640 mmol, 3.00 equiv.) in THF (3.0 mL) and water (3.0 mL) was stirred at room temperature for 15 h. LCMS showed the reaction was complete. The resulting solution was acidified to pH 5~6 with 2N HCl and concentrated under reduced pressure. The crude product was purified by prep-HPLC (Column: XB ridge Shield RP18 OBD Column, 30*150 mm, 5 μm; Mobile Phase A: Water (10 mmoL/L $NH_4HCO_3$+0.1% $NH_3 \cdot H_2O$), Mobile Phase B: ACN; Flow rate: 60 mL/min; Gradient: 24% B to 46% B in 7 min; 254/210 nm; RT: 6.38 min) to give (3R)-1-(5-((3-fluorophenyl)ethynyl)-2,3-dihydro-1H-inden-1-yl)piperidine-3-carboxylic acid isomer 1 (7a, 46.8 mg, 60%) as a solid.

LCMS (ESI, m/z): 364 $[M+H]^+$. Analytic Conditions: Poroshell EVO C18, 3.0*50 mm, 2.6 μm; Mobile Phase A: Water/5 mM $NH_4HCO_3$. Mobile Phase B: ACN; Flow rate: 1.20 mL/min; Gradient: 10% B to 95% B in 2.0 min, hold at 95% B for 0.6 min, 95% B to 10% B in 0.15 min; 254 nm; RT: 1.146 min.

$^1H$ NMR (400 MHz, Methanol-$d_4$) δ 7.69 (d, J=8.0 Hz, 1H), 7.53-7.49 (m, 2H), 7.45-7.40 (m, 1H), 7.37-7.35 (m, 1H), 7.30-7.26 (m, 1H), 7.18-7.13 (m, 1H), 4.89-4.87 (m, 1H), 3.19-2.97 (m, 6H), 2.67-2.61 (m, 1H), 2.47-2.43 (m, 2H), 2.05-1.82 (m, 4H).

$^{19}F$ NMR (376 MHz, Methanol-$d_4$) δ −114.903.

Chiral Separation of methyl (3R)-1-(5-((3-fluorophenyl)ethynyl)-2,3-dihydro-1H-inden-1-yl)piperidine-3-carboxylate

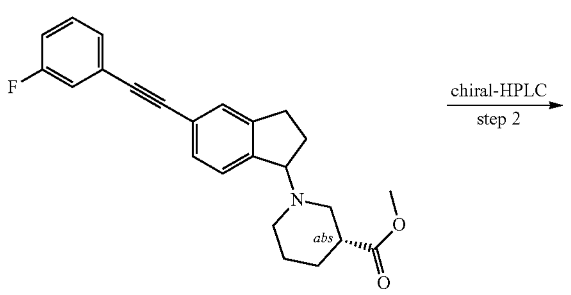

-continued

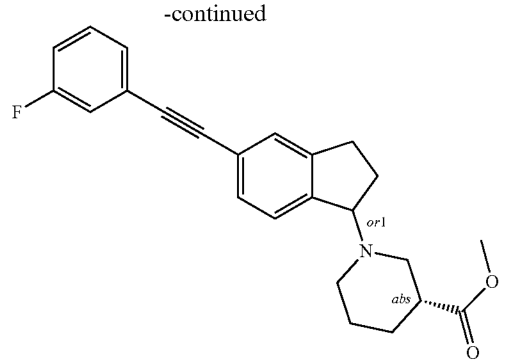

chiral separation 2

The racemic methyl (3R)-1-(5-((3-fluorophenyl)ethynyl)-2,3-dihydro-1H-inden-1-yl)-piperidine-3-carboxylate (200 mg) was separated by chiral-HPLC (Column: CHIRALPAK IG, 2*25 cm, 5 μm; Mobile Phase A: Hex (8 mmol/L $NH_3$·MeOH, Mobile Phase B: IPA; Flow rate: 20 mL/min; Gradient: 20% B to 20% B in 8.5 min; 220/254 nm; RT: 5.278 min; RT2: 6.92 min) to afford the chiral separation 2 isomer (70 mg, 99% e.e.) as an oil.

Synthesis of (3R)-1-(5-((3-fluorophenyl)ethynyl)-2,3-dihydro-1H-inden-1-yl)piperidine-3-carboxylic acid from chiral separation 2

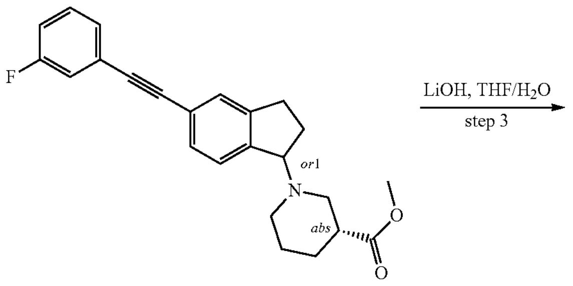

chiral separation 2

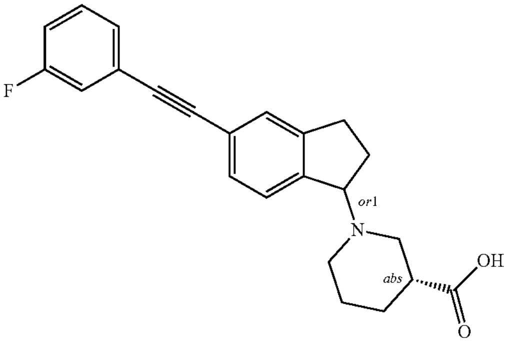

chiral separation 2

A solution of methyl (3R)-1-(5-((3-fluorophenyl)ethynyl)-2,3-dihydro-1H-inden-1-yl)-piperidine-3-carboxylate isomer 2 (70 mg, 0.185 mmol, 1.00 equiv.) and LiOH (15 mg, 0.555 mmol, 3.00 equiv.) in THF (3.0 mL) and water (3.0 mL) was stirred at room temperature for 15 h. LCMS showed the reaction was complete. The resulting solution was acidified to pH 5-6 with 2N HCl and concentrated under reduced pressure. The crude product was purified by prep-HPLC (Column: XB ridge Shield RP18 OBD Column, 30*150 mm, 5 μm; Mobile Phase A: Water (10 mmoL/L $NH_4HCO_3$+0.1% $NH_3$·$H_2O$), Mobile Phase B: ACN; Flow rate: 60 mL/min; Gradient: 24% B to 46% B in 7 min; 254/210 nm; RT: 6.38 min) to give (3R)-1-(5-((3-fluorophenyl)ethynyl)-2,3-dihydro-1H-inden-1-yl)piperidine-3-carboxylic acid isomer 2 (7b, 43.4 mg, 64%) as a solid.

LCMS (ESI, m/z): 364 $[M+H]^+$. Analytic Conditions: Poroshell EVO C18, 3.0*50 mm, 2.6 μm; Mobile Phase A: Water/5 mM $NH_4HCO_3$. Mobile Phase B: ACN; Flow rate: 1.20 mL/min; Gradient: 10% B to 95% B in 2.0 min, hold at 95% B for 0.6 min, 95% B to 10% B in 0.15 min; 254 nm; RT: 1.145 min.

$^1$H NMR (400 MHz, Methanol-$d_4$) δ 7.60-7.51 (m, 3H), 7.45-7.40 (m, 1H), 7.37-7.35 (m, 1H), 7.30-7.26 (m, 1H), 7.18-7.13 (m, 1H), 4.87-4.85 (m, 1H), 3.24-2.97 (m, 6H), 2.67-2.61 (m, 1H), 2.56-2.49 (m, 2H), 1.96-1.84 (m, 4H).

Example S8. (2S)-1-(5-((3-fluorophenyl)ethynyl)-2,3-dihydro-1H-inden-1-yl)piperidine-2-carboxylic acid (8a and 8b)

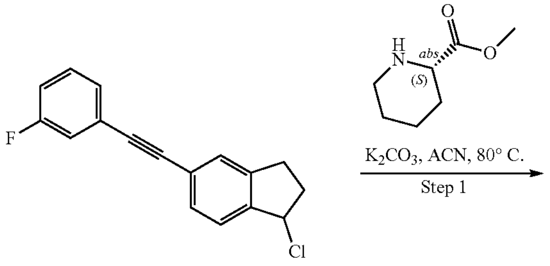

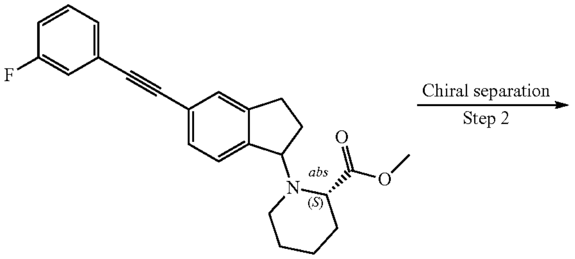

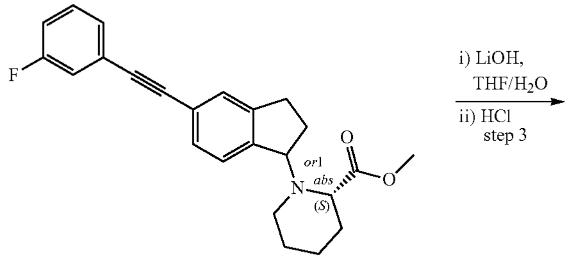

chiral separation 1

-continued

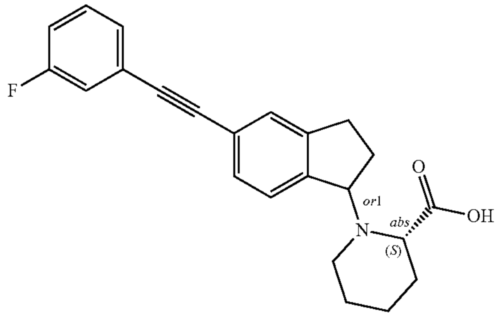

chiral separation 1

Synthesis of methyl (2S)-1-(5-((3-fluorophenyl) ethynyl)-2,3-dihydro-1H-inden-1-yl)piperidine-2-carboxylate

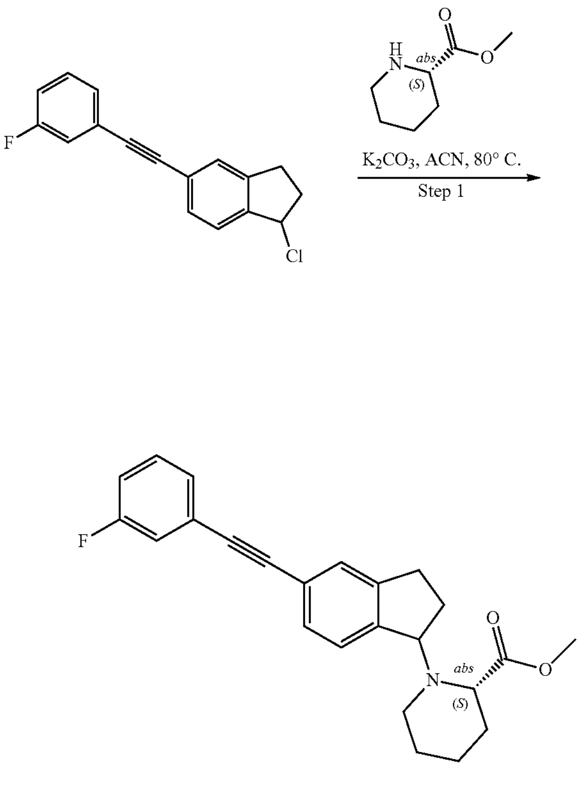

To a solution of 1-chloro-5-((3-fluorophenyl)ethynyl)-2,3-dihydro-1H-indene (750 mg, 2.770 mmol, 1.00 equiv.), methyl (S)-piperidine-2-carboxylate (793 mg, 5.540 mmol, 2.00 equiv.) in MeCN (8.0 mL) were added $K_2CO_3$ (1.1 g, 8.310 mmol, 3.00 equiv). The resulting mixture was stirred at 80° C. for 2 days. LCMS showed the reaction was complete. The reaction mixture was filtered and the filtrate was concentrated under reduced pressure. The residue was purified by flash chromatography on silica gel (PE:EA=9:1) to give methyl (2S)-1-(5-((3-fluorophenyl)ethynyl)-2,3-dihydro-1H-inden-1-yl)piperidine-2-carboxylate (190 mg, 18%) as an oil. LCMS (ESI, m/z): 378 $[M+H]^+$.

Chiral Separation of methyl (2S)-1-(5-((3-fluorophenyl)ethynyl)-2,3-dihydro-1H-inden-1-yl)piperidine-2-carboxylate

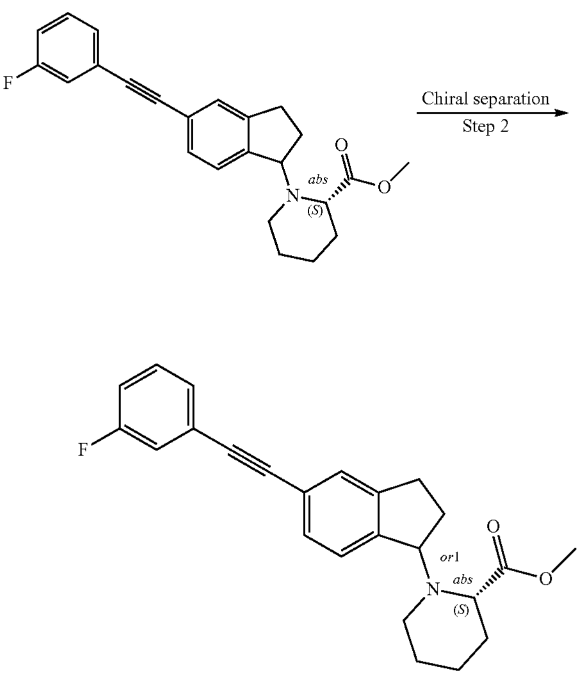

chiral separation 1

Racemic methyl (2S)-1-(5-((3-fluorophenyl)ethynyl)-2,3-dihydro-1H-inden-1-yl)-piperidine-2-carboxylate (190 mg) was separated by Chiral SFC (Column: CHIRALPAK IG, 2*25 cm, 5 μm; Mobile Phase A: Hex (8 mmol/L $NH_3$·MeOH)-HPLC, Mobile Phase B:EtOH-HPLC; Flow rate: 20 mL/min; Gradient: 7% B to 7% B in 8.5 min; 220/254 nm; Rt1: 4.995 min; Rt2: 6.813 min) to afford chiral methyl (2S)-1-(5-((3-fluoro-phenyl)ethynyl)-2,3-dihydro-1H-inden-1-yl)piperidine-2-carboxylate (enantiomer 1, 60 mg) and (enantiomer 2, 53 mg) as oils.

Synthesis of (2S)-1-(5-((3-fluorophenyl)ethynyl)-2,3-dihydro-1H-inden-1-yl)piperidine-2-carboxylic acid

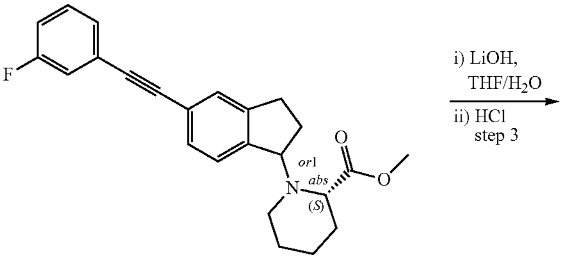

chiral separation 1

-continued

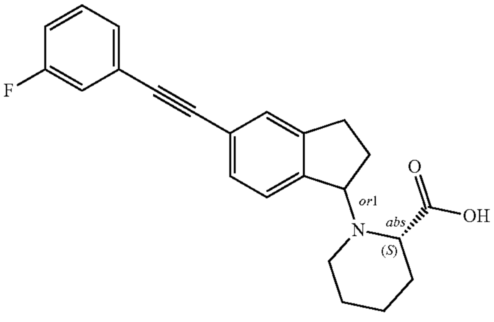

chiral separation 1

-continued

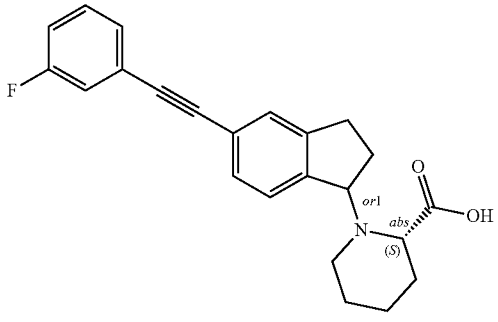

chiral separation 2

A mixture of (2S)-1-(5-((3-fluoro-phenyl)ethynyl)-2,3-dihydro-1H-inden-1-yl)piperidine-2-carboxylate (enantiomer 1, 60 mg, 0.160 mmol, 1.00 equiv.), $LiOH \cdot H_2O$ (20 mg, 0.480 mmol, 3.00 equiv.) in THF (1.0 mL) and water (1.0 mL) was stirred at 60° C. for 3 days. LCMS showed the reaction was complete. The resulting mixture was adjusted to pH 5~6 with 2N HCl and concentrated under reduced pressure. The residue was purified by preparative HPLC (Column: XBridge Prep C18 OBD Column, 19×150 mm 5 m; Mobile Phase A: water (10 mmol/L $NH_4HCO_3$), Mobile Phase B: ACN; Flow rate: 25 mL/min; Gradient: 20% B to 50% B in 7 min; 254/210 nm; RT: 6.55 min) to give corresponding enantiomer of (2S)-1-(5-((3-fluorophenyl)ethynyl)-2,3-dihydro-1H-inden-1-yl)piperidine-2-carboxylic acid (8a, 14.9 mg, 25%) as a solid.

$^1H$ NMR (400 MHz, Methanol-$d_4$) δ 7.68 (d, J=8.4 Hz, 1H), 7.50-7.48 (m, 2H), 7.42-7.37 (m, 1H), 7.34-7.32 (m, 1H), 7.26-7.23 (m, 1H), 7.15-7.10 (m, 1H), 5.30 (s, 1H), 3.57-3.50 (m, 1H), 3.12-2.95 (m, 2H), 2.85-2.73 (m, 2H), 2.52-2.47 (m, 1H), 2.35-2.21 (m, 2H), 1.93-1.82 (m, 2H), 1.73-1.65 (m, 2H), 1.57-1.52 (m, 1H).

$^{19}F$ NMR (376 MHz, Methanol-$d_4$) δ −114.88.

LCMS (ESI, m/z): 364 $[M+H]^+$. Analytic Conditions: column: EVO C18 Column 3.0*50 mm, 2.6 μm; mobile Phase A: Water/5 mM $NH_4HCO_3$, mobile Phase B: Acetonitrile; flow rate: 1.20 mL/min; gradient: 10% B to 95% B in 2.00 min, hold at 95% for 0.60 min, 95% B to 10% B in 0.25 min; 254 nm; RT: 1.180 min.

Synthesis of (2S)-1-(5-((3-fluorophenyl)ethynyl)-2,3-dihydro-1H-inden-1-yl)piperidine-2-carboxylic acid

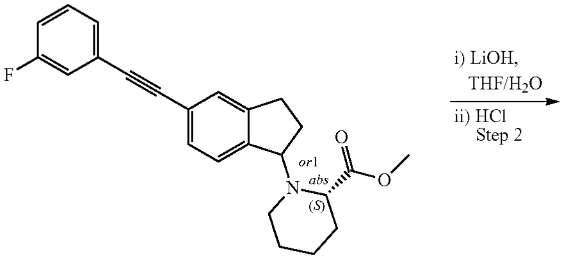

chiral separation 2

A mixture of methyl (2S)-1-(5-((3-fluoro-phenyl)ethynyl)-2,3-dihydro-1H-inden-1-yl)piperidine-2-carboxylate (enantiomer 2, 53 mg, 0.14 mmol, 1.00 equiv.), $LiOH \cdot H_2O$ (18 mg, 0.480 mmol, 3.00 equiv.) in THF (1.0 mL) and water (1.0 mL) was stirred at 60° C. for 3 days. LCMS showed the reaction was complete. The resulting mixture was adjusted to pH 5-6 with 2N HCl and concentrated under reduced pressure. The residue was purified by preparative HPLC (Column: XBridge Prep C18 OBD Column, 19×150 mm 5 m; Mobile Phase A: water (10 mmol/L $NH_4HCO_3$), Mobile Phase B: ACN; Flow rate: 25 mL/min; Gradient: 20% B to 50% B in 7 min; 254/210 nm; RT: 6.55 min) to give corresponding enantiomer of (2S)-1-(5-((3-fluorophenyl)ethynyl)-2,3-dihydro-1H-inden-1-yl)piperidine-2-carboxylic acid (8b, 12.8 mg, 25%) as a solid.

$^1H$ NMR (400 MHz, Methanol-$d_4$) δ 7.66 (d, J=7.6 Hz, 1H), 7.58 (s, 1H), 7.52 (d, J=8.0 Hz, 1H), 7.46-7.40 (m, 1H), 7.38-7.35 (m, 1H), 7.30-7.27 (m, 1H), 7.19-7.13 (m, 1H), 5.30 (d, J=8.8 Hz, 1H), 3.68-3.59 (m, 1H), 3.30-3.19 (m, 2H), 3.08-3.00 (m, 1H), 2.71-2.60 (m, 1H), 2.52-2.46 (m, 1H), 2.28-2.24 (m, 2H), 1.94-1.80 (m, 4H), 1.40-1.32 (m, 1H).

$^{19}F$ NMR (376 MHz, Methanol-$d_4$) δ −114.88.

LCMS (ESI, m/z): 364 $[M+H]^+$. Analytic Conditions: column: EVO C18 Column 3.0*50 mm, 2.6 μm; mobile Phase A: Water/5 mM $NH_4HCO_3$, mobile Phase B: Acetonitrile; flow rate: 1.20 mL/min; gradient: 10% B to 95% B in 2.00 min, hold at 95% for 0.60 min, 95% B to 10% B in 0.25 min; 254 nm; RT: 1.171 min.

Example S9. (2R)-1-(5-((3-fluorophenyl)ethynyl)-2,3-dihydro-1H-inden-1-yl)piperidine-2-carboxylic acid (9a and 9b)

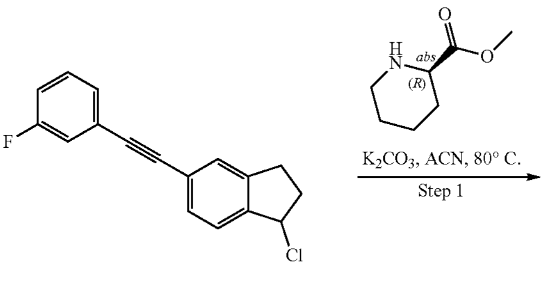

-continued

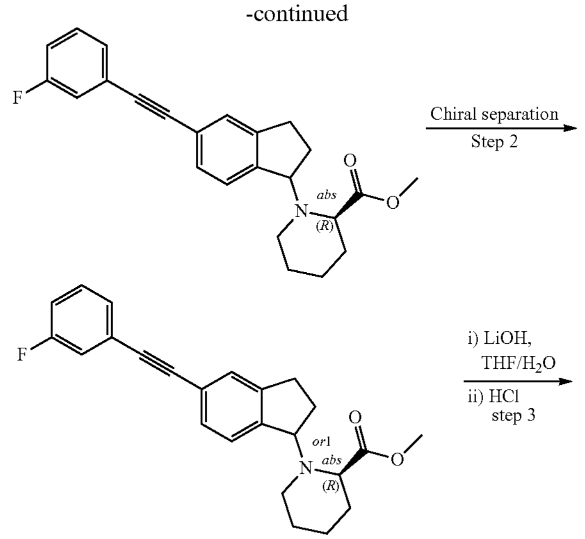

chiral separation 1

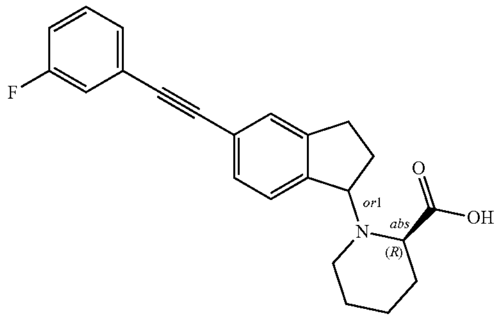

chiral separation 1

Synthesis of methyl (2R)-1-(5-((3-fluorophenyl) ethynyl)-2,3-dihydro-1H-inden-1-yl)piperidine-2-carboxylate

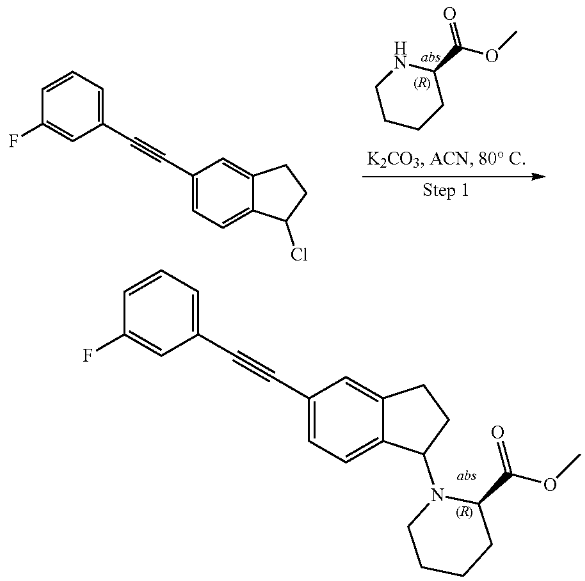

To a solution of 1-chloro-5-((3-fluorophenyl)ethynyl)-2,3-dihydro-1H-indene (980 mg, 3.620 mmol, 1.00 equiv.), methyl (R)-piperidine-2-carboxylate (1.04 g, 7.240 mmol, 2.00 equiv.) in MeCN (8.0 mL) were added $K_2CO_3$ (2.0 g, 10.860 mmol, 3.00 equiv.). The resulting mixture was stirred at 80° C. for 2 days. LCMS showed the reaction was complete. The reaction mixture was filtered and the filtrate was concentrated under reduced pressure. The residue was purified by flash chromatography on silica gel (PE:EA=9:1) to give methyl (2R)-1-(5-((3-fluorophenyl)ethynyl)-2,3-dihydro-1H-inden-1-yl)piperidine-2-carboxylate (379 mg, 28%) as an oil. LCMS (ESI, m/z): 378 $[M+H]^+$.

Chiral Separation of methyl (2R)-1-(5-((3-fluorophenyl)ethynyl)-2,3-dihydro-1H-inden-1-yl)-piperidine-2-carboxylate

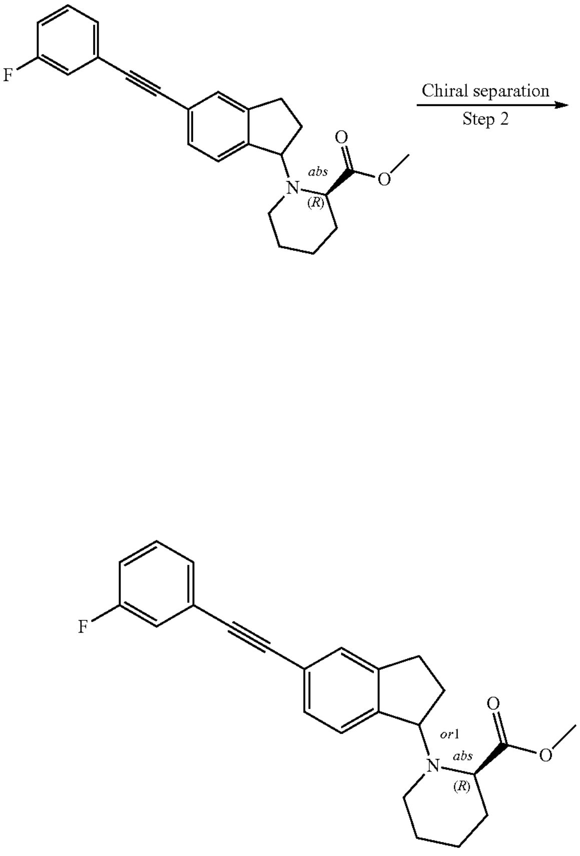

chiral separation 1

Racemic methyl (2R)-1-(5-((3-fluorophenyl)ethynyl)-2,3-dihydro-1H-inden-1-yl)-piperidine-2-carboxylate (190 mg) was separated by Chiral HPLC (Column: CHIRALPAK IG, 2*25 cm, 5 μm; Mobile Phase A: Hex (8 mmol/L $NH_3$·MeOH)-HPLC, Mobile Phase B: EtOH-HPLC; Flow rate: 20 mL/min; Gradient: 10% B to 10% B in 9 min; 220/254 nm; RT1: 5.802 min; RT2: 7.402 min; Injection volume: 0.8 ml; Number Of Runs: 4) to afford 126 mg of chiral separation 1 isomer and 133 mg of chiral separation 2 isomer as an oil. LCMS (ESI, m/z): 378 $[M+H]^+$.

Synthesis of (2R)-1-(5-((3-fluorophenyl)ethynyl)-2,3-dihydro-1H-inden-1-yl)piperidine-2-carboxylic acid

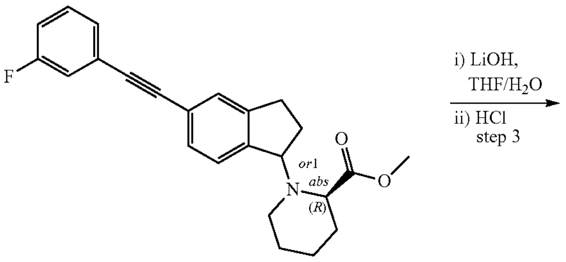

chiral separation 1

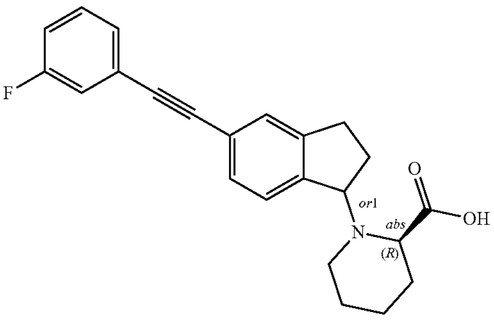

chiral separation 1

A mixture of methyl (2R)-1-(5-((3-fluorophenyl)ethynyl)-2,3-dihydro-1H-inden-1-yl)-piperidine-2-carboxylate (isomer 1, 126 mg, 0.330 mmol, 1.00 equiv.), $LiOH{\cdot}H_2O$ (40 mg, 0.990 mmol, 3.00 equiv.) in THF (2.0 mL) and water (2.0 mL) was stirred at 60° C. for 3 days. LCMS showed the reaction was complete. The resulting mixture was adjusted to pH 5-6 with 2N HCl and concentrated under reduced pressure. The residue was purified by preparative HPLC (Column: XBridge Prep C18 OBD Column, 19×150 mm 5 m; Mobile Phase A: water (10 mmol/L $NH_4HCO_3$), Mobile Phase B: ACN; Flow rate: 25 mL/min; Gradient: 28% B to 42% B in 7 min; 254/210 nm; RT: 6.53 min) to give the corresponding enantiomer of (2R)-1-(5-((3-fluorophenyl)ethynyl)-2,3-dihydro-1H-inden-1-yl)piperidine-2-carboxylic acid (9a, 36.5 mg, 30%) as a solid.

$^1H$ NMR (400 MHz, Methanol-$d_4$) δ 7.53 (d, J=7.6 Hz, 1H), 7.44 (s, 1H), 7.39 (d, J=8.0 Hz, 1H), 7.33-7.28 (m, 1H), 7.26-7.23 (m, 1H), 7.18-7.14 (m, 1H), 7.06-7.01 (m, 1H), 5.14-5.10 (m, 1H), 3.52-3.49 (m, 1H), 3.19-3.05 (m, 2H), 2.93-2.86 (m, 1H), 2.54-2.48 (m, 1H), 2.37-2.35 (m, 1H), 2.12-2.08 (m, 2H), 1.81-1.66 (m, 4H), 1.30-1.18 (m, 1H).

$^{19}F$ NMR (376 MHz, Methanol-$d_4$) δ −114.83.

LCMS (ESI, m/z): 364 $[M+H]^+$. Analytic Conditions: column: EVO C18 Column 3.0*50 mm, 2.6 µm; mobile Phase A: Water/5 mM $NH_4HCO_3$, mobile Phase B: Acetonitrile; flow rate: 1.20 mL/min; gradient: 10% B to 95% B in 2.00 min, hold at 95% for 0.60 min, 95% B to 10% B in 0.25 min; 254 nm; RT: 1.176 min.

Synthesis of (2R)-1-(5-((3-fluorophenyl)ethynyl)-2,3-dihydro-1H-inden-1-yl)piperidine-2-carboxylic acid

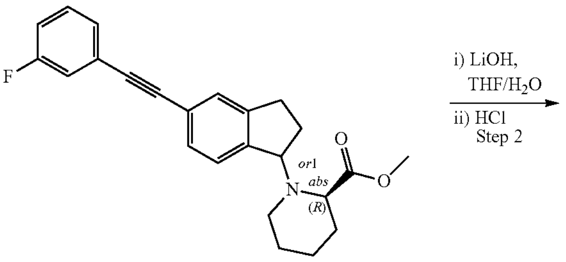

chiral separation 2

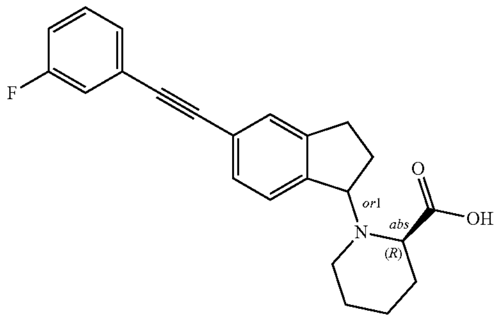

chiral separation 2

A mixture of methyl (2R)-1-(5-((3-fluorophenyl)ethynyl)-2,3-dihydro-1H-inden-1-yl)-piperidine-2-carboxylate (isomer 2, 133 mg, 0.350 mmol, 1.00 equiv.), $LiOH{\cdot}H_2O$ (40 mg, 1.050 mmol, 3.00 equiv.) in THF (2.0 mL) and water (2.0 mL) was stirred at 60° C. for 3 days. LCMS showed the reaction was complete. The resulting mixture was adjusted to pH 5-6 with 2N HCl and concentrated under reduced pressure. The residue was purified by preparative HPLC (Column: XBridge Prep C18 OBD Column, 19×150 mm 5 µm; Mobile Phase A: water (10 mmol/L $NH_4HCO_3$), Mobile Phase B: ACN; Flow rate: 25 mL/min; Gradient: 28% B to 42% B in 7 min; 254/210 nm; RT: 6.70 min) to give the corresponding enantiomer of (2R)-1-(5-((3-fluorophenyl)ethynyl)-2,3-dihydro-1H-inden-1-yl)piperidine-2-carboxylic acid (9b, 5 mg, 3.8%) as a solid.

$^1H$ NMR (400 MHz, Methanol-$d_4$) δ 7.68 (d, J=8.0 Hz, 1H), 7.50-7.47 (m, 2H), 7.45-7.39 (m, 1H), 7.36-7.34 (m, 1H), 7.29-7.25 (m, 1H), 7.17-7.12 (m, 1H), 5.27-5.19 (m, 1H), 3.59-3.49 (m, 1H), 3.10-2.92 (m, 2H), 2.75-2.67 (m, 2H), 2.55-2.45 (m, 1H), 2.35-2.12 (m, 2H), 1.93-1.84 (m, 2H), 1.75-1.67 (m, 2H), 1.57-1.48 (m, 1H).

$^{19}F$ NMR (376 MHz, Methanol-$d_4$) δ −114.92.

LCMS (ESI, m/z): 364 $[M+H]^+$. Analytic Conditions: column: EVO C18 Column 3.0*50 mm, 2.6 µm; mobile Phase A: Water/5 mM $NH_4HCO_3$, mobile Phase B: Acetonitrile; flow rate: 1.20 mL/min; gradient: 10% B to 95% B in 2.00 min, hold at 95% for 0.60 min, 95% B to 10% B in 0.25 min; 254 nm; RT: 1.174 min.

Example S10. (1R,5S,8s)-3-(5-((3-fluorophenyl)ethynyl)-2,3-dihydro-1H-inden-1-yl)-3-azabicyclo[3.2.1]-octane-8-carboxylic acid (10)

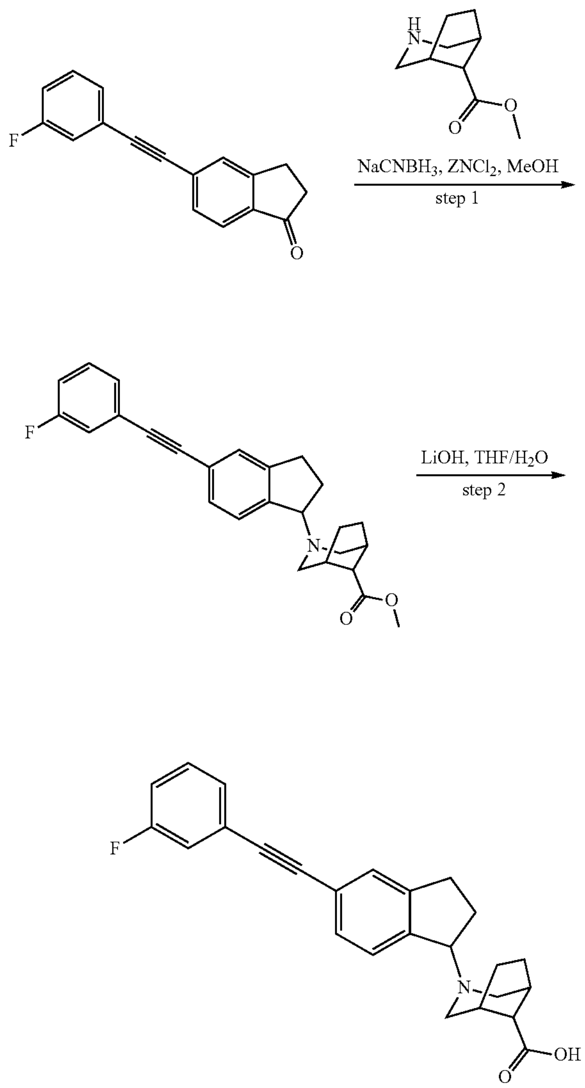

Synthesis of methyl (1R,5S,8s)-3-(5-((3-fluorophenyl)ethynyl)-2,3-dihydro-1H-inden-1-yl)-3-azabicyclo[3.2.1]octane-8-carboxylate

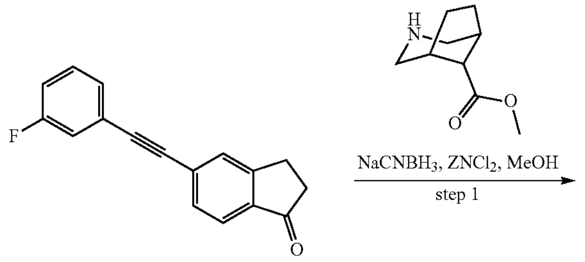

-continued

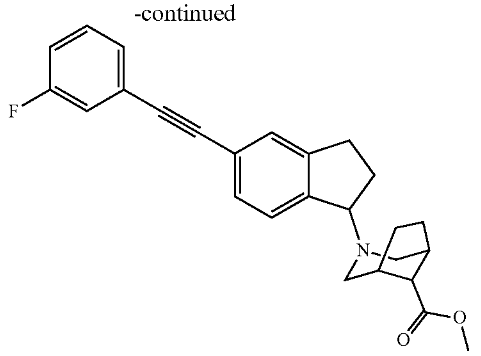

A solution of $NaBH_3CN$ (113 mg, 1.800 mmol, 3.00 equiv.) and $ZnCl_2$ (2.0 M in THF, 0.6 mL, 1.200 mmol, 2.00 equiv.) in methanol (5 mL) was stirred at room temperature for 15 m. Then 5-((3-fluorophenyl)ethynyl)-2,3-dihydro-1H-inden-1-one (150 mg, 0.600 mmol, 1.00 equiv) and methyl (1R,5S,8s)-3-azabicyclo[3.2.1]octane-8-carboxylate (122 mg, 0.720 mmol, 1.20 equiv.) were added. The resulting mixture was stirred at 60° C. for 72 h. LCMS showed the reaction was complete. The mixture was filtered through Celite and the filtrate was concentrated under vacuum. The residue was purified by Flash column chromatography on C18 silica (eluted with water (5 mM $NH_4HCO_3$)/ACN, 20/80) to give methyl (R,5S,8s)-3-(5-((3-fluorophenyl)ethynyl)-2,3-dihydro-1H-inden-1-yl)-3-azabicyclo[3.2.1]octane-8-carboxylate (60 mg, 25s) as a solid. LCMS (ESI, m/z): 404 $[M+H]^+$.

Synthesis of (1R,5S,8s)-3-(5-((3-fluorophenyl)ethynyl)-2,3-dihydro-1H-inden-1-yl)-3-aza-bicyclo[3.2.1]-octane-8-carboxylic acid

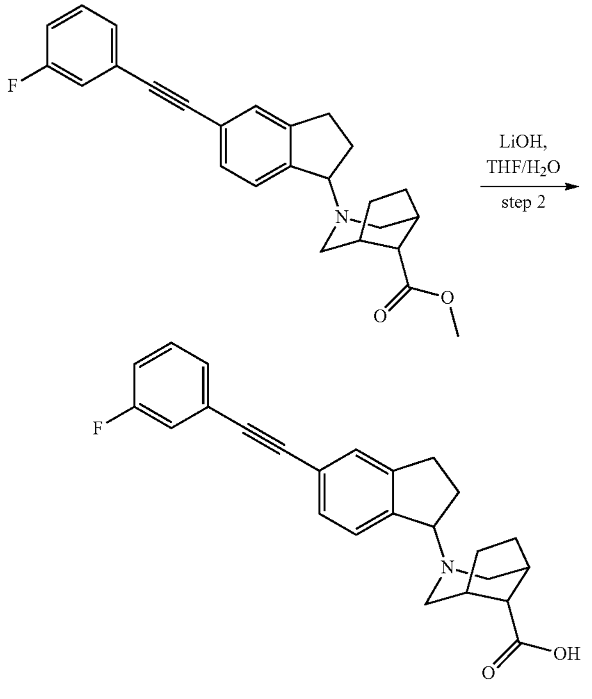

To a solution of methyl (1R,5S,8s)-3-(5-((3-fluorophenyl)ethynyl)-2,3-dihydro-1H-inden-1-yl)-3-azabicyclo[3.2.1]

octane-8-carboxylate (60 mg, 0.150 mmol, 1.00 equiv.) in THF (1 mL) and water (0.3 mL) was added $LiOH \cdot H_2O$ (19 mg, 0.450 mmol, 3.00 equiv.). The reaction was stirred at 80° C. for 48 h. LCMS showed the reaction was complete. The reaction mixture was acidified to pH 4-5 by adding 1N HCl, and then was concentrated under reduced pressure. The residue was purified by C18 Flash column chromatography (eluted with water (5 mM $NH_4HCO_3$)/ACN, 35/65) to give (1R,5S,8s)-3-(5-((3-fluorophenyl)ethynyl)-2,3-dihydro-1H-inden-1-yl)-3-azabicyclo-[3.2.1]-octane-8-carboxylic acid (10, 22.5 mg, 38%) as a solid.

$^1$H NMR (300 MHz, DMSO-$d_6$) δ 7.52-7.39 (m, 4H), 7.34-7.26 (m, 3H), 4.36-4.27 (m, 1H), 2.88-2.74 (m, 3H), 2.49-2.42 (m, 2H), 2.2.35-2.24 (m, 4H), 2.05-2.00 (m, 2H), 1.69-1.58 (m, 4H).

$^{19}$F NMR (282 MHz, DMSO-$d_6$) δ −115.0.

LCMS (ESI, m/z): 390 $[M+H]^+$. Analytic Conditions: column: Shim-pack XR-ODS Column 3.0*50 mm, 2.2 μm; mobile Phase A: water/0.05% TFA, mobile Phase B: acetonitrile/0.05% TFA; flow rate: 1.20 mL/min; gradient: 30% B to 60% B in 2.5 min, 60% B to 95% B in 0.5 min, hold at 95% for 0.6 min, 95% B to 5% B in 0.1 min; 254/220 nm; RT: 1.939 min.

Example S11. 5-(5-((2-fluorophenyl)ethynyl)-2,3-dihydro-1H-inden-1-yl)-5-azaspiro[2.5]octane-8-carboxylic acid (11)

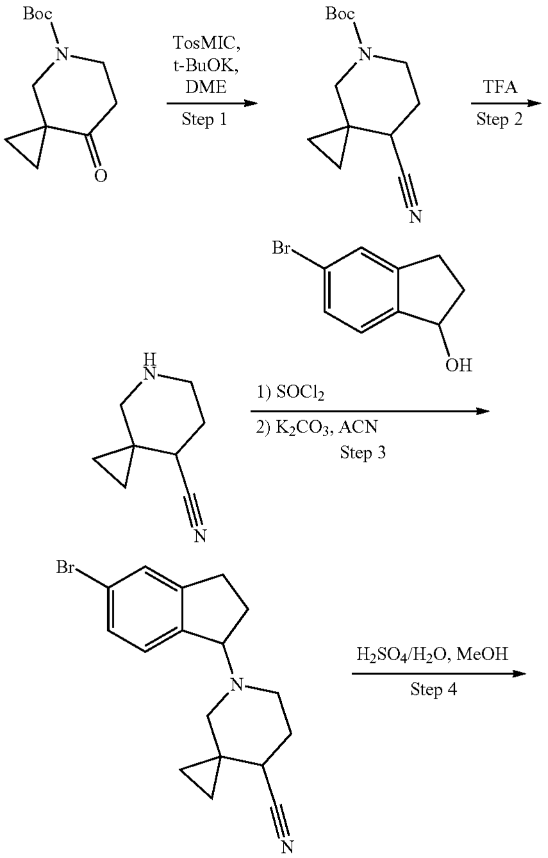

-continued

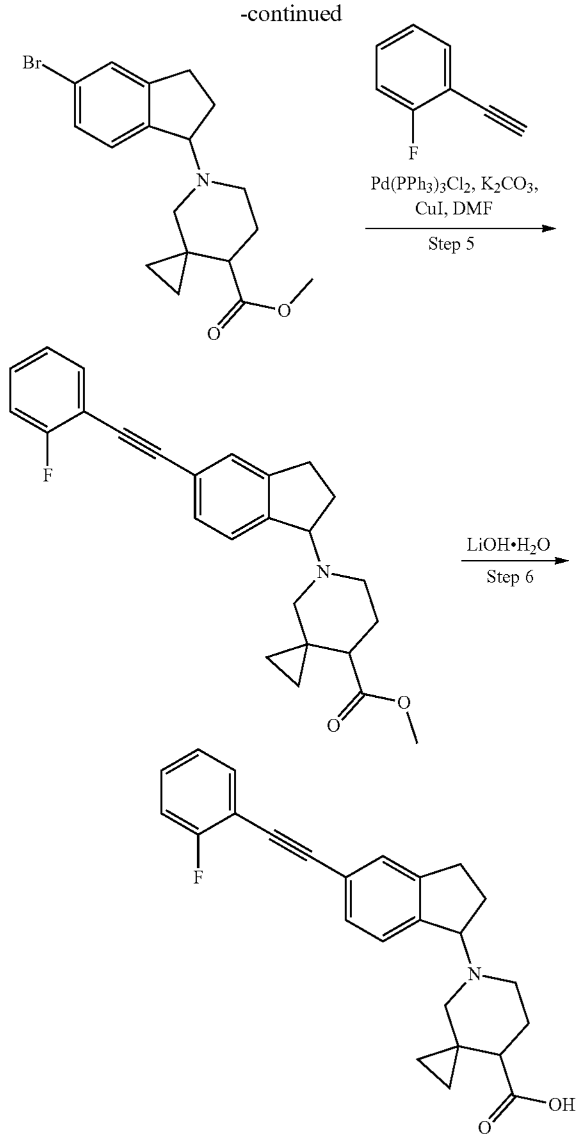

Synthesis of tert-butyl 8-cyano-5-azaspiro[2.5]octane-5-carboxylate

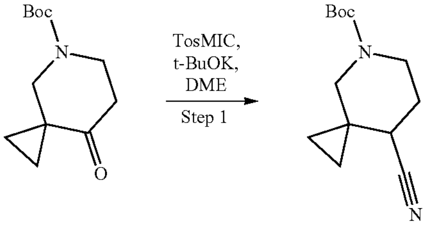 [SMILES: CC(C)(C)OC(=O)N1CCC(=O)C2(CC2)C1 ; CC(C)(C)OC(=O)N1CCC(C#N)C2(CC2)C1]

To a solution of tert-butyl 8-oxo-5-azaspiro[2.5]octane-5-carboxylate (1.0 g, 4.440 mmol, 1.00 equiv.), 1-(1-iodo-ethylsulfonyl)-4-methyl-benzene (1.8 g, 5.770 mmol, 1.20 equiv.) in DME (5.0 mL) was added t-BuOK (1.2 g, 10.65 mmol, 2.40 equiv.) at 0° C. The resulting mixture was stirred at room temperature for 8 h, and then was quenched with the water (20 mL) and diluted with ethyl acetate (20 mL). The separated aqueous layer was extracted with ethyl acetate (20 mL*3). The combined organic layers were dried over anhydrous $Na_2SO_4$ and concentrated under vacuum. The residue was purified by flash column chromatography on C18 silica (eluted with water (5 mM $NH_4HCO_3$)/ACN, 20/80) to give tert-butyl 8-cyano-5-azaspiro[2.5]octane-5-carboxylate (657 mg, 62%) as an oil. LCMS (ESI, m/z): 181 $[M+H]^+$.

Synthesis of 5-azaspiro[2.5]octane-8-carbonitrile

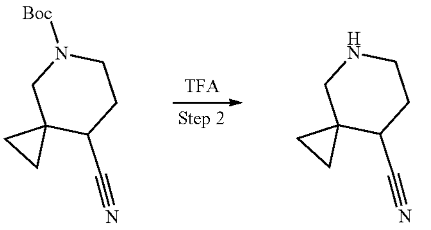 [SMILES: CC(C)(C)OC(=O)N1CCC(C#N)C2(CC2)C1 ; N#CC1CCNCC12CC2]

To a solution of tert-butyl 8-cyano-5-azaspiro[2.5]octane-5-carboxylate (432 mg, 1.828 mmol, 1.00 equiv.) in DCM (3.0 mL) was added TFA (0.3 mL). The reaction was stirred at room temperature for 1 h. TLC showed the reaction was complete. The pH value of the solution was adjusted to 9~10 by adding sat. aq. $Na_2CO_3$. The resulting solution was diluted with water (10 mL) and DCM (20 mL). The separated organic layer was concentrated under vacuum to give 5-aza-spiro[2.5]octane-8-carbonitrile (crude) (350 mg, 140%) as a solid. LCMS (ESI, m/z): 137 $[M+H]^+$.

Synthesis of 5-(5-bromo-2,3-dihydro-1H-inden-1-yl)-5-azaspiro[2.5]octane-8-carbonitrile

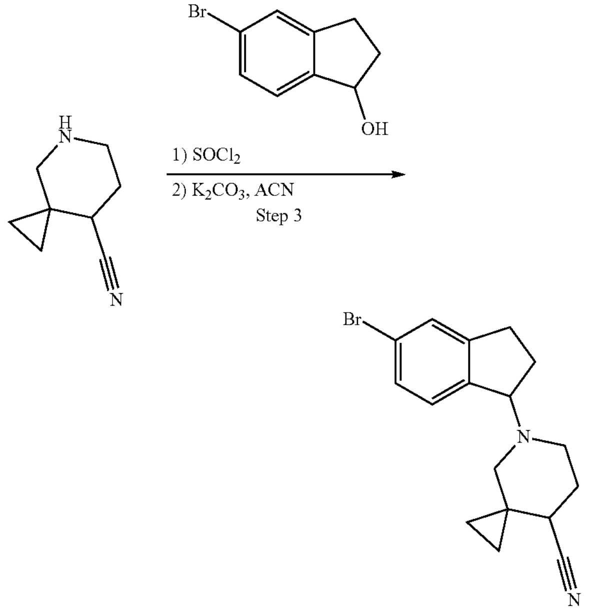

To a stirred solution of 5-bromo-2,3-dihydro-1H-inden-1-ol (348 mg, 1.630 mmol, 1.00 equiv) in DCM (3.0 mL) was added $SOCl_2$ (5.0 mL). The reaction was stirred for 4 h at room temperature. TLC showed the reaction was complete. The reaction mixture was concentrated under reduced pressure. The crude was used in the next step. $K_2CO_3$ (519 mg, 4.900 mmol, 3.00 equiv) and 5-azaspiro[2.5]octane-8-carbonitrile (444 mg, 3.267 mmol, 2.00 equiv) was added to the crude in MeCN (3.0 mL). The reaction was stirred for 12 h at room temperature. LCMS showed the reaction was complete. The solvent was removed under reduced pressure and the remaining oil was purified by flash column chromatography on C18 silica (eluted with eluted with water (5 mM $NH_4HCO_3$)/ACN, 25/75) to give 5-(5-bromo-2,3-dihydro-1H-inden-1-yl)-5-azaspiro[2.5]octane-8-carbonitrile (400 mg, 73%) as a solid. LCMS (ESI, m/z): 331 $[M+H]^+$.

Synthesis of methyl 5-(5-bromo-2,3-dihydro-1H-inden-1-yl)-5-azaspiro[2.5]octane-8-carboxylate

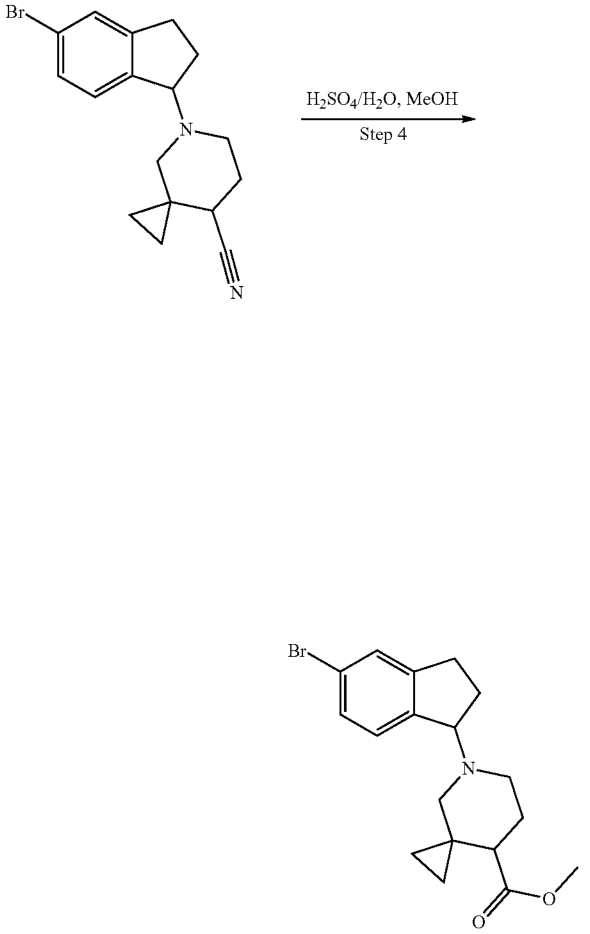

To a solution of the compound 5-(5-bromo-2,3-dihydro-1H-inden-1-yl)-5-aza-spiro[2.5]octane-8-carbonitrile (360 mg, 1.087 mmol, 1.00 equiv) in methanol (5.0 mL) was added $H_2O$ (5.0 mL) and $H_2SO_4$ (5.0 mL). The reaction was stirred for 12 h at 90° C., LCMS showed the reaction was complete. The solvent was removed by evaporation and the remaining oil was purified by flash column chromatography on C18 silica (eluted with eluted with water (5 mM $NH_4HCO_3$)/ACN, 30/70) to give methyl 5-(5-bromo-2,3-dihydro-1H-inden-1-yl)-5-azaspiro[2.5]octane-8-carboxylate (200 mg, 50%) as an oil. LCMS (ESI, m/z): 364 $[M+H]^+$.

Synthesis of methyl 5-(5-((2-fluorophenyl)ethynyl)-2,3-dihydro-1H-inden-1-yl)-5-azaspiro-[2.5]octane-8-carboxylate

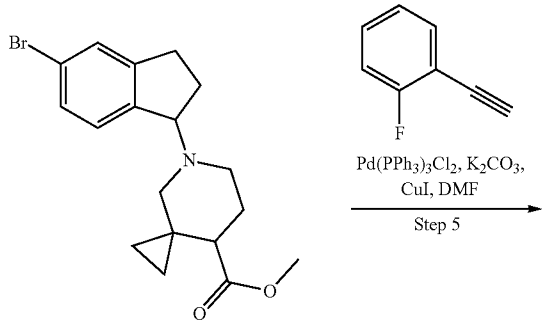

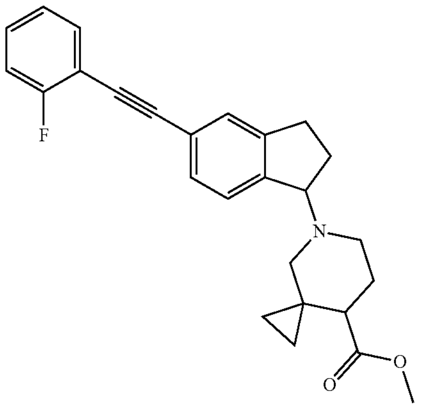

A solution of methyl 5-(5-bromo-2,3-dihydro-1H-inden-1-yl)-5-azaspiro[2.5]octane-8-carboxylate (160 mg, 0.440 mmol, 1.00 equiv), 1-ethynyl-2-fluoro-benzene (158 mg, 1.320 mmol, 3.00 equiv), $Pd(PPh_3)_2Cl_2$ (30 mg, 0.040 mmol, 0.10 equiv), $K_2CO_3$ (181 mg, 1.320 mmol, 3.00 equiv) and CuI (4 mg, 0.020 mmol, 0.05 equiv) in DMF (10.0 mL) was stirred for 12 h at 80° C. under nitrogen atmosphere. LCMS showed the reaction was complete. The mixture was filtered through a diatomite pad and the filtrate was concentrated under vacuum. The residue was purified by flash column chromatography on C18 silica (eluted with eluted with water (5 mM $NH_4HCO_3$)/ACN, 40/60) to afford methyl 5-(5-((2-fluorophenyl)ethynyl)-2,3-dihydro-1H-inden-1-yl)-5-azaspiro[2.5]octane-8-carboxylate (146 mg, 82%) as an oil. LCMS (ESI, m/z): 404 $[M+H]^+$.

Synthesis of 5-(5-((2-fluorophenyl)ethynyl)-2,3-dihydro-1H-inden-1-yl)-5-azaspiro[2.5]octane-8-carboxylic acid

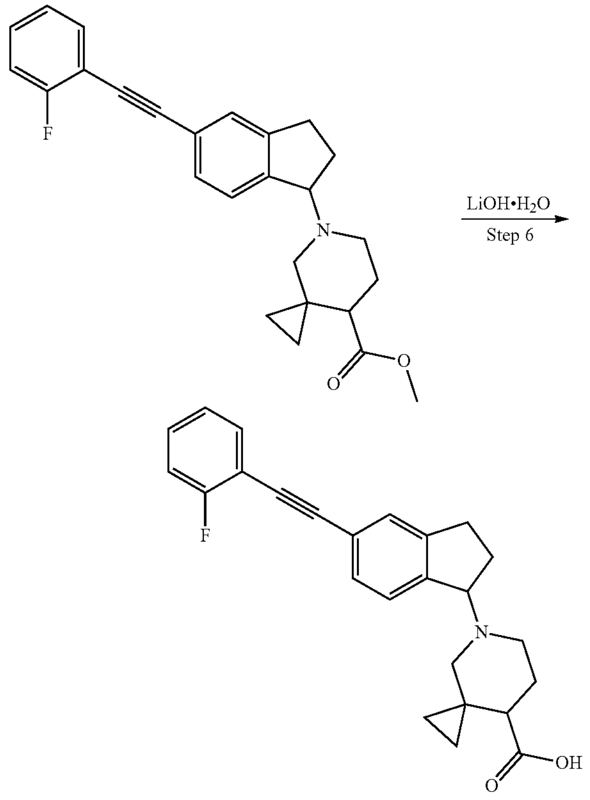

To a solution of the compound methyl 5-(5-((2-fluorophenyl)ethynyl)-2,3-dihydro-1H-inden-1-yl)-5-azaspiro[2.5]octane-8-carboxylate (146 mg, 0.360 mmol, 1.00 equiv) in THF (4.0 mL) and water (0.8 mL) was added $LiOH \cdot H_2O$ (91 mg, 2.170 mmol, 3.00 equiv). The reaction was stirred for 4 days at 80° C. LCMS showed the reaction was complete. THF was removed by evaporation and the remaining oil was treated with water. The pH value of the solution was adjusted to 4~5 with HCl (0.5 mol/L). The mixture was extracted with EA (2*30 mL). The organic layers were dried over anhydrous $Na_2SO_4$ and concentrated under reduced pressure. The residue was purified by prep-HPLC (Column: XBridge Shield RP18 OBD Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 20% B to 44% B in 7 min; 254/210 nm) to give 5-(5-((2-fluorophenyl)ethynyl)-2,3-dihydro-1H-inden-1-yl)-5-azaspiro[2.5]octane-8-carboxylic acid (11, 26.8 mg, 0.068 mmol, 18%) as a solid.

$^1H$ NMR (400 MHz, DMSO-$d_6$) δ 12.01 (s, 1H), 7.65-7.57 (m, 1H), 7.53-7.23 (m, 6H), 4.31-4.27 (m, 1H), 2.93-2.60 (m, 3H), 2.63-2.53 (m, 1H), 2.44-2.31 (m, 1H), 2.21-2.10 (m, 1H), 2.07-1.70 (m, 5H), 0.60-0.20 (m, 4H).

$^{19}F$ NMR (376 MHz, DMSO-$d_6$) δ −110.59.

LCMS (ESI, m/z): 390 $[M+H]^+$. Analytic Conditions: column: Titank C18 Column 3.0*50 mm, 3.0 μm; mobile Phase A: Water/5 mM $NH_4HCO_3$, mobile Phase B: acetonitrile; flow rate: 1.50 mL/min; gradient: 10% B to 95% B in 1.4 min, hold at 95% for 0.8 min, 95% B to 10% B in 0.03 min; 254 nm; RT: 1.192 min.

Example S12. 5-(5-((3-fluorophenyl)ethynyl)-2,3-dihydro-1H-inden-1-yl)-5-azaspiro[2.5]octane-8-carboxylic acid (12)

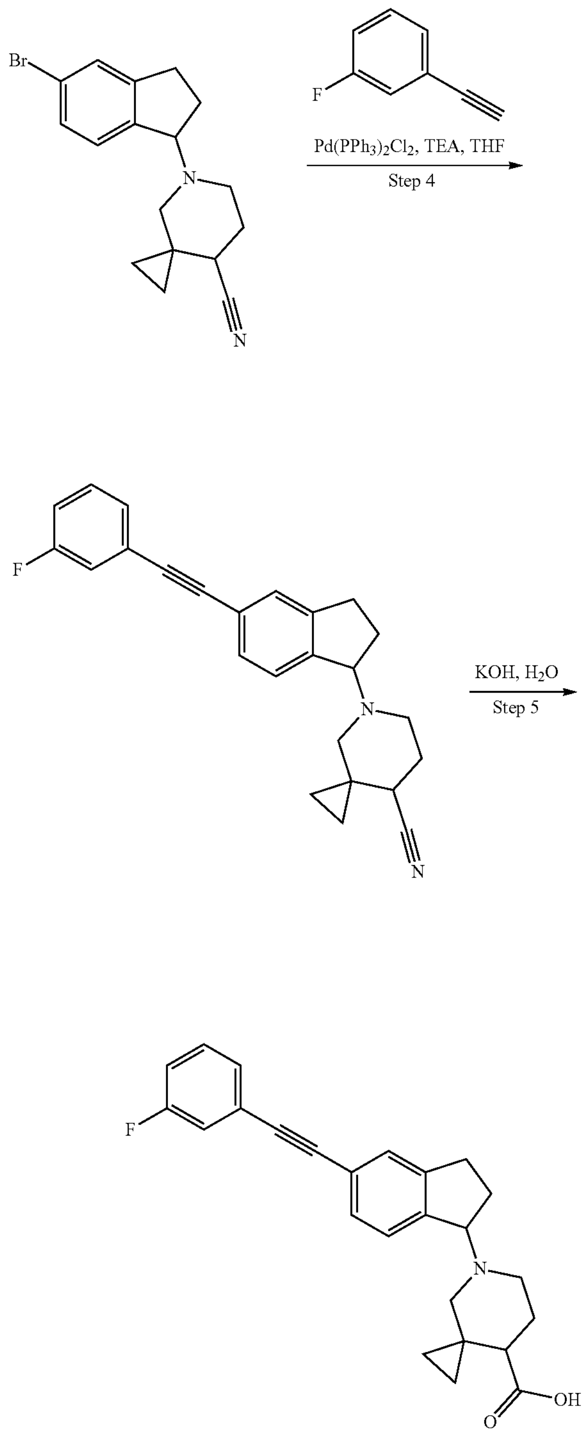

Synthesis of 5-(5-((3-fluorophenyl)ethynyl)-2,3-dihydro-1H-inden-1-yl)-5-azaspiro[2.5]octane-8-carbonitrile

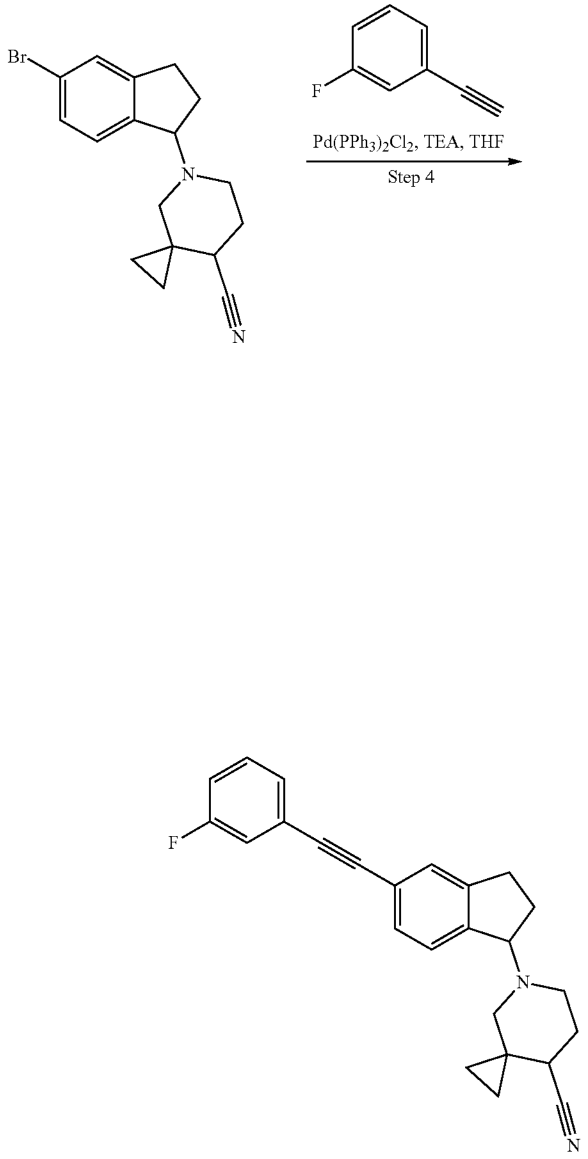

To a solution of the 5-(5-bromo-2,3-dihydro-1H-inden-1-yl)-5-azaspiro[2.5]octane-8-carbonitrile (110 mg, 0.330 mmol, 1.00 equiv.) in THF (5 mL) were added 1-ethynyl-3-fluoro-benzene (100 mg, 0.830 mmol, 2.5 equiv.), $Pd(PPh_3)_2Cl_2$ (23 mg, 0.030 mmol, 0.10 equiv.) and TEA (0.2 mL, 0.990 mmol, 3.00 equiv.). The resulting mixture was stirred at 60° C. for 12 h. LCMS showed the reaction was complete. The solid was filtered out and the filtrate was concentrated under reduced pressure. The residue was purified by flash column chromatography (eluted with PE/EtOAc, 7/1) to afford 5-(5-((3-fluorophenyl)ethynyl)-2,3-dihydro-1H-inden-1-yl)-5-azaspiro-[2.5]octane-8-carbonitrile (30 mg, 26%) as a solid. LCMS (ESI, m/z): 371 $[M+H]^+$.

Synthesis of 5-(5-((3-fluorophenyl)ethynyl)-2,3-dihydro-1H-inden-1-yl)-5-azaspiro[2.5]octane-8-carboxylic acid

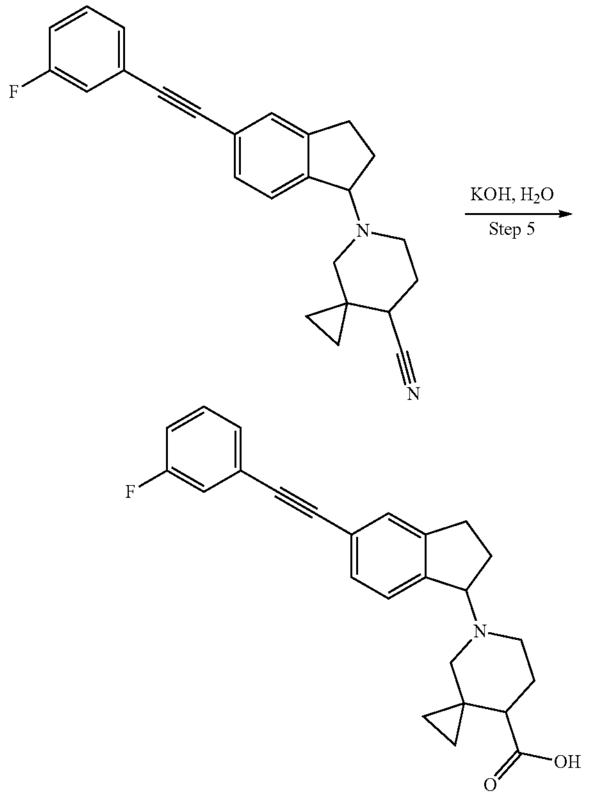

To a solution of 5-(5-((3-fluorophenyl)ethynyl)-2,3-dihydro-1H-inden-1-yl)-5-azaspiro-[2.5]octane-8-carbonitrile (30 mg, 0.080 mmol, 1.00 equiv.) in methanol (1 mL) and water (1 mL) was added KOH (45 mg, 0.810 mmol, 10.0 equiv.). The reaction was stirred at 90° C. for 80 h. LCMS showed the reaction was complete. The reaction mixture was acidified to pH 4-5 by adding 1N HCl, and then was concentrated under reduced pressure. The residue was purified by Prep-HPLC (column: Xselect CSH OBD Column 30*150 mm, 5 μm; mobile Phase A: water (10 mM $NH_4HCO_3$+0.1% $NH_3 \cdot H_2O$), mobile Phase B: ACN; flow rate: 60 mL/min; gradient: 63% B to 93% B in 7 min; 254/210 nm; RT: 6.40 min) to give 5-(5-((3-fluorophenyl)ethynyl)-2,3-dihydro-1H-inden-1-yl)-5-azaspiro[2.5]octane-8-carboxylic acid (12, 7.6 mg, 23%) as a solid.

$^1H$ NMR (400 MHz, DMSO-$d_6$) δ 7.50-7.45 (m, 1H), 7.41-7.38 (m, 4H), 7.31-7.25 (m, 2H), 4.31-4.26 (m, 1H), 2.90-2.83 (m, 1H), 2.79-2.66 (m, 2H), 2.61-2.54 (m, 1H), 2.41-2.32 (m, 1H), 2.20-2.13 (m, 1H), 2.06-1.95 (m, 2H), 1.91-1.75 (m, 3H), 0.53-0.48 (m, 1H), 0.43-0.38 (m, 1H), 0.34-0.22 (m, 2H).

$^{19}F$ NMR (376 MHz, DMSO-$d_6$) δ −114.9.

LCMS (ESI, m/z): 390 $[M+H]^+$. Analytic Conditions: column: Shim-pack XR-ODS Column 3.0*50 mm, 2.2 μm; mobile Phase A: water/0.05% TFA, mobile Phase B: acetonitrile/0.05% TFA; flow rate: 1.20 mL/min; gradient: 5% B to 100% B in 2.0 min, hold at 100% for 0.7 min, 100% B to 5% B in 0.5 min; 254 nm; RT: 1.608 min.

Example S13. (3S)-1-(5-((3-fluorophenyl)ethynyl)-2,3-dihydro-1H-inden-1-yl)pyrrolidine-3-carboxylic acid (13a and 13b)

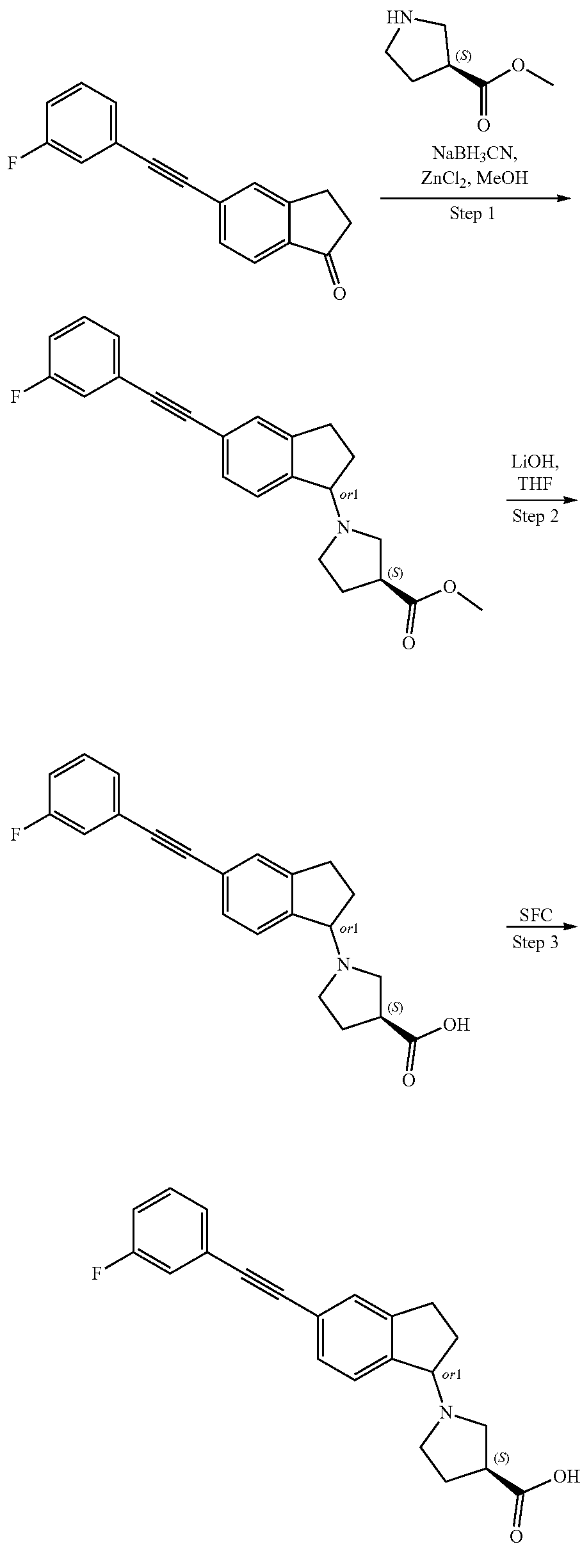

Synthesis of methyl (3S)-1-(5-((3-fluorophenyl) ethynyl)-2,3-dihydro-H-inden-yl)pyrrolidine-3-carboxylate

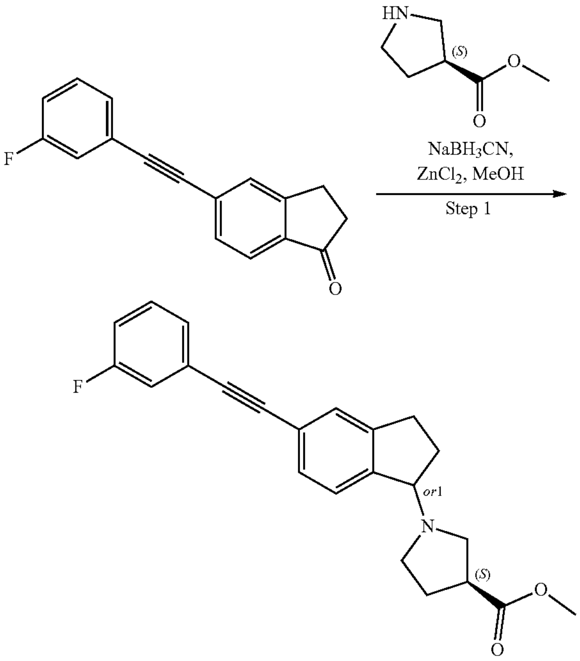

A solution of $NaBH_3CN$ (753 mg, 11.99 mmol, 3.00 equiv.) and $ZnCl_{12}$ (2.0 M in THF, 4.0 mL, 7.99 mmol, 2.00 equiv.) in methanol (8 mL) was stirred at room temperature for 15 min. Then 5-((3-fluorophenyl)ethynyl)-2,3-dihydro-1H-inden-1-one (1.0 g, 4.00 mmol, 1.00 equiv.) and methyl (S)-pyrrolidine-3-carboxylate (1.5 g, 11.99 mmol, 3.00 equiv.) were added. The resulting mixture was stirred at 60° C. for 12 h. LCMS showed the reaction was complete. The mixture was filtered through Celite and the filtrate was concentrated under vacuum. The residue was purified by Flash column chromatography on silica gel (eluted with PE/EtOAc, 1/1) to give methyl (3S)-1-(5-((3-fluorophenyl) ethynyl)-2,3-dihydro-1H-inden-1-yl)pyrrolidine-3-carboxylate (400 mg, 28%) as a solid. LCMS (ESI, m/z): 364 $[M+H]^+$.

Synthesis of (3S)-1-(5-((3-fluorophenyl)ethynyl)-2,3-dihydro-1H-inden-1-yl)pyrrolidine-3-carboxylic acid

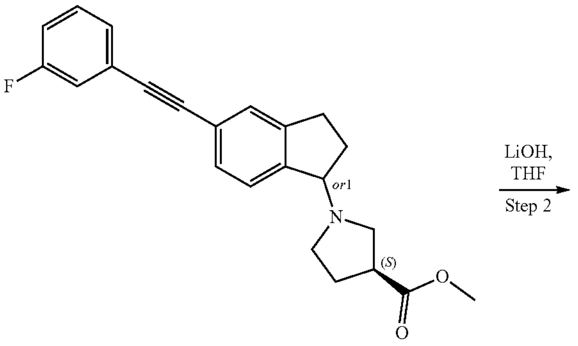

-continued

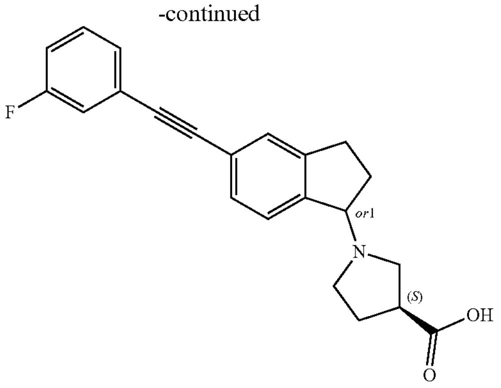

To a solution of compound methyl (3S)-1-(5-((3-fluorophenyl)ethynyl)-2,3-dihydro-1H-inden-1-yl)pyrrolidine-3-carboxylate (200 mg, 0.550 mmol, 1.00 equiv.) in THF (3 mL) and water (0.5 mL) was added $LiOH{\cdot}H_2O$ (46 mg, 1.100 mmol, 2.00 equiv). The resulting mixture was stirred at room temperature for 24 h. LCMS showed the reaction was complete. The reaction mixture was acidified to pH 4-5 by adding 1N HCl, and then was concentrated under reduced pressure. The resulted in (3S)-1-(5-((3-fluorophenyl)ethynyl)-2,3-dihydro-1H-inden-1-yl)-pyrrolidine-3-carboxylic acid (180 mg, 99%) as a solid. LCMS (ESI, m/z): 350 $[M+H]^+$.

Chiral Separation of (3S)-1-(5-((3-fluorophenyl) ethynyl)-2,3-dihydro-1H-inden-1-yl)pyrrolidine-3-carboxylic acid

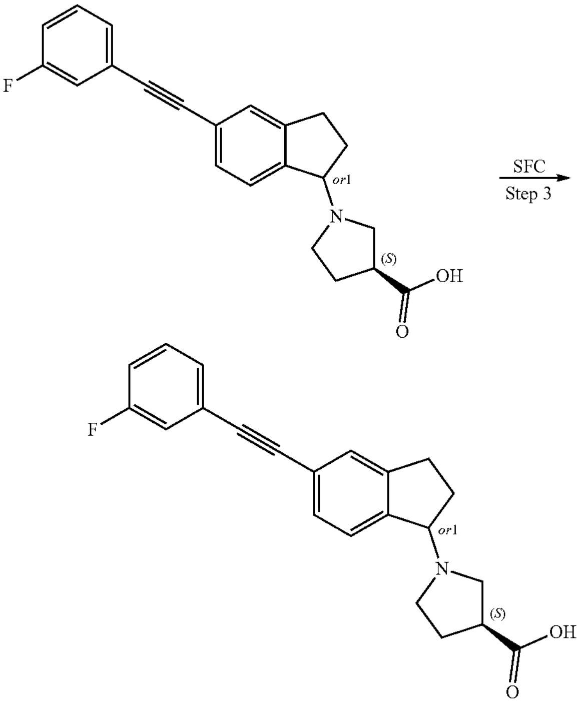

Racemic (3S)-1-(5-((3-fluorophenyl)ethynyl)-2,3-dihydro-1H-inden-1-yl)pyrrolidine-3-carboxylic acid (100 mg) was resolved by Prep-SFC (column: CHIRALPAK IG, 20*250 mm, m; mobile phase A: $CO_2$, mobile phase B:

EtOH/ACN (1/1, 2 mM $NH_3$-MeOH); flow rate: 45 mL/min; gradient: 50% B; 220 nm; RT: 5.98 min) to give chiral separation 1 of (3S)-1-(5-((3-fluorophenyl)ethynyl)-2,3-dihydro-1H-inden-1-yl)pyrrolidine-3-carboxylic acid (13a, 32.5 mg, 33%) as a solid.

$^1$H NMR (300 MHz, methanol-$d_4$) δ 7.65-7.50 (m, 3H), 7.42-7.33 (m, 2H), 7.29-7.24 (m, 1H), 7.17-7.12 (m, 1H), 4.97-4.94 (m, 1H), 3.69-3.63 (m, 1H), 3.53-3.42 (m, 3H), 3.26-3.18 (m, 2H), 3.07-2.99 (m, 1H), 2.61-2.34 (m, 3H), 2.27-2.21 (m, 1H).

$^{19}$F NMR (282 MHz, methanol-$d_4$) δ −114.8.

LCMS (ESI, m/z): 350 $[M+H]^+$. Analytic Conditions: column: Shim-pack XR-ODS Column 3.0*50 mm, 2.2 μm; mobile phase A: water/0.05% TFA, mobile phase B: acetonitrile/0.05% TFA; flow rate: 1.20 mL/min; gradient: 5% B to 100% B in 2.0 min, hold at 100% for 0.7 min, 100% B to 5% B in 0.5 min; 254/220 nm; RT: 1.597 min.

Chiral Separation of methyl (3S)-1-(5-((3-fluorophenyl)ethynyl)-2,3-dihydro-1H-inden-1-yl)pyrrolidine-3-carboxylate

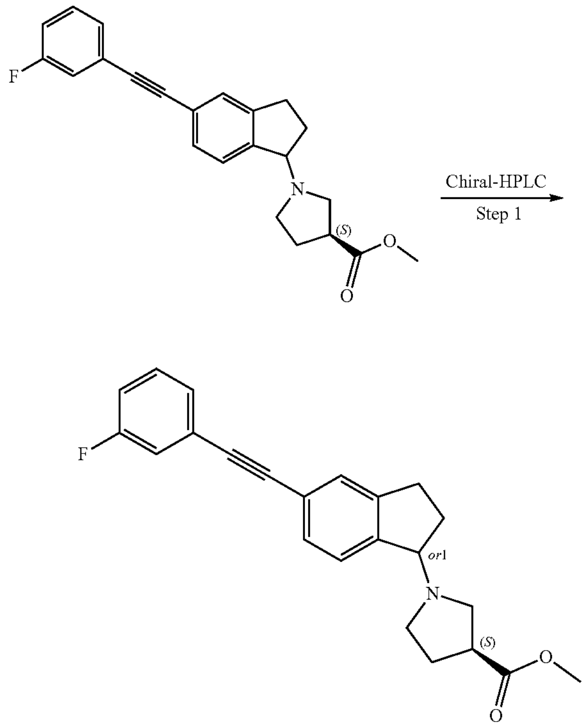

Racemic methyl (3S)-1-(5-((3-fluorophenyl)ethynyl)-2,3-dihydro-1H-inden-1-yl)-pyrrolidine-3-carboxylate (150 mg) was separated by preparative chiral HPLC (Column: CHIRALPAK IA, 2*25 cm, 5 μm; Mobile Phase A: Hex (0.10% TFA)-HPLC, Mobile Phase B: EtOH-HPLC; Flow rate: 20 mL/min; Gradient: 20% B to 20% B in 23 min; 220/254 nm; RT1: 10.778 min; RT2: 15.769 min; Injection Volume: 1 mL; Number Of Runs: 7) to afford the chiral separation 2 isomer of methyl (3 S)-1-(5-((3-fluorophenyl)ethynyl)-2,3-dihydro-1H-inden-1-yl)-pyrrolidine-3-carboxylate (60 mg) as an oil. LCMS (ESI, m/z): 364 $[M+H]^+$.

Synthesis of (3S)-1-(5-((3-fluorophenyl)ethynyl)-2,3-dihydro-1H-inden-1-yl)pyrrolidine-3-carboxylic acid

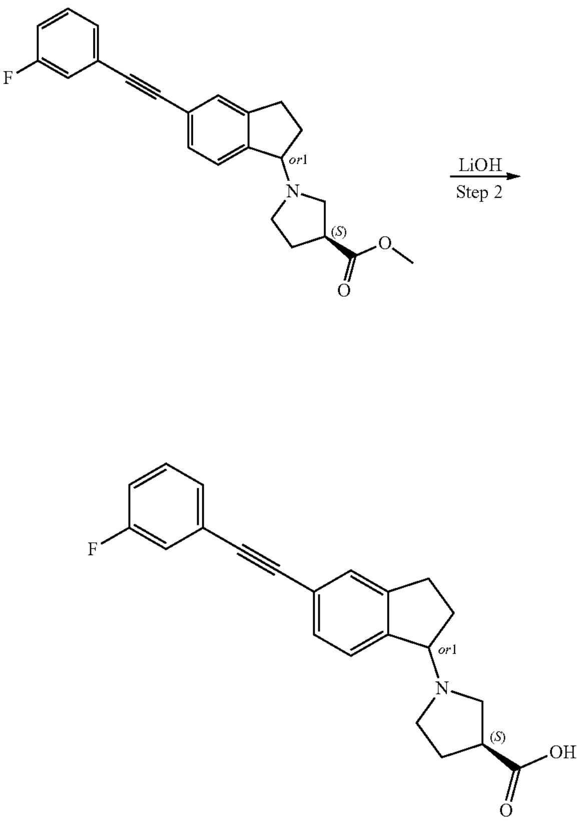

To a solution of methyl rel-(3S)-1-[5-[2-(3-fluorophenyl)ethynyl]indan-1-yl]pyrrolidine-3-carboxylate (60 mg, 0.160 mmol, 1.00 equiv.) in THF (3 mL) and water (0.5 mL) was added LiOH·$H_2O$ (24 mg, 0.600 mmol, 3.00 equiv.). The resulting mixture was stirred at room temperature for 24 h. LCMS showed the reaction was complete. The reaction mixture was acidified to pH 4-5 by adding 1N HCl, and then was concentrated under reduced pressure. The residue was purified by flash column chromatography on C18 silica (MeCN in water (0.05% $NH_4HCO_3$), from 30% to 46% in 7 min; 70 mL/min, 254/210 nm) to give the corresponding enantiomer of (3S)-1-(5-((3-fluorophenyl)ethynyl)-2,3-dihydro-1H-inden-1-yl)pyrrolidine-3-carboxylic acid (13b, 46.9 mg, 78%) as a solid. LCMS (ESI, m/z): 350 $[M+H]^+$.

$^1$H NMR (300 MHz, methanol-$d_4$) δ 7.62-7.48 (m, 3H), 7.44-7.33 (m, 2H), 7.28-7.24 (m, 1H), 7.17-7.11 (m, 1H), 4.84-4.82 (m, 1H), 3.60-3.54 (m, 1H), 3.49-3.34 (m, 3H), 3.26-3.17 (m, 2H), 3.09-2.96 (m, 1H), 2.58-2.43 (m, 2H), 2.30-2.20 (m, 2H).

$^{19}$F NMR (282 MHz, methanol-$d_4$) δ 114.85

LCMS (ESI, m/z): 350 $[M+H]^+$. Analytic Conditions: column: Shim-pack XR-ODS Column 3.0*50 mm, 2.2 μm; mobile phase A: water/0.05% TFA, mobile phase B: acetonitrile/0.05% TFA; flow rate: 1.20 mL/min; gradient: 5% B to 100% B in 2.0 min, hold at 100% for 0.7 min, 100% B to 5% B in 0.5 min; 254/220 nm; RT: 1.602 min.

Example S14. (3R)-1-(5-((3-fluorophenyl)ethynyl)-2,3-dihydro-1H-inden-1-yl)pyrrolidine-3-carboxylic acid (14a and 14b)

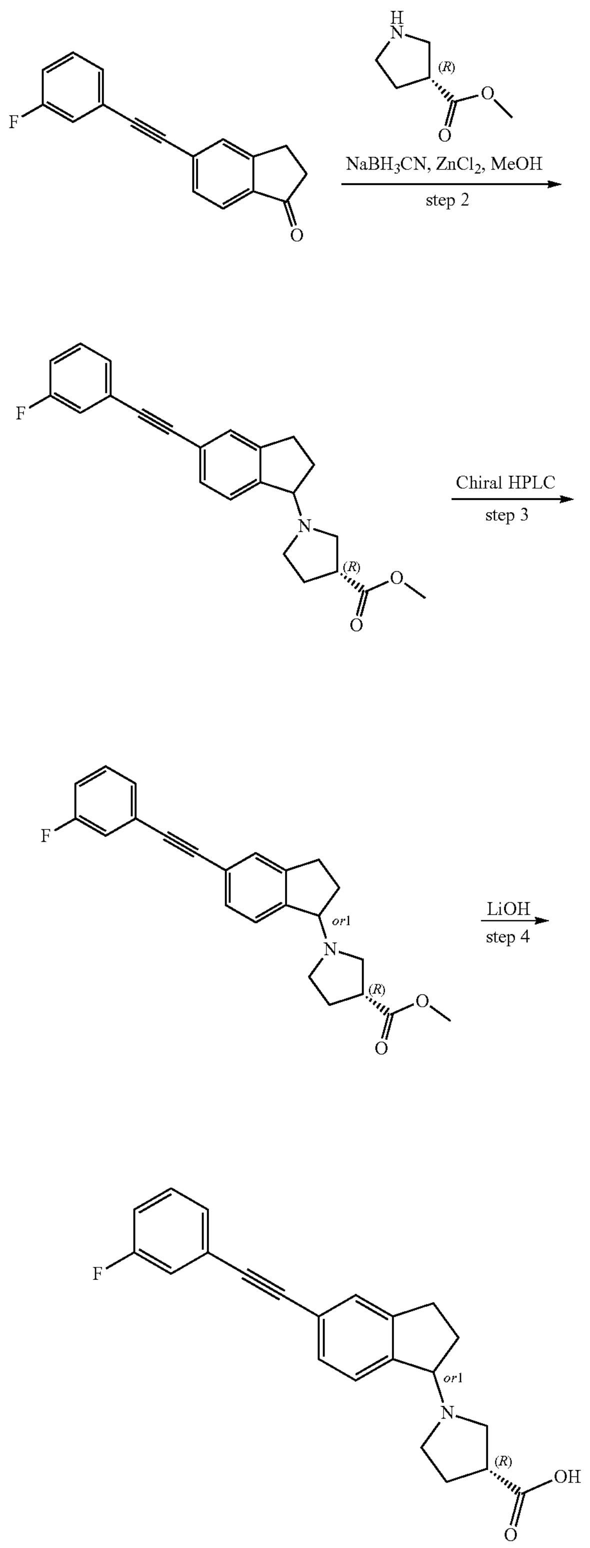

Synthesis of methyl (3R)-1-(5-((3-fluorophenyl)ethynyl)-2,3-dihydro-1H-inden-1-yl)pyrrolidine-3-carboxylate

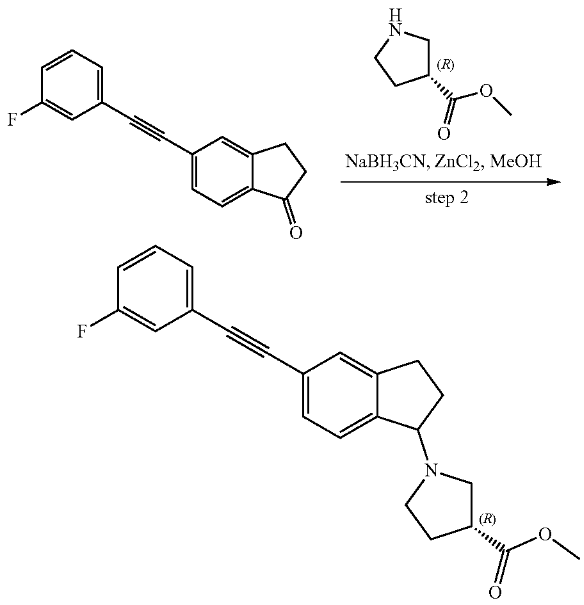

To a stirred solution of 5-((3-fluorophenyl)ethynyl)-2,3-dihydro-1H-inden-1-one (1.0 g, 3.995 mmol, 1.00 equiv.) and methyl rac-(3R)-pyrrolidine-3-carboxylate (1.5 g, 11.990 mmol, 3.00 equiv.) in methanol (12.0 mL) were added $NaBH_3CN$ (753 mg, 11.990 mmol, 3.00 equiv.) and $ZnCl_2$ (2M in THF, 4.0 mL, 7.990 mmol, 2.00 equiv.). The mixture solution was stirred at 60° C. for 16 h. Desired product could be detected by LCMS. The reaction mixture was quenched with water (50 mL) and was extracted with DCM (3*40 mL). The organic layers were combined, and washed with brine and dried over anhydrous $Na_2SO_4$, and concentrated under vacuum. The residue was purified by Flash column chromatography on C18 silica (Mobile Phase A: Water (10 mmol/L $NH_4HCO_3$), Mobile Phase B: ACN; Flow rate: 100 mL/min; Gradient: 75% B to 85% B in 4 min; 254/210 nm.) to afford (3R)-1-(5-((3-fluorophenyl)ethynyl)-2,3-dihydro-1H-inden-1-yl)-pyrrolidine-3-carboxylate (400 mg, 27%) as a solid. LCMS (ESI, m/z): 364 $[M+H]^+$.

Chiral Separation of (3R)-1-(5-((3-fluorophenyl)ethynyl)-2,3-dihydro-1H-inden-1-yl)-pyrrolidine-3-carboxylate

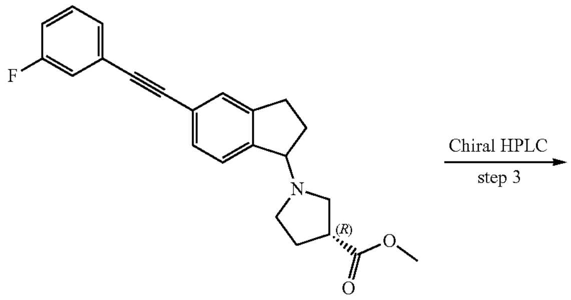

-continued

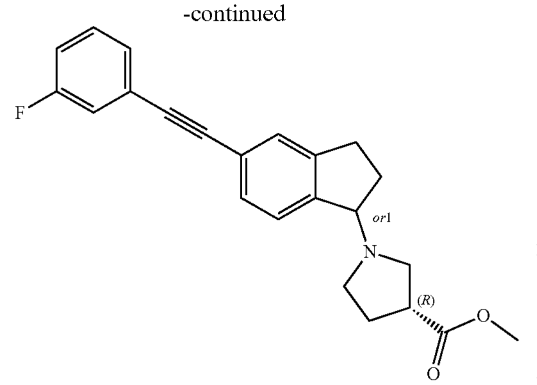

The racemate (400 mg) was resolved by Prep-Chiral HPLC (Column: CHIRALPAK IA, 2*25 cm, 5 m; Mobile Phase A: Hex (8 mmol/L $NH_3$·MeOH)-HPLC, Mobile Phase B: EtOH-HPLC; Flow rate: 20 mL/min; Gradient: 20% B to 20% B in 10 min; 220/254 nm; RT1: 5.741 min; RT2: 7.442 min; Injection Volume: 0.5 mL; Number Of Runs: 15) to afford 150 mg of isomer 1 and 150 mg of isomer 2. LCMS (ESI, m/z): 364 $[M+H]^+$.

Synthesis of (3R)-1-(5-((3-fluorophenyl)ethynyl)-2,3-dihydro-1H-inden-1-yl)pyrrolidine-3-carboxylic acid

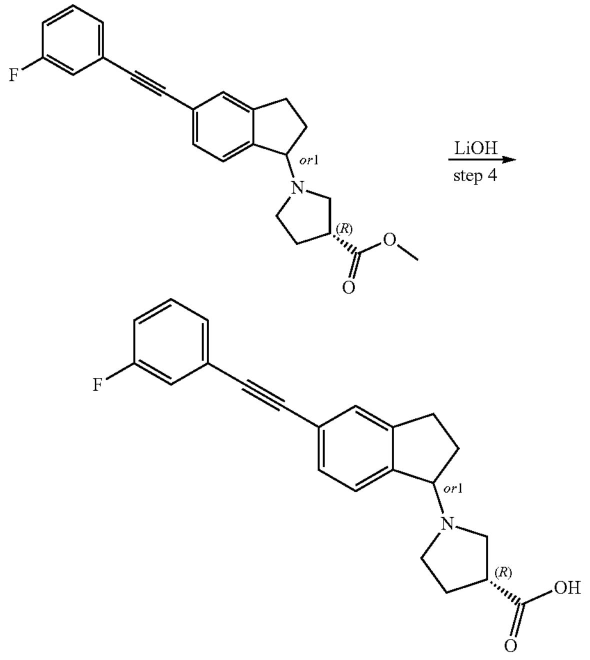

To a stirred solution of (3R)-1-(5-((3-fluorophenyl)ethynyl)-2,3-dihydro-1H-inden-1-yl)pyrrolidine-3-carboxylate (enantiomer 1, 50 mg, 0.140 mmol, 1.00 equiv.) in THF (2 mL) and water (2 mL) were added LiOH·$H_2O$ (17 mg, 0.410 mmol, 3.00 equiv.). The mixture solution was stirred at room temperature for 2 h under air atmosphere. Desired product could be detected by LCMS. The resulting mixture was adjusted to pH 5~6 with 2N HCl and concentrated under reduced pressure. The residue was purified by flash chromatography on C18 silica (Mobile Phase A: Water (0.1% HCl), Mobile Phase B: ACN; Flow rate: 60 mL/min; Gradient: 14% B to 44% B in 7 min; 254/210 nm) to afford the corresponding enantiomer of (3R)-1-(5-((3-fluoro-phenyl)ethynyl)-2,3-dihydro-1H-inden-1-yl)pyrrolidine-3-carboxylic acid (14a, 19.5 mg, 40%) as a semi-solid.

$^1$H NMR (300 MHz, Methanol-$d_4$) δ 7.69 (d, J=8.1 Hz, 1H), 7.59 (s, 1H), 7.54-7.51 (m, 1H), 7.46-7.40 (m, 1H), 7.39-7.34 (m, 1H), 7.29-7.25 (m, 1H), 7.19-7.12 (m, 1H), 5.01 (dd, J=7.8, 2.7 Hz, 1H), 3.70-3.36 (m, 4H), 3.30-3.23 (m, 2H), 3.09-2.99 (m, 1H), 2.67-2.33 (m, 4H).

$^{19}$F NMR (282 MHz, $CDCl_3$-d) δ −112.644.

LCMS (ESI, m/z): 350 $[M+H]^+$. Analytic Conditions: column: Shim-pack XR-ODS Column 3.0*50 mm, 2.2 μm; mobile Phase A: water/0.05% TFA, mobile Phase B: acetonitrile/0.05% TFA; flow rate: 1.20 mL/min; gradient: 5% B to 95% B in 1.99 min, hold at 95% for 0.7 min, 95% B to 5% B in 0.05 min; 254 nm; RT: 1.677 min.

Synthesis of (3R)-1-(5-((3-fluorophenyl)ethynyl)-2,3-dihydro-1H-inden-1-yl)pyrrolidine-3-carboxylic acid

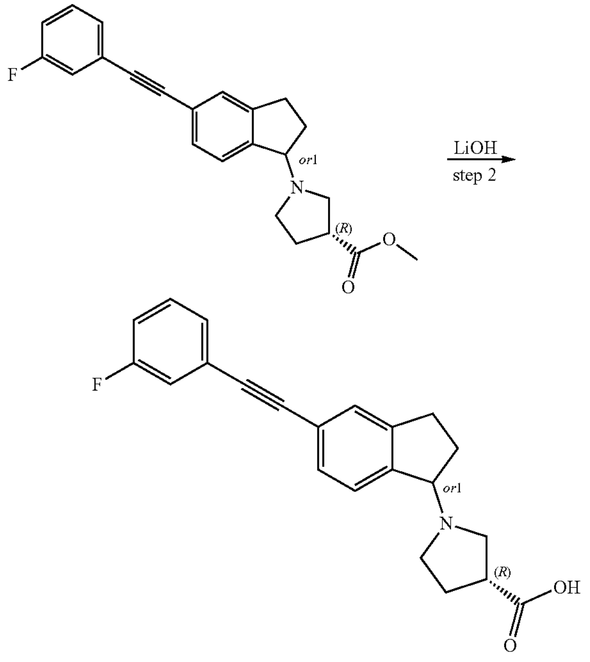

To a stirred solution of (3R)-1-(5-((3-fluorophenyl)ethynyl)-2,3-dihydro-1H-inden-1-yl)pyrrolidine-3-carboxylate (enantiomer 2, 50 mg, 0.140 mmol, 1.00 equiv.) in THF (2 mL) and water (2 mL) were added LiOH·$H_2O$ (17 mg, 0.410 mmol, 3.00 equiv.). The mixture solution was stirred at room temperature for 2 h under air atmosphere. Desired product could be detected by LCMS. The resulting mixture was adjusted to pH 5-6 with 2N HCl and concentrated under reduced pressure. The residue was purified by flash chromatography on C18 silica (Mobile Phase A: Water (0.1% HCl), Mobile Phase B: ACN; Flow rate: 60 mL/min; Gradient: 14% B to 44% B in 7 min; 254/210 nm) to afford the corresponding enantiomer of (3R)-1-(5-((3-fluoro-phenyl)ethynyl)-2,3-dihydro-1H-inden-1-yl)pyrrolidine-3-carboxylic acid (14b, 16.0 mg, 33%) as a semi-solid.

$^1$H NMR (300 MHz, Methanol-$d_4$) δ 7.68 (d, J=7.8 Hz, 1H), 7.59 (s, 1H), 7.54-7.51 (m, 1H), 7.46-7.30 (m, 2H), 7.30-7.25 (m, 1H), 7.19-7.12 (m, 1H), 5.02 (dd, J=7.8, 2.7 Hz, 1H), 3.72-3.37 (m, 5H), 3.28-3.23 (m, 1H), 3.09-2.99 (m, 1H), 2.67-2.57 (m, 1H), 2.54-2.43 (m, 2H), 2.34-2.25 (m, 1H).

$^{19}F$ NMR (282 MHz, $CDCl_3$-d) δ −112.636.

LCMS (ESI, m/z): 390 $[M+H]^+$. Analytic Conditions: column: Xbridge Shield RP18, 4.6*50 mm, 3.5 μm; mobile Phase A: 0.04% $NH_3 \cdot H_2O$, mobile Phase B: acetonitrile; flow rate: 1.20 mL/min; gradient: 10% B to 95% B in 1.99 min, hold at 95% for 0.79 min, 95% B to 10% B in 0.06 min; 254 nm; RT: 1.160 min.

Example S15. (1R,5R)-3-(5-((2,6-dichlorophenyl) ethynyl)-2,3-dihydro-1H-inden-1-yl)-3-azabicyclo [3.1.0]-hexane-1-carboxylic acid (15)

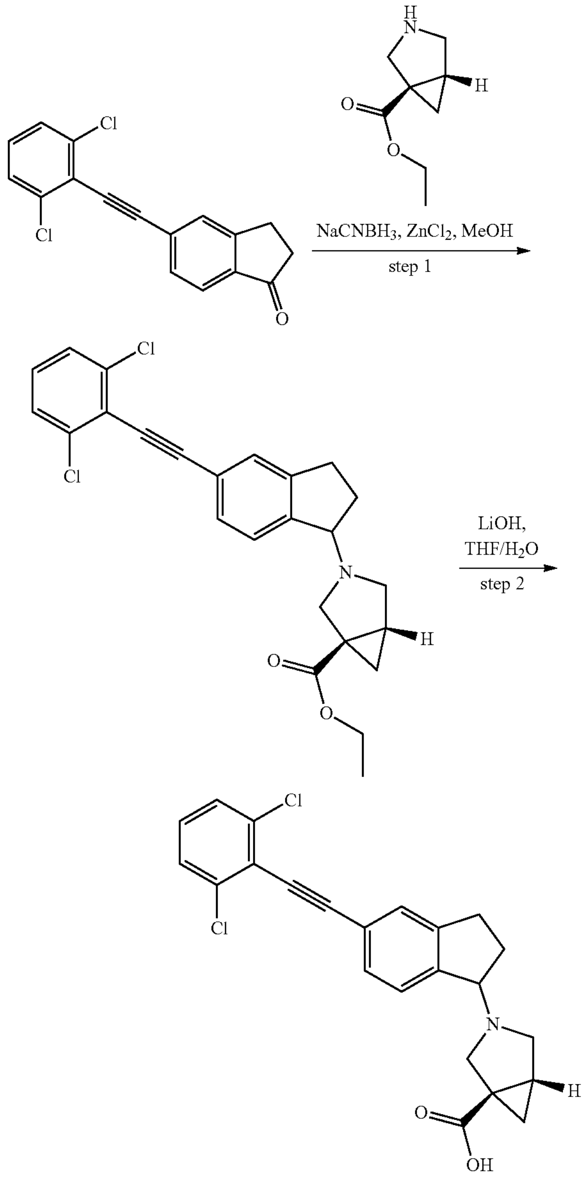 [SMILES: O=C1CCc2cc(C#Cc3c(Cl)cccc3Cl)ccc21 ; CCOC(=O)[C@@]12CNC[C@@H]1C2 ; CCOC(=O)[C@]12C[C@H]1CN(C1CCc3cc(C#Cc4c(Cl)cccc4Cl)ccc31)C2 ; O=C(O)[C@]12C[C@H]1CN(C1CCc3cc(C#Cc4c(Cl)cccc4Cl)ccc31)C2]

Synthesis of ethyl (1R,5R)-3-(5-((2,6-dichlorophenyl)ethynyl)-2,3-dihydro-1H-inden-1-yl)-3-aza-bicyclo[3.1.0]hexane-1-carboxylate

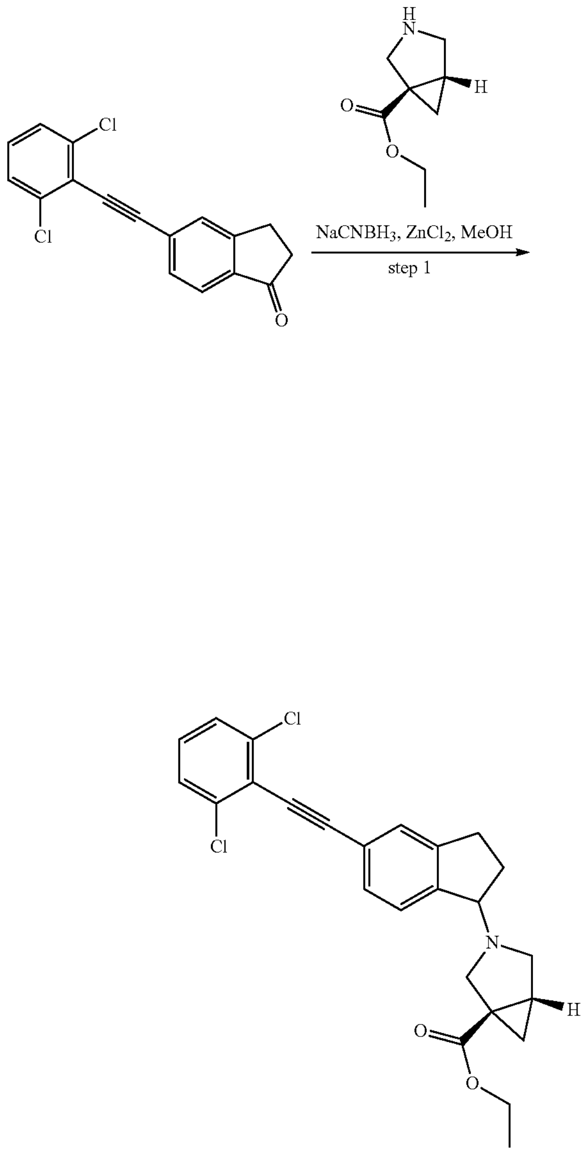

To a stirred solution of 5-((2,6-dichlorophenyl)ethynyl)-2,3-dihydro-1H-inden-1-one (100 mg, 0.332 mmol, 1.00 equiv.) in methanol (5.0 mL) were added ethyl (1R,5R)-3-azabicyclo[3.1.0]hexane-1-carboxylate (77 mg, 0.498 mmol, 1.50 equiv.) and $NaCNBH_3$ (84 mg, 1.328 mmol, 4.00 equiv.) and $ZnCl_2$ (2.0 M in THF, 0.33 mL, 0.664 mmol, 2.00 equiv.). The resulting mixture was stirred at 70° C. under nitrogen atmosphere for 48 h. LCMS showed that the reaction was complete. The reaction mixture was concentrated under reduced pressure. The residue was purified by Flash column chromatography (eluted with PE/EtOAc, 3/1) to afford ethyl (1R,5R)-3-(5-((2,6-dichlorophenyl)ethynyl)-2,3-dihydro-1H-inden-1-yl)-3-aza-bicyclo[3.1.0] hexane-1-carboxylate (124 mg, 85%) as a semi-solid. LCMS (ESI, m/z): 440 $[M+H]^+$.

Synthesis of (1R,5R)-3-(5-((2,6-dichlorophenyl) ethynyl)-2,3-dihydro-1H-inden-1-yl)-3-aza-bicyclo [3.1.0]hexane-1-carboxylic acid

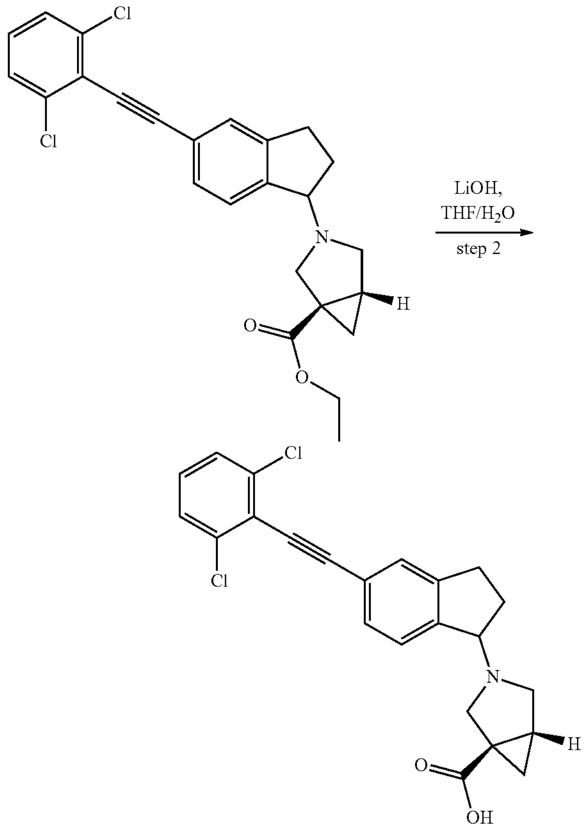

To a stirred solution of ethyl (1R,5R)-3-(5-((2,6-dichlorophenyl)ethynyl)-2,3-dihydro-1H-inden-1-yl)-3-azabicyclo[3.1.0]hexane-1-carboxylate (124 mg, 0.282 mmol, 1.00 equiv.) in water (2.0 mL)/THF (2.0 mL) were added LiOH·$H_2O$ (47 mg, 1.126 mmol, 4.00 equiv.). The resulting mixture was stirred at room temperature for 72 h. LCMS showed that the reaction was complete. The reaction mixture was acidified to pH 4-5 by adding 1N HCl, and then was concentrated under reduced pressure. The residue was purified by preparative HPLC (column: Sunfire prep C18 column, 30*150 mm, 5 μm; mobile Phase A: water (0.05% HCl), mobile Phase B: ACN; flow rate: 60 mL/min; gradient: 25% B to 40% B in 7 min; 254/210 nm; RT: 6.12 min) to afford (1R,5R)-3-(5-((2,6-dichlorophenyl)ethynyl)-2,3-dihydro-1H-inden-1-yl)-3-aza-bicyclo[3.1.0]hexane-1-carboxylic acid (15, 48.3 mg, 41%) as a solid.

$^1H$ NMR (400 MHz, Methanol-$d_4$) δ 7.76-7.71 (m, 1H), 7.64 (s, 1H), 7.59-7.57 (m, 1H), 7.51-7.49 (m, 2H), 7.39-7.34 (m, 1H), 5.07-5.01 (m, 1H), 4.04-3.74 (m, 4H), 3.30-3.28 (m, 1H), 3.08-3.02 (m, 1H), 2.64-2.58 (m, 1H), 2.49-2.40 (m, 2H), 1.76-1.66 (m, 1H), 1.52-1.39 (m, 1H).

LCMS (ESI, m/z): 412 $[M+H]^+$. Analytic Conditions: column: Shim-pack XR-ODS Column 3*50 mm, 2.2 μm; mobile Phase A: water/0.05% TFA, mobile Phase B: acetonitrile/0.05% TFA; flow rate: 1.20 mL/min; gradient: 5% B to 95% B in 2.0 min, hold at 95% for 0.7 min, 95% B to 5% B in 0.05 min; 254 nm; RT: 1.651 min.

Example S16. (1R,5S,6r)-3-(5-((3-fluorophenyl) ethynyl)-2,3-dihydro-1H-inden-1-yl)-3-azabicyclo [3.1.0]-hexane-6-carboxylic acid (16)

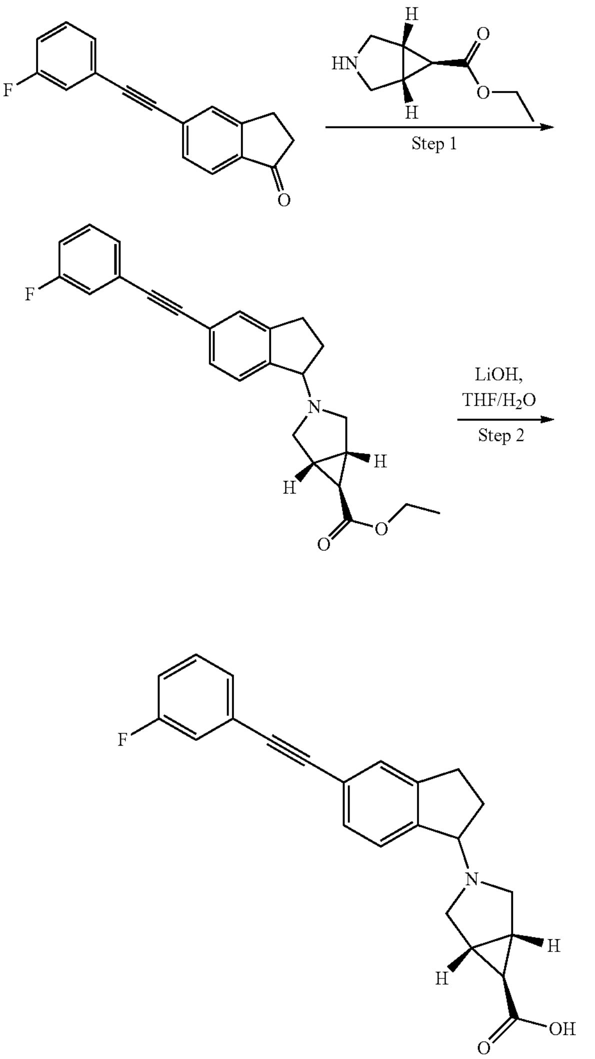

Synthesis of ethyl (1R,5S,6r)-3-(5-((3-fluorophenyl) ethynyl)-2,3-dihydro-1H-inden-1-yl)-3-azabicyclo [3.1.0]hexane-6-carboxylate

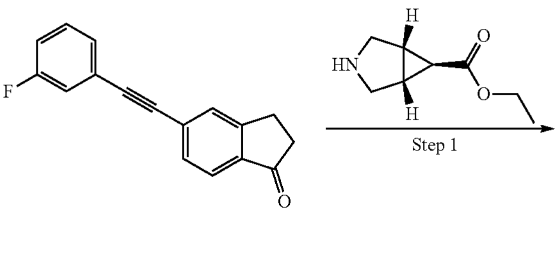

-continued

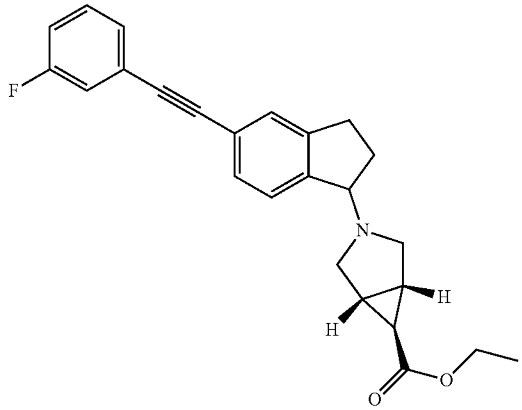

To a solution of $NaBH_3CN$ (110 mg, 1.760 mmol, 4.00 equiv.) in methanol (2.0 mL) was added $ZnCl_2$ (2M in 2-Me-THF, 0.44 mL, 0.880 mmol, 2.00 equiv.). The resulting solution was stirred at room temperature for 5-10 min. Then 5-((3-fluorophenyl)ethynyl)-2,3-dihydro-1H-inden-1-one (110 mg, 0.440 mmol, 1.00 equiv.) and ethyl (1R,5S,6r)-3-azabicyclo[3.1.0]hexane-6-carboxylate (102 mg, 0.660 mmol, 1.50 equiv.) were added. The resulting mixture was stirred at 60° C. for 16 h under nitrogen atmosphere. LCMS showed the reaction was complete. The reaction mixture was concentrated under reduced pressure. The residue was purified by flash chromatography on silica gel with ethyl acetate/petroleum ether (1/7) to give ethyl (1R,5S,6r)-3-(5-((3-fluorophenyl)ethynyl)-2,3-dihydro-1H-inden-1-yl)-3-azabicyclo[3.1.0]hexane-6-carboxylate (83 mg, 48%) as a semi-solid. LCMS (ESI, m/z): 390 $[M+H]^+$.

Synthesis of (1R,5S,6r)-3-(5-((3-fluorophenyl)ethynyl)-2,3-dihydro-1H-inden-1-yl)-3-azabicyclo[3.1.0]hexane-6-carboxylic acid

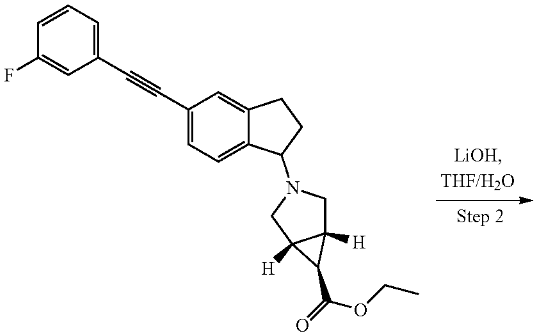

-continued

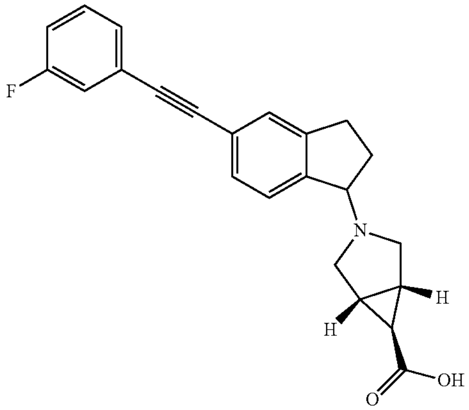

A solution of ethyl (1R,5S,6r)-3-(5-((3-fluorophenyl)ethynyl)-2,3-dihydro-1H-inden-1-yl)-3-azabicyclo[3.1.0]hexane-6-carboxylate (83 mg, 0.212 mmol, 1.00 equiv.) and $LiOH \cdot H_2O$ (51 mg, 1.272 mmol, 6.00 equiv.) in THF (1.0 mL) and water (1.0 mL) was stirred at 80° C. for 14 h. LCMS showed the reaction was complete. The solution was adjusted to pH 4-5 with 1N HCl, and then was concentrated under vacuum. The residue was purified by Prep-HPLC (Column: XBridge Prep C18 OBD Column, 19×150 mm 5 μm; Mobile Phase A: water (10 mmol/L $NH_4HCO_3$), Mobile Phase B: ACN; Flow rate: 25 mL/min; Gradient: 25% B to 45% B in 7 min; 210/254 nm; RT: 6.42 min) to afford (1R,5S,6r)-3-(5-((3-fluorophenyl)ethynyl)-2,3-dihydro-1H-inden-1-yl)-3-azabicyclo[3.1.0]hexane-6-carboxylic acid (16, 4.0 mg, 5.2%) as a solid.

$^1H$ NMR (400 MHz, Methanol-$d_4$) δ 7.58-7.54 (m, 2H), 7.49 (d, J=8.0 Hz, 1H), 7.46-7.40 (m, 1H), 7.37 (d, J=8.0 Hz, 1H), 7.28 (d, J=9.6 Hz, 1H), 7.18-7.14 (m, 1H), 4.75-4.60 (m, 1H), 3.51-3.39 (m, 4H), 3.21-3.15 (m, 1H), 3.05-2.95 (m, 1H), 2.47-2.38 (m, 2H), 2.16-2.10 (m, 2H), 1.84-1.76 (m, 1H).

$^{19}F$ NMR (376 MHz, Methanol-$d_4$) δ −114.89.

LCMS (ESI, m/z): 362 $[M+H]^+$. Analytic Conditions: EVO C18, 3.0*50 mm, 2.6 μm; Mobile Phase A: Water/5 mM $NH_4HCO_3$, Mobile Phase B: Acetonitrile; Flow rate: 1.20 mL/min; Gradient: 10% B to 95% B in 2.0 min, hold at 95% B for 0.6 min, 95% B to 10% B in 0.15 min; 254 nm; RT: 1.250 min.

Example S17. (1R,5S,6s)-3-(5-((3-fluorophenyl)ethynyl)-2,3-dihydro-1H-inden-1-yl)-3-azabicyclo[3.1.0]-hexane-6-carboxylic acid (17)

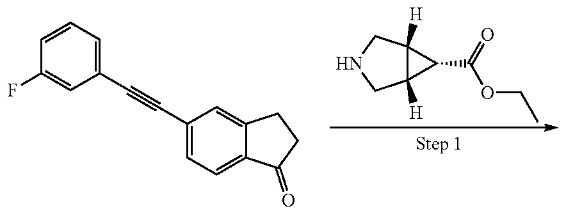

-continued

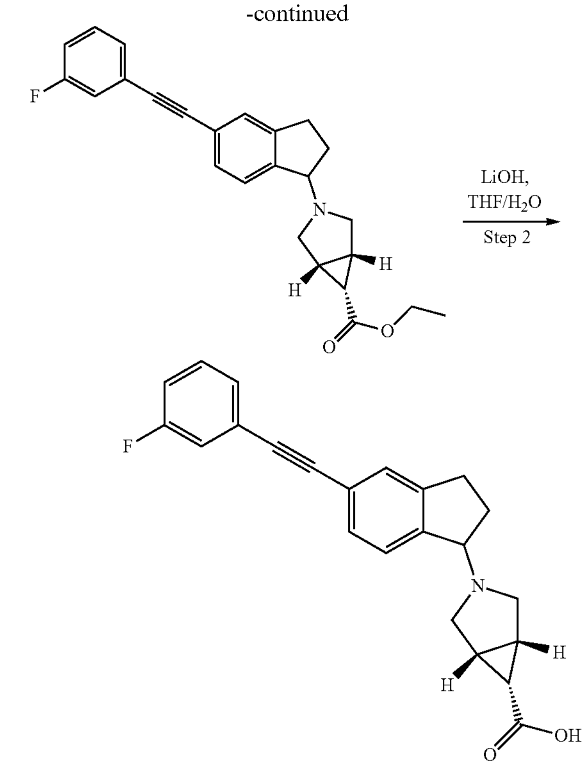

Synthesis of ethyl (1R,5S,6s)-3-(5-((3-fluorophenyl)ethynyl)-2,3-dihydro-1H-inden-1-yl)-3-azabicyclo[3.1.0]hexane-6-carboxylate

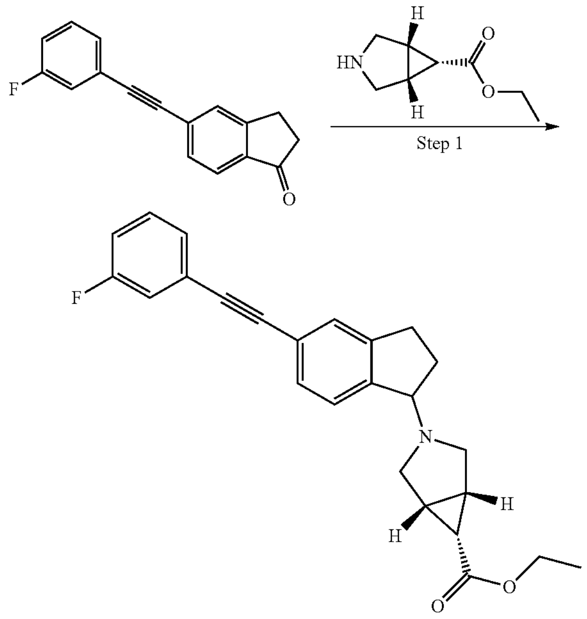

To a solution of $NaBH_3CN$ (110 mg, 1.760 mmol, 4.00 equiv.) in methanol (2.0 mL) was added $ZnCl_2$ (2M in 2-Me-THF, 0.44 mL, 0.880 mmol, 2.00 equiv.). The resulting solution was stirred at room temperature for 5-10 min. Then 5-((3-fluorophenyl)ethynyl)-2,3-dihydro-1H-inden-1-one (110 mg, 0.440 mmol, 1.00 equiv.) and ethyl (1R,5S,6s)-3-azabicyclo[3.1.0]hexane-6-carboxylate (102 mg, 0.660 mmol, 1.50 equiv.) were added. The resulting mixture was stirred at 60° C. for 16 h under nitrogen atmosphere. LCMS showed the reaction was complete. The reaction mixture was concentrated under reduced pressure. The residue was purified by flash chromatography on silica gel with ethyl acetate/petroleum ether (1/7) to give ethyl (1R,5S,6s)-3-(5-((3-fluorophenyl)ethynyl)-2,3-dihydro-1H-inden-1-yl)-3-azabicyclo[3.1.0]hexane-6-carboxylate (17, 130 mg, 75%) as a semi-solid. LCMS (ESI, m/z): 390 $[M+H]^+$.

Example S18. 1-(5-((2,6-dichlorophenyl)ethynyl)-2,3-dihydro-1H-inden-1-yl)azetidine-3-carboxylic acid (18)

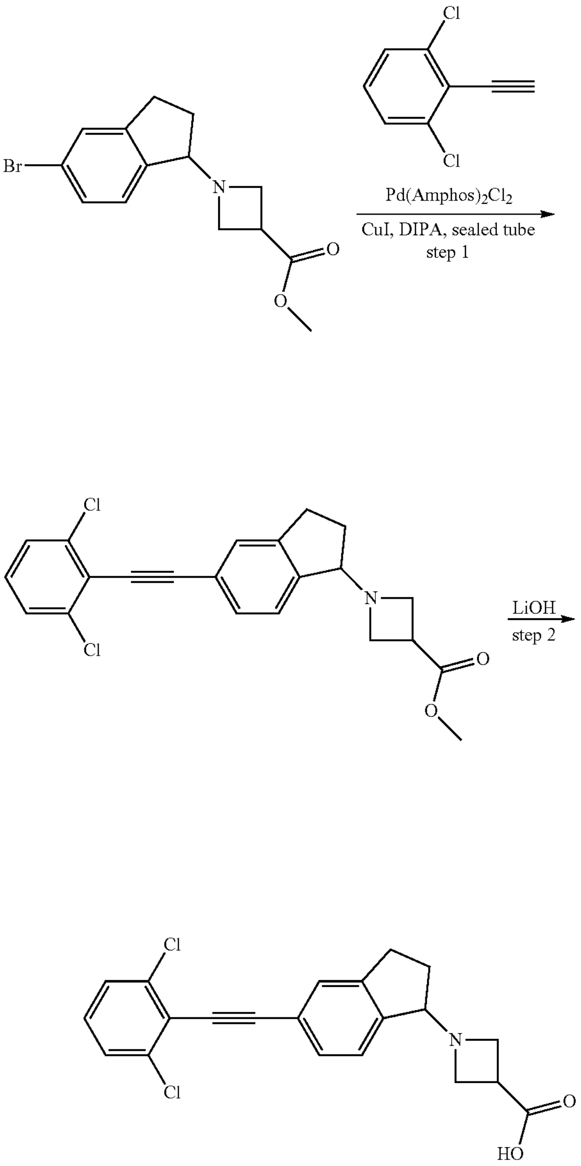

Synthesis of methyl 1-(5-((2,6-dichlorophenyl)ethynyl)-2,3-dihydro-1H-inden-1-yl)-azetidine-3-carboxylate

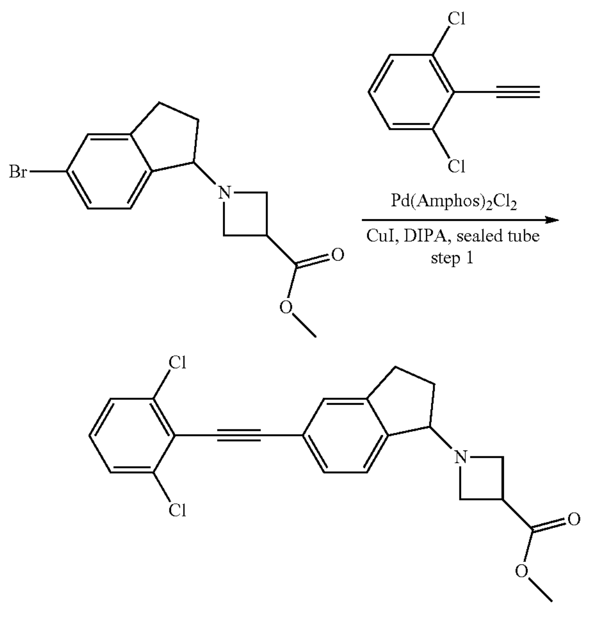

A mixture of methyl 1-(5-bromo-2,3-dihydro-1H-inden-1-yl)azetidine-3-carboxylate (12.0 g, 38.690 mmol, 1.00 equiv), 1,3-dichloro-2-ethynyl-benzene (16.5 g, 96.710 mmol, 2.50 equiv), Pd(Amphos)$_2$Cl$_2$ (1.4 g, 1.930 mmol, 0.05 equiv) and CuI (737 mg, 3.870 mmol, 0.10 equiv) in DIPA (240 mL, 0.161 mol/L) was stirred at 45° C. for 16 hours under a nitrogen atmosphere. TLC showed the reaction was complete and the mixture was quenched with $NaHCO_3$ (sat. aq, 500 mL) and extracted with DCM (500 mL×3). The combined organic phase was dried over $Na_2SO_4$, filtered and concentrated under reduced pressure. The crude product was purified by flash chromatography (PE:EA=3:1) to give the desired product methyl 1-(5-((2,6-dichlorophenyl)ethynyl)-2,3-dihydro-1H-inden-1-yl)azetidine-3-carboxylate (12.0 g, 77%) as a solid. LCMS (ESI, m/z): 400 [M+H]$^+$.

Synthesis of 1-(5-((2,6-dichlorophenyl)ethynyl)-2,3-dihydro-1H-inden-1-yl)azetidine-3-carboxylic acid

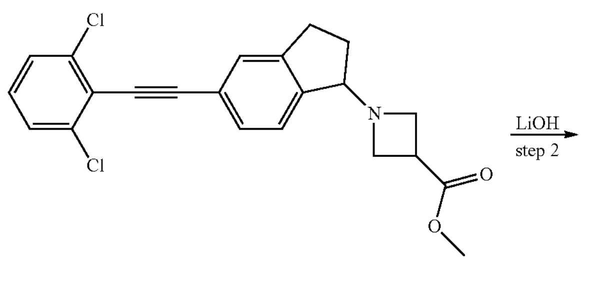

-continued

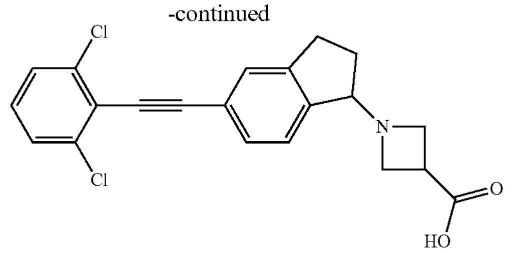

A mixture of methyl 1-(5-((2,6-dichlorophenyl)ethynyl)-2,3-dihydro-1H-inden-1-yl)-azetidine-3-carboxylate (12.0 g, 29.980 mmol, 1.00 equiv), LiOH (2.2 g, 89.930 mmol, 3.00 equiv) in THF (100 mL) and Water (100 mL) was stirred at 25° C. for 0.5 hours. TLC showed the reaction was complete. The mixture was quenched with HCl (2 N, 500 mL) and extracted with DCM (500 mL×3). The combined organic phase was dried over $Na_2SO_4$, filtered and concentrated under reduced pressure. The crude product was purified by reverse flash chromatography (MeCN:$H_2O$=2:3) to give the desired product 1-(5-((2,6-dichlorophenyl)-ethynyl)-2,3-dihydro-1H-inden-1-yl)azetidine-3-carboxylic acid (18, 7.15 g, 62%, >99% ee) as a solid. $^1$H NMR (400 MHz, Methanol-d$_4$) δ 7.50-7.25 (m, 5H), 7.22-7.08 (m, 1H), 4.65-4.75 (m, 1H), 4.23-4.10 (m, 2H), 4.10-3.94 (m, 2H), 3.27-3.15 (m, 1H), 3.07-2.92 (m, 1H), 2.90-2.73 (m, 1H), 2.44-2.21 (m, 1H), 2.09-1.92 (m, 1H). LCMS (ESI, m/z): 386 [M+H]$^+$.

Example S19. 1-(5-((3-fluorophenyl)ethynyl)-2,3-dihydro-1H-inden-1-yl)azetidine-3-carboxylic acid (19)

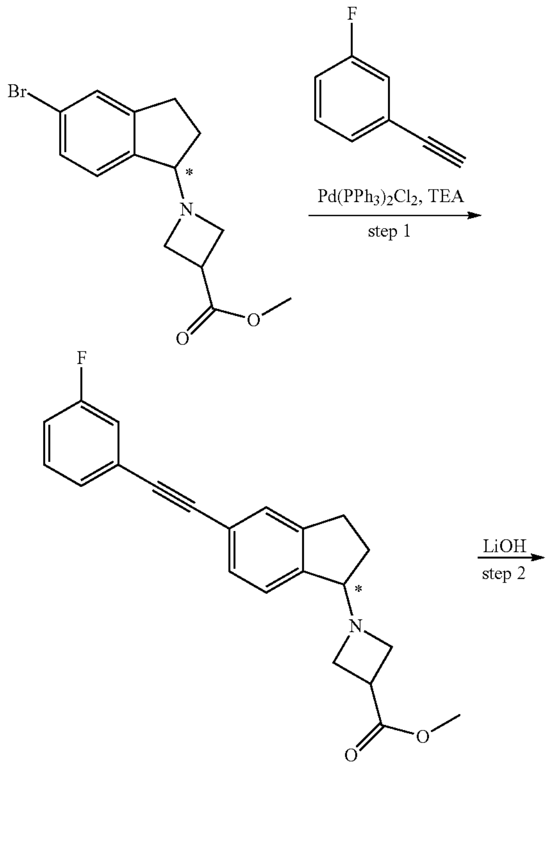

-continued

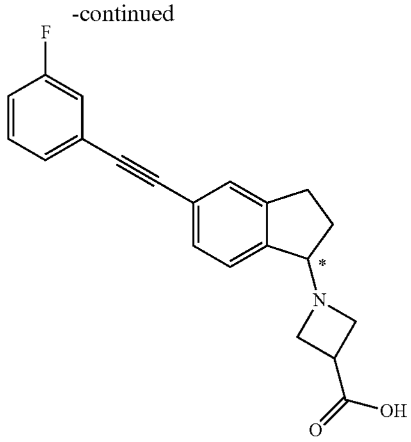

Synthesis of methyl 1-(5-((3-fluorophenyl)ethynyl)-2,3-dihydro-1H-inden-1-yl)azetidine-3-carboxylate

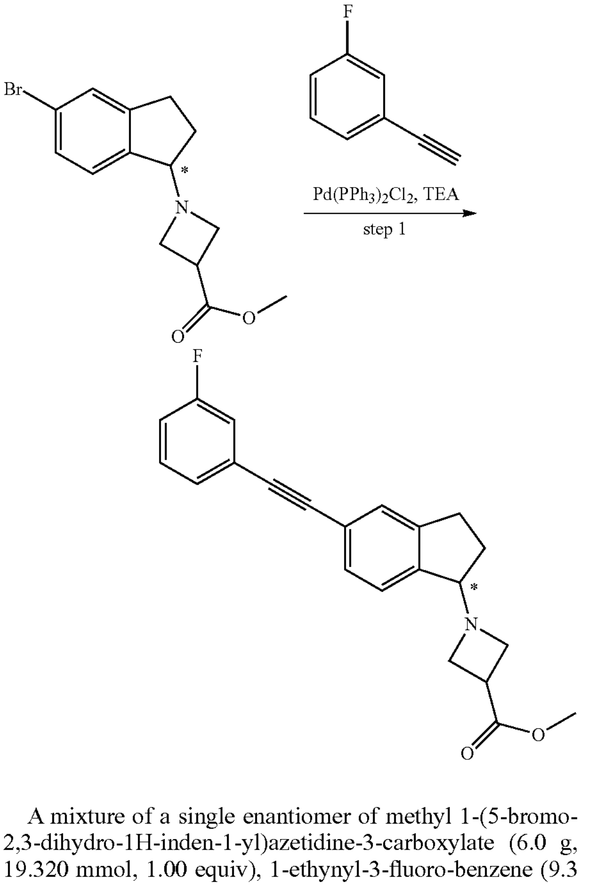

A mixture of a single enantiomer of methyl 1-(5-bromo-2,3-dihydro-1H-inden-1-yl)azetidine-3-carboxylate (6.0 g, 19.320 mmol, 1.00 equiv), 1-ethynyl-3-fluoro-benzene (9.3 g, 77.280 mmol, 4.00 equiv), $Pd(PPh_3)_2Cl_2$ (1.3 g, 1.932 mmol, 0.10 equiv) and TEA (8.1 mL, 57.960 mmol, 3.00 equiv) in THF (100.0 mL) was stirred at 60° C. for 12 h under a nitrogen atmosphere. LCMS showed the reaction was complete. The mixture was quenched with sat. aq. $NaHCO_3$ (100 mL) and extracted with DCM (3*100 mL). The combined organic layers were dried over anhydrous $Na_2SO_4$ and concentrated under reduced pressure. The residue was purified by flash chromatography on silica gel (PE/EA, 2/1) to give the corresponding enantiomer of methyl 1-(5-((3-fluorophenyl)ethynyl)-2,3-dihydro-1H-inden-1-yl)azetidine-3-carboxylate (5.5 g, 77%) as an oil. LCMS (ESI, m/z): 350 $[M+H]^+$.

Synthesis of 1-(5-((3-fluorophenyl)ethynyl)-2,3-dihydro-1H-inden-1-yl)azetidine-3-carboxylic acid

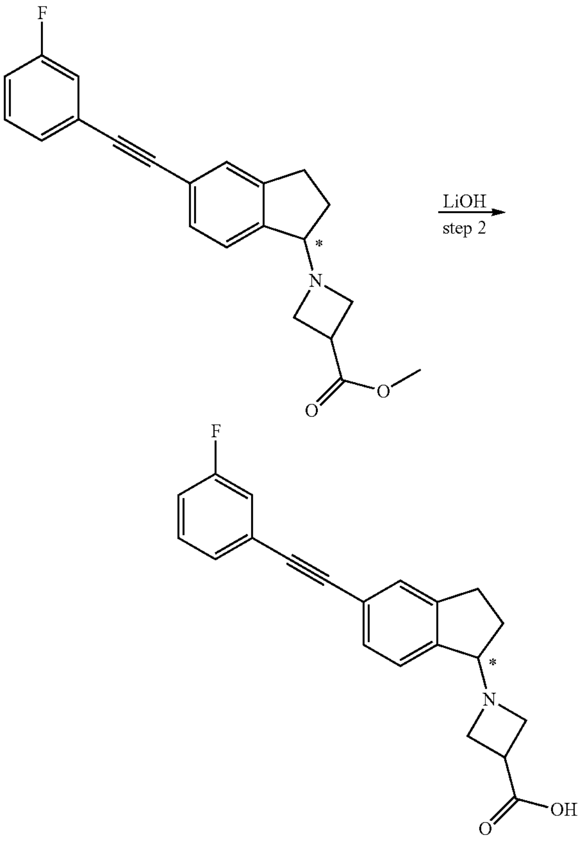

A mixture of a single enantiomer of methyl 1-(5-((3-fluorophenyl)ethynyl)-2,3-dihydro-1H-inden-1-yl)-azetidine-3-carboxylate (5.0 g, 14.310 mmol, 1.00 equiv) and LiOH (2.7 g, 114.48 mmol, 8.00 equiv) in THF (25.0 mL) and water (25.0 mL) was stirred at 60° C. for 0.5 h. LCMS showed the reaction was complete. The reaction mixture was acidified to 3-4 with 2N HCl and concentrated under reduced pressure. The residue was purified by flash column chromatography on C18 silica (Mobile Phase A: Water (10 mmol/L $NH_4HCO_3$), Mobile Phase B: ACN; Flow rate: 100 mL/min; Gradient: 60% B to 75% B in 5 min; 254/210 nm) to give the respective enantiomer of 1-(5-((3-fluorophenyl)ethynyl)-2,3-dihydro-1H-inden-1-yl)azetidine-3-carboxylic acid (19, 3.31 g, 68%) as a solid.

$^1$H NMR (400 MHz, Methanol-$d_4$) δ 7.61-7.54 (m, 2H), 7.53-7.47 (m, 1H), 7.47-7.39 (m, 1H), 7.39-7.33 (m, 1H), 7.32-7.24 (m, 1H), 7.20-7.12 (m, 1H), 4.92-4.88 (m, 1H), 4.37 (t, J=8.8 Hz, 2H), 4.28-4.18 (m, 2H), 3.47-3.34 (m, 1H), 3.24-3.12 (m, 1H), 3.08-2.96 (m, 1H), 2.60-2.45 (m, 1H), 2.25-2.16 (m, 1H).

$^{19}$F NMR (376 MHz, Methanol-$d_4$) δ −114.856.

LCMS (ESI, m/z): 336 $[M+H]^+$. Analytic Conditions: Shim-pack XR-ODS, 3.0*50 mm, 2.2 μm; Mobile Phase A: Water/0.05% TFA, Mobile Phase B: Water/0.05% TFA;

Flow rate: 1.20 mL/min; Gradient: 5% B to 95% B in 2.0 min, 254 nm; RT: 1.583 min.

Example S20. 1-(5-((2,5-difluorophenyl)ethynyl)-2,3-dihydro-1H-inden-1-yl)azetidine-3-carboxylicacid (20)

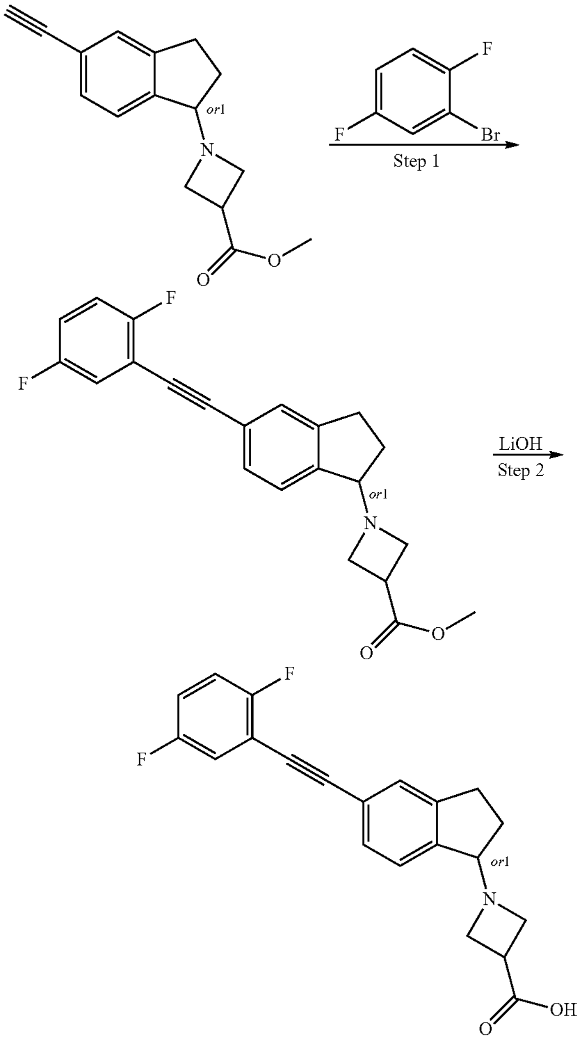

Synthesis of methyl 1-(5-((2,5-difluorophenyl)ethynyl)-2,3-dihydro-1H-inden-1-yl)azetidine-3-carboxylate

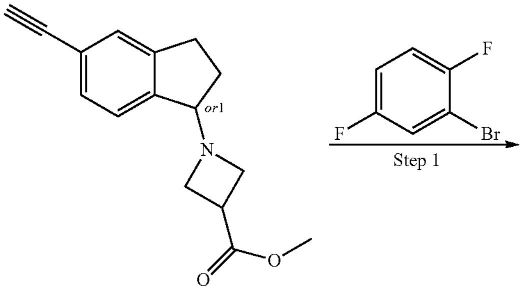

-continued

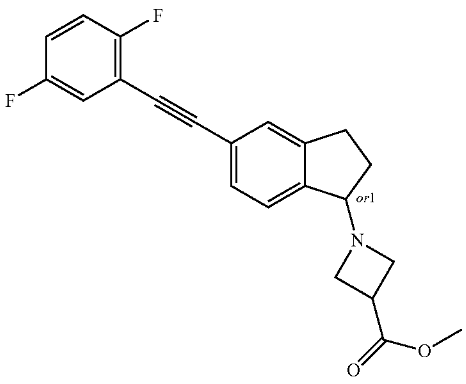

To a solution of a single enantiomer of methyl 1-(5-ethynyl-2,3-dihydro-1H-inden-1-yl)azetidine-3-carboxylate (150 mg, 0.590 mmol, 1.00 equiv), 2-bromo-1,4-difluorobenzene (125 mg, 0.650 mmol, 1.10 equiv) and $K_2CO_3$ (243 mg, 1.76 mmol, 3.00 equiv) in DMF (3.0 mL) was added XPhos Pd G3 (50 mg, 0.060 mmol, 0.10 equiv). The flask was evacuated and flushed five times with nitrogen. The mixture was stirred at 70° C. under nitrogen atmosphere overnight. LCMS showed that the reaction complete. The resulting mixture was diluted with water and extracted with ethyl acetate. The combined organic layers were washed with brine, dried over anhydrous $Na_2SO_4$ and concentrated under reduced pressure. The residue was purified by silica gel chromatography (eluted with ethyl acetate/petroleum ether, 1/2) to give one enantiomer of methyl 1-(5-((2,5-difluorophenyl)ethynyl)-2,3-dihydro-1H-inden-1-yl)azetidine-3-carboxylate (130 mg, 60%) as an oil. LCMS (ESI, m/z): 368 $[M+H]^+$.

Synthesis of 1-(5-((2,5-difluorophenyl)ethynyl)-2,3-dihydro-1H-inden-1-yl)azetidine-3-carboxylic acid

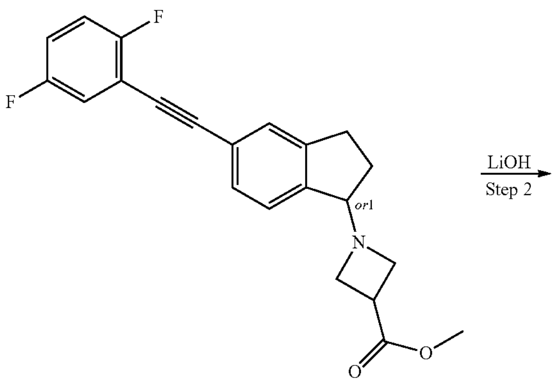

-continued

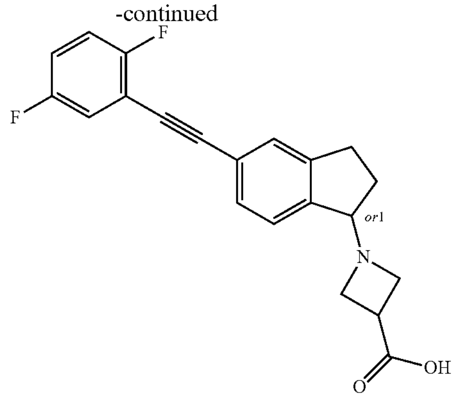

To a solution of a single enantiomer of methyl 1-(5-((2,5-difluorophenyl)ethynyl)-2,3-dihydro-1H-inden-1-yl)azetidine-3-carboxylate (130 mg, 0.350 mmol, 1.00 equiv.) in THF (3.0 mL) and Water (0.3 mL) was added LiOH·$H_2O$ (30 mg, 0.710 mmol, 2.00 equiv.). The mixture was stirred at room temperature overnight. LCMS showed that the reaction was complete. The reaction mixture was acidified to pH 4-5 by adding 1N HCl and then was concentrated under reduced pressure. The residue was purified by Prep-HPLC (Column: XSelect CSH Prep C18 OBD Column, 19*250 mm, 5 μm; Mobile Phase A: water (0.05% HCl), Mobile Phase B: ACN; Flow rate: 25 mL/min; Gradient: 22% B to 47% B in 7 min, hold at 47% B for 1 min; 254/210 nm; RT: 7.33 min) to give the corresponding enantiomer of 1-(5-((2,5-difluorophenyl)ethynyl)-2,3-dihydro-1H-inden-1-yl)azetidine-3-carboxylic acid (20, 80.9 mg, 64%) as a solid.

$^1$H NMR (400 MHz, Methanol-$d_4$) δ 7.62-7.58 (m, 2H), 7.51 (dd, J=7.6, 1.2 Hz, 1H), 7.33-7.29 (m, 1H), 7.24-7.14 (m, 2H), 5.00 (dd, J=7.6, 2.8 Hz, 1H), 4.54-4.50 (m, 2H), 4.43-4.37 (m, 2H), 3.74-3.65 (m, 1H), 3.24-3.16 (m, 1H), 3.07-3.00 (m, 1H), 2.60-2.50 (m, 1H), 2.26-2.18 (m, 1H).

$^{19}$F NMR (376 MHz, Methanol-$d_4$) δ −117.8, −120.5.

LCMS (ESI, m/z): 354 $[M+H]^+$. Analytic Conditions: Shim-pack XR-ODS, 3.0*50 mm, 2.2 μm; Mobile Phase A: water/0.05% TFA, Mobile Phase B: Acetonitrile/0.05% TFA; Flow rate: 1.20 mL/min; Gradient: 5% B to 100% B in 2.0 min, hold at 100% B for 0.7 min, 100% B to 5% B in 0.05 min; 254 nm; RT: 1.542 min.

Example S21. 2-(5-((2,6-dichlorophenyl)ethynyl)-2,3-dihydro-1H-inden-1-yl)-2-azaspiro[3.3]heptane-6-carboxylic acid (21)

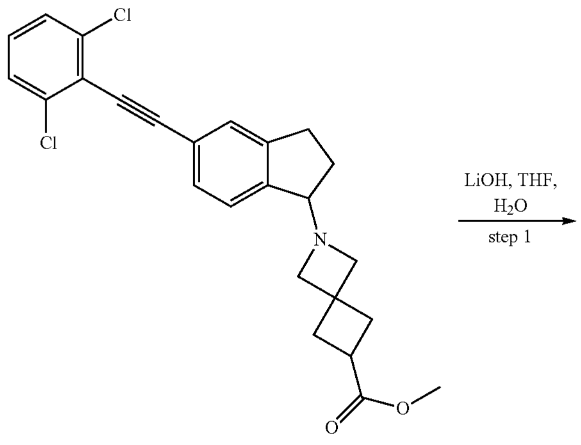

-continued

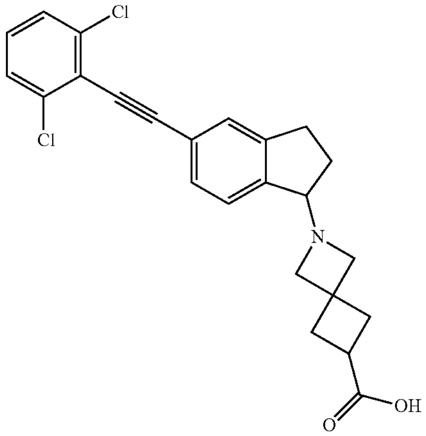

A solution of methyl 2-[5-[2-(2,6-dichlorophenyl)ethynyl]indan-1-yl]-2-azaspiro[3.3]-heptane-6-carboxylate (50 mg, 0.110 mmol, 1.00 equiv.) and LiOH (8 mg, 0.330 mmol, 3.00 equiv.) in THF (1.0 mL) and water (1.0 mL) was stirred at room temperature for 15 h. LCMS showed the reaction was complete. The resulting solution was acidified to pH 5~6 with 2N HCl and concentrated under reduced pressure. The residue was purified by prep-HPLC (Column: X Bridge Shield RP18 OBD Column, 30*150 mm, 5 μm; Mobile Phase A: water (10 mM $NH_4HCO_3$), Mobile Phase B: ACN; Flow rate: 60 mL/min; Gradient: 15% B to 45% B in 7 min; 254/210 nm; RT: 6.63 min) to give 2-(5-((2,6-dichlorophenyl)ethynyl)-2,3-dihydro-1H-inden-1-yl)-2-azaspiro[3.3]heptane-6-carboxylic acid (21, 14.3 mg, 29.5%) as a solid.

LCMS (ESI, m/z): 426 $[M+H]^+$. Analytic Conditions: HALO C18, 3.0*30 mm, 2.0 μm; Mobile Phase A: water+0.05% TFA. Mobile Phase B: Acetonitrile+0.05% TFA; Flow rate: 1.20 mL/min; Gradient: 5% B to 100% B in 1.2 min, hold at 100% B for 0.6 min, 100% B to 5% B in 0.03 min; 254 nm; RT: 1.038 min.

$^1$H NMR (300 MHz, DMSO-$d_6$) δ 7.60 (d, J=11.2 Hz, 2H), 7.46-7.43 (m, 2H), 7.40-7.31 (m, 2H), 3.73-3.71 (m, 1H), 3.32-3.28 (m, 2H), 3.19-3.14 (m, 3H), 2.96-2.84 (m, 2H), 2.782.72 (m, 1H), 2.20-2.19 (m, 3H), 2.04-1.97 (m, 1H), 1.81-1.78 (m, 1H).

Example S22. 1-(5-(2,6-dichlorophenethyl)-2,3-dihydro-1H-inden-1-yl)piperidine-4-carboxylic acid (22a and 22b)

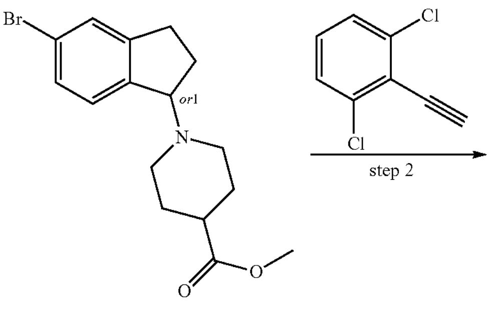

-continued

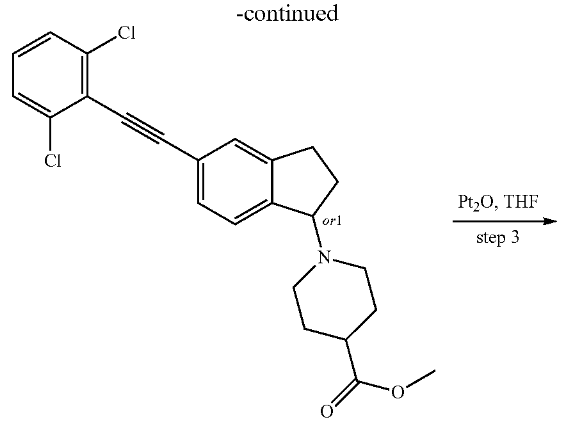

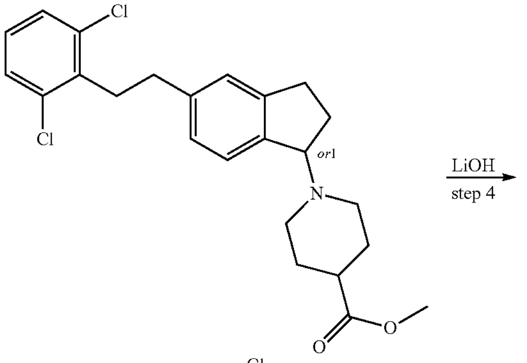

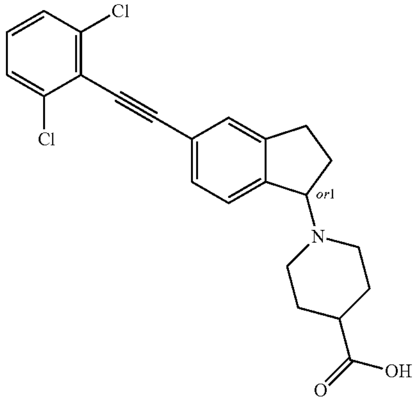

chiral separation 1

Synthesis of methyl 1-(5-((2,6-dichlorophenyl)ethynyl)-2,3-dihydro-1H-inden-1-yl)piperidine-4-carboxylate

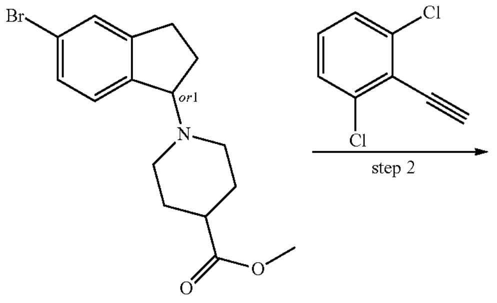

-continued

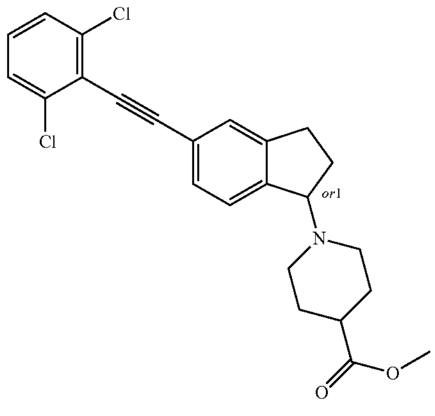

A mixture of methyl 1-(5-bromo-2,3-dihydro-1H-inden-1-yl)piperidine-4-carboxylate (500 mg, 1.480 mmol, 1.00 equiv), 1,3-dichloro-2-ethynyl-benzene (505 mg, 2.960 mmol, 2.00 equiv), $Pd(PPh_3)_2Cl_2$ (103 mg, 0.148 mmol, 0.10 equiv) and TEA (0.3 mL, 4.440 mmol, 3.00 equiv) in THF (10.0 mL) was stirred at 60° C. for 12 hours under a nitrogen atmosphere. LCMS showed the reaction was complete. The reaction mixture was quenched with water (10 mL) and extracted with EtOAc (3*10 mL). The combined organic layers were dried over anhydrous $Na_2SO_4$ and concentrated under reduced pressure. The residue was purified by flash column chromatography on silica gel (PE: EA=1:1) to give methyl 1-(5-((2,6-dichlorophenyl)ethynyl)-2,3-dihydro-1H-inden-1-yl)piperidine-4-carboxylate (350 mg, 55%) as an oil. LCMS (ESI, m/z): 428 $[M+H]^+$.

Synthesis of methyl 1-(5-(2,6-dichlorophenethyl)-2,3-dihydro-1H-inden-1-yl)piperidine-4-carboxylate

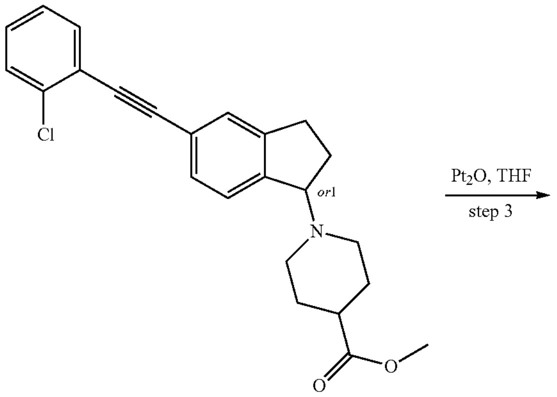

-continued

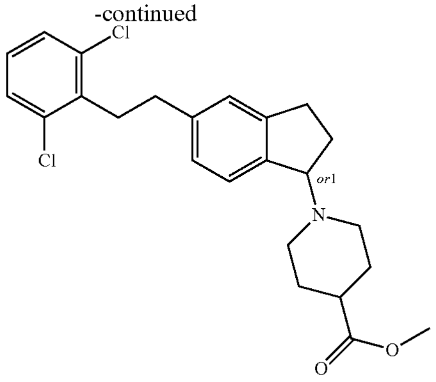

A mixture of methyl 1-(5-((2,6-dichlorophenyl)ethynyl)-2,3-dihydro-1H-inden-1-yl)piperidine-4-carboxylate (350 mg, 0.817 mmol, 1.00 equiv) and $PtO_2$ (70 mg, 0.20 w/w) in methanol (8.0 mL) was stirred at 25° C. for 1 h under an atmosphere of hydrogen. LCMS showed the reaction was complete. The solid was filtered out. The filtrate was concentrated under reduced pressure to give methyl 1-(5-(2,6-dichlorophenethyl)-2,3-dihydro-1H-inden-1-yl)piperidine-4-carboxylate (200 mg, crude) as an oil. LCMS (ESI, m/z): 432 $[M+H]^+$.

Synthesis of 1-(5-(2,6-dichlorophenethyl)-2,3-dihydro-1H-inden-1-yl)piperidine-4-carboxylic acid

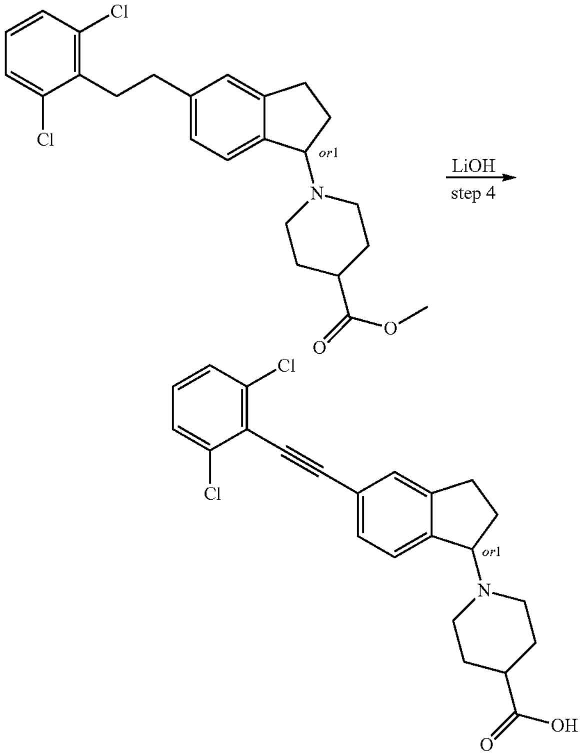

chiral separation 1

A mixture of methyl 1-(5-(2,6-dichlorophenethyl)-2,3-dihydro-1H-inden-1-yl)piperidine-4-carboxylate (200 mg, 0.460 mmol, 1.00 equiv) and $LiOH{\cdot}H_2O$ (97 mg, 2.300 mmol, 5.00 equiv) in water/THF (2/2 mL) was stirred at room temperature for 1 h. LCMS showed the reaction was complete. The pH value of the solution was adjusted to 3~4 with 1N HCl. The resulting mixture was concentrated under reduced pressure and the crude product was purified by Prep-HPLC (Column: YMC-Actus Triart C18, 30*250 mm, 5 m; Mobile Phase A: Water (10 MMOL/L $NH_4HCO_3$+0.1% $NH_3H_2O$), Mobile Phase B: ACN; Flow rate: 60 mL/min; Gradient: 30% B to 50% B in 7 min; 254/210 nm; RT: 6.42 min) to give 1-(5-(2,6-dichlorophenethyl)-2,3-dihydro-1H-inden-1-yl)piperidine-4-carboxylic acid (22a, 88.9 mg, 46%) as a solid.

$^1$H NMR (400 MHz, DMSO-$d_6$) δ 12.00 (s, 1H), 7.48 (d, J=8.0 Hz, 2H), 7.34-7.25 (m, 1H), 7.20 (d, J=7.6 Hz, 1H), 7.14-7.05 (m, 2H), 4.27 (s, 1H), 3.15-3.06 (m, 2H), 2.93-2.64 (m, 5H), 2.50 (s, 1H), 2.35-2.05 (m, 3H), 1.99 (d, J=7.2 Hz, 2H), 1.89-1.69 (m, 2H), 1.62-1.43 (m, 2H).

LCMS (ESI, m/z): 418 $[M+H]^+$. Analytic Conditions: column: EVO C18 Column 3.0*50 mm, 2.6 μm; mobile Phase A: Water/5 mM $NH_4HCO_3$, mobile Phase B: acetonitrile; flow rate: 1.20 mL/min; gradient: 10% B to 95% B in 1.99 min, hold at 95% for 0.6 min, 95% B to 10% B in 0.15 min; 220 nm; RT: 1.225 min.

Synthesis of 1-(5-(2,6-dichlorophenethyl)-2,3-dihydro-1H-inden-1-yl)piperidine-4-carboxylic acid

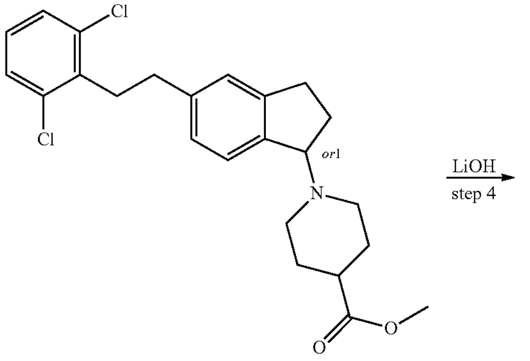

chiral separation 1

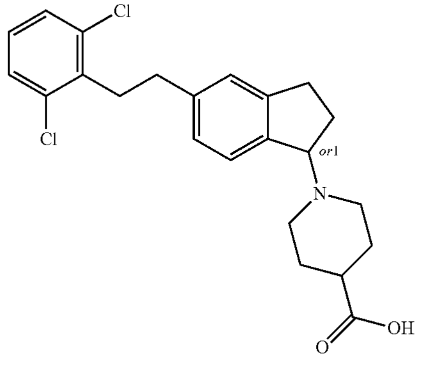

chiral separation 2

A mixture of methyl 1-(5-(2,6-dichlorophenethyl)-2,3-dihydro-1H-inden-1-yl)piperidine-4-carboxylate (200 mg, 0.460 mmol, 1.00 equiv) and $LiOH{\cdot}H_2O$ (97 mg, 2.300 mmol, 5.00 equiv) in water/THF (2/2 mL) was stirred at room temperature for 1 h. LCMS showed the reaction was complete. The pH value of the solution was adjusted to 3~4 with 1N HCl. The resulting mixture was concentrated under reduced pressure and the crude product was purified by Prep-HPLC (Column: YMC-Actus Triart C18, 30*250 mm, 5 m; Mobile Phase A: Water (10 MMOL/L $NH_4HCO_3$+0.1% $NH_3{\cdot}H_2O$), Mobile Phase B: ACN; Flow rate: 60 mL/min; Gradient: 30% B to 50% B in 7 min; 254/210 nm; RT: 6.42 min) to give 1-(5-(2,6-dichlorophenethyl)-2,3-dihydro-1H-inden-1-yl)piperidine-4-carboxylic acid (22b, 105.2 mg, 54%) as a solid.

$^1$H NMR (400 MHz, DMSO-$d_6$) δ 12.02 (s, 1H), 7.48 (d, J=8.0 Hz, 2H), 7.34-7.25 (m, 1H), 7.20 (d, J=7.6 Hz, 1H), 7.13-7.05 (m, 2H), 4.26 (t, J=7.2 Hz, 1H), 3.15-3.06 (m, 2H), 2.91-2.68 (m, 5H), 2.46 (s, 1H), 2.29-2.12 (m, 3H), 2.09-1.95 (m, 2H), 1.88-1.70 (m, 2H), 1.67-1.38 (m, 2H).

LCMS (ESI, m/z): 418 $[M+H]^+$. Analytic Conditions: column: EVO C18, 3.0*50 mm, 2.6 μm; mobile Phase A: Water/5 mM $NH_4HCO_3$, mobile Phase B: acetonitrile; flow rate: 1.20 mL/min; gradient: 10% B to 95% B in 1.99 min, hold at 95% for 0.6 min, 95% B to 10% B in 0.15 min; 220 nm; RT: 1.227 min.

Example S23. 1-(5-(2-(2,6-dichlorophenyl)acetyl)-2,3-dihydro-1H-inden-1-yl)piperidine-4-carboxylic acid (23)

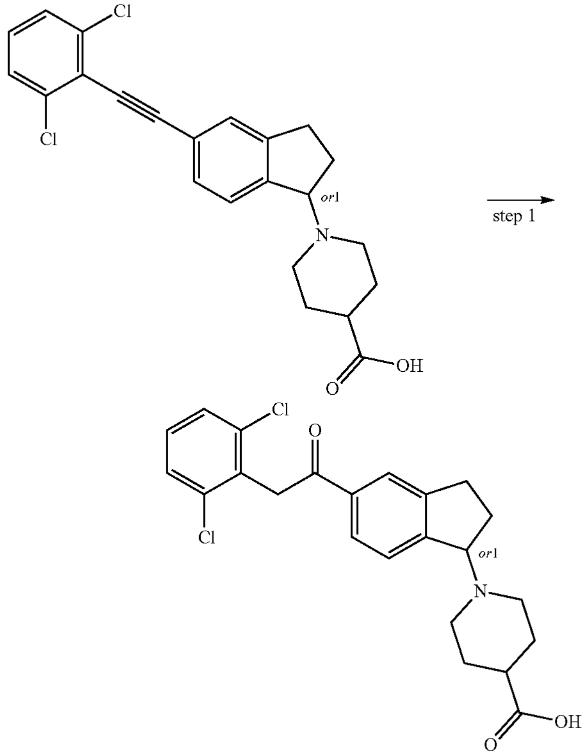

A solution of a single enantiomer of 1-(5-((2,6-dichlorophenyl)ethynyl)-2,3-dihydro-1H-inden-1-yl)piperidine-4-carboxylic acid (600 mg, 1.45 mmol, 1.00 equiv) in acetic acid (2 mL) and TfOH (1 mL, 11.3 mmol, 7.00 equiv) was stirred at 150° C. for 8 h under microwave irradiation. LCMS showed the reaction was complete. The solvent was removed under reduced pressure and the residue was purified by chiral-HPLC (Column: CHIRALPAK IG, 2*25 cm, 5 μm; Mobile Phase A: Hex (0.3% TFA):EtOH=60:40, Mobile Phase B: IPA; Flow rate: 20 mL/min; Gradient: 30% B to 30% B in 27 min; 220/254 nm; RT: 16.438 min) and prep-HPLC (Column: Sunfire prep C18 column, 30*150 mm, 5 m; Mobile Phase A: Water (0.05% HCl), Mobile Phase B: ACN; Flow rate: 60 mL/min; Gradient: 12% B to 42% B in 7 min, 254/210 nm; RT: 6.43 min) to obtain (R)-1-(5-(2-(2,6-dichlorophenyl)acetyl)-2,3-dihydro-1H-inden-1-yl)piperidine-4-carboxylic acid (23, 5 mg, 0.771%) as a solid.

$^1$H NMR (400 MHz, Methanol-$d_4$) δ 8.18 (s, 1H), 8.14 (dd, J=8.0, 1.6 Hz, 1H), 7.81 (d, J=8.0 Hz, 1H), 7.45 (d, J=8.0 Hz, 2H), 7.34-7.30 (m, 1H), 5.07 (dd, J=8.4, 3.2 Hz, 1H), 4.82 (s, 2H), 3.57-3.50 (m, 2H), 3.32-3.10 (m, 5H), 2.71-2.54 (m, 2H), 2.28-2.20 (m, 2H), 2.05-1.90 (m, 2H).

LCMS (ESI, m/z): 432$[M+H]^+$. Analytic Conditions: Shim-pack XR-ODS C18, 3.0*50 mm, 2.2 μm; Mobile Phase A: water/0.05% TFA, Mobile Phase B: Acetonitrile/0.05% TFA; Flow rate: 1.20 mL/min; Gradient: 5% B to 100% B in 2.0 min, hold at 100% B for 0.7 min, 100% B to 5% B in 0.2 min; 254 nm; RT: 1.512 min.

Example S24. 1-(5-(2-(2,6-dichlorophenyl)-2-oxoethyl)-2,3-dihydro-1H-inden-1-yl)piperidine-4-carboxylic acid (24)

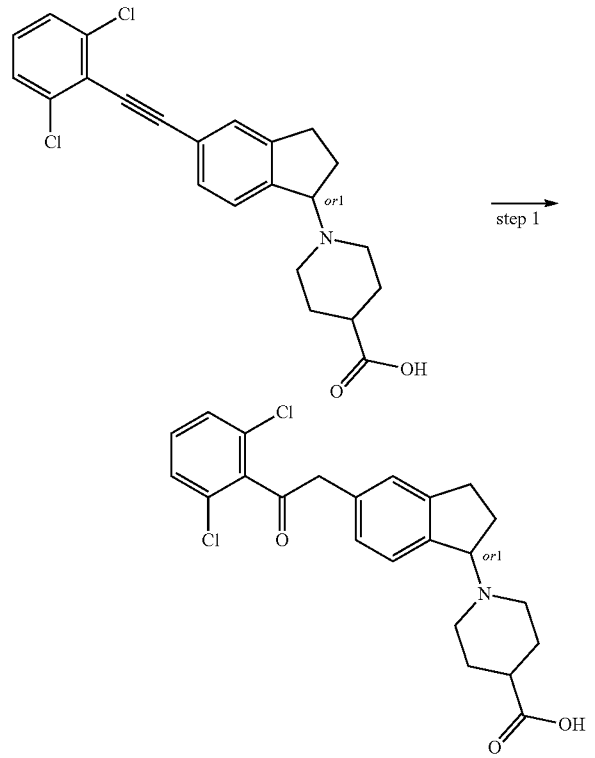

A solution of a single enantiomer of 1-(5-((2,6-dichlorophenyl)ethynyl)-2,3-dihydro-1H-inden-1-yl)piperidine-4-carboxylic acid (600 mg, 1.45 mmol, 1.00 equiv) in acetic acid (2 mL) and TfOH (1 mL, 11.3 mmol, 7.00 equiv) was stirred at 150° C. for 8 h under microwave irradiation. LCMS showed the reaction was complete. The solvent was removed under reduced pressure and the residue was purified by chiral-HPLC (Column: CHIRALPAK IG, 2*25 cm, 5 μm; Mobile Phase A: Hex (0.3% TFA):EtOH=60:40, Mobile Phase B: IPA; Flow rate: 20 mL/min; Gradient: 30% B to 30% B in 27 min; 220/254 nm; RT2: 24.691 min) and prep-HPLC (Column: Sunfire prep C18 column, 30*150 mm, 5 μm; Mobile Phase A: water (0.05% HCl), Mobile Phase B: ACN; Flow rate: 60 mL/min; Gradient: 12% B to 42% B in 7 min,; 254/210 nm; RT: 6.25 min) to obtain a single enantiomer of 1-(5-(2-(2,6-dichlorophenyl)-2-oxo-ethyl)-2,3-dihydro-1H-inden-1-yl)piperidine-4-carboxylic acid (24, 20 mg, 3.19%) as a solid.

$^1$H NMR (400 MHz, Methanol-$d_4$) δ 7.58 (d, J=8.0 Hz, 1H), 7.47-7.41 (m, 3H), 7.32-7.26 (m, 2H), 4.96-4.92 (m, 1H), 4.25 (s, 2H), 3.55-3.51 (m, 1H), 3.33-3.30 (m, 1H), 3.22-3.10 (m, 2H), 3.03-2.86 (m, 2H), 2.65-2.47 (m, 3H), 2.30-2.19 (m, 2H), 1.97-1.76 (m, 2H).

LCMS (ESI, m/z): 432[M+H]$^+$. Analytic Conditions: Shim-pack XR-ODS C18, 3.0*50 mm, 2.2 m; Mobile Phase A: water/0.05% TFA, Mobile Phase B: Acetonitrile/0.05% TFA; Flow rate: 1.20 mL/min; Gradient: 5% B to 100% B in 2.0 min, hold at 100% B for 0.7 min, 100% B to 5% B in 0.2 min; 254 nm; RT: 1.533 min.

Example S25. 1-(5-(2-chlorophenethyl)-2,3-dihydro-1H-inden-1-yl)piperidine-4-carboxylic acid (25a and 25b)

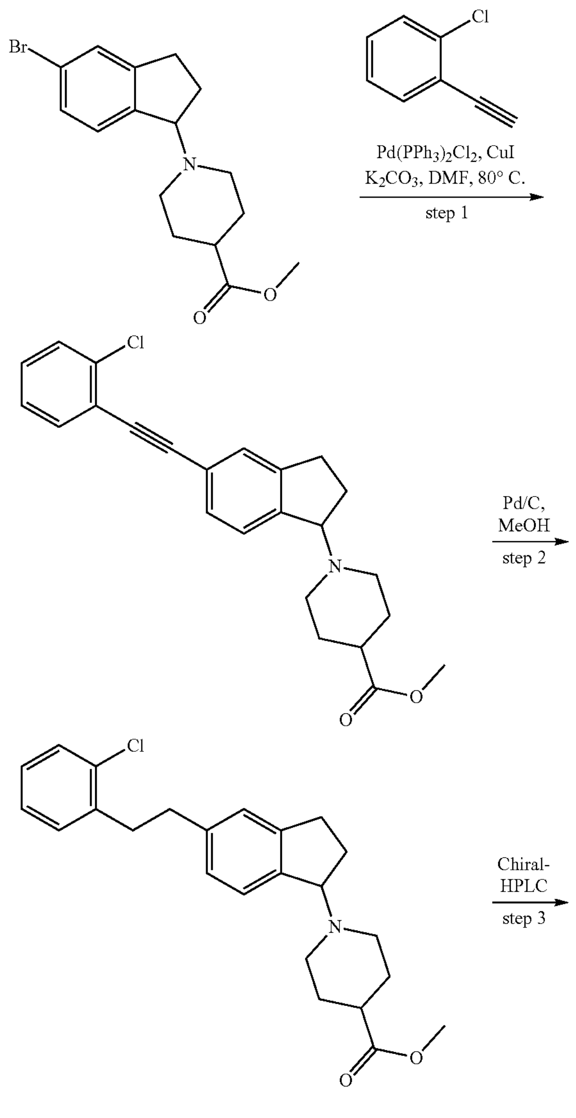

-continued

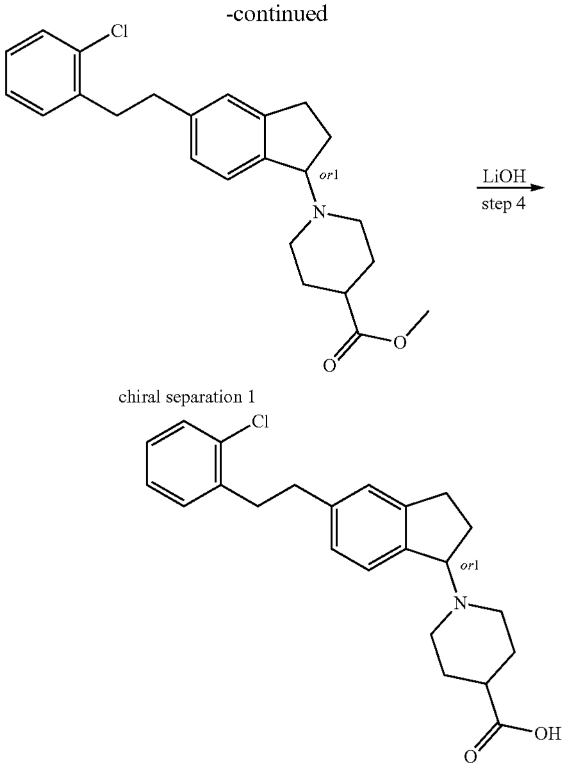

chiral separation 1

Synthesis of methyl 1-(5-((2-chlorophenyl)ethynyl)-2,3-dihydro-1H-inden-1-yl)piperidine-4-carboxylate

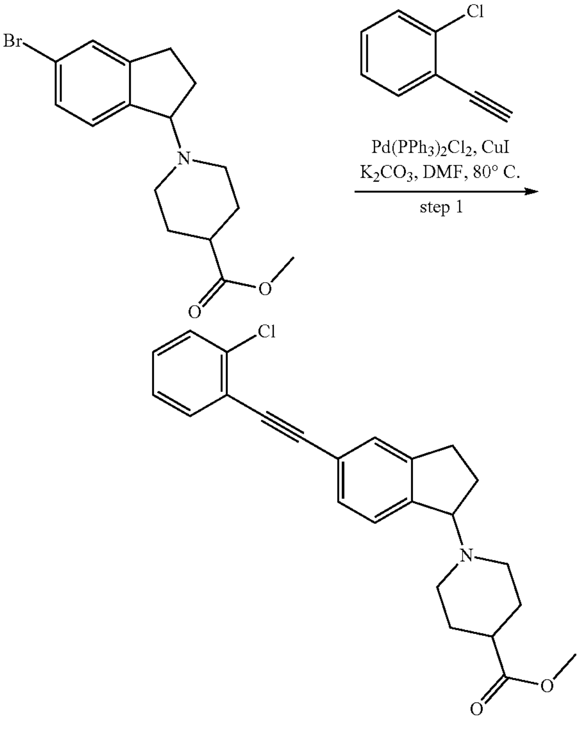

To a stirred solution of methyl 1-(5-bromo-2,3-dihydro-1H-inden-1-yl)piperidine-4-carboxylate (500 mg, 1.480 mmol, 1.00 equiv.) in DMF (4 mL) was added 1-chloro-2-ethynyl-benzene (606 mg, 4.43 mmol, 3.00 equiv.), $Pd(PPh_3)_2Cl_2$ (20 mg, 0.150 mmol, 0.100 equiv.), CuI (57.3 mg, 0.300 mmol, 0.200 equiv.) and $K_2CO_3$ (0.84 mL, 4.43 mmol, 3.00 equiv.). The resulting solution was stirred at 80° C. overnight. LCMS showed the reaction was complete. The mixture was concentrated under reduced pressure. The residue was purified by flash chromatography on silica gel (eluted with ethyl acetate/petroleum ether, 1/2) to afford methyl 1-(5-((2-chlorophenyl)ethynyl)-2,3-dihydro-1H-inden-1-yl)piperidine-4-carboxylate (512 mg, 87.9%) as an oil. LCMS (ESI, m/z): 394 $[M+H]^+$.

Synthesis of methyl 1-(5-(2-chlorophenethyl)-2,3-dihydro-1H-inden-1-yl)piperidine-4-carboxylate

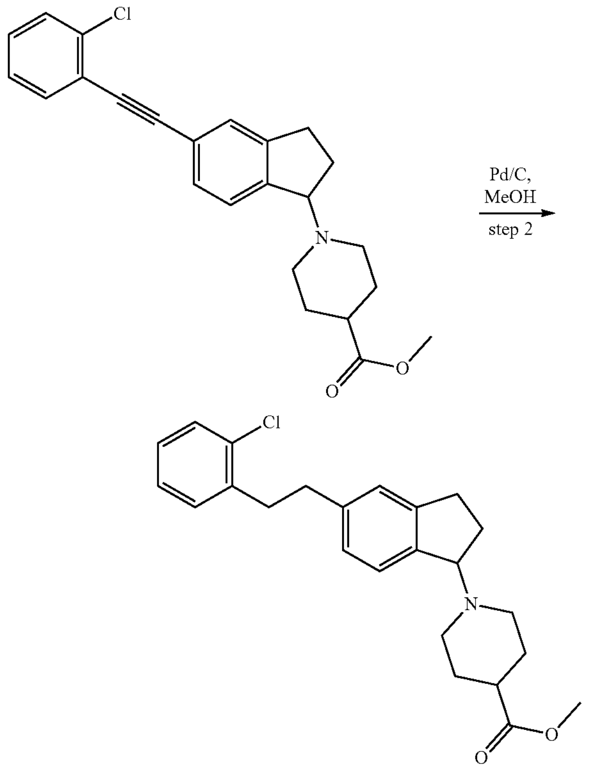 [SMILES: COC(=O)C1CCN(C2CCc3cc(C#Cc4ccccc4Cl)ccc32)CC1 ; COC(=O)C1CCN(C2CCc3cc(CCc4ccccc4Cl)ccc32)CC1]

To a stirred solution of methyl 1-(5-((2-chlorophenyl)ethynyl)-2,3-dihydro-1H-inden-1-yl)piperidine-4-carboxylate (512 mg, 1.30 mmol, 1.00 equiv.) in methanol (5 mL) was added Pd/C (51 mg, 10% w/w). The resulting mixture was stirred at room temperature overnight under hydrogen atmosphere. LCMS showed the reaction was complete. The reaction mixture was filtered through Celite, and the filter cake was washed with methanol (3*50 mL). The mixture was concentrated under reduced pressure. The crude product was purified by flash chromatography on silica gel (eluted with ethyl acetate/petroleum ether, 1/2) to afford methyl 1-(5-(2-chlorophenethyl)-2,3-dihydro-1H-inden-1-yl)piperidine-4-carboxylate (457 mg, 77.1%) as an oil. LCMS (ESI, m/z): 398 $[M+H]^+$.

Chiral Separation of methyl 1-(5-(2-chlorophenethyl)-2,3-dihydro-1H-inden-1-yl)piperidine-4-carboxylate

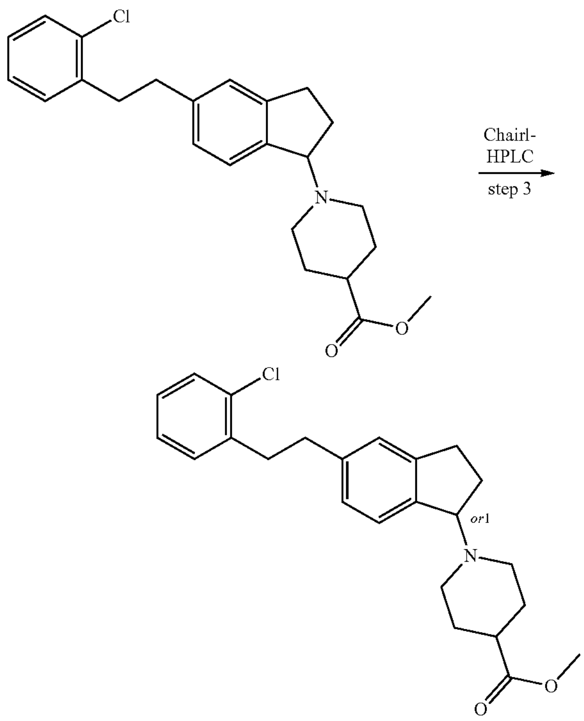

chiral separation 1

457 mg of the racemate was separated by Chairl-HPLC (Column: CHIRALPAK IG, 2.0*25 cm, 5 μm; Mobile Phase A: Hex (8 mmol/L $NH_3\cdot$MeOH)-HPLC, Mobile Phase B: EtOH-HPLC; Flow rate: 16 mL/min; Gradient: 50% B to 50% B in 14 min; 220/254 nm; RT1: 7.002 min; RT2: 9.054 min; Injection Volume: 1.1 mL; Number Of Runs: 8) to give the chiral separation 1 isomer (192 mg, 100% e.e.) and the chiral separation 2 isomer (190 mg, 100% e.e).

Synthesis of 1-(5-(2-chlorophenethyl)-2,3-dihydro-1H-inden-1-yl)piperidine-4-carboxylic acid

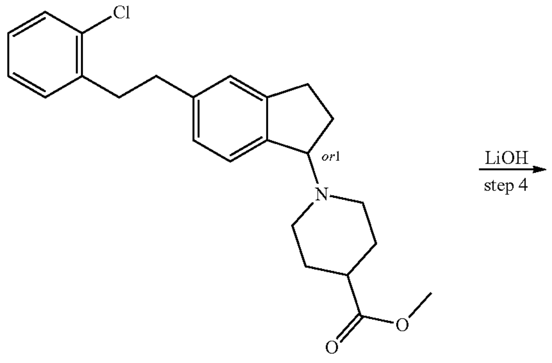

chiral separation 1

-continued

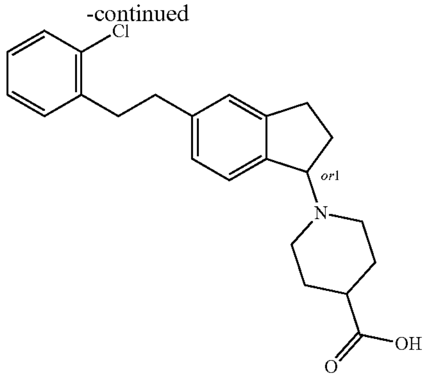

chiral separation 1

A mixture of methyl 1-(5-(2-chlorophenethyl)-2,3-dihydro-1H-inden-1-yl)piperidine-4-carboxylate (chiral separation 1, 180 mg, 0.450 mmol, 1.00 equiv.) and LiOH (32.5 mg, 1.36 mmol, 3.00 equiv.) in THF (2 mL) and water (2 mL) was stirred at room temperature for 0.5 h. LCMS showed the reaction was complete. The pH value of the solution was adjusted to 3-4 with 2N HCl, and was concentrated under reduced pressure. The residue was purified by Prep-HPLC (Column: XBridge Prep C18 OBD Column, 5 μm, 19*150 mm; Mobile Phase A: Water (10 mM $NH_4HCO_3$+0.1% $NH_3 \cdot H_2O$), Mobile Phase B: ACN; Flow rate: 60 mL/min; Gradient: 2% B to 8% B in 10 min; 210/254 nm; RT: 7.68 min) to give the respective enantiomer of 1-(5-(2-chlorophenethyl)-2,3-dihydro-1H-inden-1-yl)piperidine-4-carboxylic acid (25a, 85.5 mg, 0.222 mmol, 49.1% yield) as a solid.

$^1$H NMR (300 MHz, DMSO-$d_6$) δ 12.00 (br, 1H), 7.43-7.33 (m, 2H), 7.28-7.20 (m, 2H), 7.16 (d, J=10.4 Hz, 1H), 7.09-7.04 (m, 2H), 4.23 (t, J=9.2 Hz, 1H), 2.97-2.92 (m, 2H), 2.83-2.71 (m, 5H), 2.48-2.43 (m, 1H), 2.28-2.09 (m, 3H), 2.00-1.93 (m, 2H), 1.82-1.72 (m, 2H), 1.63-1.40 (m, 2H).

LCMS (ESI, m/z): 384 $[M+H]^+$. Analytic Conditions: Shim-pack XR-ODS C18, 3.0*50 mm, 2.2 μm; Mobile Phase A: Water/0.05% TFA, Mobile Phase B: Acetonitrile/0.05% TFA; Flow rate: 1.20 mL/min; Gradient: 5% B to 100% B in 2.0 min, hold at 100% B for 0.7 min, 100% B to 5% B in 0.2 min; 220 nm; RT: 1.655 min.

Synthesis of the Respective Enantiomer of 1-(5-(2-chlorophenethyl)-2,3-dihydro-1H-inden-1-yl)piperidine-4-carboxylic acid

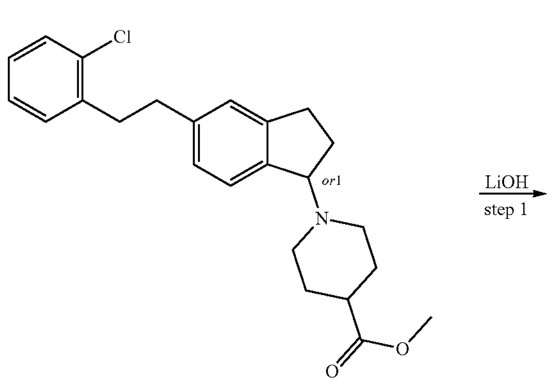

chiral separation 2

-continued

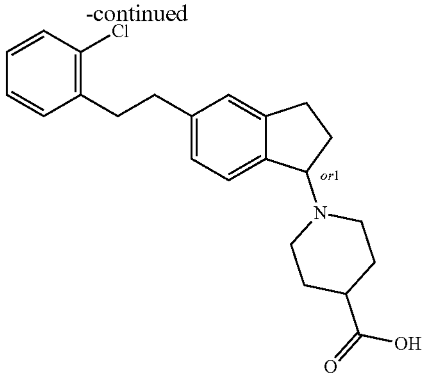

chiral separation 2

A mixture of methyl 1-(5-(2-chlorophenethyl)-2,3-dihydro-1H-inden-1-yl)piperidine-4-carboxylate (chiral separation 2, 192 mg, 0.450 mmol, 1.00 equiv) and LiOH (61 mg, 1.36 mmol, 3.00 equiv) in THF (2 mL) and water (2 mL) was stirred at room temperature for 0.5 h. LCMS showed the reaction was complete. The pH value of the solution was adjusted to 3-4 with 2N HCl, and was concentrated under reduced pressure. The residue was purified by Prep-HPLC (Column: XBridge Prep C18 OBD, 5 μm, 19*150 mm; Mobile Phase A: water (10 mM $NH_4HCO_3$+0.1% $NH_3H_2O$), Mobile Phase B: ACN; Flow rate: 60 mL/min; Gradient: 22% B to 52% B in 7 min; 210/254 nm; RT: 5.95 min) to give the respective enantiomer of 1-(5-(2-chlorophenethyl)-2,3-dihydro-1H-inden-1-yl)piperidine-4-carboxylic acid (25b, 108.1 mg, 61.8%) as a solid.

$^1$H NMR (300 MHz, DMSO-$d_6$) δ 12.00 (br, 1H), 7.43-7.33 (m, 2H), 7.26-7.22 (m, 2H), 7.16 (d, J=10.4 Hz, 1H), 7.09-7.04 (m, 2H), 4.26-4.21 (m, 1H), 2.97-2.92 (m, 2H), 2.83-2.71 (m, 5H), 2.48-2.43 (m, 1H), 2.28-2.08 (m, 3H), 2.00-1.93 (m, 2H), 1.82-1.72 (m, 2H), 1.63-1.40 (m, 2H).

LCMS (ESI, m/z): 384 $[M+H]^+$. Analytic Conditions: Shim-pack XR-ODS C18, 3.0*50 mm, 2.2 m; Mobile Phase A: Water/0.05% TFA, Mobile Phase B: Acetonitrile/0.05% TFA; Flow rate: 1.20 mL/min; Gradient: 5% B to 100% B in 2.0 min, hold at 100% B for 0.7 min, 100% B to 5% B in 0.2 min; 220 nm; RT: 1.653 min.

Example S26. 1-(5-(3-fluorophenethyl)-2,3-dihydro-1H-inden-1-yl)piperidine-4-carboxylic acid (26a and 26b)

Synthesis of 1-(5-(3-fluorophenethyl)-2,3-dihydro-1H-inden-1-yl)piperidine-4-carboxylic acid

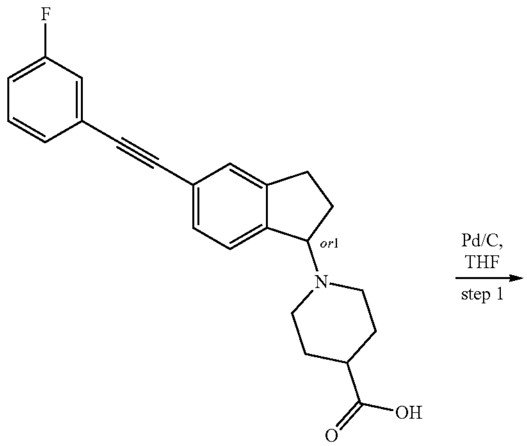

-continued

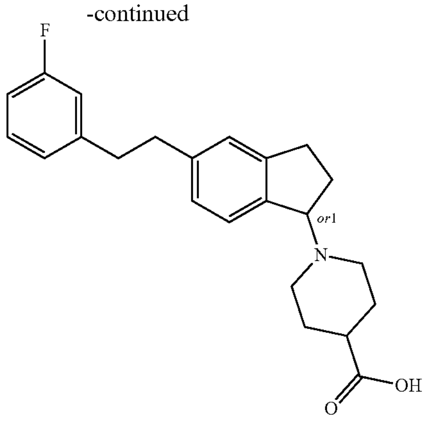

A mixture of one enantiomer of 1-(5-((3-fluorophenyl)ethynyl)-2,3-dihydro-1H-inden-1-yl)piperidine-4-carboxylic acid (200 mg, 0.550 mmol, 1.00 equiv) and $PtO_2$ (40 mg, 0.20 w/w) in methanol (5.0 mL). was stirred at 25° C. for 1 h under an atmosphere of hydrogen. LCMS showed the reaction was complete. The solid was filtered out. The filtrate was concentrated under reduced pressure to give the desired product (200 mg, crude) as an oil. The crude product was purified by Prep-HPLC (Column: XBridge Shield RP18 OBD Column, 5 μm, 19*150 mm; Mobile Phase A: water (10 mM $NH_4HCO_3$+0.1% $NH_3·H_2O$), Mobile Phase B: ACN; Flow rate: 60 mL/min; Gradient: 18% B to 48% B in 7 min; 210/254 nm; RT: 6.22 min) to afford the desired product 1-(5-(3-fluorophenethyl)-2,3-dihydro-1H-inden-1-yl)piperidine-4-carboxylic acid (26a, 90.8 mg, 45%) as a solid.

$^1$H NMR (300 MHz, DMSO-$d_6$) δ 12.05 (s, 1H), 7.36-7.24 (m, 1H), 7.21-6.97 (m, 6H), 4.23 (t, J=6.9 Hz, 1H), 2.84-2.66 (m, 7H), 2.44 (s, 1H), 2.32-2.04 (m, 3H), 2.04-1.90 (m, 2H), 1.84-1.68 (m, 2H), 1.66-1.36 (m, 2H).

$^{19}$F NMR (376 MHz, Methanol-$d_4$) δ −116.135.

LCMS (ESI, m/z): 368 $[M+H]^+$. Analytic Conditions: column: Titank C18 Column 3.0*50 mm, 3.0 μm; mobile Phase A: Water+5 mM $NH_4HCO_3$, mobile Phase B: acetonitrile; flow rate: 1.50 mL/min; gradient: 10% B to 95% B in 1.39 min, hold at 95% for 0.7 min, 95% B to 10% B in 0.03 min; 210 nm; RT: 1.137 min.

Synthesis of 1-(5-(3-fluorophenethyl)-2,3-dihydro-1H-inden-1-yl)piperidine-4-carboxylic acid

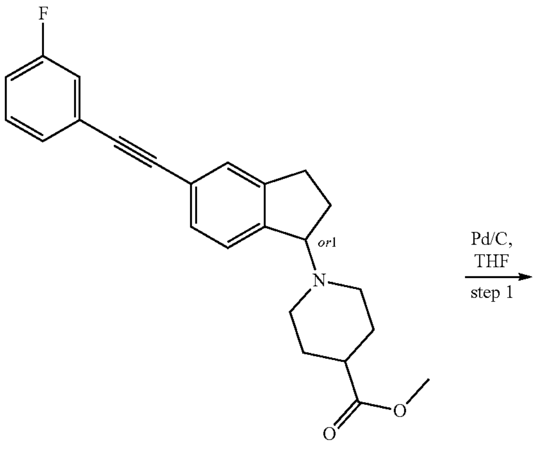

-continued

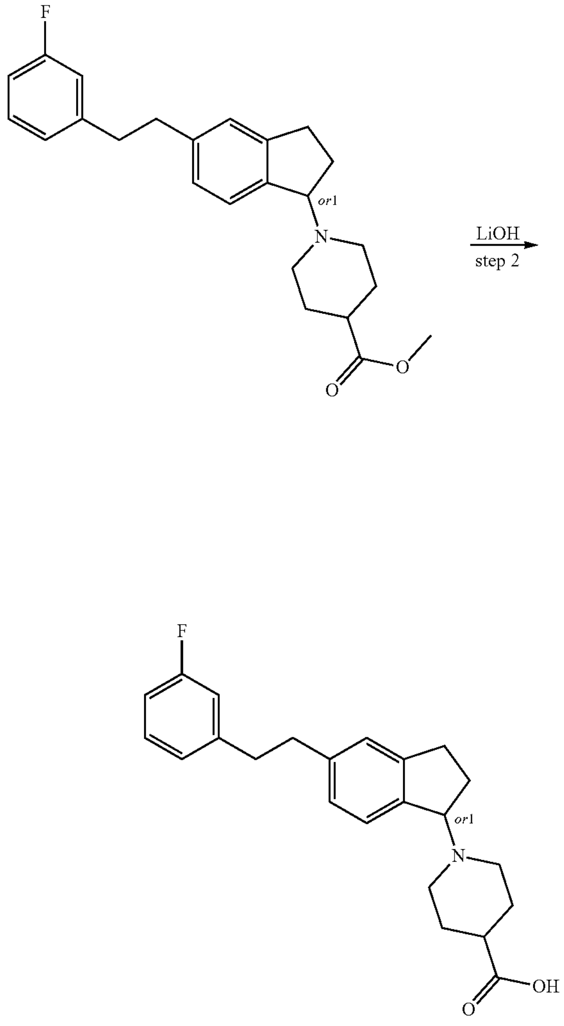

Synthesis of methyl 1-(5-(3-fluorophenethyl)-2,3-dihydro-1H-inden-1-yl)piperidine-4-carboxylate

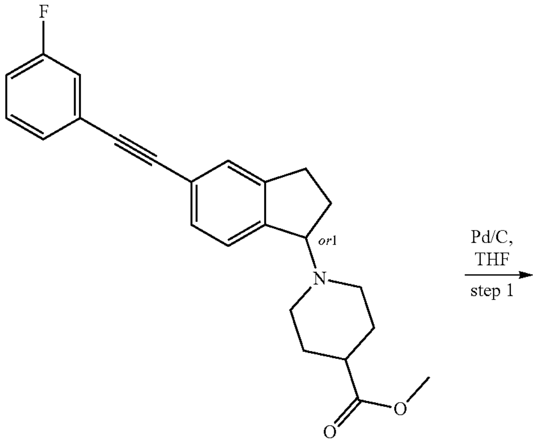

-continued

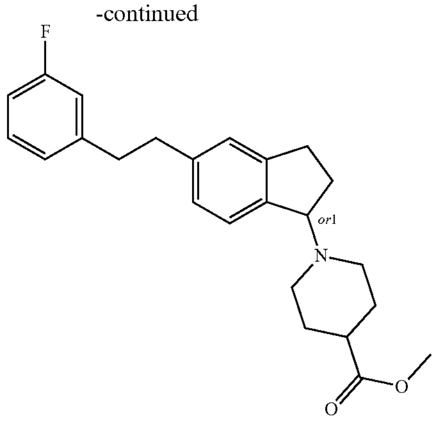

A mixture of the other enantiomer of methyl 1-(5-((3-fluorophenyl)ethynyl)-2,3-dihydro-1H-inden-1-yl)piperidine-4-carboxylate (300 mg, 0.790 mmol, 1.00 equiv) and Pd/C (60 mg, w/w=0.2) in methanol (5.0 mL) was stirred at room temperature for 12 h under an atmosphere of hydrogen. LCMS showed the reaction was complete. The solid was filtered out. The filtrate was concentrated under reduced pressure to give methyl 1-(5-(3-fluorophenethyl)-2,3-dihydro-1H-inden-1-yl)piperidine-4-carboxylate (150 mg, 50%) as an oil. LCMS (ESI, m/z): 382 [M+H]$^+$.

Synthesis of 1-(5-(3-fluorophenethyl)-2,3-dihydro-1H-inden-1-yl)piperidine-4-carboxylic acid

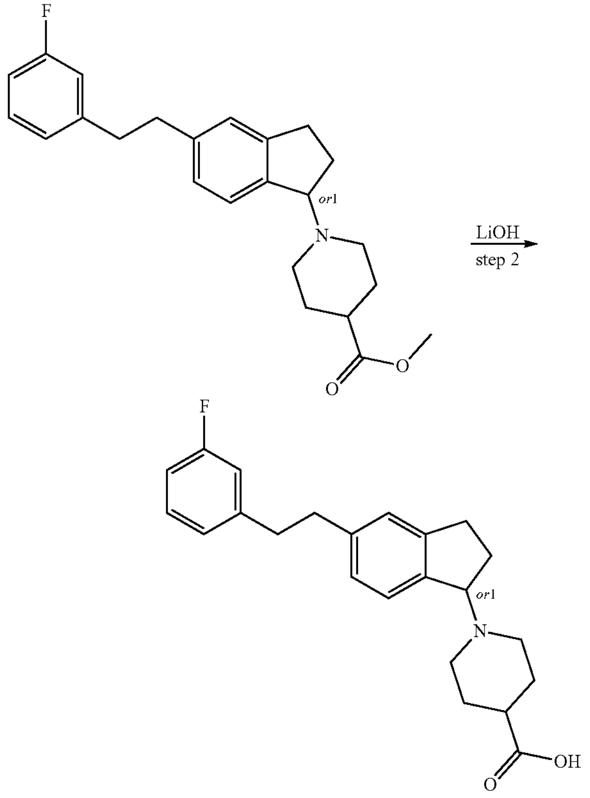

A mixture of methyl 1-(5-(3-fluorophenethyl)-2,3-dihydro-1H-inden-1-yl)piperidine-4-carboxylate (150 mg, 0.390 mmol, 1.00 equiv) and $LiOH \cdot H_2O$ (83 mg, 1.950 mmol, 5.00 equiv) in THF/water (1/1, 4 mL) was stirred at room temperature for 1 h. LCMS showed the reaction was complete. The pH value of the solution was adjusted to 3-4 with 1N HCl. The resulting mixture was concentrated under reduced pressure and the crude product was purified by Prep-HPLC (Column: XBridge Shield RP18 OBD Column, 5 μm, 19*150 mm; Mobile Phase A: Water (10 mM $NH_4HCO_3$+0.1% $NH_3 \cdot H_2O$), Mobile Phase B: ACN; Flow rate: 60 mL/min; Gradient: 18% B to 48% B in 7 min; 210/254 nm; RT: 6.17 min) to give 1-(5-(3-fluorophenethyl)-2,3-dihydro-1H-inden-1-yl)piperidine-4-carboxylic acid (26b, 47.7 mg, 32%) as a solid.

$^1$H NMR (300 MHz, DMSO-$d_6$) δ 12.01 (s, 1H), 7.37-7.14 (m, 1H), 7.14-6.97 (m, 6H), 4.23 (t, J=6.7 Hz, 1H), 2.88-2.62 (m, 7H), 2.44 (s, 1H), 2.33-2.09 (m, 3H), 2.08-1.92 (m, 2H), 1.80-1.69 (m, 2H), 1.61-1.33 (m, 2H).

$^{19}$F NMR (376 MHz, DMSO-$d_6$) δ −116.147.

LCMS (ESI, m/z): 368 [M+H]$^+$. Analytic Conditions: column: Titank C18 Column 3.0*50 mm, 3.0 μm; mobile Phase A: Water+5 mM $NH_4HCO_3$, mobile Phase B: acetonitrile; flow rate: 1.50 mL/min; gradient: 10% B to 95% B in 1.39 min, hold at 95% for 0.7 min, 95% B to 10% B in 0.03 min; 210 nm; RT: 1.131 min.

Example S27. 1-(5-(3-chlorophenethyl)-2,3-dihydro-1H-inden-1-yl)piperidine-4-carboxylic acid (27a and 27b)

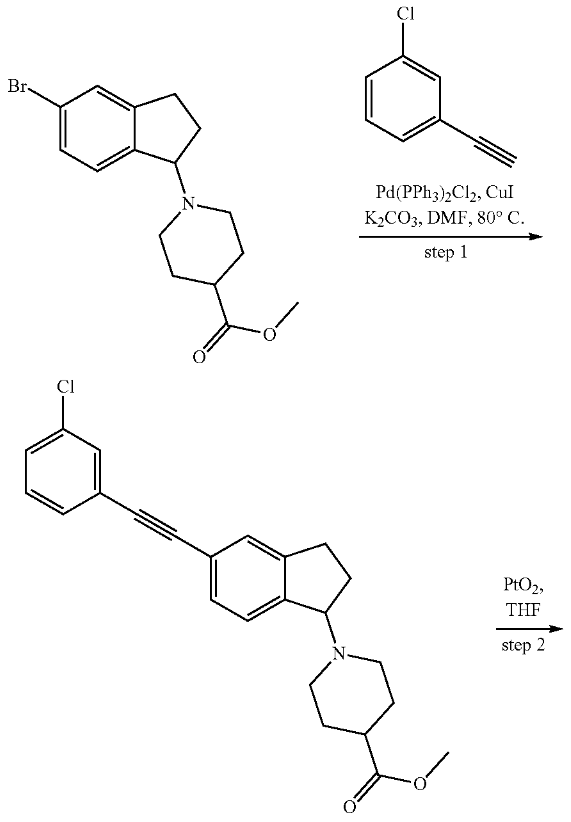

-continued

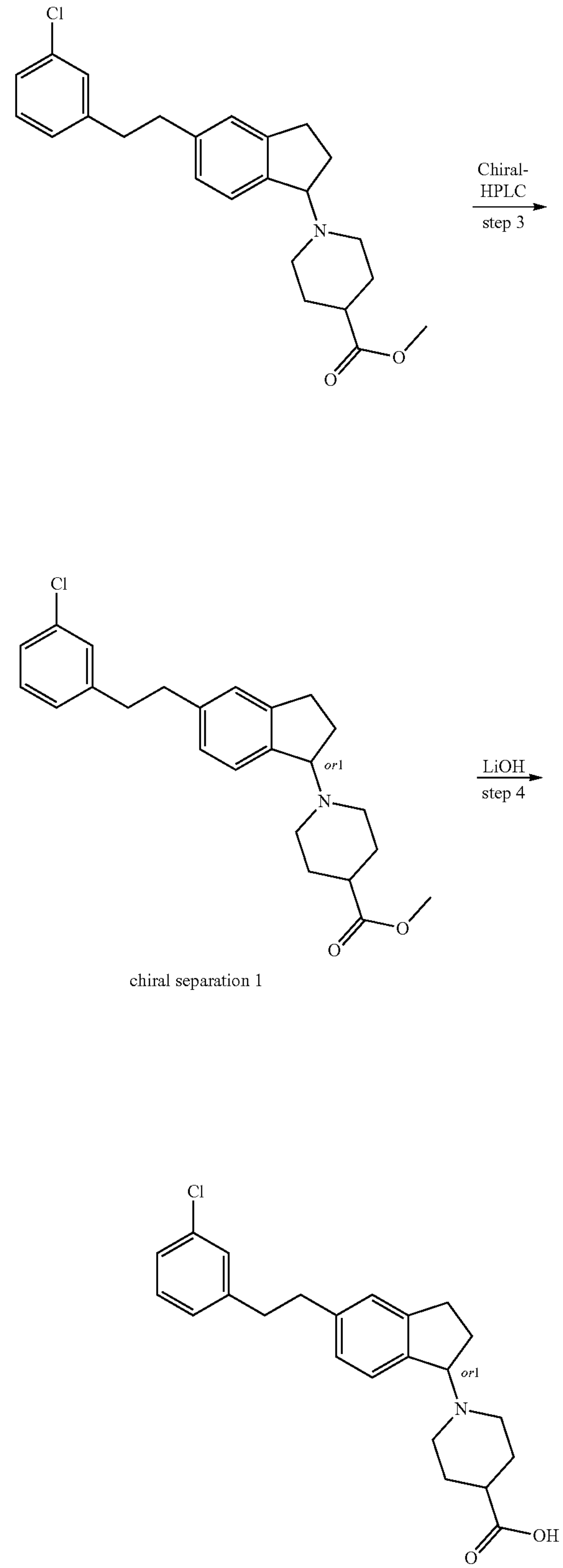

chiral separation 1 chiral separation 1

Synthesis of methyl 1-(5-((3-chlorophenyl)ethynyl)-2,3-dihydro-1H-inden-1-yl)piperidine-4-carboxylate

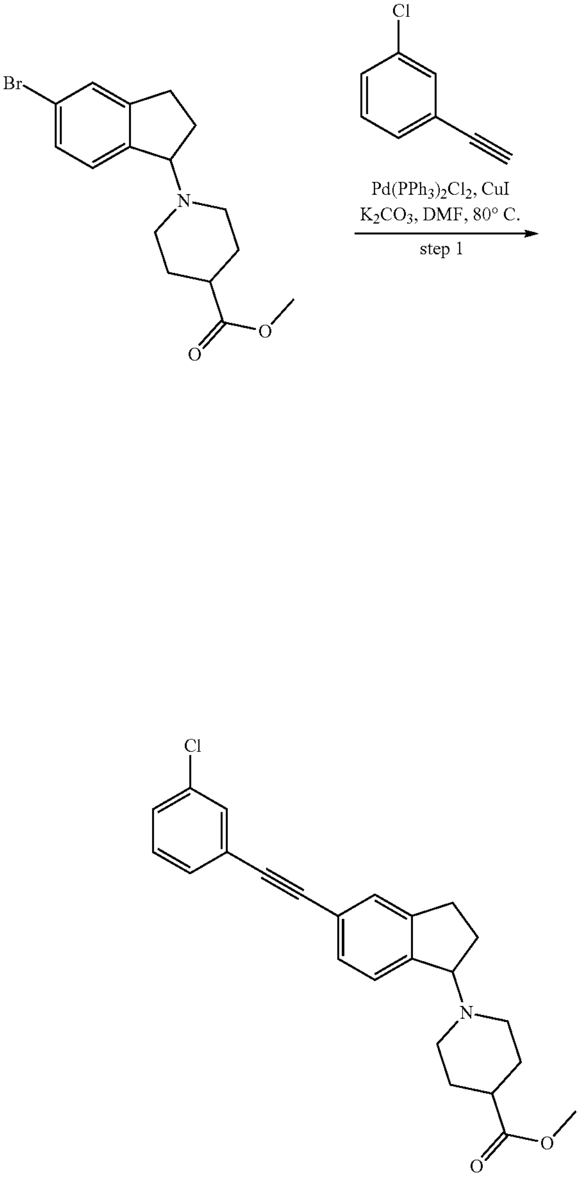

A solution of methyl 1-(5-bromo-2,3-dihydro-1H-inden-1-yl)piperidine-4-carboxylate (1.0 g, 2.96 mmol, 3.00 equiv.), 1-chloro-2-ethynyl-benzene (1.2 g, 8.88 mmol, 3.00 equiv.), $Pd(PPh_3)_2Cl_2$ (207 mg, 0.296 mmol, 0.10 equiv.), CuI (56 mg, 0.296 mmol, 0.10 equiv.) and $K_2CO_3$ (897 mg, 8.88 mmol, 3.00 equiv.) in DMF (10 mL) was stirred at 80° C. for 15 h under $N_2$ atmosphere. LCMS showed the reaction was complete. The resulting solution was diluted with 20 mL of water and extracted with ethyl acetate (3*10 mL). The combined organic layers were washed with brine, dried over anhydrous $Na_2SO_4$ and concentrated under reduced pressure. The residue was purified by flash chromatography on silica gel (PE/EA=30%) to give methyl 1-(5-((3-chlorophenyl)ethynyl)-2,3-dihydro-1H-inden-1-yl)piperidine-4-carboxylate (580 mg, 50%) as an oil. LCMS (ESI, m/z): 394 $[M+H]^+$.

Synthesis of methyl 1-(5-(3-chlorophenethyl)-2,3-dihydro-1H-inden-1-yl)piperidine-4-carboxylate

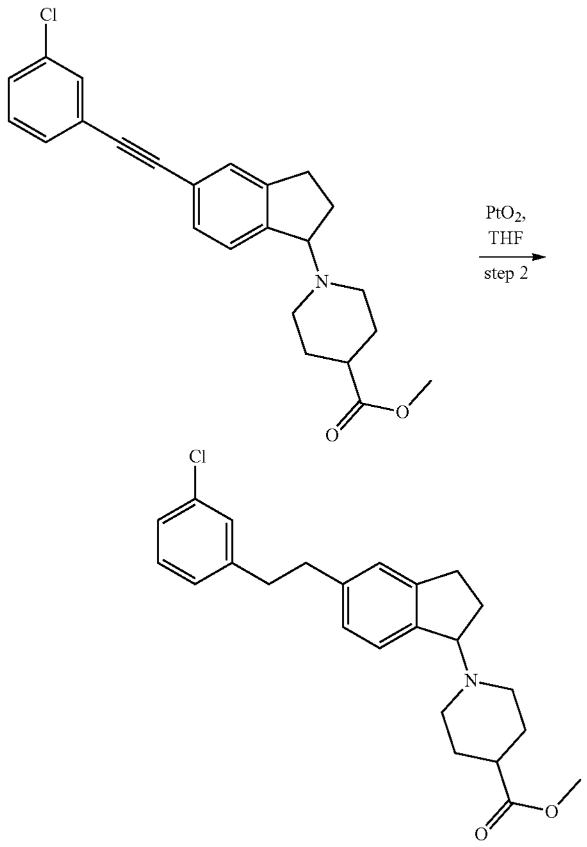

A solution of methyl 1-(5-((3-chlorophenyl)ethynyl)-2,3-dihydro-1H-inden-1-yl)piperidine-4-carboxylate (580 mg, 1.47 mmol, 1.00 equiv.) and $PtO_2$ (110 mg, 0.2 w/w) in THF (3 mL) was stirred at room temperature for 1 h under $H_2$ atmosphere. TLC showed the reaction was complete. The resulting solution was concentrated under reduced pressure. The residue was purified by flash chromatography on silica gel (EA/PE=50%) to give methyl 1-(5-(3-chlorophenethyl)-2,3-dihydro-1H-inden-1-yl)piperidine-4-carboxylate (300 mg, 51%) as an oil. LCMS (ESI, m/z): 398 $[M+H]^+$.

Chiral Separation.

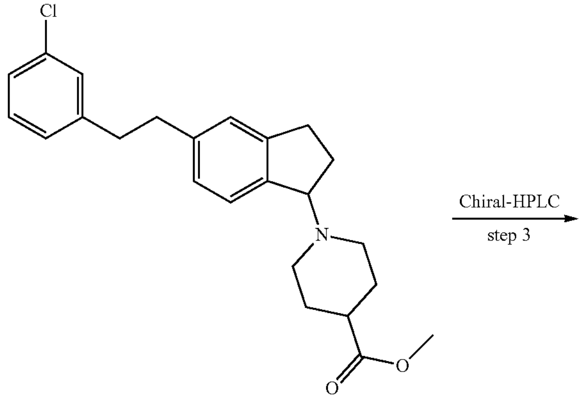

-continued

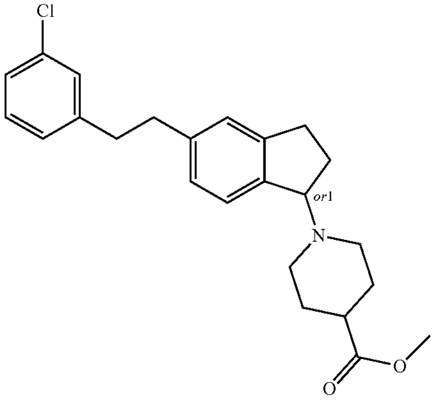

chiral separation 1

The racemic methyl 1-(5-(3-chlorophenethyl)-2,3-dihydro-1H-inden-1-yl)piperidine-4-carboxylate (300 mg) was separated by chiral-HPLC (Column: CHIRALPAK IG, 2*25 cm, 5 μm; Mobile Phase A: Hex (8 mmol/L $NH_3$-MeOH)-HPLC, Mobile Phase B: EtOH-HPLC; Flow rate: 20 mL/min; Gradient: 20% B to 20% B in 13 min; 220/254 nm; RT1: 7.219 min; RT2: 8.912 min) to afford the chiral separation 1 isomer (110 mg, 100% e.e.) as an oil. LCMS (ESI, m/z): 398 $[M+H]^+$.

Synthesis of 1-(5-(3-chlorophenethyl)-2,3-dihydro-1H-inden-1-yl)piperidine-4-carboxylic acid

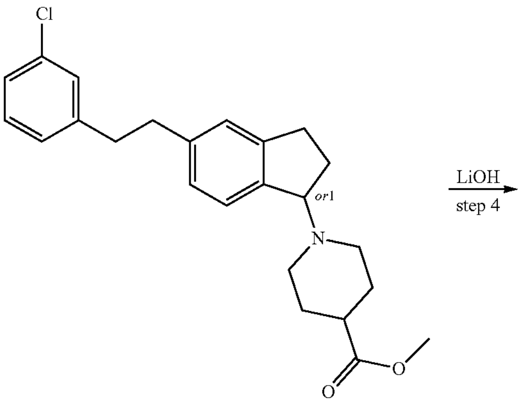

chiral separation 1

-continued

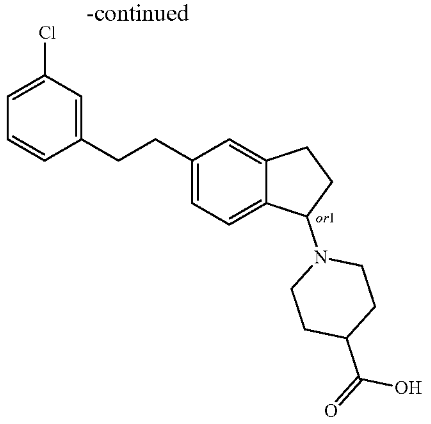

chiral separation 1

-continued

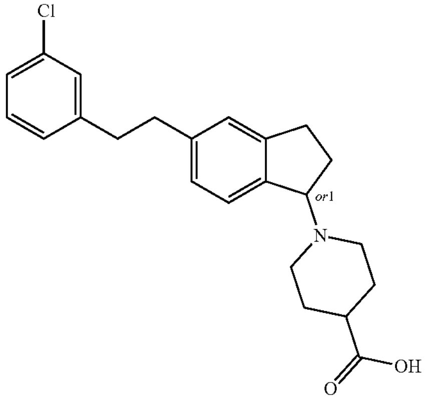

chiral separation 2

A solution of methyl 1-(5-(3-chlorophenethyl)-2,3-dihydro-1H-inden-1-yl)piperidine-4-carboxylate (chiral separation 1, 110 mg, 0.280 mmol, 1.00 equiv.) and LiOH (20 mg, 0.830 mmol, 3.00 equiv.) in THF (2.0 mL) and water (1.0 mL) was stirred at room temperature for 1 h. LCMS showed the reaction was complete. The resulting solution was purified by prep-HPLC (Column: YMC-Actus Triart C18, 30*250 mm, 5 μm; Mobile Phase A: water (10 mmoL/L $NH_4HCO_3$+0.1% $NH_3 \cdot H_2O$), Mobile Phase B: ACN; Flow rate: 60 mL/min; Gradient: 25% B to 55% B in 7 min; 254/210 nm; RT: 6.28 min) to give one enantiomer of 1-(5-(3-chlorophenethyl)-2,3-dihydro-1H-inden-1-yl)piperidine-4-carboxylic acid (27a, 47.5 mg, 45%) as a solid.

LCMS (ESI, m/z): 384$[M+H]^+$. Analytic Conditions: EVO C18, 3.0*50 mm, 2.6 m; Mobile Phase A: Water/5mMNH$_4$HCO$_3$. Mobile Phase B: ACN; Flow rate: 1.20 mL/min; Gradient: 10% B to 95% B in 2.0 min, hold at 95% B for 0.6 min, 95% B to 10% B in 0.15 min; 210 nm; RT: 1.167 min.

$^1$H NMR (300 MHz, DMSO-$d_6$) δ 7.33-7.19 (m, 4H), 7.16-7.14 (m, 1H), 7.08-7.02 (m, 2H), 4.25-4.20 (m, 1H), 2.85-2.65 (m, 7H), 2.50-2.44 (m, 1H), 2.27-2.08 (m, 3H), 2.01-1.93 (m, 2H), 1.82-1.72 (m, 2H), 1.63-1.43 (m, 2H).

Synthesis of 1-(5-(3-chlorophenethyl)-2,3-dihydro-1H-inden-1-yl)piperidine-4-carboxylic acid

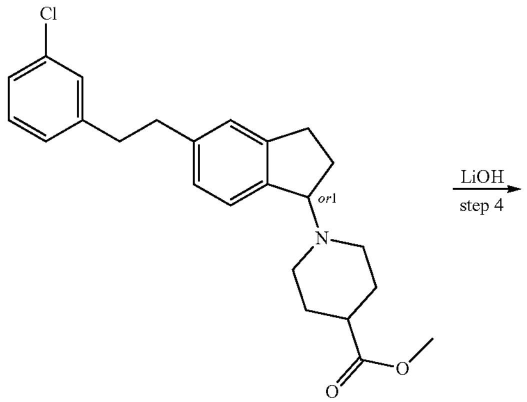

chiral separation 2

A solution of the other enantiomer of methyl 1-(5-(3-chlorophenethyl)-2,3-dihydro-1H-inden-1-yl)piperidine-4-carboxylate (chiral separation 2, 150 mg, 0.377 mmol, 1.00 equiv.) and LiOH (26 mg, 1.13 mmol, 3.00 equiv.) in THF (2.0 mL) and water (1.0 mL) was stirred at room temperature for 1 h. LCMS showed the reaction was complete. The resulting solution was purified by prep-HPLC (Column: YMC-Actus Triart C18, 30*250 mm, 5 μm; Mobile Phase A: water (10 mmoL/L $NH_4HCO_3$+0.1% $NH_3 \cdot H_2O$), Mobile Phase B: ACN; Flow rate: 60 mL/min; Gradient: 25% B to 55% B in 7 min; 254/210 nm; RT: 6.28 min) to give the corresponding enantiomer of 1-(5-(3-chlorophenethyl)-2,3-dihydro-1H-inden-1-yl)piperidine-4-carboxylic acid (27b, 48.0 mg, 33%) as a solid.

LCMS (ESI, m/z): 384 $[M+H]^+$. Analytic Conditions: EVO C18, 3.0*50 mm, 2.6 μm; Mobile Phase A: Water/5 mM $NH_4HCO_3$. Mobile Phase B: ACN; Flow rate: 1.20 mL/min; Gradient: 10% B to 95% B in 2.0 min, hold at 95% B for 0.6 min, 95% B to 10% B in 0.15 min; 210 nm; RT: 1.151 min.

$^1$H NMR (300 MHz, DMSO-$d_6$) δ 7.33-7.14 (m, 5H), 7.08-7.02 (m, 2H), 4.26-4.21 (m, 1H), 2.87-2.65 (m, 7H), 2.50-2.45 (m, 1H), 2.27-2.08 (m, 3H), 2.01-1.93 (m, 2H), 1.82-1.72 (m, 2H), 1.63-1.43 (m, 2H).

Example S28. 1-(5-(2,6-difluorophenethyl)-2,3-dihydro-1H-inden-1-yl)piperidine-4-carboxylic acid (28a and 28b)

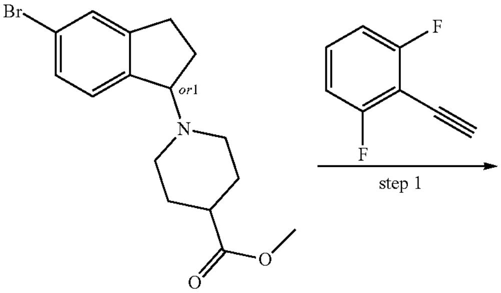

-continued

-continued

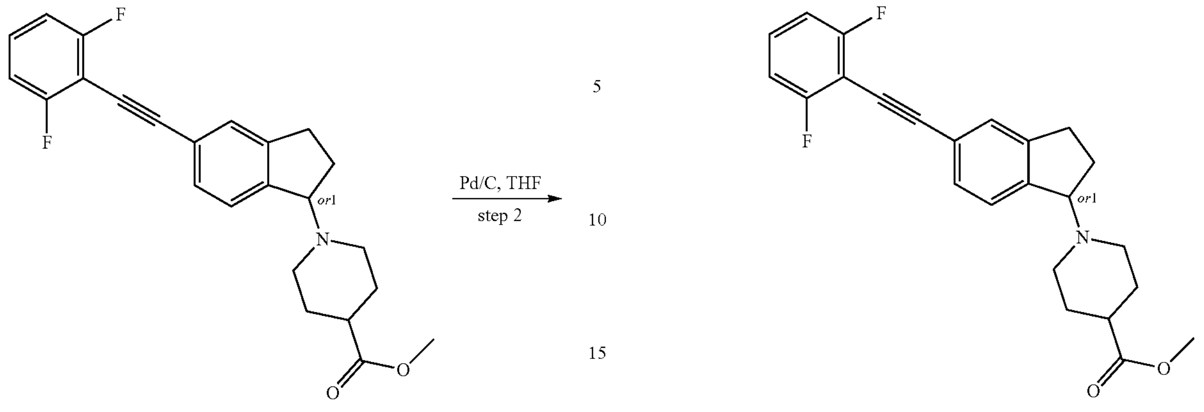

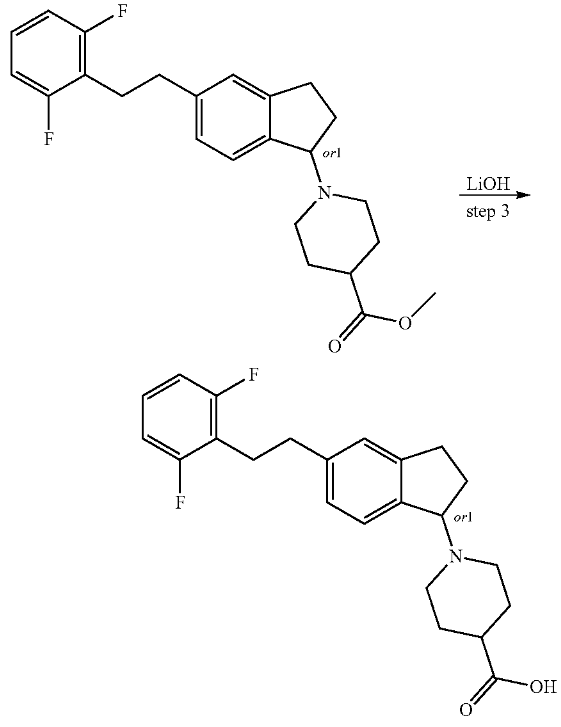

chiral separation 1

Synthesis of methyl 1-(5-((2,6-difluorophenyl)ethynyl)-2,3-dihydro-1H-inden-1-yl)piperidine-4-carboxylate

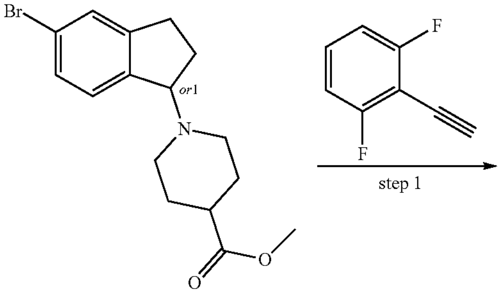

To a solution of one enantiomer of methyl 1-(5-bromo-2,3-dihydro-1H-inden-1-yl)piperidine-4-carboxylate (300 mg, 0.890 mmol, 1.00 equiv.) in DMF (4.0 mL) were added $K_2CO_3$ (367 mg, 2.660 mmol, 3.00 equiv.), $Pd(PPh_3)_2Cl_2$ (124 mg, 0.180 mmol, 0.200 equiv.) and CuI (84 mg, 0.440 mmol, 0.050 equiv.) at room temperature. The resulting solution was stirred at 60° C. for 12 h under nitrogen atmosphere. LCMS showed the reaction was complete. The reaction mixture was diluted with ethyl acetate (30 mL) and filtered. The filtration was washed with brine and dried over anhydrous $Na_2SO_4$ and concentrated under reduced pressure. The residue was purified by flash chromatography on silica gel with ethyl acetate/petroleum ether (1/2) to give methyl 1-(5-((2,6-difluorophenyl)ethynyl)-2,3-dihydro-1H-inden-1-yl)piperidine-4-carboxylate (300 mg, 850%) as a semi-solid. LCMS (ESI, m/z). 396 $[M+H]^+$.

Synthesis of methyl 1-(5-(2,6-difluorophenethyl)-2,3-dihydro-1H-inden-1-yl)piperidine-4-carboxylate

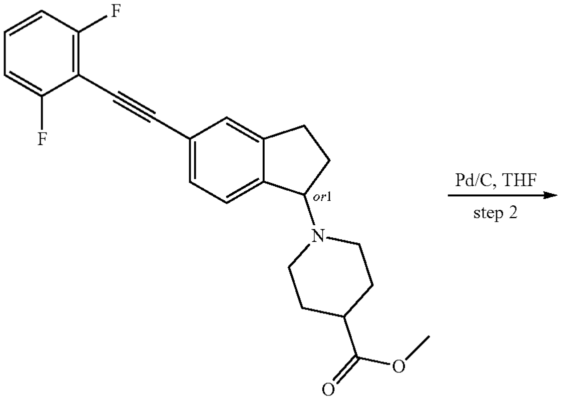

-continued

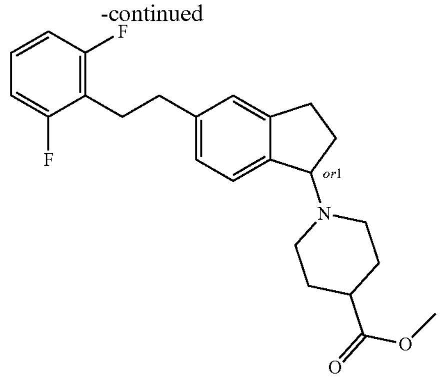

To a solution of methyl 1-(5-((2,6-difluorophenyl)ethynyl)-2,3-dihydro-1H-inden-1-yl)piperidine-4-carboxylate (300 mg, 0.760 mmol, 1.00 equiv) in methanol (10 mL) was added Pd/C (300 mg, 1.00 w/w). The reaction mixture was stirred at room temperature for 10 h under hydrogen atmosphere. LCMS showed the reaction was complete. The resulting mixture was filtered through Celite and the filtration was concentrated under reduced pressure to afford crude product methyl 1-(5-(2,6-difluorophenethyl)-2,3-dihydro-1H-inden-1-yl)piperidine-4-carboxylate (200 mg) as a solid, which was used in the next step without further purification. LCMS (ESI, m/z): 400 $[M+H]^+$.

Synthesis of 1-(5-(2,6-difluorophenethyl)-2,3-dihydro-1H-inden-1-yl)piperidine-4-carboxylic acid

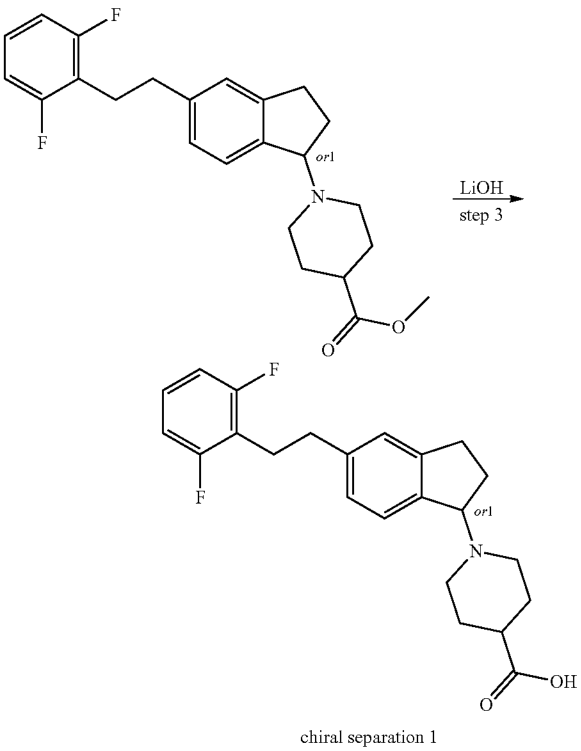

A solution of methyl 1-(5-(2,6-difluorophenethyl)-2,3-dihydro-1H-inden-1-yl)piperidine-4-carboxylate (150 mg, 0.380 mmol, 1.00 equiv), $LiOH·H_2O$ (47.2 mg, 1.13 mmol, 3.00 equiv.) in THF (1.0 mL) and water (1.0 mL) was stirred at room temperature for 1 h. LCMS showed the reaction was complete. The solution was adjusted to pH 4-5 with 1N HCl, and then was concentrated under vacuum. The residue was purified by Prep-HPLC (10 mmol/L $NH_4HCO_{3+0.1}$% $NH_3·H_2O$), Mobile Phase B: ACN; Flow rate: 60 mL/min; Gradient: 25% B to 45% B in 7 min; 210/254 nm; RT: 4.77 min) to afford one enantiomer of 1-(5-(2,6-difluorophenethyl)-2,3-dihydro-1H-inden-1-yl)piperidine-4-carboxylic acid (28a, 60.3 mg, 41%) as a solid.

$^1H$ NMR (300 MHz, Methanol-$d_4$) δ 7.43 (d, J=7.5 Hz, 1H), 7.24-7.19 (m, 1H), 7.16 (s, 1H), 7.11 (d, J=7.8 Hz, 1H), 6.89 (t, J=7.8 Hz, 2H), 4.82-4.77 (m, 1H), 3.37-3.35 (m, 1H), 3.15-3.04 (m, 2H), 2.98-2.83 (m, 7H), 2.46-2.33 (m, 3H), 2.10-1.80 (m, 4H).

$^{19}F$ NMR (282 MHz, Methanol-$d_4$) δ −118.08.

LCMS (ESI, m/z): 386 $[M+H]^+$. Analytic Conditions: column: Titank C18 Column 3.0*50 mm, 2.6 m; mobile Phase A: Water/5 mM $NH_4HCO_3$, mobile Phase B: Acetonitrile; flow rate: 1.20 mL/min; gradient: 10% B to 95% B in 1.40 min, hold at 95% for 0.80 min, 95% B to 10% B in 0.03 min; 254 nm; RT: 1.157 min.

Compound 28b was obtained following the same procedures as described above with the other enantiomer of methyl 1-(5-bromo-2,3-dihydro-1H-inden-1-yl)piperidine-4-carboxylate.

Example S29. 2-(5-(2,6-dichlorophenethyl)-2,3-dihydro-1H-inden-1-yl)-2-azaspiro[3.3]heptane-6-carboxylic acid (29)

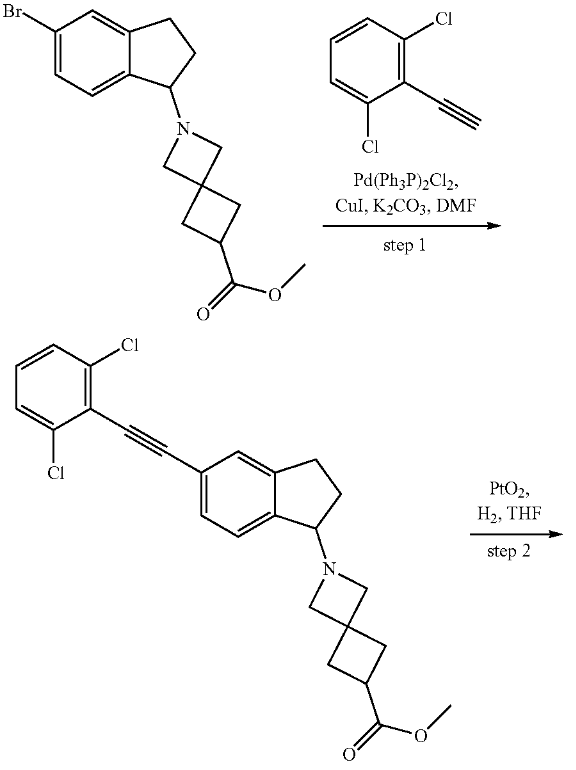

-continued

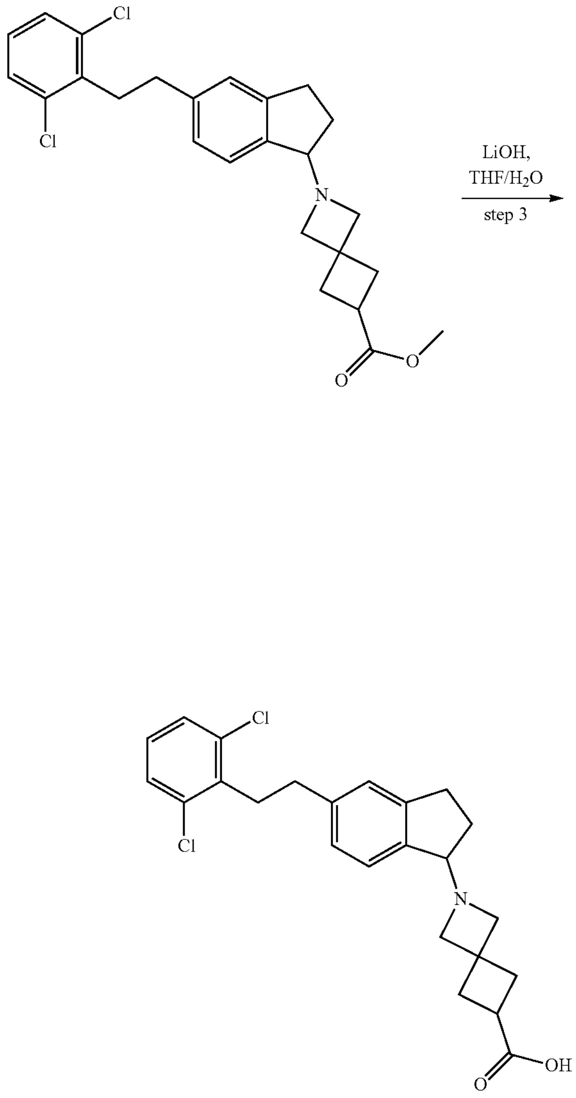

Synthesis of methyl 2-(5-((2,6-dichlorophenyl)ethynyl)-2,3-dihydro-1H-inden-1-yl)-2-azaspiro[3.3]heptane-6-carboxylate

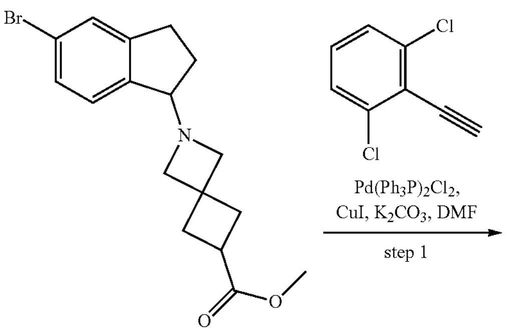

-continued

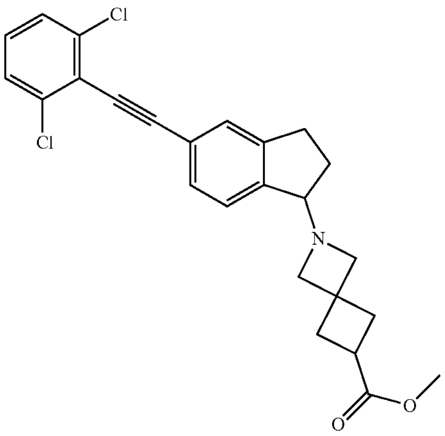

A mixture of methyl 2-(5-bromo-2,3-dihydro-1H-inden-1-yl)-2-azaspiro[3.3]heptane-6-carboxylate (400 mg, 1.14 mmol, 1.00 equiv.), 1,3-dichloro-2-ethynyl-benzene (293 mg, 1.71 mmol, 1.50 equiv.), $Pd(PPh_3)_2Cl_2$ (80 mg, 0.110 mmol, 0.10 equiv.), CuI (22 mg, 0.110 mmol, 0.10 equiv.) and $K_2CO_3$ (474 mg, 3.430 mmol, 3.00 equiv.) in DMF (10 mL) was stirred at 80° C. for 15 h under $N_2$ atmosphere. LCMS showed the reaction was complete. The resulting solution was diluted with 20 mL of water, then extracted with ethyl acetate (3×20 mL). The combined organic layers were washed with brine, dried over anhydrous $Na_2SO_4$ and concentrated under reduced pressure. The residue was purified by flash chromatography on silica gel (EA/PE=50%) to give methyl 2-(5-((2,6-dichlorophenyl)ethynyl)-2,3-dihydro-1H-inden-1-yl)-2-azaspiro[3.3]heptane-6-carboxylate (200 mg, 39.8%) as an oil. LCMS (ESI, m/z): 440 $[M+H]^+$.

Synthesis of methyl 2-(5-(2,6-dichlorophenethyl)-2,3-dihydro-1H-inden-1-yl)-2-azaspiro[3.3]heptane-6-carboxylate

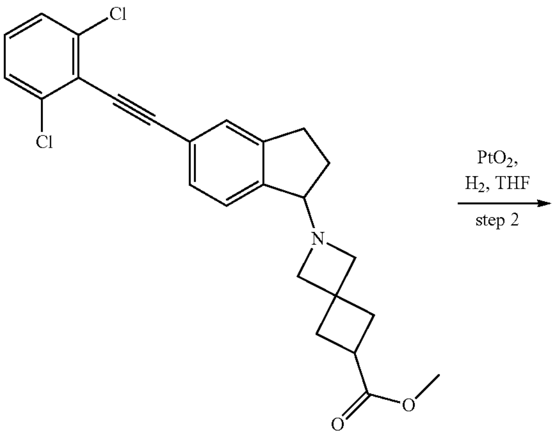

-continued

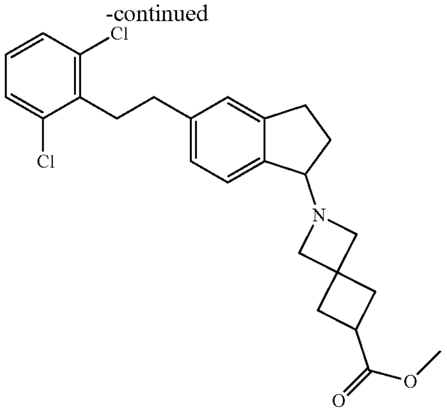

A mixture of methyl 2-(5-((2,6-dichlorophenyl)ethynyl)-2,3-dihydro-1H-inden-1-yl)-2-azaspiro[3.3]heptane-6-carboxylate (150 mg, 0.350 mmol, 1.00 equiv.) and $PtO_2$ (15 mg, 0.070 mmol, 0.2 w/w) in THF (5.0 mL) was stirred at room temperature for 15 h under $H_2$ atmosphere. LCMS showed the reaction was complete. The reaction mixture was filtered and the filtrate was concentrated under reduced pressure. The obtained crude product methyl 2-(5-(2,6-dichlorophenethyl)-2,3-dihydro-1H-inden-1-yl)-2-azaspiro[3.3]heptane-6-carboxylate was used directly for the next step without further purification. LCMS (ESI, m/z): 444 $[M+H]^+$.

Synthesis of 2-(5-(2,6-dichlorophenethyl)-2,3-dihydro-1H-inden-1-yl)-2-azaspiro[3.3]heptane-6-carboxylic acid

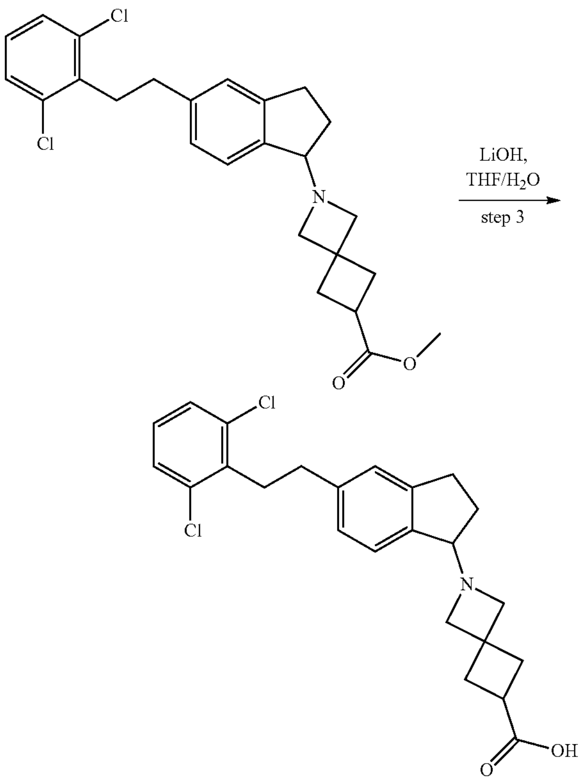

A solution of methyl 2-(5-(2,6-dichlorophenethyl)-2,3-dihydro-1H-inden-1-yl)-2-azaspiro[3.3]heptane-6-carboxylate (30 mg, 0.070 mmol, 1.00 equiv.) and LiOH (5 mg, 0.210 mmol, 3.00 equiv.) in THF (1.0 mL) and water (1.0 mL) was stirred at room temperature for 1 h. LCMS showed the reaction was complete. The resulting solution was acidified to pH 5-6 with 2N HCl and concentrated under reduced pressure. The residue was purified by prep-HPLC (Column: XB ridge Prep OBD C18 Column, 19*250 mm, 5 μm; Mobile Phase A: water (10 mM $NH_4HCO_3$), Mobile Phase B: ACN; Flow rate: 60 mL/min; Gradient: 32% B to 53% B in 7 min, hold at 53% B for 1 min; 254/210 nm; RT: 7.92 min) to give the desired product 2-(5-(2,6-dichlorophenethyl)-2,3-dihydro-1H-inden-1-yl)-2-azaspiro[3.3]heptane-6-carboxylic acid (29, 10.2 mg, 34%) as a solid.

LCMS (ESI, m/z): 430 $[M+H]^+$. Analytic Conditions: Poroshell EVO C18, 3.0*50 mm, 2.6 μm; Mobile Phase A: water/5 mM $NH_4HCO_3$, Mobile Phase B: ACN; Flow rate: 1.20 mL/min; Gradient: 10% B to 95% B in 2.0 min, hold at 95% B for 0.6 min, 95% B to 10% B in 0.15 min; 210 nm; RT: 1.219 min.

$^1H$ NMR (400 MHz, DMSO-$d_6$) δ 7.49 (d, J=8.0 Hz, 2H), 7.30 (t, J=8.0 Hz, 1H), 7.18 (d, J=7.6 Hz, 1H), 7.12 (s, 1H), 7.03 (d, J=7.6 Hz, 1H), 3.66-3.64 (m, 1H), 3.27-3.24 (m, 1H), 3.17-3.047 (m, 4H), 3.02 (d, J=7.2 Hz, 1H), 2.93-2.85 (m, 2H), 2.75-2.67 (m, 3H), 2.27-2.19 (m, 4H), 1.99-1.94 (m, 1H), 1.79-1.73 (m, 1H).

Example S30. 1-(5-(3-chloro-4-cyclopropylphenyl)-2,3-dihydro-1H-inden-1-yl)azetidine-3-carboxylic acid (30a and 30b)

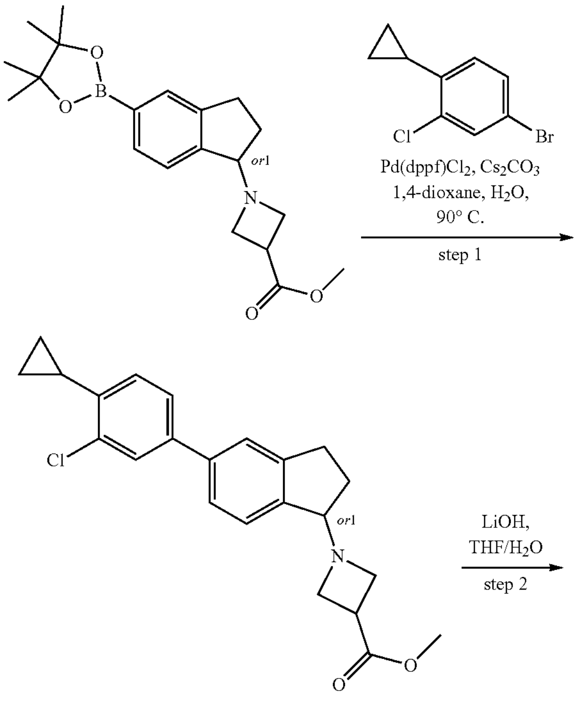

-continued

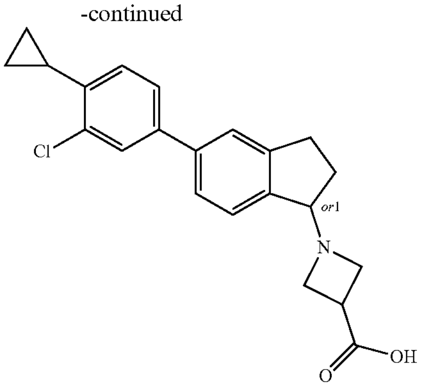

Synthesis of methyl 1-(5-(3-chloro-4-cyclopropylphenyl)-2,3-dihydro-1H-inden-1-yl)-azetidine-3-carboxylate

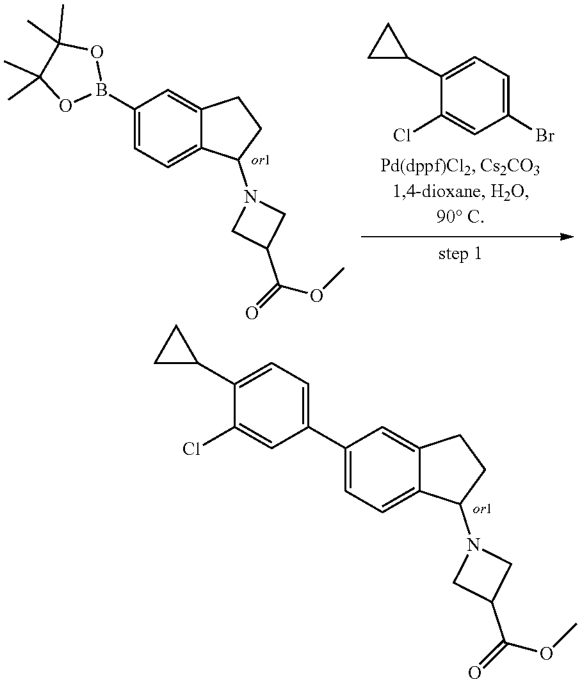

A mixture of a single enantiomer of methyl 1-(5-(4,4,5,5-tetramethyl-1,3,2-dioxaborolan-2-yl)-2,3-dihydro-1H-inden-1-yl)azetidine-3-carboxylate (200 mg, 0.560 mmol, 1.00 equiv.), 4-bromo-2-chloro-1-cyclopropyl-benzene (120 mg, 0.560 mmol, 1.00 equiv.), $Pd(dppf)Cl_2$ (82 mg, 0.112 mmol, 0.20 equiv.) and $Cs_2CO_3$ (548 mg, 1.68 mmol, 3.00 equiv.) in 1,4-dioxane (5.0 mL) and water (0.5 mL) was stirred at 90° C. for 2 h under $N_2$ atmosphere. LCMS showed the reaction was complete. The resulting solution was diluted with 20 mL of water, then extracted with ethyl acetate (3*20 mL). The combined organic layers were washed with brine, and dried over anhydrous $Na_2SO_4$ and concentrated under reduced pressure. The residue was purified by flash chromatography on silica gel (EA/PE=30%) to give a single enantiomer of methyl 1-(5-(3-chloro-4-cyclopropylphenyl)-2,3-dihydro-1H-inden-1-yl)azetidine-3-carboxylate (120 mg, 56%) as an oil. LCMS (ESI, m/z): 382 $[M+H]^+$.

Synthesis of 1-(5-(3-chloro-4-cyclopropylphenyl)-2,3-dihydro-1H-inden-1-yl)azetidine-3-carboxylic acid

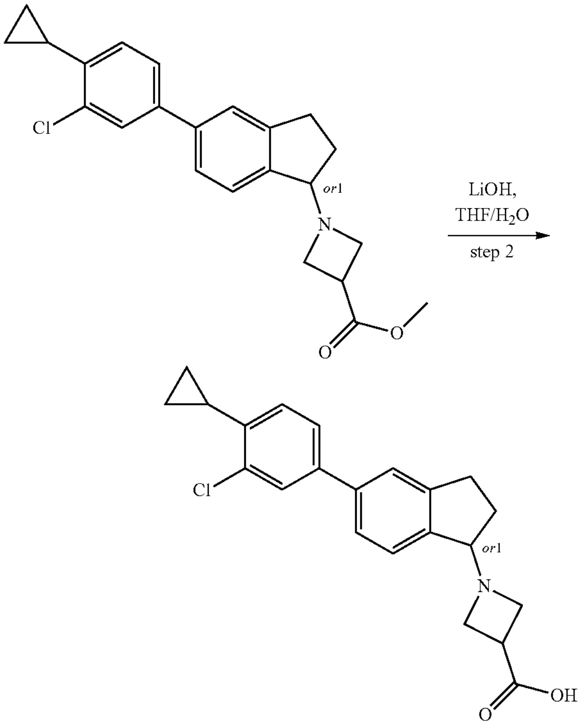

A solution of a single enantiomer of methyl 1-(5-(3-chloro-4-cyclopropylphenyl-2,3-dihydro-1H-inden-1-yl) azetidine-3-carboxylate (120 mg, 0.360 mmol, 1.00 equiv.) and LiOH (26 mg, 1.08 mmol, 3.00 equiv.) in THF (2.0 mL) and water (1.0 mL) was stirred at room temperature for 15 h. LCMS showed the reaction was complete. The resulting solution was acidified to PH 5~6 with 2N HCl and concentrated under reduced pressure. The residue was purified by prep-HPLC (Column: YMC-Actus Triart C18, 30*250, 5 μm; Mobile Phase A: water (10 mM $NH_4HCO_3$+0.1% $NH_3 \cdot H_2O$), Mobile Phase B: ACN; Flow rate: 60 mL/min; Gradient: 20% B to 50% B in 7 min; 254/210 nm; RT: 7.00 min) to give a single enantiomer of 1-(5-(3-chloro-4-cyclopropylphenyl)-2,3-dihydro-1H-inden-1-yl)azetidine-3-carboxylic acid (30a, 23.5 mg, 20%) as a solid.

LCMS (ESI, m/z): 368 $[M+H]^+$. Analytic Conditions: EVO C18, 3.0*50 mm, 2.6 μm; Mobile Phase A: Water/5 mM $NH_4HCO_3$. Mobile Phase B: ACN; Flow rate: 1.20 mL/min; Gradient: 10% B to 95% B in 2.0 min, hold at 95% B for 0.6 min, 95% B to 10% B in 0.15 min; 254 nm; RT: 1.217 min.

$^1H$ NMR (400 MHz, DMSO-$d_6$) δ 7.67 (d, J=2.0 Hz, 1H), 7.53-7.50 (m, 2H), 7.43 (dd, J=8.0, 2.0 Hz, 1H), 7.35 (d, J=8.0 Hz, 1H), 7.09 (d, J=8.0 Hz, 1H), 3.84 (s, 1H), 3.55-3.48 (m, 2H), 3.24-3.15 (m, 3H), 3.01-2.93 (m, 1H), 2.83-2.76 (m, 1H), 2.20-2.14 (m, 1H), 2.10-2.01 (m, 1H), 1.89-1.82 (m, 1H), 1.06-0.97 (m, 2H), 0.78-0.72 (m, 2H).

Synthesis of 1-(5-(3-chloro-4-cyclopropylphenyl)-2,3-dihydro-1H-inden-1-yl)azetidine-3-carboxylic acid

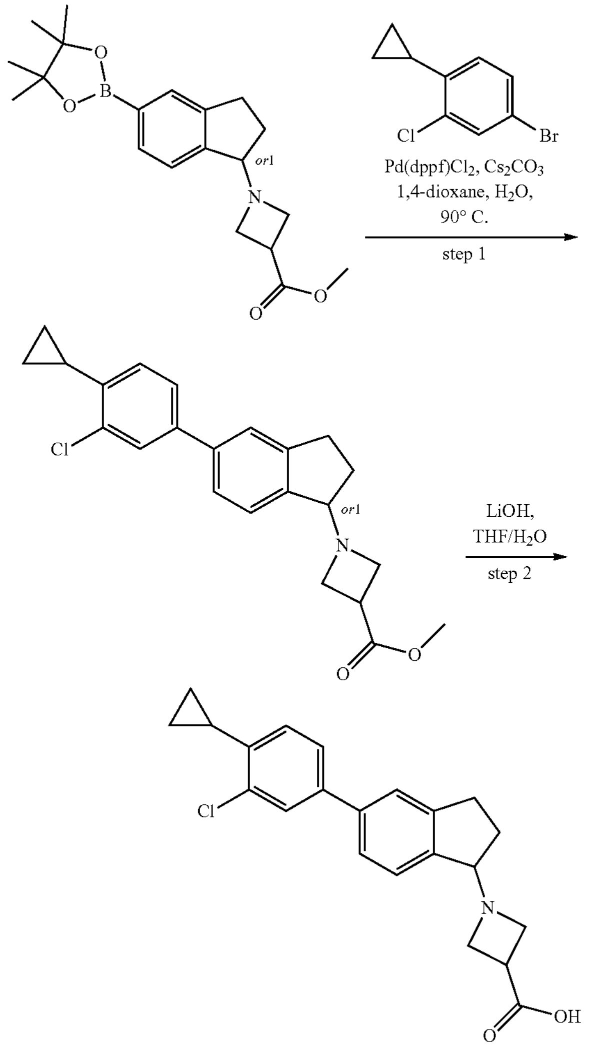

Synthesis of methyl 1-(5-(3-chloro-4-cyclopropylphenyl)-2,3-dihydro-1H-inden-1-yl)azetidine-3-carboxylate

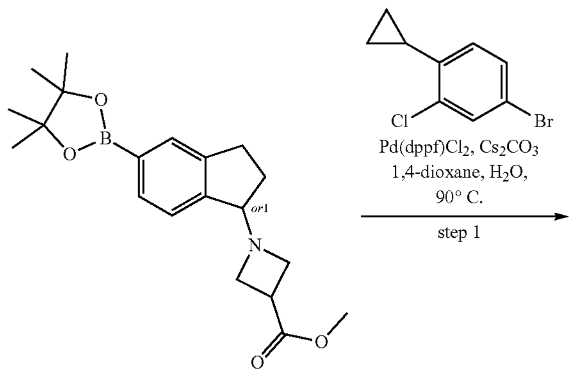

-continued

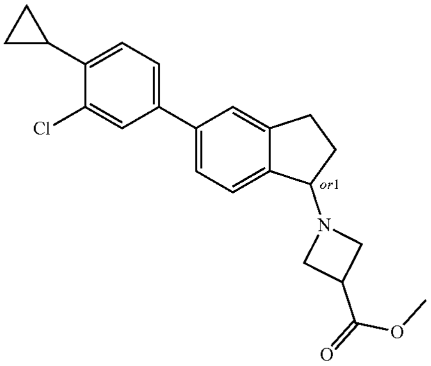

A mixture of the other enantiomer of methyl 1-(5-(4,4,5,5-tetramethyl-1,3,2-dioxaborolan-2-yl)-2,3-dihydro-1H-inden-1-yl)azetidine-3-carboxylate (200 mg, 0.560 mmol, 1.00 equiv.), 4-bromo-2-chloro-1-cyclopropyl-benzene (120 mg, 0.560 mmol, 1.00 equiv.), $Pd(dppf)Cl_2$ (82 mg, 0.112 mmol, 0.20 equiv.) and $Cs_2CO_3$ (548 mg, 1.68 mmol, 3.00 equiv.) in 1,4-dioxane (5.0 mL) and water (0.5 mL) was stirred at 90° C. for 2 h under $N_2$ atmosphere. LCMS showed that the reaction was complete. The reaction mixture was diluted with 20 mL of water, then extracted with ethyl acetate (3*20 mL). The combined organic layers were washed with brine, and dried over anhydrous $Na_2SO_4$ and concentrated under reduced pressure. The residue was purified by flash chromatography on silica gel (EA/PE=30%) to give the other enantiomer of methyl 1-(5-(3-chloro-4-cyclopropylphenyl)-2,3-dihydro-1H-inden-1-yl)azetidine-3-carboxylate (120 mg, 64%) as an oil. LCMS (ESI, m/z): 382 $[M+H]^+$.

Synthesis of 1-(5-(3-chloro-4-cyclopropylphenyl)-2,3-dihydro-1H-inden-1-yl)azetidine-3-carboxylic acid

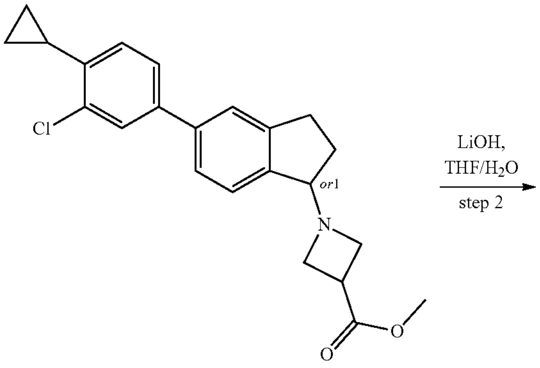

-continued

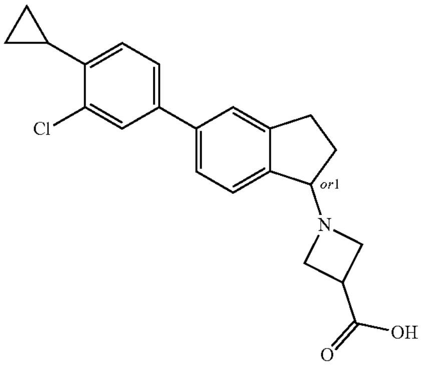

A solution of the other enantiomer of methyl 1-(5-(3-chloro-4-cyclopropylphenyl)-2,3-dihydro-1H-inden-1-yl)azetidine-3-carboxylate (120 mg, 0.360 mmol, 1.00 equiv.) and LiOH (26 mg, 1.08 mmol, 3.00 equiv.) in THF (2.0 mL) and water (1.0 mL) was stirred at room temperature for 15 h. LCMS showed the reaction was complete. The resulting solution was acidified to pH 5~6 with 2N HCl and concentrated under reduced pressure. The residue was purified by prep-HPLC (Column: YMC-Actus Triart C18, 30*250 mm, 5 μm; Mobile Phase A: water (10 mM $NH_4HCO_3$+0.1% $NH_3 \cdot H_2O$), Mobile Phase B: ACN; Flow rate: 60 mL/min; Gradient: 20% B to 50% B in 7 min; 254/210 nm; RT: 7.00 min) to give the other enantiomer of 1-(5-(3-chloro-4-cyclopropylphenyl)-2,3-dihydro-1H-inden-1-yl)azetidine-3-carboxylic acid (30b, 30.7 mg, 24.0%) as a solid.

LCMS (ESI, m/z): 368 $[M+H]^+$. Analytic Conditions: EVO C18, 3.0*50 mm, 2.6 μm; Mobile Phase A: Water/5 mM $NH_4HCO_3$. Mobile Phase B: ACN; Flow rate: 1.20 mL/min; Gradient: 10% B to 95% B in 2.0 min, hold at 95% B for 0.6 min, 95% B to 10% B in 0.15 min; 254 nm; RT: 1.217 min.

$^1H$ NMR (400 MHz, DMSO-$d_6$) δ 7.67 (d, J=2.0 Hz, 1H), 7.52-7.50 (m, 2H), 7.43 (dd, J=8.0, 2.0 Hz, 1H), 7.34 (d, J=8.0 Hz, 1H), 7.09 (d, J=8.0 Hz, 1H), 3.81-3.78 (m, 1H), 3.55-3.48 (m, 2H), 3.24-3.15 (m, 3H), 2.98-2.92 (m, 1H), 2.82-2.75 (m, 1H), 2.20-2.13 (m, 1H), 2.08-1.99 (m, 1H), 1.85-1.81 (m, 1H), 1.05-1.00 (m, 2H), 0.76-0.72 (m, 2H).

Example S31. 1-(5-(4-cyclopropyl-3-fluorophenyl)-2,3-dihydro-1H-inden-1-yl)azetidine-3-carboxylic acid (31a and 31b)

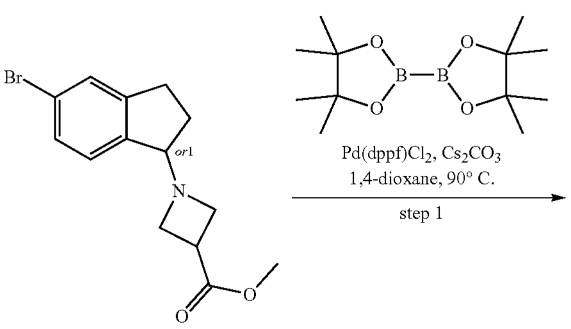

-continued

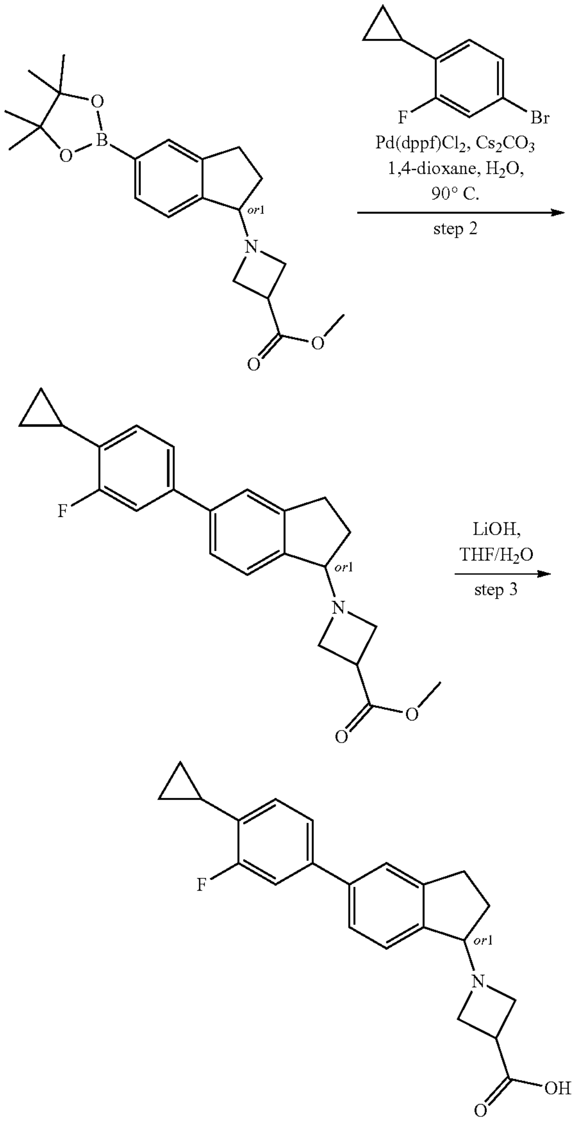

Synthesis of methyl 1-(5-(4,4,5,5-tetramethyl-1,3,2-dioxaborolan-2-yl)-2,3-dihydro-1H-inden-1-yl)azetidine-3-carboxylate

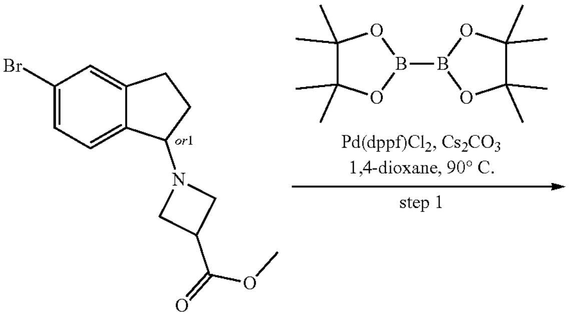

-continued

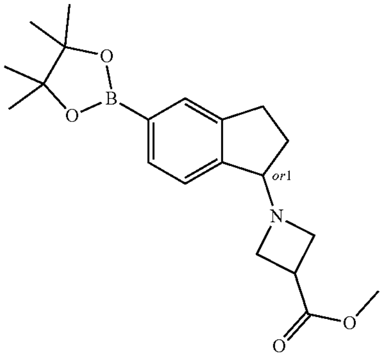

A mixture of one enantiomer of methyl 1-(5-bromo-2,3-dihydro-1H-inden-1-yl)azetidine-3-carboxylate (1.0 g, 3.22 mmol, 1.00 equiv.), bis(pinacolato)diboron (1.23 g, 4.84 mmol, 1.00 equiv.), Pd(dppf)$Cl_2$ (472 mg, 0.640 mmol, 0.20 equiv.) and AcOK (948 mg, 9.67 mmol, 3.00 equiv.) in 1,4-dioxane (10 mL) was stirred at 90° C. for 2 h under $N_2$ atmosphere. LCMS showed the reaction was complete. The resulting solution was diluted with 20 mL of water, then extracted with ethyl acetate (3*20 mL). The combined organic layers were washed with brine, and dried over anhydrous $Na_2SO_4$ and concentrated under reduced pressure. The residue was purified by flash chromatography on silica gel (EA/PE=19%) to give the corresponding enantiomer of methyl 1-(5-(4,4,5,5-tetramethyl-1,3,2-dioxaborolan-2-yl)-2,3-dihydro-1H-inden-1-yl)-azetidine-3-carboxylate (720 mg, 65%) as an oil. LCMS (ESI, m/z): 358 $[M+H]^+$.

Synthesis of methyl 1-(5-(4-cyclopropyl-3-fluorophenyl)-2,3-dihydro-1H-inden-1-yl)azetidine-3-carboxylate

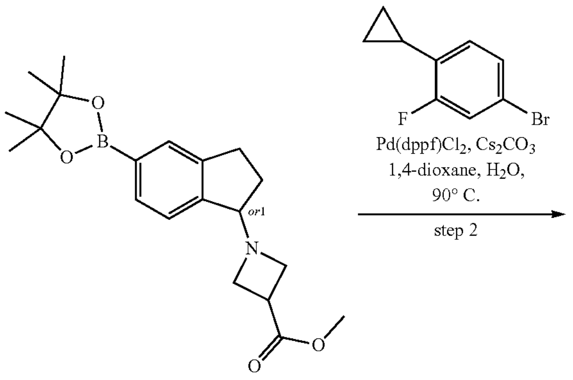

-continued

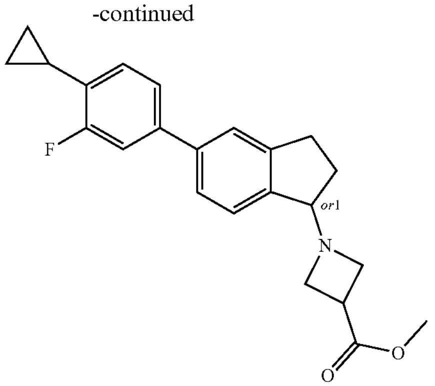

A solution of one enantiomer of methyl 1-(5-(4,4,5,5-tetramethyl-1,3,2-dioxaborolan-2-yl)-2,3-dihydro-1H-inden-1-yl)azetidine-3-carboxylate (200 mg, 0.560 mmol, 1.00 equiv.), 4-bromo-1-cyclopropyl-2-fluoro-benzene (120 mg, 0.560 mmol, 1.00 equiv.), Pd(dppf)$Cl_2$ (82 mg, 0.112 mmol, 0.20 equiv.) and $Cs_2CO_3$ (548 mg, 1.68 mmol, 3.00 equiv.) in 1,4-dioxane (5.0 mL) and water (0.5 mL) was stirred at 90° C. for 2 h under $N_2$ atmosphere. LCMS showed the reaction was complete. The resulting solution was diluted with 10 ml of water, then extracted with ethyl acetate (3*10 mL). The combined organic layers were washed with brine, and dried over anhydrous $Na_2SO_4$ and concentrated under reduced pressure. The residue was purified by flash chromatography on silica gel (EA/PE=30%) to give one enantiomer of methyl 1-(5-(4-cyclopropyl-3-fluorophenyl)-2,3-dihydro-1H-inden-1-yl)azetidine-3-carboxylate (90 mg, 44%) as an oil. LCMS (ESI, m/z): 366 $[M+H]^+$.

Synthesis of 1-(5-(4-cyclopropyl-3-fluorophenyl)-2,3-dihydro-1H-inden-1-yl)azetidine-3-carboxylic acid

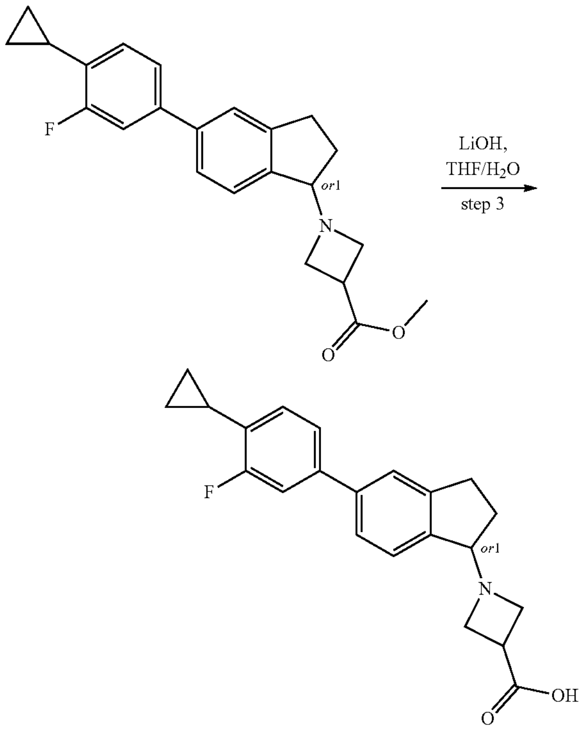

A solution of one enantiomer of methyl 1-(5-(4-cyclopropyl-3-fluorophenyl)-2,3-dihydro-1H-inden-1-yl)azetidine-3-carboxylate (130 mg, 0.360 mmol, 1.00 equiv.) and LiOH (26 mg, 1.08 mmol, 3.00 equiv.) in THF (2.0 mL) and water (1.0 mL) was stirred at room temperature for 15 h. LCMS showed the reaction was complete. The resulting solution was acidified to pH 5~6 with 2N HCl and concentrated under reduced pressure. The crude product was purified by prep-HPLC (Column: YMC-Actus Triart C18, 30*250 mm, 5 μm; Mobile Phase A: water (10 mmoL/L $NH_4HCO_3$+0.1% $NH_3{\cdot}H_2O$), Mobile Phase B: ACN; Flow rate: 60 mL/min; Gradient: 20% B to 50% B in 7 min; 254/210 nm; RT: 6.42 min) to give the corresponding enantiomer of 1-(5-(4-cyclopropyl-3-fluorophenyl)-2,3-dihydro-1H-inden-1-yl)azetidine-3-carboxylic acid (31a, 25.8 mg, 29%) as a solid.

LCMS (ESI, m/z): 352 $[M+H]^+$. Analytic Conditions: EVO C18, 3.0*50 mm, 2.6 μm; Mobile Phase A: water/5 mM $NH_4HCO_3$. Mobile Phase B: ACN; Flow rate: 1.20 mL/min; Gradient: 10% B to 95% B in 2.0 min, hold at 95% B for 0.6 min, 95% B to 10% B in 0.15 min; 254 nm; RT: 1.141 min.

$^1H$ NMR (400 MHz, Methanol-$d_4$) δ 7.60-7.52 (m, 3H), 7.37-7.30 (m, 2H), 7.03 (t, J=8.0 Hz, 1H), 4.75 (dd, J=7.6, 2.8 Hz, 1H), 4.28-4.23 (m, 2H), 4.17-4.08 (m, 2H), 3.41-3.35 (m, 1H), 3.24-3.16 (m, 1H), 3.06-2.98 (m, 1H), 2.53-2.43 (m, 1H), 2.22-2.09 (m, 2H), 1.06-0.97 (m, 2H), 0.83-0.76 (m, 2H).

$^{19}F$ NMR (376 MHz, Methanol-$d_4$) δ −122.338.

Synthesis of methyl 1-(5-(4,4,5,5-tetramethyl-1,3,2-dioxaborolan-2-yl)-2,3-dihydro-1H-inden-1-yl)azetidine-3-carboxylate

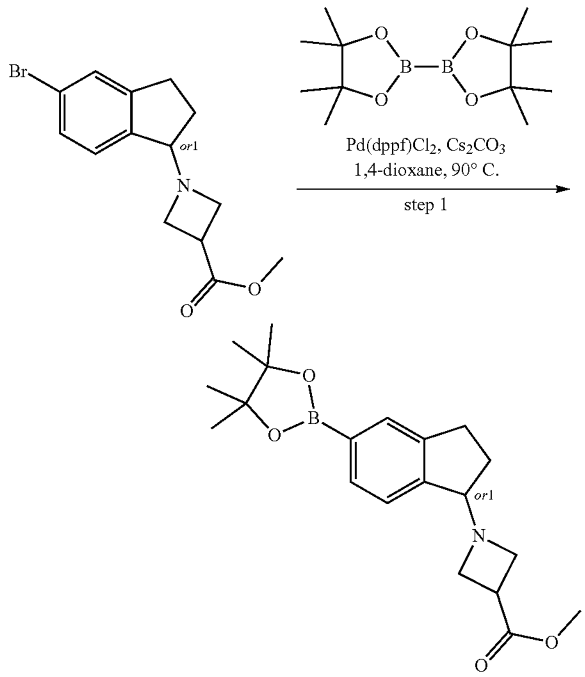

A mixture of the other enantiomer of methyl 1-(5-bromo-2,3-dihydro-1H-inden-1-yl)azetidine-3-carboxylate (1.0 g, 3.22 mmol, 1.00 equiv.), bis(pinacolato)diboron (1.23 g, 4.84 mmol, 1.00 equiv.), $Pd(dppf)Cl_2$ (472 mg, 0.640 mmol, 1.00 equiv.) and AcOK (948 mg, 9.67 mmol, 1.00 equiv.) in 1,4-dioxane (10 mL) was stirred at 90° C. for 2 h under $N_2$ atmosphere. TLC showed that the reaction was complete. The reaction mixture was diluted with 20 mL of water, then extracted with ethyl acetate (3*20 mL). The combined organic layers were washed with brine, and dried over anhydrous $Na_2SO_4$ and concentrated under reduced pressure. The residue was purified by flash chromatography on silica gel (EA/PE=19%) to give the other enantiomer of methyl 1-(5-(4,4,5,5-tetramethyl-1,3,2-dioxaborolan-2-yl)-2,3-dihydro-1H-inden-1-yl)azetidine-3-carboxylate (810 mg, 70%) as an oil. LCMS (ESI, m/z): 358 $[M+H]^+$.

Synthesis of methyl 1-(5-(4-cyclopropyl-3-fluorophenyl)-2,3-dihydro-1H-inden-1-yl)azetidine-3-carboxylate

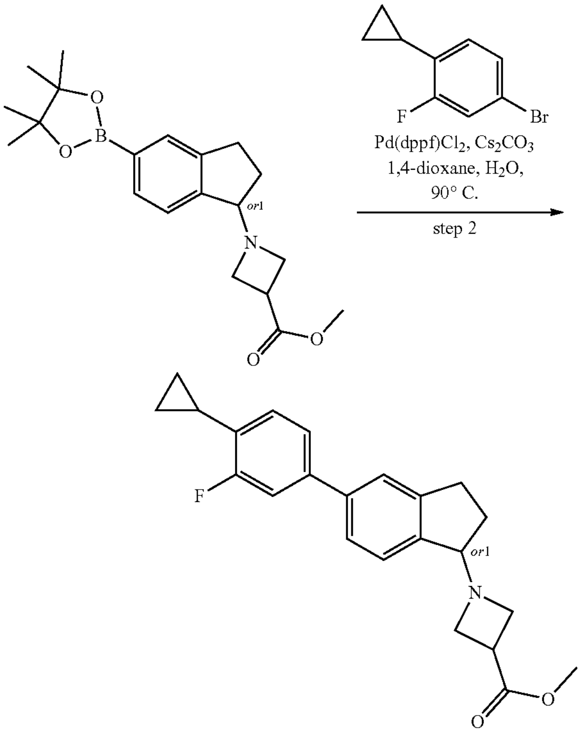

A mixture of the other enantiomer of methyl 1-(5-(4,4,5,5-tetramethyl-1,3,2-dioxaborolan-2-yl)-2,3-dihydro-1H-inden-1-yl)azetidine-3-carboxylate (200 mg, 0.560 mmol, 1.00 equiv.), 4-bromo-1-cyclopropyl-2-fluoro-benzene (120 mg, 0.560 mmol, 1.00 equiv.), $Pd(dppf)Cl_2$ (82 mg, 0.112 mmol, 0.200 equiv.) and $Cs_2CO_3$ (548 mg, 1.680 mmol, 3.00 equiv.) in 1,4-dioxane (5.0 mL) and water (0.5 mL) was stirred at 90° C. for 2 h under $N_2$ atmosphere. LCMS showed the reaction was complete. The resulting solution was diluted with 20 mL of water, then extracted with ethyl acetate (3*20 mL). The combined organic layers were washed with brine, and dried over anhydrous $Na_2SO_4$ and concentrated under reduced pressure. The residue was purified by flash chromatography on silica gel (EA/PE=30%) to yield the other enantiomer of methyl 1-(5-(4-cyclopropyl-3-fluorophenyl)-2,3-dihydro-1H-inden-1-yl)azetidine-3-carboxylate (130 mg, 64%) as an oil. LCMS (ESI, m/z): 366 $[M+H]^+$.

Synthesis of 1-(5-(4-cyclopropyl-3-fluorophenyl)-2,3-dihydro-1H-inden-1-yl)azetidine-3-carboxylic acid

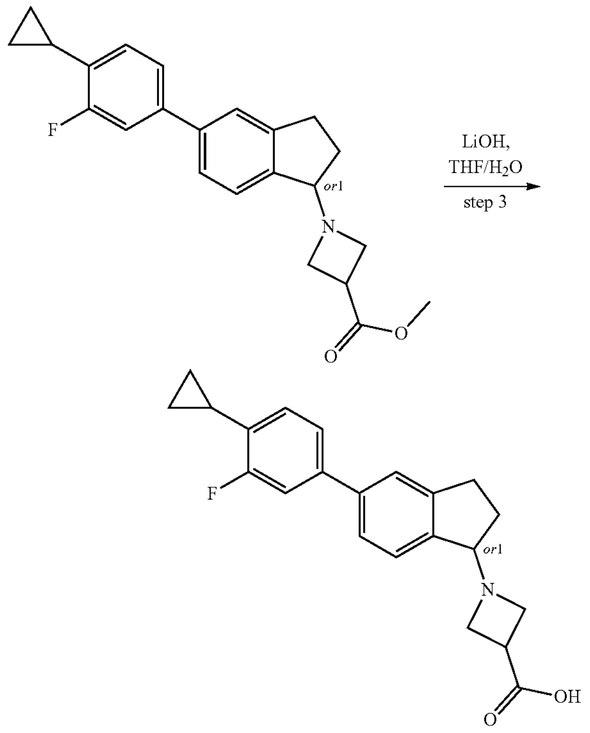

A solution of the other enantiomer of methyl 1-(5-(4-cyclopropyl-3-fluorophenyl)-2,3-dihydro-1H-inden-1-yl)azetidine-3-carboxylate (130 mg, 0.360 mmol, 1.00 equiv.) and LiOH (26 mg, 1.08 mmol, 3.00 equiv.) in THF (2.0 mL) and water (1.0 mL) was stirred at room temperature for 15 h. LCMS showed the reaction was complete. The resulting solution was acidified to pH 5~6 with 2N HCl and concentrated under reduced pressure. The crude product was purified by prep-HPLC (Column: YMC-Actus Triart C18, 30*250 mm, 5 μm; Mobile Phase A: Water (10 mM $NH_4HCO_3$+0.1% $NH_3·H_2O$), Mobile Phase B: ACN; Flow rate: 60 mL/min; Gradient: 20% B to 50% B in 7 min; 254/210 nm; RT: 6.42 min) to give the corresponding enantiomer of 1-(5-(4-cyclopropyl-3-fluorophenyl)-2,3-dihydro-1H-inden-1-yl)azetidine-3-carboxylic acid (31b, 38.2 mg, 31%) as a solid.

LCMS (ESI, m/z): 352 $[M+H]^+$. Analytic Conditions: EVO C18, 3.0*50 mm, 2.6 μm; Mobile Phase A: water/5 mM $NH_4HCO_3$. Mobile Phase B: ACN; Flow rate: 1.20 mL/min; Gradient: 10% B to 95% B in 2.0 min, hold at 95% B for 0.6 min, 95% B to 10% B in 0.15 min; 254 nm; RT: 1.122 min.

$^1H$ NMR (400 MHz, Methanol-$d_4$) δ 7.60-7.52 (m, 3H), 7.37-7.29 (m, 2H), 7.03 (t, J=8.0 Hz, 1H), 4.81 (dd, J=7.6, 2.8 Hz, 1H), 4.34-4.29 (m, 2H), 4.22-4.14 (m, 2H), 3.41-3.35 (m, 1H), 3.25-3.17 (m, 1H), 3.06-2.98 (m, 1H), 2.54-2.45 (m, 1H), 2.25-2.09 (m, 2H), 1.08-0.97 (m, 2H), 0.83-0.75 (m, 2H).

$^{19}F$ NMR (376 MHz, Methanol-$d_4$) δ −114.9.

Example S32. 1-(5-(3-chloro-4-cyclopropylphenyl)-2,3-dihydro-1H-inden-1-yl)piperidine-4-carboxylic acid (32a and 32b)

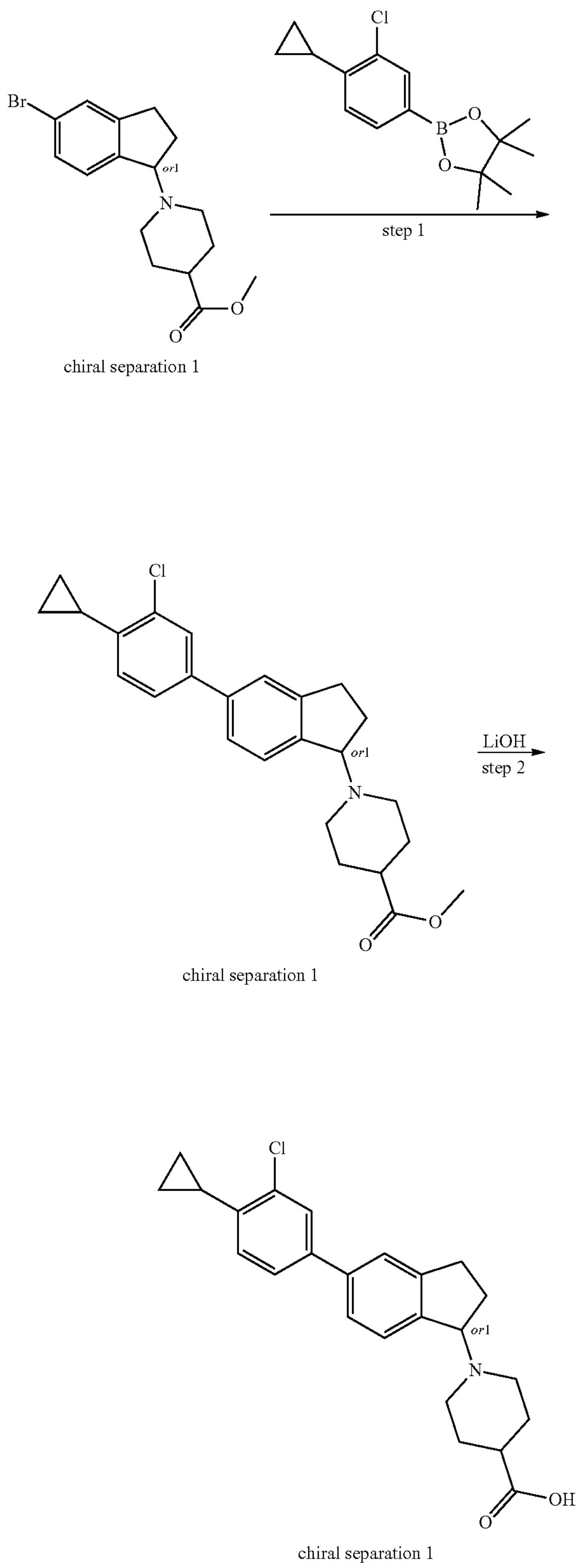

Synthesis of methyl 1-(5-(3-chloro-4-cyclopropylphenyl)-2,3-dihydro-1H-inden-1-yl)piperidine-4-carboxylate

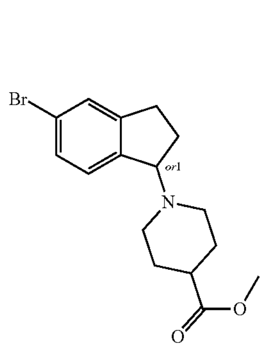

chiral separation 1

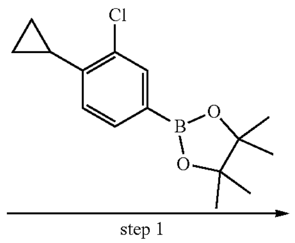

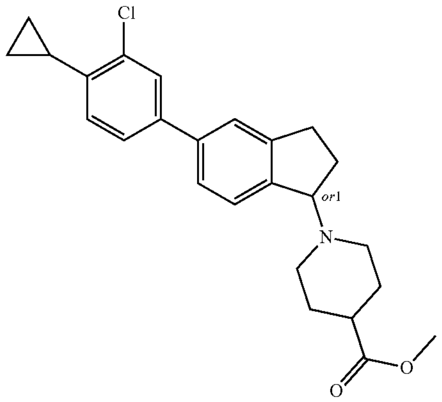

chiral separation 1

To a stirred solution of one enantiomer of methyl 1-(5-bromo-2,3-dihydro-1H-inden-1-yl)piperidine-4-carboxylate (200 mg, 0.590 mmol, 1.00 equiv.) and 2-(3-chloro-4-cyclopropyl-phenyl)-4,4,5,5-tetramethyl-1,3,2-dioxaborolane (329 mg, 1.18 mmol, 2.00 equiv.) in toluene (2 mL) and water (1 mL) were added Pd(dtbpf)$Cl_2$ (46.1 mg, 0.060 mmol, 0.100 equiv.) and $K_3PO_4$ (375 mg, 1.77 mmol, 3.00 equiv.) under nitrogen atmosphere. The resulting mixture was stirred at 90° C. for 4 h. LCMS showed the reaction was complete. The mixture was concentrated under reduced pressure. The residue was purified by flash chromatography on silica gel (eluted with ethyl acetate/petroleum ether, 1/1) to afford methyl one enantiomer of 1-(5-(3-chloro-4-cyclopropylphenyl)-2,3-dihydro-1H-inden-1-yl)piperidine-4-carboxylate (131 mg, 54.0%) as an oil. LCMS (ESI, m/z): 410 $[M+H]^+$.

Synthesis of 1-(5-(3-chloro-4-cyclopropylphenyl)-2,3-dihydro-1H-inden-1-yl)piperidine-4-carboxylic acid

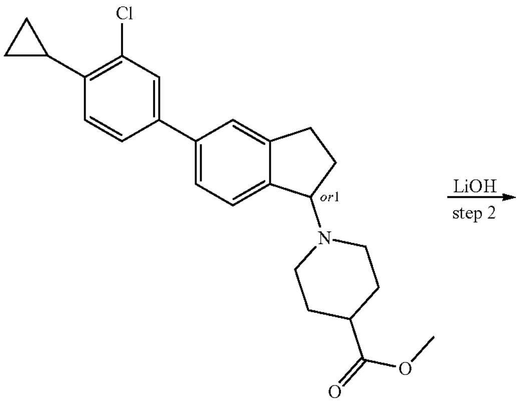

chiral separation 1

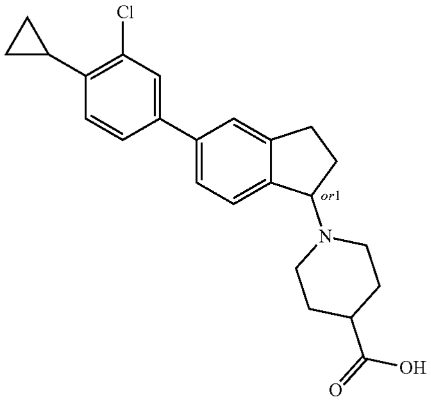

chiral separation 1

To a solution of one enantiomer of methyl 1-(5-(3-chloro-4-cyclopropylphenyl)-2,3-dihydro-1H-inden-1-yl)piperidine-4-carboxylate (131 mg, 0.320 mmol, 1.00 equiv.) in THF (2 mL) and water (2 mL) was added LiOH (23 mg, 0.960 mmol, 3.00 equiv.). The resulting solution was stirred at room temperature for 30 min. LCMS showed the reaction was complete. The reaction mixture was acidified to pH 3-4 with 1N HCl, and then was concentrated under reduced pressure. The residue was purified by HPLC (Column: Sunfire prep C18 column, 30*150 mm, 5 μm; Mobile Phase A: water (0.05% HCl), Mobile Phase B: ACN; Flow rate: 60 mL/min; Gradient: 22% B to 40% B in 10 min; 254/210 nm; RT: 8.80 min) to afford one enantiomer of 1-(5-(3-chloro-4-cyclopropylphenyl)-2,3-dihydro-1H-inden-1-yl)piperidine-4-carboxylic acid (32a, 41 mg, 32.3%) as a solid.

$^1H$ NMR (300 MHz, methanol-$d_4$) δ 7.70-7.58 (m, 4H), 7.49 (dd, J=8.1, 1.8 Hz, 1H), 7.08 (d, J=8.1 Hz, 1H), 5.01-4.97 (m, 1H), 3.57-3.52 (m, 1H), 3.41-3.34 (m, 1H), 3.28-2.98 (m, 4H), 2.65-2.54 (m, 3H), 2.67-2.20 (m, 3H), 2.04-1.84 (m, 2H), 1.09-1.02 (m, 2H), 0.76-0.71 (m, 2H).

LCMS (ESI, m/z): 396 $[M+H]^+$. Analytic Conditions: Shim-pack XR-ODS C18, 3.0*50 mm, 2.2 μm; Mobile Phase A: Water/0.05% TFA, Mobile Phase B: Acetonitrile/0.05% TFA; Flow rate: 1.20 mL/min; Gradient: 20% B to 60% B in 2.5 min, 60% B to 95% B in 0.5 min, hold at 95% B for 0.6 min, 95% B to 5% B in 0.1 min; 254 nm; RT: 2.345 min.

Synthesis of 1-(5-(3-chloro-4-cyclopropylphenyl)-2,3-dihydro-1H-inden-1-yl)piperidine-4-carboxylic acid

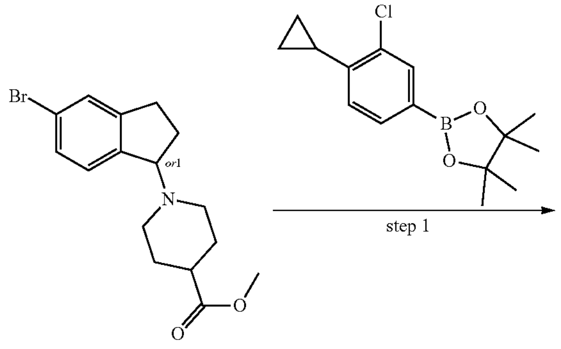

chiral separation 2

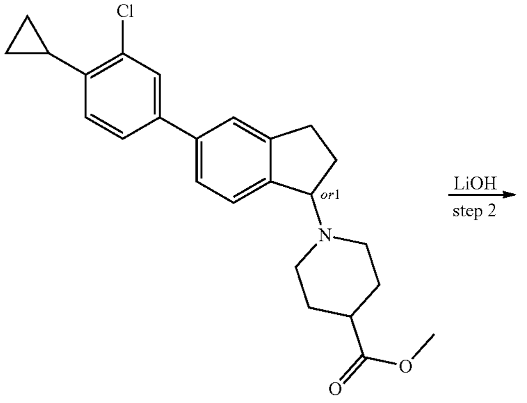

chiral separation 2

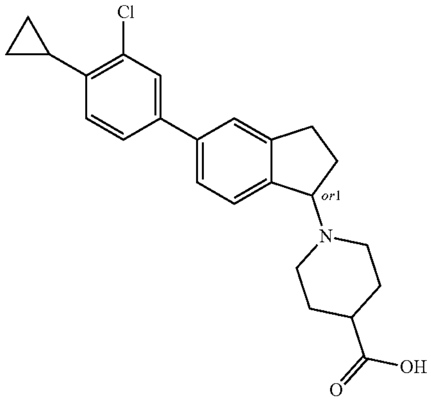

chiral separation 2

Synthesis of methyl 1-(5-(3-chloro-4-cyclopropylphenyl)-2,3-dihydro-1H-inden-1-yl)-piperidine-4-carboxylate

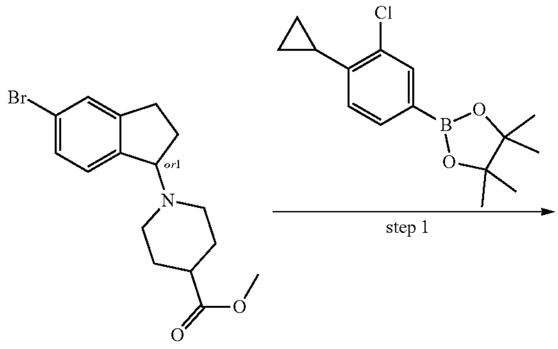

chiral separation 2

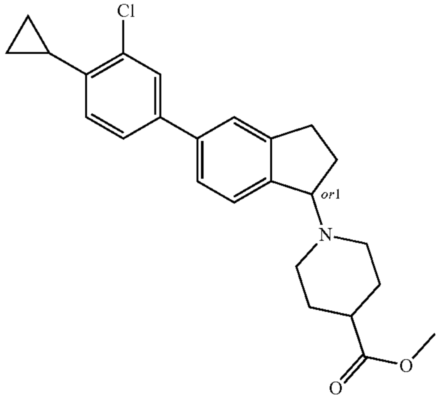

chiral separation 2

To a stirred solution of methyl 1-(5-bromo-2,3-dihydro-1H-inden-1-yl)piperidine-4-carboxylate (200 mg, 0.590 mmol, 1.00 equiv.) and 2-(3-chloro-4-cyclopropyl-phenyl)-4,4,5,5-tetramethyl-1,3,2-dioxaborolane (329 mg, 1.18 mmol, 2.00 equiv.) in toluene (2 mL) and water (1 mL) were added Pd(DTBPF)$Cl_2$ (46.1 mg, 0.060 mmol, 0.100 equiv.) and $K_3PO_4$ (375 mg, 1.77 mmol, 3.00 equiv.). The resulting mixture was stirred at 90° C. for 4 h. LCMS showed the reaction was complete. The mixture was concentrated under reduced pressure. The residue was purified by flash chromatography on silica gel (eluted with ethyl acetate/petroleum ether, 1/1) to afford methyl 1-(5-(3-chloro-4-cyclopropylphenyl)-2,3-dihydro-1H-inden-1-yl)piperidine-4-carboxylate (268 mg, 89.5%) as an oil. LCMS (ESI, m/z): 410[M+H]$^+$.

Synthesis of 1-(5-(3-chloro-4-cyclopropylphenyl)-2,3-dihydro-1H-inden-1-yl)piperidine-4-carboxylic acid

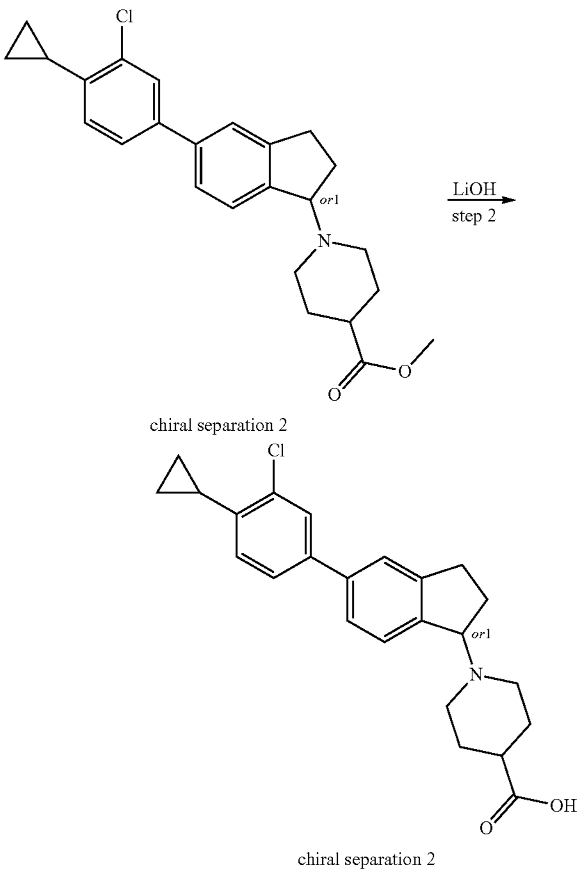

To a solution of methyl 1-(5-(3-chloro-4-cyclopropylphenyl)-2,3-dihydro-1H-inden-1-yl)piperidine-4-carboxylate (268 mg, 0.320 mmol, 1.00 equiv.) in THF (2 mL) and water (2 mL) was added LiOH (47 mg, 0.960 mmol, 3.00 equiv.). The resulting solution was stirred at room temperature for 30 min. LCMS showed the reaction was complete. The reaction mixture was acidified to pH 3-4 with 1N HCl, and then was concentrated under reduced pressure. The residue was purified by HPLC (Column: Sunfire prep C18 column, 30*150 mm, 5 μm; Mobile Phase A: water (0.05% HCl), Mobile Phase B: ACN; Flow rate: 60 mL/min; Gradient: 22% B to 40% B in 10 min; 254/210 nm; RT: 8.80 min) to afford 1-(5-(3-chloro-4-cyclopropylphenyl)-2,3-dihydro-1H-inden-1-yl)piperidine-4-carboxylic acid (32b, 41 mg, 31.18%) as a solid.

$^1$H NMR (400 MHz, Methanol-$d_4$) δ 7.70-7.67 (m, 1H), 7.65-7.63 (m, 2H), 7.61-7.57 (m, 1H), 7.49 (dd, J=8.0, 2.0 Hz, 1H), 7.08 (d, J=8.0 Hz, 1H), 5.00-4.98 (m, 1H), 3.58-3.54 (m, 1H), 3.38-3.34 (m, 1H), 3.27-2.98 (m, 4H), 2.65-2.54 (m, 3H), 2.67-2.20 (m, 3H), 2.02-1.81 (m, 2H), 1.08-1.01 (m, 2H), 0.75-0.71 (m, 2H).

LCMS (ESI, m/z): 396 $[M+H]^+$. Analytic Conditions: Shim-pack XR-ODS C18, 3.0*50 mm, 2.2 μm; Mobile Phase A: Water/0.05% TFA, Mobile Phase B: Acetonitrile/0.05% TFA; Flow rate: 1.20 mL/min; Gradient: 5% B to 95% B in 2.0 min, hold at 95% B for 0.7 min, 95% B to 5% B in 0.3 min; 254 nm; RT: 1.170 min.

Example S33. 1-(5-(3-chloro-4-isopropylphenyl)-2,3-dihydro-1H-inden-1-yl)piperidine-4-carboxylic acid (33)

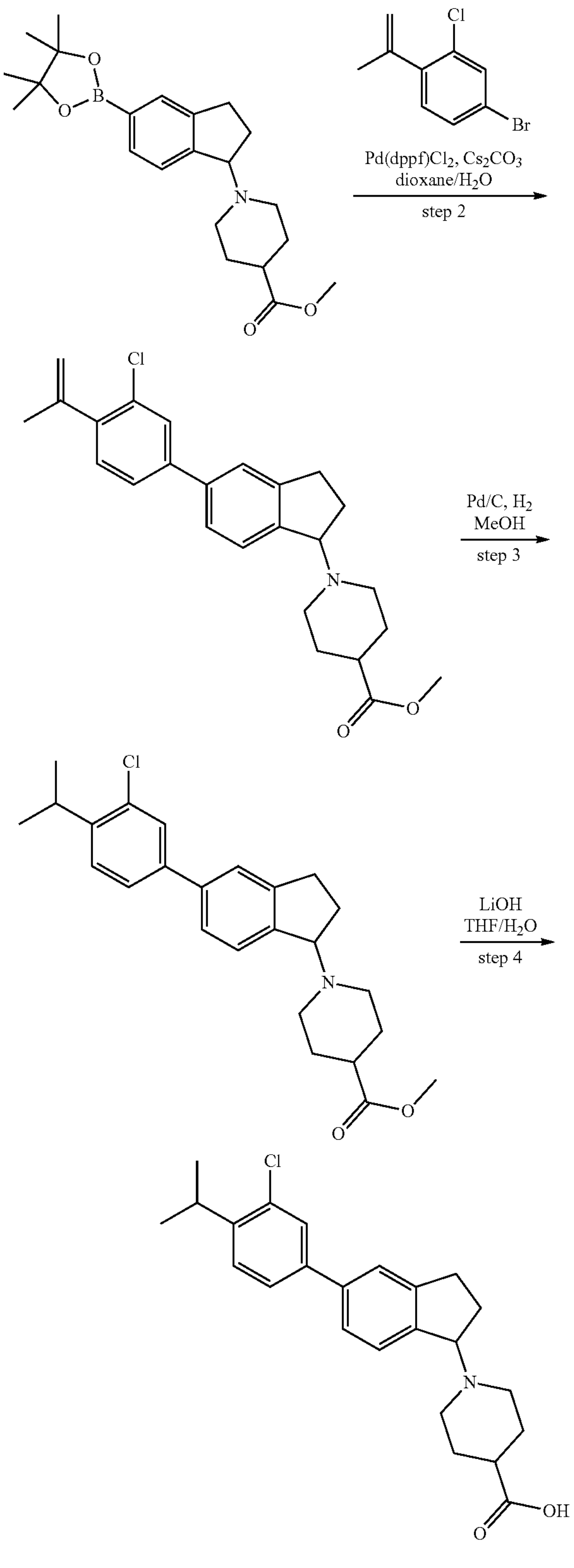

Synthesis of methyl 1-(5-(3-chloro-4-(prop-1-en-2-yl)phenyl)-2,3-dihydro-1H-inden-1-yl)piperidine-4-carboxylate

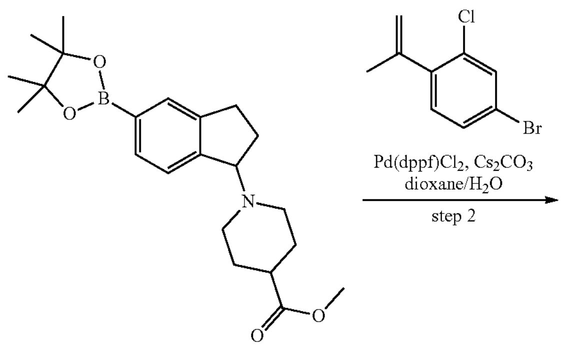

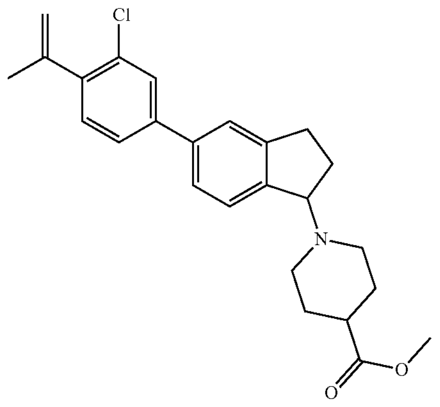

To a stirred solution of 4-bromo-2-chloro-1-isopropenylbenzene (300 mg, 1.300 mmol, 1.00 equiv.), $Pd(dppf)Cl_2$ (189 mg, 0.260 mmol, 0.20 equiv.) and $Cs_2CO_3$ (1.27 g, 3.890 mmol, 3.00 equiv.) in 1,4-dioxane (10 mL) and water (1 mL) was added methyl 1-(5-(4,4,5,5-tetramethyl-1,3,2-dioxaborolan-2-yl)-2,3-dihydro-1H-inden-1-yl)piperidine-4-carboxylate (749 mg, 1.9400 mmol, 1.50 equiv.). The resulting mixture was stirred at 90° C. for 1 d. LCMS showed the reaction was complete. The reaction mixture was diluted with water (20 mL), extracted with EtOAc (3*15 mL). The combined organic layers were washed with brine (15 mL), dried over anhydrous $Na_2SO_4$ concentrated under reduced pressure. The residue was purified by flash chromatography on silica gel (eluted with PE/EtOAc, 6/1) to afford methyl 1-(5-(3-chloro-4-(prop-1-en-2-yl)phenyl)-2,3-dihydro-1H-inden-1-yl)piperidine-4-carboxylate (230 mg, 43.2%). LCMS (ESI, m/z): 410 $[M+H]^+$.

Synthesis of methyl 1-(5-(3-chloro-4-isopropylphenyl)-2,3-dihydro-1H-inden-1-yl)piperidine-4-carboxylate

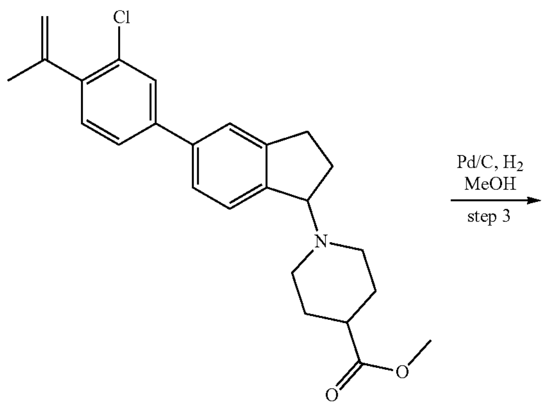

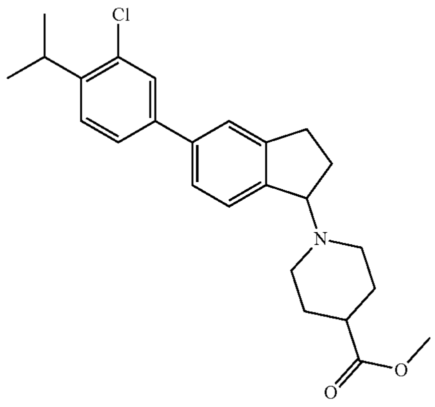

To a stirred solution of methyl 1-(5-(3-chloro-4-(prop-1-en-2-yl)phenyl)-2,3-dihydro-1H-inden-1-yl)piperidine-4-carboxylate (50 mg, 0.1200 mmol, 1.00 equiv.) in MeOH (2 mL) was added Pd/C (8 mg, 0.16 w/w). The resulting mixture was evacuated and flushed three times with nitrogen and then with hydrogen. The mixture was stirred at room temperature under hydrogen atmosphere for 2 h. LCMS showed the reaction was complete. The reaction mixture was filtered through Celite, and the filtrate was concentrated under reduced pressure to afford methyl 1-(5-(3-chloro-4-isopropylphenyl)-2,3-dihydro-1H-inden-1-yl)piperidine-4-carboxylate (37 mg) as a crude, which was used directly in the next step. LCMS (ESI, m/z): 412 $[M+H]^+$.

Synthesis of 1-(5-(3-chloro-4-isopropylphenyl)-2,3-dihydro-1H-inden-1-yl)piperidine-4-carboxylic acid

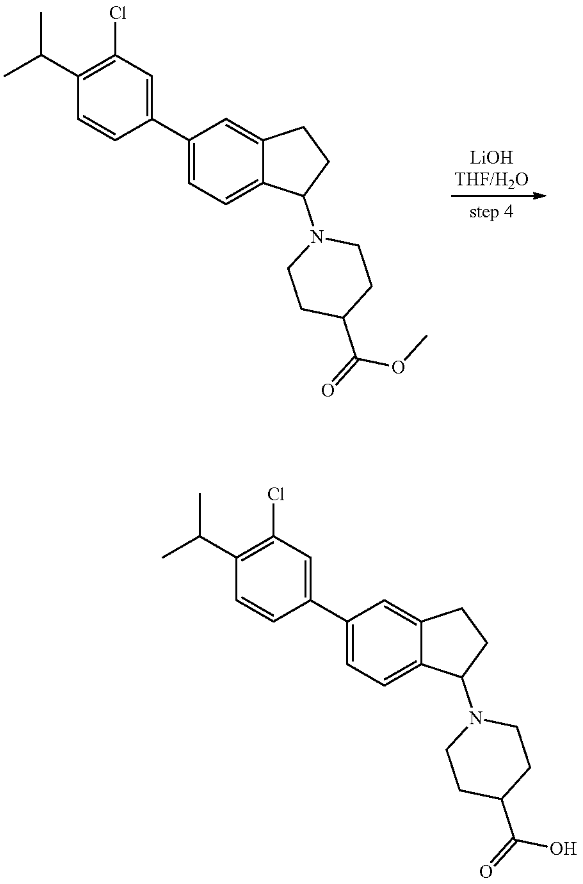

To a solution of methyl 1-(5-(3-chloro-4-isopropylphenyl)-2,3-dihydro-1H-inden-1-yl)piperidine-4-carboxylate (37 mg, 0.090 mmol, 1.00 equiv.) in THF (1.5 mL) and Water (1.5 mL) was added LiOH·$H_2O$ (11 mg, 0.2700 mmol, 3.00 equiv.). The resulting mixture was stirred at room temperature for 3 h. LCMS showed the reaction was complete. The reaction mixture was acidified to pH 4-5 by adding 1N HCl, and then was concentrated under reduced pressure. The residue was purified by Prep-HPLC (column: X select CSH F-Phenyl OBD Column 19*150 mm 5 m; mobile phase A: water (0.05% HCl), mobile phase B: ACN; flow rate: 60 mL/min; gradient: 23% B to 41% B in 7 min, hold at 41% B for 1 min; 210/254 nm; RT: 7.92 min) to afford 1-(5-(3-chloro-4-isopropylphenyl)-2,3-dihydro-1H-inden-1-yl)piperidine-4-carboxylic acid (33, 8.8 mg, 23.9%) as a solid.

$^1H$ NMR (300 MHz, DMSO-$d_6$) δ 10.59 (s, 1H), 7.89 (d, J=7.8 Hz, 1H), 7.73-7.65 (m, 4H), 7.52 (d, J=7.8 Hz, 1H), 4.99-4.96 (m, 1H), 3.33-2.90 (m, 8H), 2.51-2.43 (m, 2H), 2.14-1.85 (m, 5H), 1.27 (d, J=6.6 Hz, 6H).

LCMS (ESI, m/z): 398 $[M+H]^+$. Analytic Conditions: column: Shim-pack XR-ODS C18 100A Column 3.0*50 mm, 2.2 μm; mobile phase A: water/0.05% TFA, mobile phase B: acetonitrile/0.05% TFA; flow rate: 1.20 mL/min; gradient: 5% B to 95% B in 2.0 min, hold at 95% B for 0.7 min, 95% B to 5% B in 0.05 min; 254 nm; RT: 2.013 min.

Example S34. (3R)-1-(5-(3-chloro-4-cyclopropylphenyl)-2,3-dihydro-1H-inden-1-yl)pyrrolidine-3-carboxylic acid (34a and 34b)

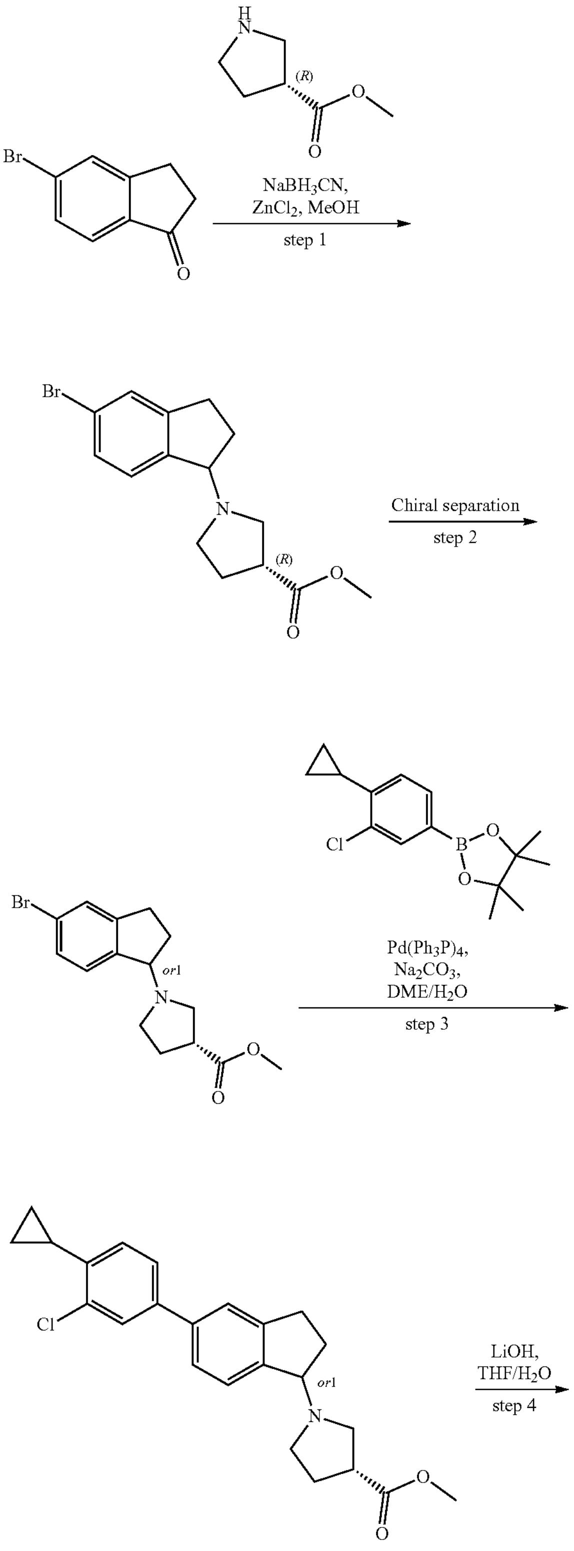

Chiral separation 1

-continued

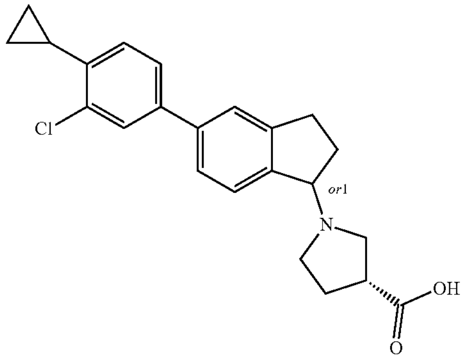

Chiral separation 1

Synthesis of methyl (3R)-1-(5-bromo-2,3-dihydro-1H-inden-1-yl)pyrrolidine-3-carboxylate

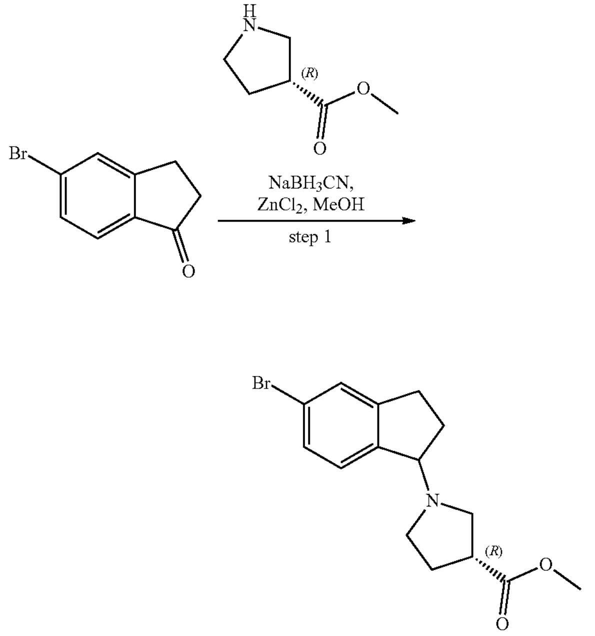

To a stirred solution of methyl (R)-pyrrolidine-3-carboxylate (1.84 g, 14.2 mmol, 2.00 equiv.) and 5-bromo-2,3-dihydro-1H-inden-1-one (1.50 g, 7.11 mmol, 1.00 equiv.) in methanol (20 mL) were added $NaBH_3CN$ (1.82 g, 28.4 mmol, 4.00 equiv.) and $ZnCl_2$ (1.9 M in THF, 7.11 mL, 14.2 mmol, 2.00 equiv.). The resulting solution was stirred at 80° C. overnight. LCMS showed that the reaction was complete. The reaction mixture was concentrated under reduced pressure. The residue was diluted with water (50 mL), extracted with DCM (3*20 mL). The combined organic layers were washed with brine and dried over anhydrous $Na_2SO_4$, and concentrated under reduce pressure. The residue was purified by flash chromatography on silica gel (eluted with PE/EtOAc, 3/1) to afford methyl (3R)-1-(5-bromo-2,3-dihydro-1H-inden-1-yl)pyrrolidine-3-carboxylate (1.60 g, 69.4%) as an oil. LCMS (ESI, m/z): 324 $[M+H]^+$.

Chiral Separation of methyl (3R)-1-(5-bromo-2,3-dihydro-1H-inden-1-yl)pyrrolidine-3-carboxylate

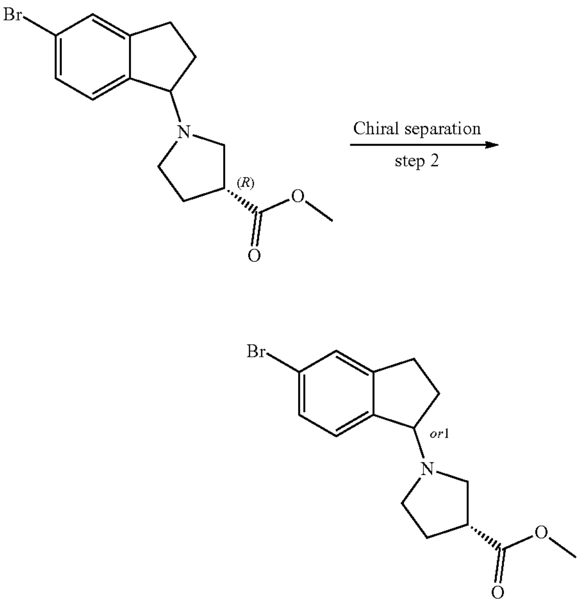

3.50 g of racemic methyl (3R)-1-(5-bromo-2,3-dihydro-1H-inden-1-yl)pyrrolidine-3-carboxylate was separated by SFC (column: CHIRAL ART Amylose-C NEO, 3*25 cm, 5 μm; mobile phase A: $CO_2$, mobile phase B: IPA; flow rate: 100 mL/min; gradient: 20% B; 220 nm) to afford the Chiral Separation 1 enantiomer (1.40 g, 96.1% e.e.) with the retention time at 2.53 min, the Chiral Separation 2 enantiomer (1.30 g, 99.2% e.e.) at 2.88 min.

Synthesis of methyl (3R)-1-(5-(3-chloro-4-cyclopropylphenyl)-2,3-dihydro-1H-inden-1-yl)pyrrolidine-3-carboxylate

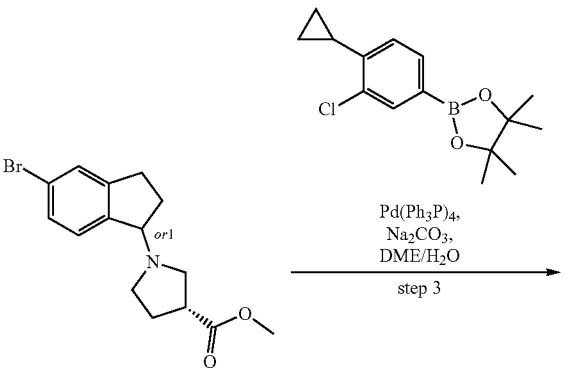

Chiral separation 1

-continued

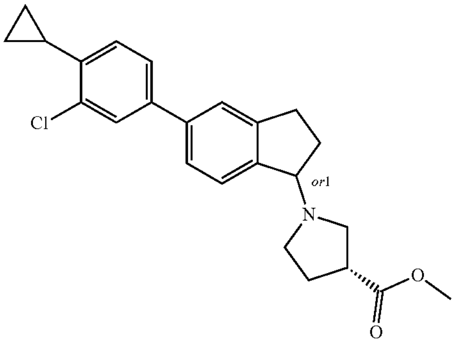

Chiral separation 1

To a stirred solution of Chiral separation 1 enantiomer of methyl (3R)-1-(5-bromo-2,3-dihydro-1H-inden-1-yl)pyrrolidine-3-carboxylate (150 mg, 0.460 mmol, 1.00 equiv.) and 2-(3-chloro-4-cyclopropyl-phenyl)-4,4,5,5-tetramethyl-1,3,2-dioxaborolane (141 mg, 0.510 mmol, 1.10 equiv.) in 1,2-dimethoxyethane (2 mL) and water (0.5 mL) were added $Pd(PPh_3)_4$ (53.5 mg, 0.050 mmol, 0.100 equiv.) and $Na_2CO_3$ (147 mg, 1.39 mmol, 3.00 equiv.). The resulting mixture was stirred at 90° C. for 4 h under nitrogen atmosphere. LCMS showed that the reaction was complete. The reaction solution was filtered through Celite and the filtrate was concentrated under reduced pressure. The residue was purified by flash chromatography on silica gel (eluted with PE/EtOAc, 1/1) to give the corresponding enantiomer of methyl (3R)-1-(5-(3-chloro-4-cyclopropylphenyl)-2,3-dihydro-1H-inden-1-yl)pyrrolidine-3-carboxylate (100 mg, 54.6%) as an oil. LCMS (ESI, m/z): 396 $[M+H]^+$.

Synthesis of (3R)-1-(5-(3-chloro-4-cyclopropylphenyl)-2,3-dihydro-1H-inden-1-yl)pyrrolidine-3-carboxylic acid

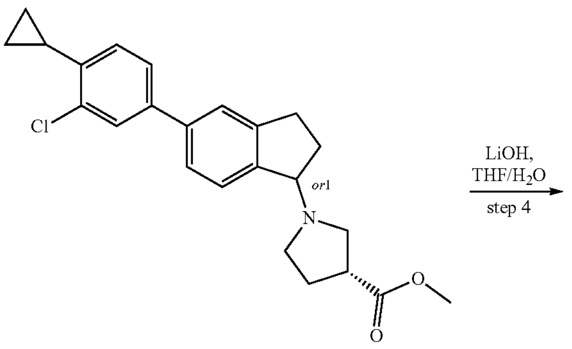

Chiral separation 1

-continued

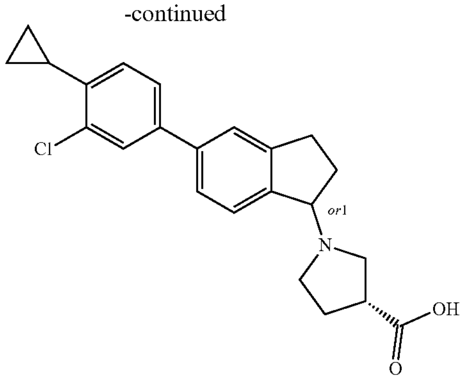

Chiral separation 1

To a stirred solution of methyl (3R)-1-(5-(3-chloro-4-cyclopropylphenyl)-2,3-dihydro-1H-inden-1-yl)pyrrolidine-3-carboxylate (60.0 mg, 0.150 mmol, 1.00 equiv.) in THF (2.5 mL) was added a solution of $LiOH·H_2O$ (20.0 mg, 0.480 mmol, 3.00 equiv.) in water (0.5 mL). The resulting solution was stirred at room temperature for 2 h. The reaction mixture was acidified to pH 4-5 by adding 1N HCl, and then was concentrated under reduced pressure. The residue was purified by Prep-HPLC (column: YMC-Actus Triart C18, 30*250, 5 μm; mobile phase A: water (10 mmol/L $NH_4HCO_3$+0.1% $NH_3·H_2O$), mobile phase B: ACN; flow rate: 60 mL/min; gradient: 25% B to 55% B in 7 min; 210/254 nm; RT: 6.38 min) to obtain the respective enantiomer of (3R)-1-(5-(3-chloro-4-cyclopropylphenyl)-2,3-dihydro-1H-inden-1-yl)-pyrrolidine-3-carboxylic acid (34a, 14.8 mg, 25.4% yield) as a solid.

$^1H$ NMR (400 MHz, methanol-$d_6$) δ 7.64-7.62 (m, 2H), 7.59 (s, 1H), 7.53 (dd, J=8.0, 2.0 Hz, 1H), 7.49 (dd, J=8.0, 2.0 Hz, 1H), 7.08 (d, J=8.0 Hz, 1H), 4.72-4.70 (m, 1H), 3.38-3.35 (m, 2H), 3.28-3.20 (m, 3H), 3.08-2.98 (m, 2H), 2.53-2.36 (m, 2H), 2.28-2.16 (m, 3H), 1.09-1.03 (m, 2H), 0.77-0.73 (m, 2H).

LCMS (ESI, m/z): 382 $[M+H]^+$. Analytic Conditions: column: EVO C18, 3.0*50 mm, 2.6 μm; mobile phase A: water/5 mM $NH_4HCO_3$, mobile phase B: acetonitrile; flow rate: 1.20 mL/min; gradient: 10% B to 95% B in 2.0 min, hold at 95% for 0.6 min, 95% B to 10% B in 0.15 min; 254 nm; RT: 1.220 min.

Synthesis of (3R)-1-(5-(3-chloro-4-cyclopropylphenyl)-2,3-dihydro-1H-inden-1-yl)pyrrolidine-3-carboxylic acid

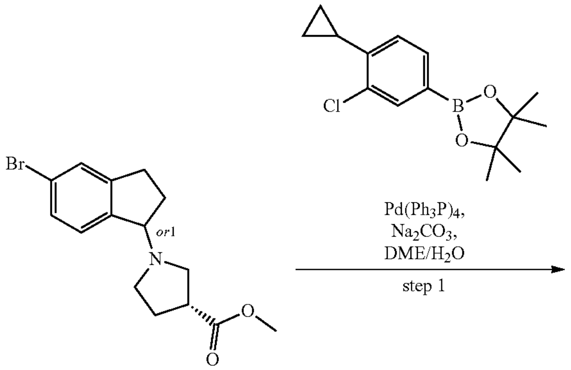

Chiral separation 2

-continued

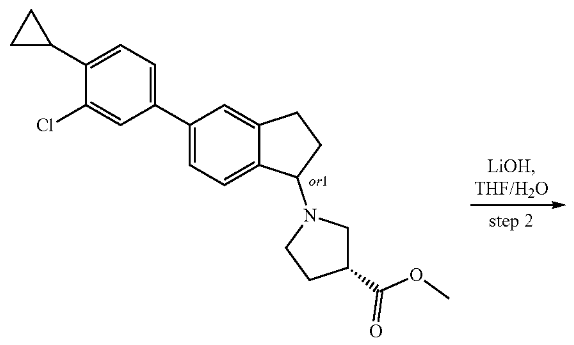

Chiral separation 2

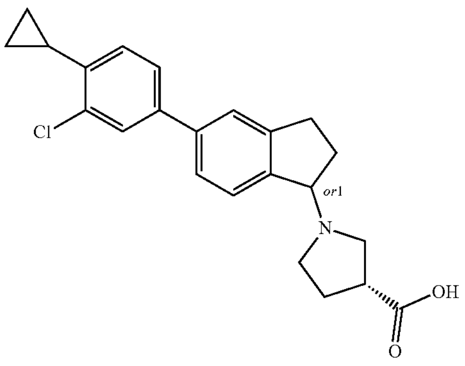

Chiral separation 2

Synthesis of methyl (3R)-1-(5-(3-chloro-4-cyclopropylphenyl)-2,3-dihydro-1H-inden-1-yl)pyrrolidine-3-carboxylate

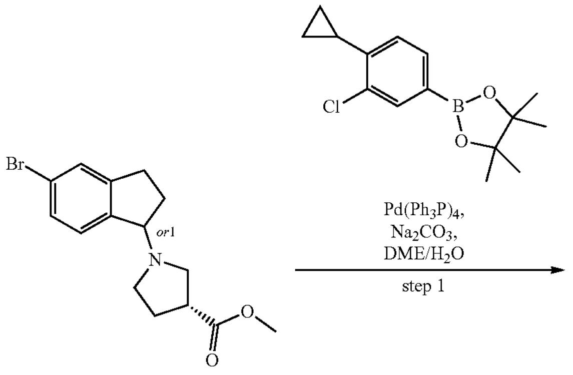

Chiral separation 2

-continued

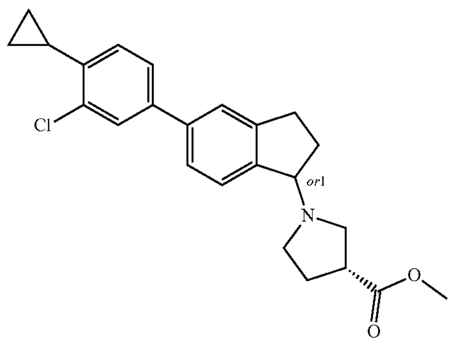

Chiral separation 2

To a stirred solution of Chiral separation 2 enantiomer of methyl (3R)-1-(5-bromo-2,3-dihydro-1H-inden-1-yl)pyrrolidine-3-carboxylate (150 mg, 0.460 mmol, 1.00 equiv.) and 2-(3-chloro-4-cyclopropyl-phenyl)-4,4,5,5-tetramethyl-1,3,2-dioxaborolane (141 mg, 0.510 mmol, 1.10 equiv.) in 1,2-dimethoxyethane (2 mL) and water (0.5 mL) were added $Pd(PPh_3)_4$ (53.5 mg, 0.050 mmol, 0.100 equiv.) and $Na_2CO_3$ (147 mg, 1.39 mmol, 3.00 equiv.). The resulting mixture was stirred at 90° C. for 4 h under nitrogen atmosphere. LCMS showed that the reaction was complete. The reaction solution was filtered through Celite and the filtrate was concentrated under reduced pressure. The residue was purified by flash chromatography on silica gel (eluted with PE/EtOAc, 1/1) to give the corresponding enantiomer of methyl (3R)-1-(5-(3-chloro-4-cyclopropylphenyl)-2,3-dihydro-1H-inden-1-yl)pyrrolidine-3-carboxylate (100 mg, 54.6%) as an oil. LCMS (ESI, m/z): 396 $[M+H]^+$.

Synthesis of (3R)-1-(5-(3-chloro-4-cyclopropylphenyl)-2,3-dihydro-1H-inden-1-yl)pyrrolidine-3-carboxylic acid

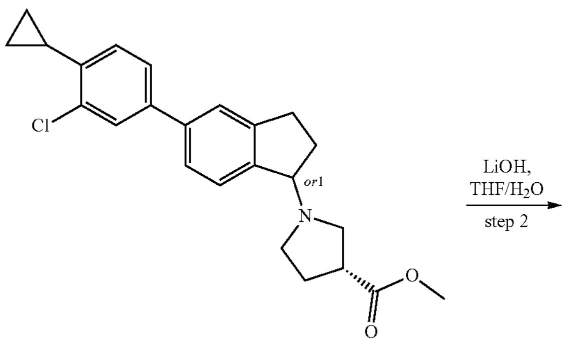

Chiral separation 2

-continued

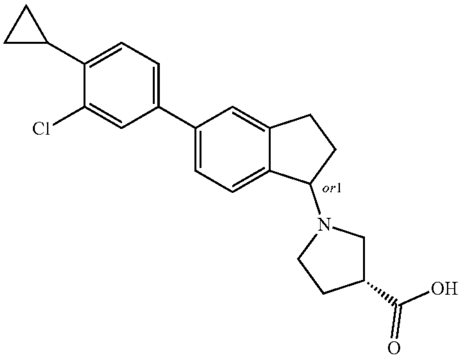

Chiral separation 2

To a solution of methyl (3R)-1-(5-(3-chloro-4-cyclopropylphenyl)-2,3-dihydro-1H-inden-1-yl)pyrrolidine-3-carboxylate (100 mg, 0.250 mmol, 1.00 equiv.) in THF (2.5 mL) was added a solution of $LiOH \cdot H_2O$ (30.0 mg, 0.710 mmol, 3.00 equiv.) in water (0.5 mL). The resulting solution was stirred at 25° C. for 2 h. The reaction mixture was acidified to pH 4-5 by adding 1N HCl, and then was concentrated under reduced pressure. The residue was purified by Prep-HPLC (column: YMC-Actus Triart C18, 30*250, 5 μm; mobile phase A: water (10 mmol/L $NH_4HCO_3$+0.1% $NH_3 \cdot H_2O$), mobile phase B: ACN; flow rate: 60 mL/min; gradient: 25% B to 45% B in 10 min, hold at 45% B for 1 min; 210/254 nm; RT: 10.02 min) to obtain the respective enantiomer of (3R)-1-(5-(3-chloro-4-cyclopropylphenyl)-2,3-dihydro-1H-inden-1-yl)pyrrolidine-3-carboxylic acid (34b, 49.5 mg, 51.1%) as a solid.

$^1$H NMR (400 MHz, methanol-$d_6$) δ 7.66-7.64 (m, 2H), 7.62 (s, 1H), 7.56 (dd, J=8.0, 2.0 Hz, 1H), 7.49 (dd, J=8.0, 2.0 Hz, 1H), 7.09 (d, J=8.0 Hz, 1H), 4.88-4.83 (m, 1H), 3.57-3.53 (m, 1H), 3.45-3.38 (m, 2H), 3.31-3.23 (m, 2H), 3.10-3.01 (m, 2H), 2.60-2.43 (m, 2H), 2.29-2.20 (m, 3H), 1.10-1.05 (m, 2H), 0.77-0.73 (m, 2H).

LCMS (ESI, m/z): 382 $[M+H]^+$. Analytic Conditions: column: EVO C18, 3.0*50 mm, 2.6 μm; mobile phase A: water/5 mM $NH_4HCO_3$, mobile phase B: acetonitrile; flow rate: 1.20 mL/min; gradient: 10% B to 95% B in 2.0 min, hold at 95% for 0.6 min, 95% B to 10% B in 0.15 min; 254 nm; RT: 1.220 min.

Example S35. (3S)-1-(5-(3-chloro-4-cyclopropylphenyl)-2,3-dihydro-1H-inden-1-yl)pyrrolidine-3-carboxylic acid (35a and 35b)

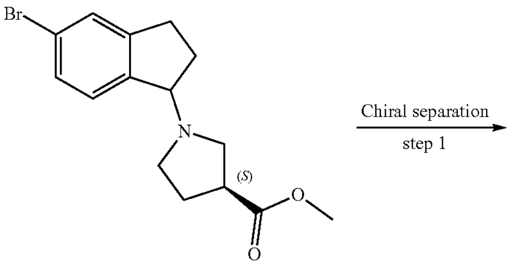

-continued

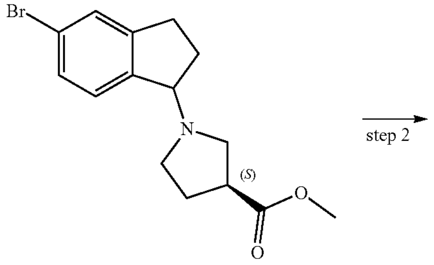

Chiral separation 2

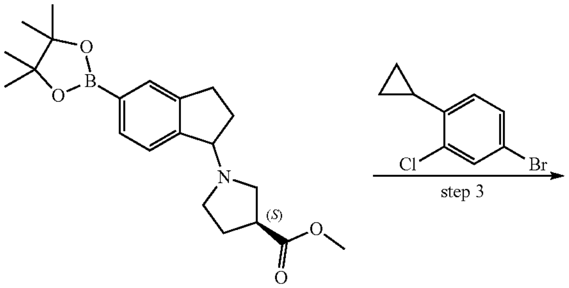

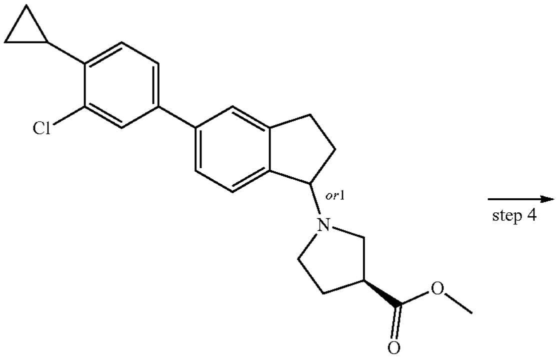

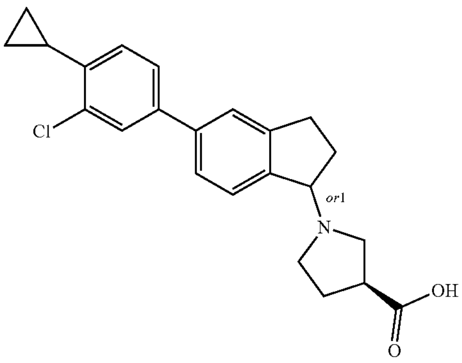

Chiral separation 2

Chiral Separation of methyl (3S)-1-(5-bromo-2,3-dihydro-1H-inden-1-yl)pyrrolidine-3-carboxylate

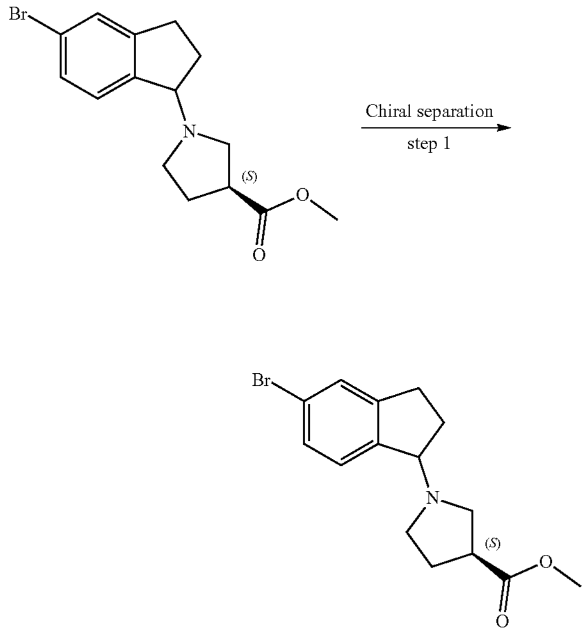

Chiral separation 2

3.00 g of the racemic product methyl (3 S)-1-(5-bromo-2,3-dihydro-1H-inden-1-yl)-pyrrolidine-3-carboxylate was separated by SFC (Column: CHIRAL ART Amylose-C NEO, 3*25 cm, 5 m; Mobile Phase A: $CO_2$, Mobile Phase B: MeOH (2 mmol/L $NH_3$-MeOH); Flow rate: 100 mL/min; Gradient: 25% B; 220 nm) to afford the Chiral Separation 1 enantiomer (1.10 g, e.e.=96.9%) with the retention time at 2.61 min, the Chiral Separation 2 enantiomer (900 mg, e.e.=98.0%) at 3.35 min.

Synthesis of methyl (3S)-1-(5-(4,4,5,5-tetramethyl-1,3,2-dioxaborolan-2-yl)-2,3-dihydro-1H-inden-1-yl) pyrrolidine-3-carboxylate

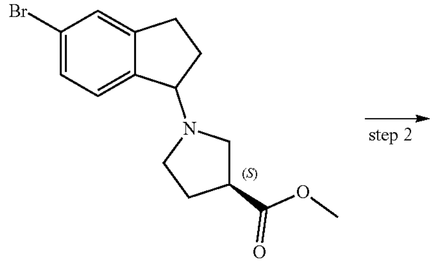

Chiral separation 2

-continued

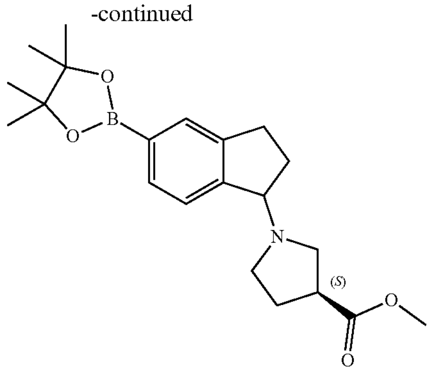

To a stirred solution of the Chiral Separation 2 enantiomer of methyl (3S)-1-(5-bromo-2,3-dihydro-1H-inden-1-yl)pyrrolidine-3-carboxylate (400 mg, 1.23 mmol, 1.00 equiv.) in 1,4-dioxane (5.0 mL) were added bis(pinacolato)diboron (469 mg, 1.85 mmol, 1.5 equiv.), $PdCl_2(dppf)CH_2Cl_2$ (100 mg, 0.120 mmol, 0.100 equiv.) and AcOK (362 mg, 3.70 mmol, 3.00 equiv.). The resulting solution was stirred at 80° C. for 2 h under nitrogen atmosphere. LCMS showed the reaction was complete. The reaction solution was concentrated under reduced pressure and the crude product was purified by flash chromatography on silica gel (EA:PE=1:4) to give the corresponding enantiomer of methyl (3S)-1-(5-(4,4,5,5-tetramethyl-1,3,2-dioxaborolan-2-yl)-2,3-dihydro-1H-inden-1-yl)pyrrolidine-3-carboxylate (300 mg, 65%) as an oil. LCMS (ESI, m/z): 372 $[M+H]^+$.

Synthesis of methyl (3S)-1-(5-(3-chloro-4-cyclopropylphenyl)-2,3-dihydro-1H-inden-1-yl)-pyrrolidine-3-carboxylate

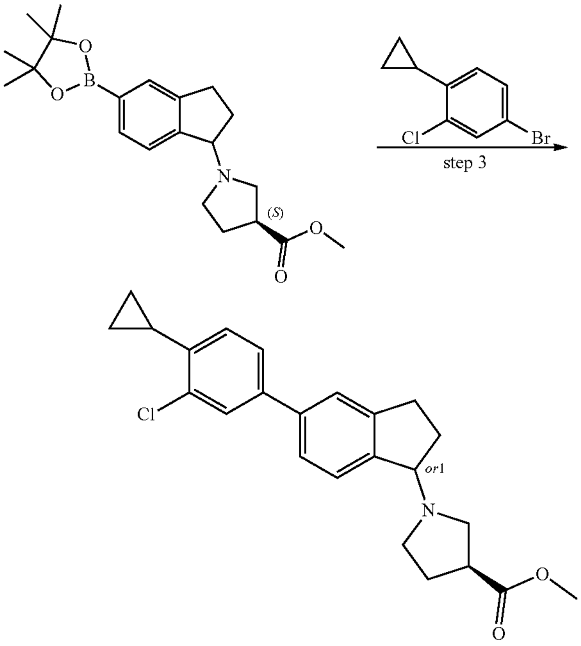

To a stirred solution of methyl (3S)-1-(5-(4,4,5,5-tetramethyl-1,3,2-dioxaborolan-2-yl)-2,3-dihydro-1H-inden-1-yl) pyrrolidine-3-carboxylate (200 mg, 0.540 mmol, 1.00 equiv.) in 1,4-dioxane (2.0 mL) were added 4-bromo-2- chloro-1-cyclopropyl-benzene (186 mg, 0.810 mmol, 1.50 equiv.), water (0.2 mL), $PdCl_2(dppf)CH_2Cl_2$ (88.0 mg, 0.110 mmol, 0.200 equiv.) and $Cs_2CO_3$ (527 mg, 1.620 mmol, 3.00 equiv.). The resulting solution was stirred at 80° C. for 2 h under nitrogen atmosphere. LCMS showed the reaction was complete. The reaction solution was filtered and the filtration concentrated under reduced pressure. The crude product was purified by flash chromatography on silica gel (EA:PE=2:3) to give the respective enantiomer of methyl (3S)-1-(5-(3-chloro-4-cyclopropylphenyl)-2,3-dihydro-1H-inden-1-yl) pyrrolidine-3-carboxylate (100 mg, 46%) as an oil. LCMS (ESI, m/z): 396 $[M+H]^+$.

Synthesis of (3S)-1-(5-(3-chloro-4-cyclopropylphenyl)-2,3-dihydro-1H-inden-1-yl)pyrrolidine-3-carboxylic acid

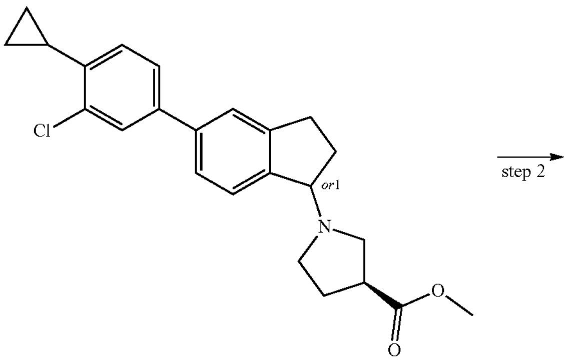

Chiral separation 1

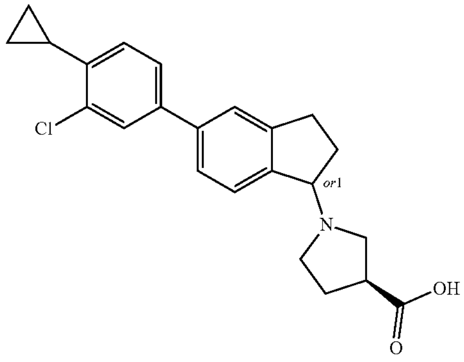

Chiral separation 1

A mixture of methyl (3S)-1-(5-(3-chloro-4-cyclopropylphenyl)-2,3-dihydro-1H-inden-1-yl)pyrrolidine-3-carboxylate (100 mg, 0.250 mmol, 1.00 equiv.) and $LiOH·H_2O$ (53.0 mg, 1.25 mmol, 5.00 equiv.) in THF (2 mL) and water (2 mL) was stirred at room temperature for 12 h. LCMS showed the reaction was complete. The resulting mixture was adjusted to pH 5-6 with 2N HCl and concentrated under reduced pressure. The residue was purified by preparative HPLC (Column: YMC-Actus Triart C18, 30*250 mm, 5 μm; Mobile Phase A: water (10 mmol/L $NH_4HCO_3$+0.1% $NH_3·H_2O$), Mobile Phase B: ACN; Flow rate: 60 mL/min; Gradient: 25% B to 55% B in 7 min; 254/210 nm; RT: 6.42 min) to give the respective enantiomer of (3S)-1-(5-(3-chloro-4-cyclopropylphenyl)-2,3-dihydro-1H-inden-1-yl) pyrrolidine-3-carboxylic acid (35a, 20 mg, 21%) as a solid. LCMS (ESI, m/z): 382 $[M+H]^+$.

$^1$H NMR (400 MHz, DMSO-$d_6$) δ 7.67 (d, J=2.0 Hz, 1H), 7.53-7.50 (m, 2H), 7.45 (dd, J=8.0, 2.0 Hz, 1H), 7.34 (d, J=8.0 Hz, 1H), 7.08 (d, J=8.0 Hz, 1H), 4.17 (d, J=6.0 Hz, 1H), 3.02-2.94 (m, 1H), 2.89-2.84 (m, 1H), 2.82-2.77 (m, 2H), 2.70-2.67 (m, 1H), 2.62-2.57 (m, 2H), 2.20-2.13 (m, 1H), 2.10-2.05 (m, 2H), 1.95-1.90 (m, 2H), 1.05-1.00 (m, 2H), 0.76-0.72 (m, 2H).

LCMS (ESI, m/z): 382 $[M+H]^+$. Analytic Conditions: column: EVO C18, 3.0*50 mm, 2.6 μm; mobile phase A: water (5 mM $NH_4HCO_3$), mobile phase B: acetonitrile; flow rate: 1.20 mL/min; gradient: 10% B to 95% B in 2.00 min, hold at 95% for 0.60 min, 95% B to 10% B in 0.15 min; 210 nm; RT: 1.204 min.

Synthesis of (3S)-1-(5-(3-chloro-4-cyclopropylphenyl)-2,3-dihydro-1H-inden-1-yl)pyrrolidine-3-carboxylic acid

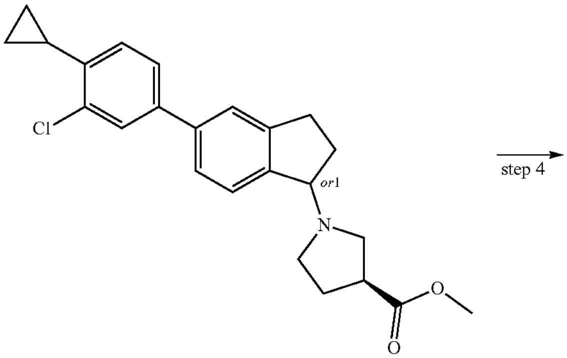

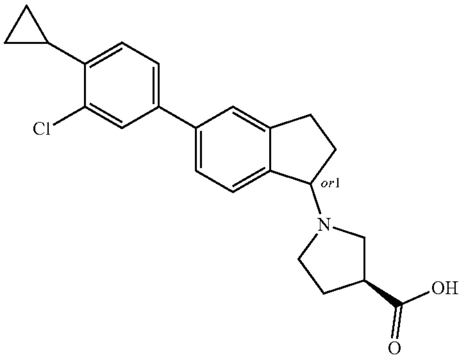

Chiral separation 2

A mixture of methyl (3S)-1-(5-(3-chloro-4-cyclopropylphenyl)-2,3-dihydro-1H-inden-1-yl)pyrrolidine-3-carboxylate (100 mg, 0.250 mmol, 1.00 equiv.) and $LiOH·H_2O$ (53 mg, 1.250 mmol, 5.00 equiv.) in THF (4.0 mL)/Water (4.0 mL) was stirred at room temperature for 12 h. LCMS showed the reaction was complete. The solution was adjusted to pH 4-5 with 1N HCl, and then was concentrated under vacuum. The residue was purified by Prep-HPLC (Column: YMC-Actus Triart C18, 30*250 mm, 5 μm; Mobile Phase A: Water (10 mmol/L $NH_4HCO_3$+0.1% $NH_3·H_2O$), Mobile Phase B: ACN; Flow rate: 60 mL/min; Gradient: 25% B to 55% B in 7 min; 254/210 nm; RT: 6.42 min) to give (3S)-1-(5-(3-chloro-4-cyclopropylphenyl)-2,3-dihydro-1H-inden-1-yl)pyrrolidine-3-carboxylic acid (35b, 40.6 mg, 42%) as a solid.

$^1$H NMR (400 MHz, DMSO-$d_6$) δ 7.68 (d, J=2.0 Hz, 1H), 7.54-7.51 (m, 2H), 7.47-7.45 (m, 1H), 7.37 (d, J=7.6 Hz,

1H), 7.09 (d, J=8.4 Hz, 1H), 4.16 (t, J=6.0 Hz, 1H), 3.03-2.87 (m, 2H), 2.85-2.76 (m, 2H), 2.74-2.70 (m, 1H), 2.64-2.57 (m, 2H), 2.21-2.14 (m, 1H), 2.12-2.07 (m, 2H), 1.96-1.86 (m, 2H), 1.06-1.01 (m, 2H), 0.77-0.73 (m, 2H).

LCMS (ESI, m/z): 382 $[M+H]^+$. Analytic Conditions: column: EVO C18, 3.0*50 mm, 2.6 μm; mobile Phase A: Water/5 mM $NH_4HCO_3$, mobile Phase B: acetonitrile; flow rate: 1.20 mL/min; gradient: 10% B to 95% B in 1.99 min, hold at 95% for 0.6 min, 95% B to 10% B in 0.15 min; 210 nm; RT: 1.203 min.

Example S36. (3R)-1-(5-(4-cyclopropyl-3-fluorophenyl)-2,3-dihydro-1H-inden-1-yl)pyrrolidine-3-carboxylic acid (36a and 36b)

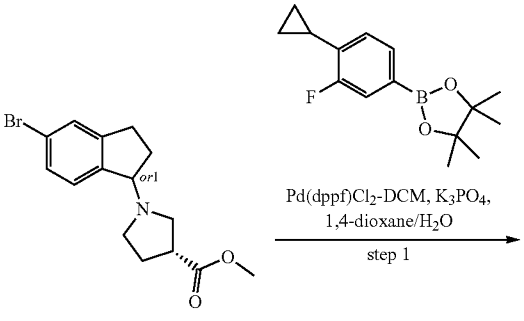

Chiral separation 1

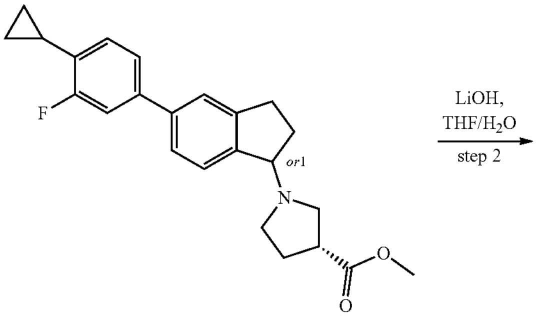

Chiral separation 1

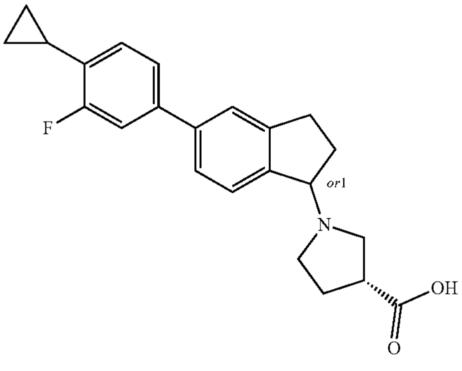

Chiral separation 1

Synthesis of methyl (3R)-1-(5-(4-cyclopropyl-3-fluorophenyl)-2,3-dihydro-1H-inden-1-yl)pyrrolidine-3-carboxylate

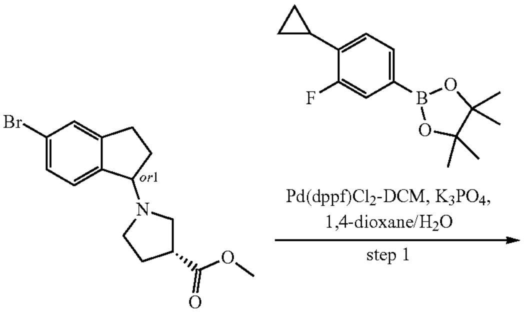

Chiral separation 1

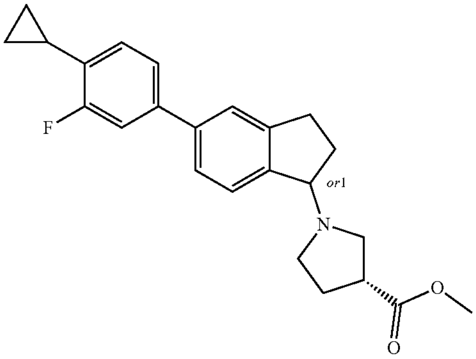

Chiral separation 1

To a solution of chiral separation 1 isomer of methyl (3R)-1-(5-bromo-2,3-dihydro-1H-inden-1-yl)pyrrolidine-3-carboxylate (200 mg, 0.620 mmol, 1.00 equiv.), $K_3PO_4$ (392 mg, 1.85 mmol, 3.00 equiv.) and 2-(4-cyclopropyl-3-fluorophenyl)-4,4,5,5-tetramethyl-1,3,2-dioxaborolane (162 mg, 0.620 mmol, 1.00 equiv,) in 1,4-dioxane (4 mL) and water (0.4 mL) was added Pd(dppf)$Cl_2$·DCM (50.4 mg, 0.060 mmol, 1.00 equiv.). The reaction mixture was stirred at 80° C. overnight under a nitrogen atmosphere. LCMS showed the reaction was complete. The reaction mixture was diluted with EA. The solid was filtered out. The filtrate was concentrated under reduce pressure and the residue was purified by flash column chromatography on silica gel (eluted with DCM/MeOH, 15/1) to give the corresponding enantiomer of methyl (3R)-1-(5-(4-cyclopropyl-3-fluorophenyl)-2,3-dihydro-1H-inden-1-yl)-pyrrolidine-3-carboxylate (50 mg, 21.3%) as a semi-solid. LCMS (ESI, m/z): 380 $[M+H]^+$.

Synthesis of (3R)-1-(5-(4-cyclopropyl-3-fluorophenyl)-2,3-dihydro-1H-inden-1-yl)-pyrrolidine-3-carboxylic acid

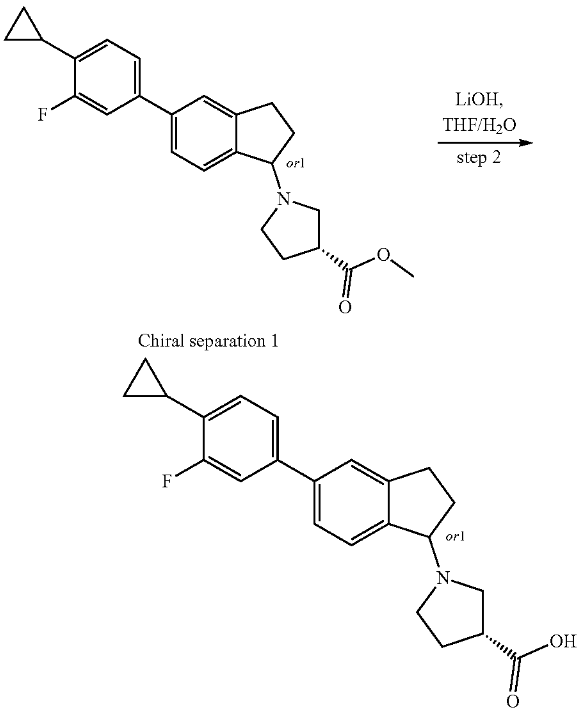

Chiral separation 1

To a stirred solution of methyl (3R)-1-(5-(4-cyclopropyl-3-fluorophenyl)-2,3-dihydro-1H-inden-1-yl)-pyrrolidine-3-carboxylate (50.0 mg, 0.130 mmol, 1.00 equiv.) in THF (1 mL) and water (1 mL) was added $LiOH \cdot H_2O$ (27.6 mg, 0.660 mmol, 1.00 equiv.). The resulting solution was stirred overnight at room temperature. LCMS showed the reaction was complete. The reaction mixture was acidified to pH 4-5 by adding 1N HCl, and then was concentrated under reduced pressure. The residue was purified by Prep-HPLC (column: Xselect CSH OBD Column 30*150 mm 5 μm; mobile phase A: water (0.05% HCl), mobile phase B: ACN; flow rate: 60 mL/min; gradient: 17% B to 43% B in 7 min; 254/210 nm; RT: 6.68 min) to afford the respective enantiomer of (3R)-1-(5-(4-cyclopropyl-3-fluorophenyl)-2,3-dihydro-1H-inden-1-yl)pyrrolidine-3-carboxylic acid (36a, 14.8 mg, 30.6%) as a solid.

$^1$H NMR (400 MHz, methanol-$d_6$) δ 7.74-7.67 (m, 2H), 7.61 (d, J=8.0 Hz, 1H), 7.40-7.33 (m, 2H), 7.05 (t, J=8.0 Hz, 1H), 5.05-5.01 (m, 1H), 3.90-3.78 (m, 1H), 3.71-3.59 (m, 2H), 3.54-3.47 (m, 1H), 3.42-3.33 (m, 1H), 3.12-3.06 (m, 1H), 2.66-2.48 (m, 3H), 2.41-2.38 (m, 1H), 2.24-2.11 (m, 2H), 1.07-1.02 (m, 2H), 0.81-0.77 (m, 2H).

$^{19}$F NMR (376 MHz, methanol-$d_6$) δ −122.2.

LCMS (ESI, m/z): 366 $[M+H]^+$. Analytic Conditions: column: Shim-pack XR-ODS Column 3.0*50 mm, 2.2 μm; mobile phase A: water/0.05% TFA, mobile phase B: acetonitrile/0.05% TFA; flow rate: 1.20 mL/min; gradient: 5% B to 100% B in 2.0 min, hold at 100% for 0.7 min, 100% B to 5% B in 0.05 min; 254 nm; RT: 1.577 min.

Synthesis of (3R)-1-(5-(4-cyclopropyl-3-fluorophenyl)-2,3-dihydro-1H-inden-1-yl)-pyrrolidine-3-carboxylic acid

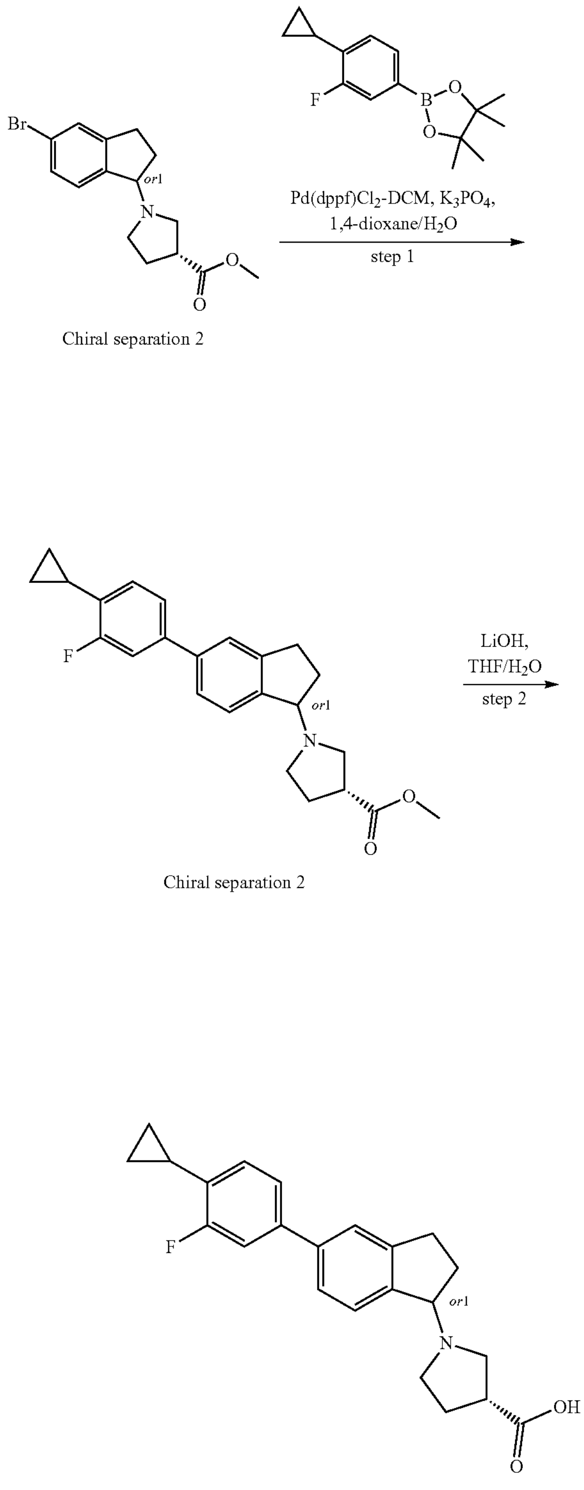

Chiral separation 2

Synthesis of methyl (3R)-1-(5-(4-cyclopropyl-3-fluorophenyl)-2,3-dihydro-1H-inden-1-yl)pyrrolidine-3-carboxylate

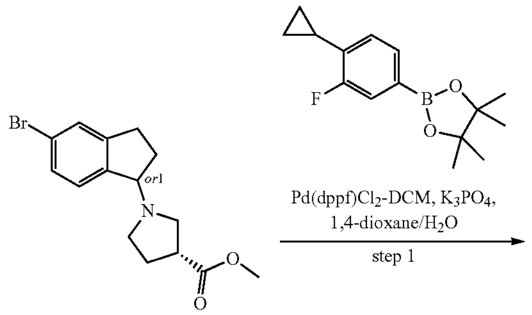

Chiral separation 2

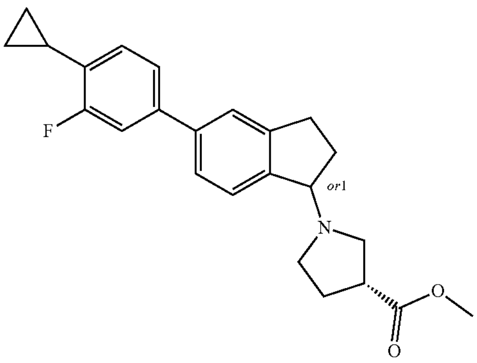

Chiral separation 2

To a solution of chiral separation 2 isomer of methyl (3R)-1-(5-bromo-2,3-dihydro-1H-inden-1-yl)pyrrolidine-3-carboxylate (150 mg, 0.460 mmol, 1.00 equiv.), $K_3PO_4$ (294 mg, 1.39 mmol, 3.00 equiv.) and 2-(4-cyclopropyl-3-fluorophenyl)-4,4,5,5-tetramethyl-1,3,2-dioxaborolane (121 mg, 0.460 mmol, 1.00 equiv.) in 1,4-dioxane (3 mL) and water (0.3 mL) was added $Pd(dppf)Cl_2$·DCM (37.8 mg, 0.050 mmol, 0.10 equiv.). The reaction mixture was stirred at 80° C. overnight under a nitrogen atmosphere. LCMS showed the reaction was complete. The reaction mixture was diluted with EA. The solid was filtered out. The filtrate was concentrated under reduce pressure and the residue was purified by flash column chromatography on silica gel (eluted with DCM/MeOH, 15/1) to give the corresponding enantiomer of methyl (3R)-1-(5-(4-cyclopropyl-3-fluorophenyl)-2,3-dihydro-1H-inden-1-yl)pyrrolidine-3-carboxylate (150 mg, 85.4%) as an oil. LCMS (ESI, m/z): 380 $[M+H]^+$.

Synthesis of (3R)-1-(5-(4-cyclopropyl-3-fluorophenyl)-2,3-dihydro-1H-inden-1-yl)pyrrolidine-3-carboxylic acid

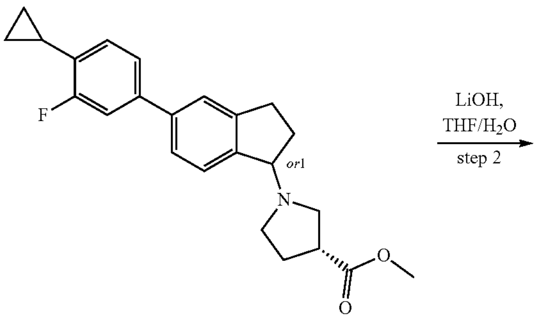

Chiral separation 2

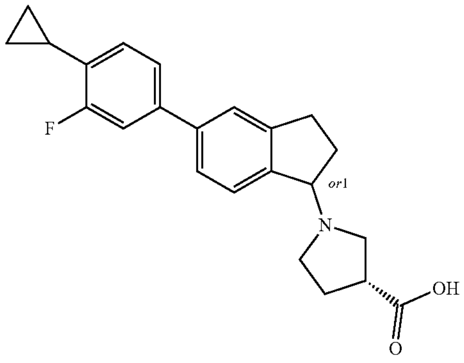

Chiral separation 2

To a solution of methyl (3R)-1-(5-(4-cyclopropyl-3-fluorophenyl)-2,3-dihydro-1H-inden-1-yl)pyrrolidine-3-carboxylate (100 mg, 0.260 mmol, 1.00 equiv.) in THF (4 mL) and water (4 mL) was added LiOH·$H_2O$ (55.3 mg, 1.32 mmol, 1.00 equiv.). The resulting solution was stirred overnight at room temperature. LCMS showed the reaction was complete. The reaction mixture was acidified to pH 4-5 by adding 1N HCl, and then was concentrated under reduced pressure. The residue was purified by Prep-HPLC (column: Xselect CSH OBD Column 30*150 mm 5 μm; mobile phase A: water (0.05% HCl), mobile phase B: ACN; flow rate: 60 mL/min; gradient: 15% B to 45% B in 7 min; 254/210 nm; RT: 6.42 min) to afford the respective enantiomer of (3R)-1-(5-(4-cyclopropyl-3-fluorophenyl)-2,3-dihydro-1H-inden-1-yl)pyrrolidine-3-carboxylic acid (36b, 33.6 mg, 34.7%) as a solid.

$^1H$ NMR (400 MHz, methanol-$d_6$) δ 7.71 (d, J=8.0 Hz, 1H), 7.67 (s, 1H), 7.63-7.58 (m, 1H), 7.40-7.32 (m, 2H), 7.05 (t, J=8.0 Hz, 1H), 5.04-5.01 (m, 1H), 3.95-3.82 (m, 1H), 3.75-3.62 (m, 1H), 3.59-3.46 (m, 2H), 3.41-3.29 (m, 2H), 3.13-3.05 (m, 1H), 2.66-2.22 (m, 4H), 2.174-2.10 (m, 1H), 1.07-1.01 (m, 2H), 0.81-0.77 (m, 2H).

$^{19}F$ NMR (376 MHz, methanol-$d_6$) δ −122.2.

LCMS (ESI, m/z): 366 $[M+H]^+$. Analytic Conditions: column: Shim-pack XR-ODS Column 3.0*50 mm, 2.2 μm; mobile phase A: water/0.05% TFA, mobile phase B: acetonitrile/0.05% TFA; flow rate: 1.20 mL/min; gradient: 20% B to 50% B in 2.7 min, 50% B to 95% B in 0.3 min, hold at 95% for 0.6 min, 95% B to 5% B in 0.1 min; 254 nm; RT: 2.656 min.

Example S37. (3S)-1-(5-(4-cyclopropyl-3-fluorophenyl)-2,3-dihydro-1H-inden-1-yl)pyrrolidine-3-carboxylic acid (37a and 37b)

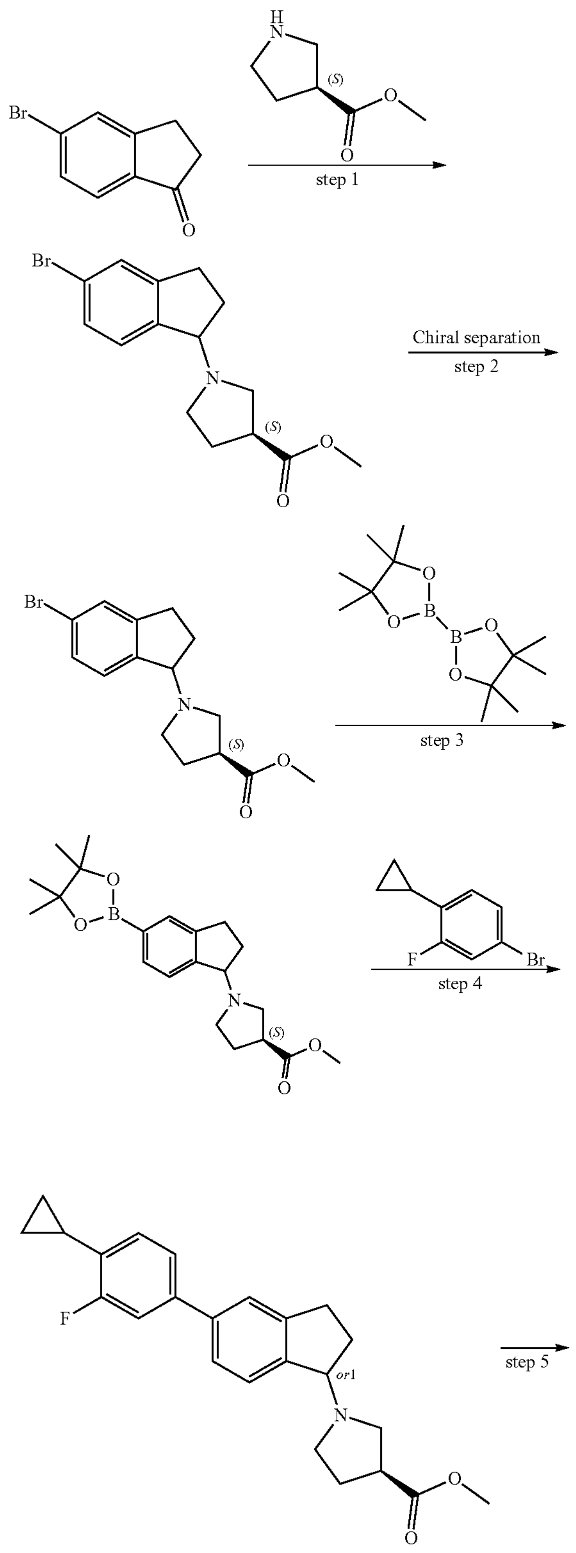

-continued

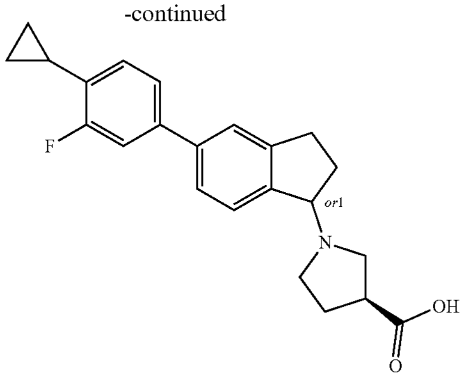

Chiral separation 1

Synthesis of methyl (3S)-1-(5-bromo-2,3-dihydro-1H-inden-1-yl)pyrrolidine-3-carboxylate

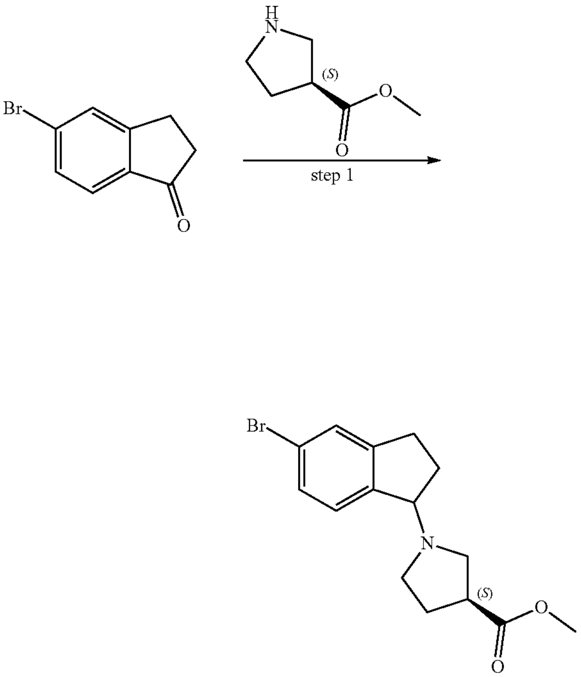

To a stirred solution of $NaBH_3CN$ (3.64 g, 56.9 mmol, 4.00 equiv.) in methanol (20 mL) was added $ZnCl_2$ (2 M in 2-Me-THF, 14.2 mL, 28.4 mmol, 2.00 equiv.). The resulting solution was stirred at room temperature for 15 min. Then methyl (S)-pyrrolidine-3-carboxylate (3.67 g, 28.4 mmol, 2.00 equiv.) and 5-bromo-2,3-dihydro-1H-inden-1-one (3.00 g, 14.2 mmol, 1.00 equiv.) were then added. The resulting mixture was stirred at 80° C. overnight. LCMS showed the reaction was complete. The reaction mixture was quenched with water (100 mL) and extracted with DCM (3*100 mL). The combined organic layers were dried over anhydrous $Na_2SO_4$ and concentrated under reduced pressure. The residue was purified by flash chromatography on silica gel with PE:EA=3:1 to afford methyl (3S)-1-(5-bromo-2,3-dihydro-1H-inden-1-yl)pyrrolidine-3-carboxylate (3.00 g, 65%) as an oil. LCMS (ESI, m/z): 324 $[M+H]^+$.

Chiral Separation of methyl (3S)-1-(5-bromo-2,3-dihydro-1H-inden-1-yl)pyrrolidine-3-carboxylate

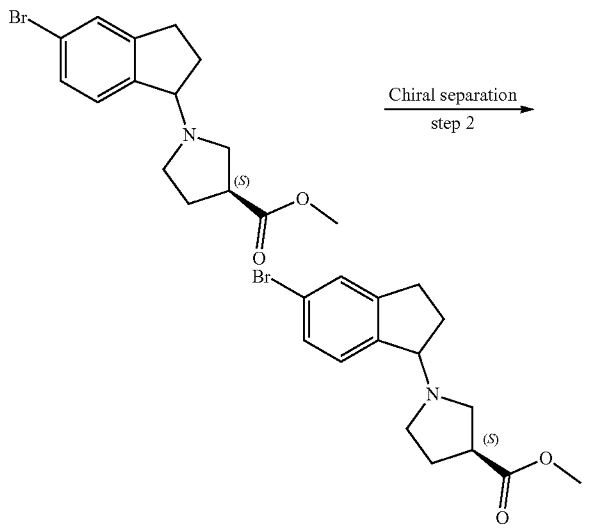

3.00 g of the racemic product was separated by SFC (Column: CHIRAL ART Amylose-C NEO, 3*25 cm, 5 m; Mobile Phase A: $CO_2$, Mobile Phase B: MeOH (2 mmol/L $NH_3$-MeOH); Flow rate: 100 mL/min; Gradient: 25% B; 220 nm) to afford the Chiral Separation 1 enantiomer (1.10 g, e.e.=96.9%) with the retention time at 2.61 min, the Chiral Separation 2 enantiomer (900 mg, e.e.=98.0%) at 3.35 min. LCMS (ESI, m/z): 324 $[M+H]^+$.

Synthesis of methyl (3S)-1-(5-(4,4,5,5-tetramethyl-1,3,2-dioxaborolan-2-yl)-2,3-dihydro-1H-inden-1-yl) pyrrolidine-3-carboxylate

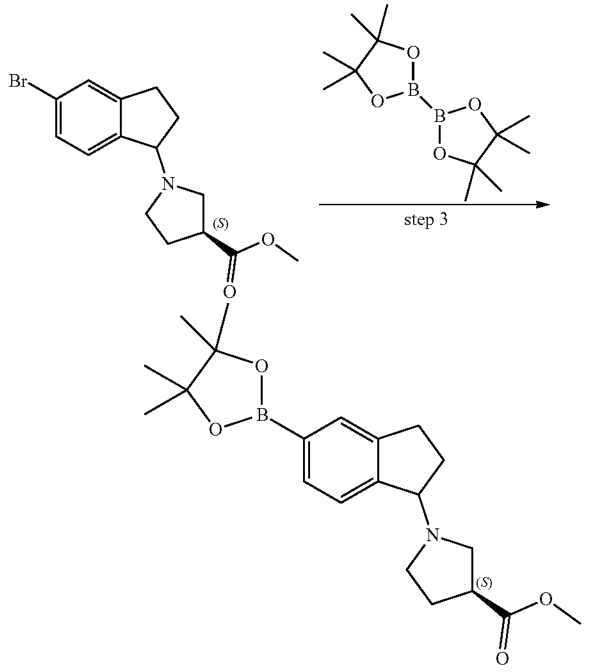

To a stirred solution of the Chiral Separation 1 enantiomer of methyl (3S)-1-(5-bromo-2,3-dihydro-1H-inden-1-yl)pyrrolidine-3-carboxylate (400 mg, 1.23 mmol, 1.00 equiv.) in 1,4-dioxane (5 mL) were added bis(pinacolato)diboron (469 mg, 1.85 mmol, 1.5 equiv.), $PdCl_2$(dppf) DCM (100 mg, 0.120 mmol, 0.100 equiv.) and AcOK (362 mg, 3.70 mmol, 3.00 equiv.). The resulting solution was stirred at 80° C. for 2 h under nitrogen atmosphere. LCMS showed the reaction was complete. The reaction solution was concentrated under reduced pressure and the crude product was purified by flash chromatography on silica gel (EA:PE=1:4) to give to give the corresponding enantiomer of methyl (3S)-1-(5-(4,4,5,5-tetramethyl-1,3,2-dioxaborolan-2-yl)-2,3-dihydro-1H-inden-1-yl)pyrrolidine-3-carboxylate (300 mg, 65%) as an oil. LCMS (ESI, m/z): 372 $[M+H]^+$.

Synthesis of methyl (3S)-1-(5-(4-cyclopropyl-3-fluorophenyl)-2,3-dihydro-1H-inden-1-yl)pyrrolidine-3-carboxylate

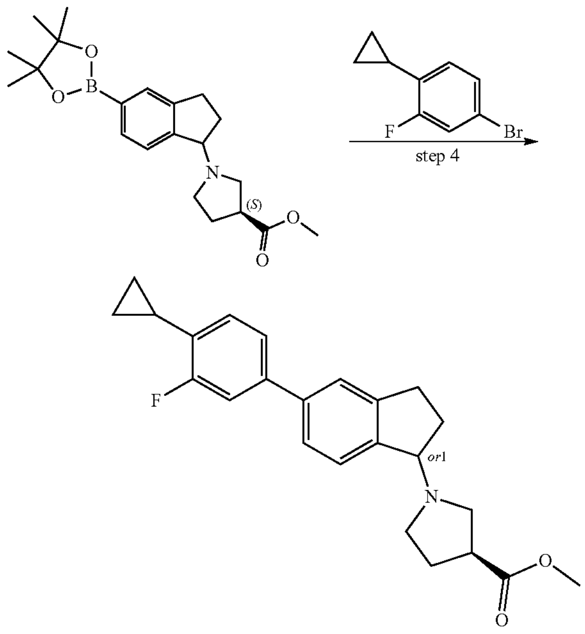

To a stirred solution of methyl (3S)-1-(5-(4,4,5,5-tetramethyl-1,3,2-dioxaborolan-2-yl)-2,3-dihydro-1H-inden-1-yl) pyrrolidine-3-carboxylate (100 mg, 0.270 mmol, 1.00 equiv.) in 1,4-dioxane (2 mL) and water (0.2 mL) were added 4-bromo-1-cyclopropyl-2-fluoro-benzene (87.0 mg, 0.400 mmol, 1.50 equiv.), $PdCl_2$(dppf) DCM (44.0 mg, 0.050 mmol, 0.200 equiv.) and $Cs_2CO_3$ (263 mg, 0.810 mmol, 3.00 equiv.). The resulting solution was stirred at 80° C. for 2 h under nitrogen atmosphere. LCMS showed the reaction was complete. The reaction solution was filtered and the filtration was concentrated under reduced pressure. The residue was purified by flash chromatography on silica gel (EA:PE=2:3) to give the respective enantiomer of methyl (3S)-1-(5-(4-cyclopropyl-3-fluorophenyl)-2,3-dihydro-1H-inden-1-yl)pyrrolidine-3-carboxylate (100 mg, 49%) as an oil. LCMS (ESI, m/z): 380 $[M+H]^+$.

Synthesis of (3S)-1-(5-(4-cyclopropyl-3-fluorophenyl)-2,3-dihydro-1H-inden-1-yl)pyrrolidine-3-carboxylic acid

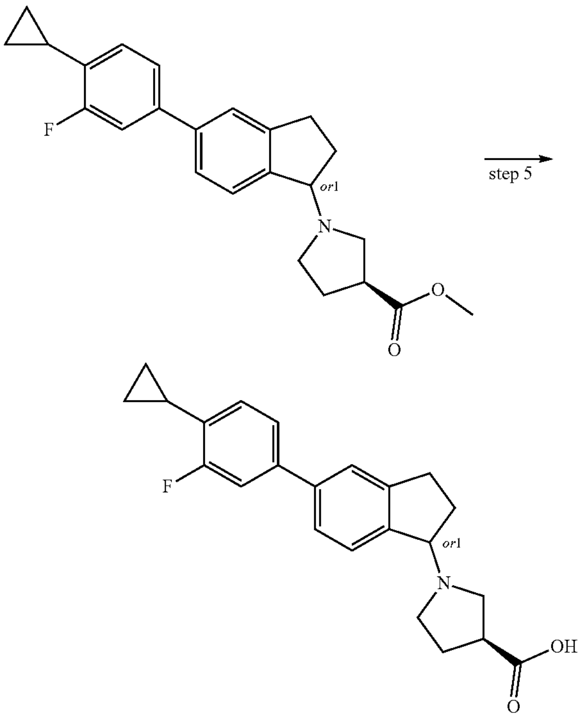

Chiral separation 1

A mixture of methyl (3S)-1-(5-(4-cyclopropyl-3-fluorophenyl)-2,3-dihydro-1H-inden-1-yl)pyrrolidine-3-carboxylate (100 mg, 0.250 mmol, 1.00 equiv.) and $LiOH{\cdot}H_2O$ (53.0 mg, 1.25 mmol, 5.00 equiv.) in THF (2 mL)/water (2 mL) was stirred at room temperature for 12 h. LCMS showed the reaction was complete. The resulting mixture was adjusted to pH 5-6 with 2N HCl and concentrated under reduced pressure. The residue was purified by preparative HPLC (Column: YMC-Actus Triart C18, 30*250.5 μm; Mobile Phase A: Water (10 mmol/L $NH_4HCO_3$+0.1% $NH_3{\cdot}H_2O$), Mobile Phase B: ACN; Flow rate: 60 mL/min; Gradient: 25% B to 55% B in 7 min; 254/210 nm; RT: 6.42 min) to give the respective enantiomer of (3S)-1-(5-(4-cyclopropyl-3-fluorophenyl)-2,3-dihydro-1H-inden-1-yl)pyrrolidine-3-carboxylic acid (37a, 36.6 mg, 37%) as a solid. LCMS (ESI, m/z): 366 $[M+H]^+$.

$^1H$ NMR (400 MHz, DMSO-$d_6$) δ 7.52 (s, 1H), 7.47-7.38 (m, 3H), 7.35 (d, J=7.6 Hz, 1H), 7.05 (t, J=8.0 Hz, 1H), 4.17 (d, J=6.0 Hz, 1H), 3.02-2.95 (m, 1H), 2.91-2.85 (m, 1H), 2.84-2.77 (m, 2H), 2.71-2.67 (m, 1H), 2.63-2.58 (m, 2H), 2.10-2.03 (m, 3H), 1.96-1.90 (m, 2H), 1.02-0.98 (m, 2H), 0.79-0.75 (m, 2H).

$^{19}F$ NMR (376 MHz, DMSO-$d_6$) δ −120.46.

LCMS (ESI, m/z): 366 $[M+H]^+$. Analytic Conditions: column: Xbridge RP18, 4.6*50 mm, 3.5 μm; mobile phase A: water/0.04% $NH_3{\cdot}H_2O$, mobile phase B: acetonitrile; flow rate: 1.20 mL/min; gradient: 10% B to 95% B in 1.75 min, hold at 95% for 1.15 min, 95% B to 10% B in 0.01 min; 254 nm; RT: 1.165 min.

Synthesis of (3S)-1-(5-(3-chloro-4-cyclopropylphenyl)-2,3-dihydro-1H-inden-1-yl)pyrrolidine-3-carboxylic acid from Chiral Separation 2

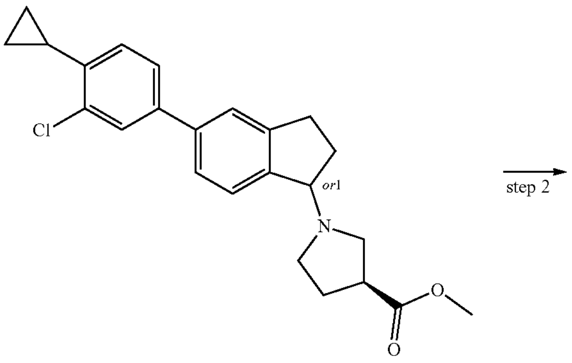

Chiral separation 2

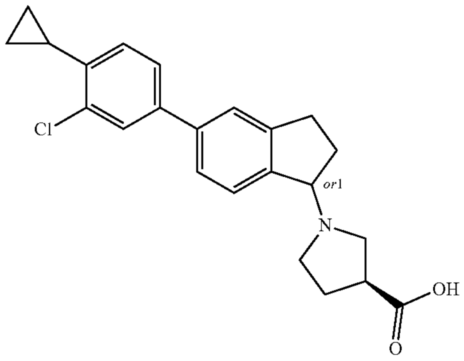

Chiral separation 2

A mixture of methyl (3S)-1-(5-(3-chloro-4-cyclopropylphenyl)-2,3-dihydro-1H-inden-1-yl)pyrrolidine-3-carboxylate (100 mg, 0.250 mmol, 1.00 equiv.) and $LiOH{\cdot}H_2O$ (53.0 mg, 1.25 mmol, 5.00 equiv.) in THF (2 mL) and water (2 mL) was stirred at room temperature for 12 h. LCMS showed the reaction was complete. The resulting mixture was adjusted to pH 5-6 with 2N HCl and concentrated under reduced pressure. The residue was purified by preparative HPLC (Column: YMC-Actus Triart C18, 30*250 mm, 5 μm; Mobile Phase A: water (10 mmol/L $NH_4HCO_3$+0.1% $NH_3{\cdot}H_2O$), Mobile Phase B: ACN; Flow rate: 60 mL/min; Gradient: 25% B to 55% B in 7 min; 254/210 nm; RT: 6.42 min) to give the respective enantiomer of (3S)-1-(5-(3-chloro-4-cyclopropylphenyl)-2,3-dihydro-1H-inden-1-yl) pyrrolidine-3-carboxylic acid (37b, 40.6 mg, 42%) as a solid. LCMS (ESI, m/z): 382 $[M+H]^+$.

$^1H$ NMR (400 MHz, DMSO-$d_6$) δ 7.68 (d, J=2.0 Hz, 1H), 7.54-7.51 (m, 2H), 7.47-7.45 (m, 1H), 7.37 (d, J=7.6 Hz, 1H), 7.08 (d, J=8.4 Hz, 1H), 4.16 (d, J=6.0 Hz, 1H), 3.03-2.95 (m, 1H), 2.92-2.87 (m, 1H), 2.84-2.79 (m, 2H), 2.73-2.70 (m, 1H), 2.64-2.59 (m, 2H), 2.21-2.14 (m, 1H), 2.12-2.07 (m, 2H), 1.96-1.90 (m, 2H), 1.06-1.01 (m, 2H), 0.77-0.73 (m, 2H).

LCMS (ESI, m/z): 382 $[M+H]^+$. Analytic Conditions: column: EVO C18, 3.0*50 mm, 2.6 μm; mobile phase A: water (5 mM $NH_4HCO_3$), mobile phase B: acetonitrile; flow rate: 1.20 mL/min; gradient: 10% B to 95% B in 2.00 min, hold at 95% for 0.60 min, 95% B to 10% B in 0.15 min; 210 nm; RT: 1.203 min.

Example S38. 1-(5-(3-chloro-4-cyclopropylphenyl)-2,3-dihydro-1H-inden-1-yl)piperidine-3-carboxylic acid (38)

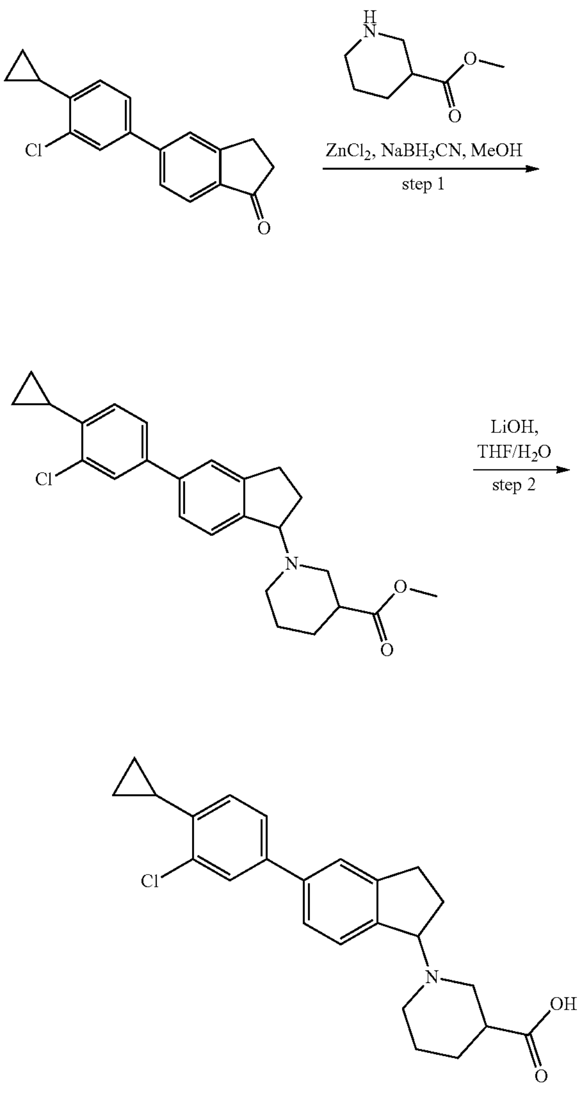

Synthesis of methyl 1-(5-(3-chloro-4-cyclopropy-lphenyl)-2,3-dihydro-1H-inden-1-yl)piperidine-3-carboxylate

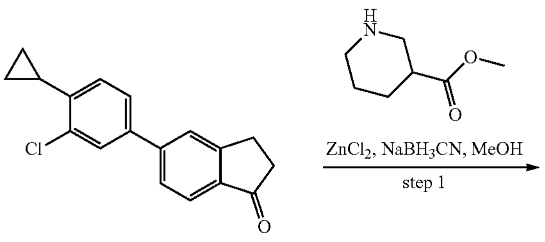

-continued

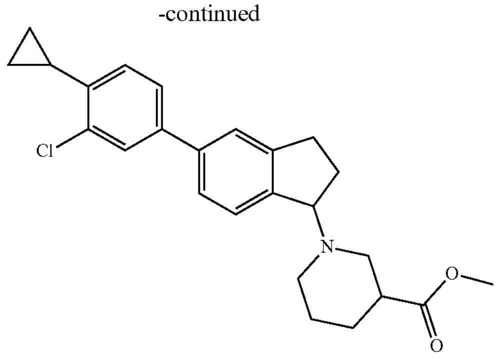

A solution of $ZnCl_2$ (2M in THF, 0.35 mL, 0.710 mmol, 1.00 equiv.) and $NaBH_3CN$ (181 mg, 2.83 mmol, 4.00 equiv.) in methanol (2 mL) was stirred at room temperature for 30 min. Then 5-(3-chloro-4-cyclopropylphenyl)-2,3-dihydro-1H-inden-1-one (200 mg, 0.710 mmol, 1.00 equiv.) and methyl piperidine-3-carboxylate (203 mg, 1.41 mmol, 2.00 equiv.) were added in portions. The resulting solution was stirred at 60° C. overnight. LCMS showed the reaction was complete. The mixture was concentrated under reduced pressure. The residue was purified by flash chromatography on silica gel with EA to afford methyl 1-(5-(3-chloro-4-cyclopropylphenyl)-2,3-dihydro-1H-inden-1-yl)piperidine-3-carboxylate (110 mg, 37.9%) as an oil. LCMS (ESI, m/z): 410 $[M+H]^+$.

Synthesis of 1-(5-(3-chloro-4-cyclopropylphenyl)-2,3-dihydro-1H-inden-1-yl)piperidine-3-carboxylic acid

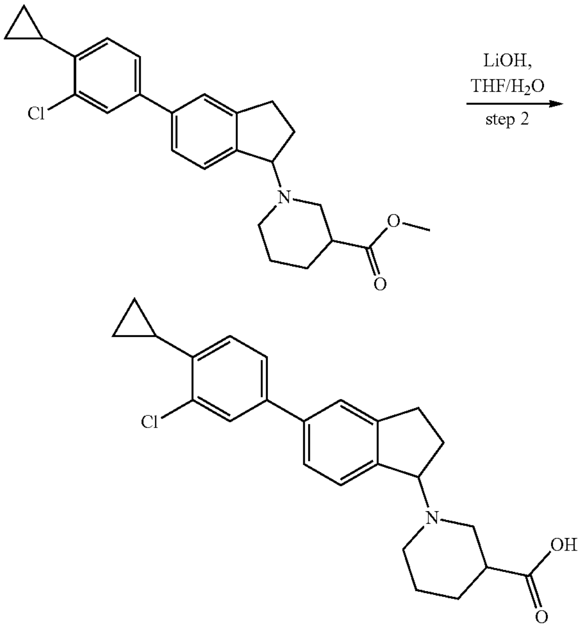

A mixture of methyl 1-(5-(3-chloro-4-cyclopropylphenyl)-2,3-dihydro-1H-inden-1-yl)piperidine-3-carboxylate (110 mg, 0.270 mmol, 1.00 equiv.) and LiOH (19 mg, 0.800 mmol, 3.00 equiv.) in THF (1 mL) and water (1 mL) was stirred at room temperature for 1 h. LCMS showed the reaction was complete. The pH of the solution was adjusted to 3-4 with 2N HCl. The resulting mixture was concentrated under reduced pressure and the crude product was purified by Prep-HPLC (Column: YMC-Triart Diol Hilic, 20*150 mm 5 μm; Mobile Phase A: water (10 mmol/L $NH_4HCO_3$+ 0.1% $NH_3 \cdot H_2O$), Mobile Phase B: ACN; Flow rate: 60 mL/min; Gradient: 20% B to 50% B in 7 min; 254/210 nm; RT: 6.73 min) to 1-(5-(3-chloro-4-cyclopropylphenyl)-2,3-dihydro-1H-inden-1-yl)piperidine-3-carboxylic acid (38, 26.4 mg, 24.7%) as a solid.

$^1$H NMR (400 MHz, Chloroform-d) δ 7.56-7.48 (m, 2H), 7.41-7.33 (m, 3H), 6.97 (d, J=8.0 Hz, 1H), 4.54-4.50 (m, 1H), 3.13-2.95 (m, 3H), 2.76-2.53 (m, 4H), 2.26-2.19 (m, 3H), 2.05-1.95 (m, 2H), 1.85-1.75 (m, 2H), 1.26-0.98 (m, 2H), 0.74-0.68 (m, 2H).

LCMS (ESI, m/z): 396 $[M+H]^+$. Analytic Conditions: Poroshell HPH-C18, 3.0*50 mm, 2.7 μm; Mobile Phase A: water/5 mM $NH_4HCO_3$, Mobile Phase B: Acetonitrile; Flow rate: 1.20 mL/min; Gradient: 10% B to 95% B in 2.0 min, hold at 95% B for 0.6 min, 95% B to 10% B in 0.15 min; 254 nm; RT: 1.311 min.

Example S39. 2-(5-(3-chloro-4-cyclopropylphenyl)-2,3-dihydro-1H-inden-1-yl)-2-azaspiro[3.3]heptane-6-carboxylic acid (39)

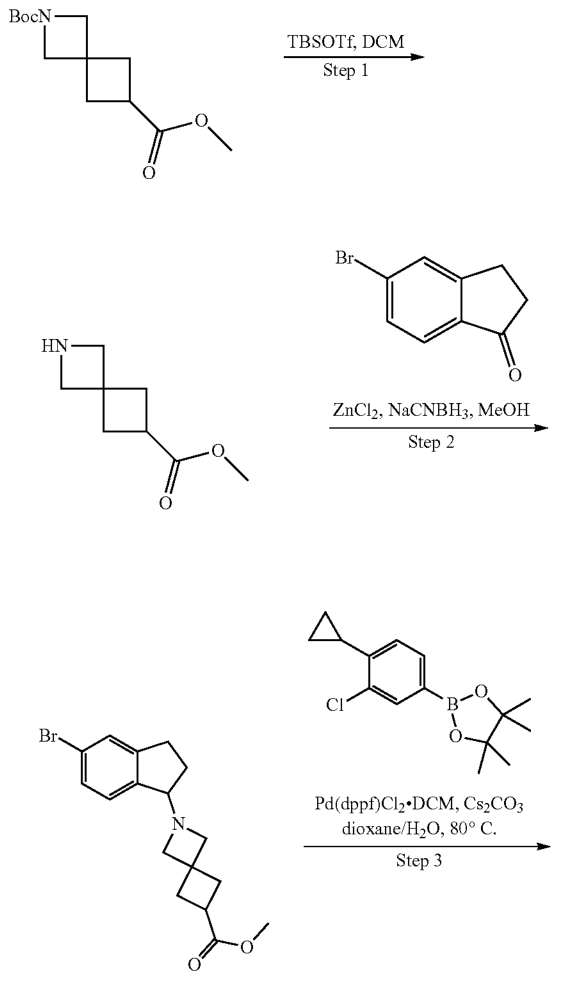

-continued

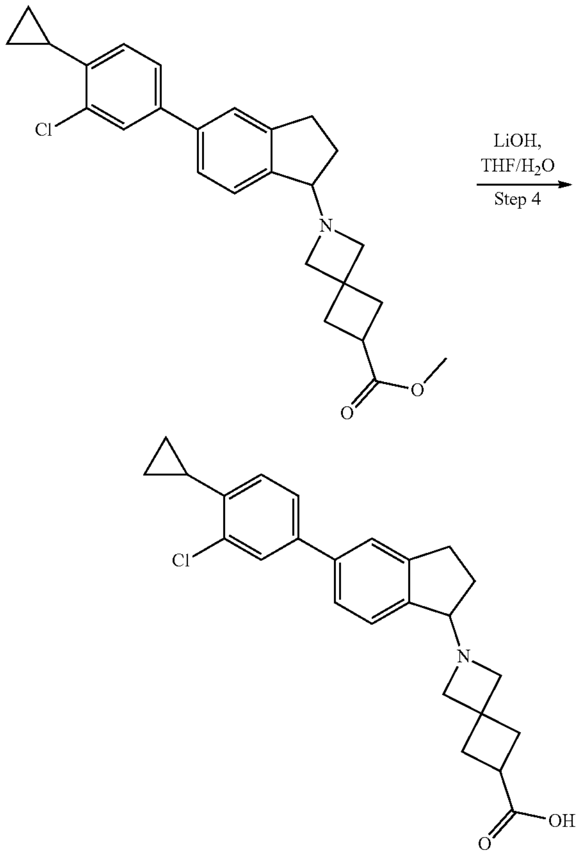

Synthesis of methyl 2-azaspiro[3.3]heptane-6-carboxylate

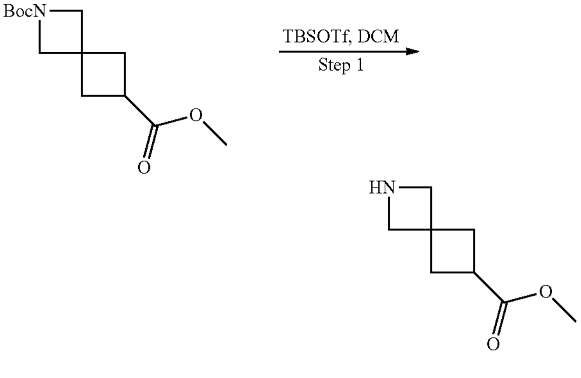

To a solution of 2-(tert-butyl) δ-methyl 2-azaspiro[3.3]heptane-2,6-dicarboxylate (1.0 g, 3.922 mmol, 1.00 equiv.) in DCM (10 mL) was added TBSOTf (2.1 g, 7.843 mmol, 2.00 equiv.) dropwise at 0° C. The resulting solution was stirred at room temperature for 2 h. LCMS showed the reaction was complete. The resulting solution was concentrated under reduce pressure. The crude methyl 2-azaspiro[3.3]heptane-6-carboxylate (700 mg) was used directly for the next step without further purification. LCMS (ESI, m/z): 156 $[M-H]^+$.

Synthesis of methyl 2-(5-bromo-2,3-dihydro-1H-inden-1-yl)-2-azaspiro[3.3]heptane-6-carboxylate

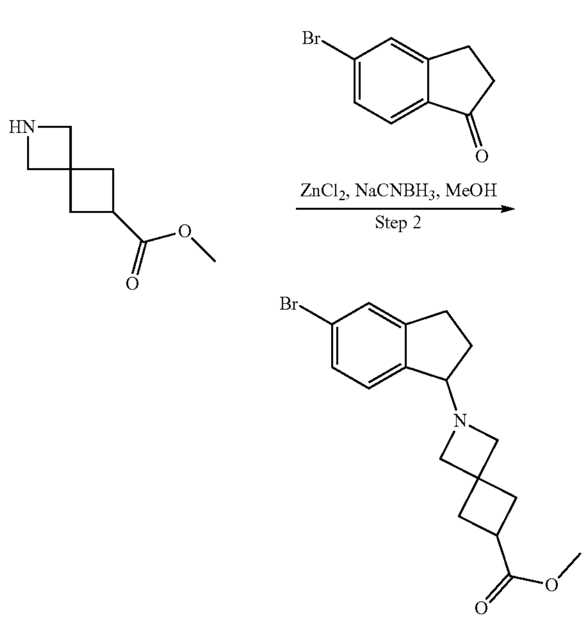

To a solution of 5-bromo-2,3-dihydro-1H-inden-1-one (400 mg, 1.896 mmol, 1.00 equiv.), $ZnCl_2$ (258 mg, 1.896 mmol, 1.00 equiv.) and methyl 2-azaspiro[3.3]heptane-6-carboxylate (353 mg, 2.275 mmol, 1.50 equiv.) in methanol (10 mL) was added $NaBH_3CN$ (358 mg, 5.688 mmol, 3.00 equiv.). The resulting solution was stirred at 80° C. overnight under a nitrogen atmosphere. LCMS showed the reaction was complete. The resulting mixture was diluted with water and extracted with DCM. The combined organic layers were washed with brine, dried over anhydrous $Na_2SO_4$, filtered and concentrated under reduced pressure. The crude product was purified by flash chromatography on C18 silica (eluted with water (0.05% TFA)/ACN, 3/1) to afford methyl 2-(5-bromo-2,3-dihydro-1H-inden-1-yl)-2-azaspiro[3.3]heptane-6-carboxylate (400 mg, 60.3%) as an oil. LCMS (ESI, m/z): 350 $[M+H]^+$.

Synthesis of methyl 2-(5-(3-chloro-4-cyclopropylphenyl)-2,3-dihydro-1H-inden-1-yl)-2-azaspiro[3.3]heptane-6-carboxylate

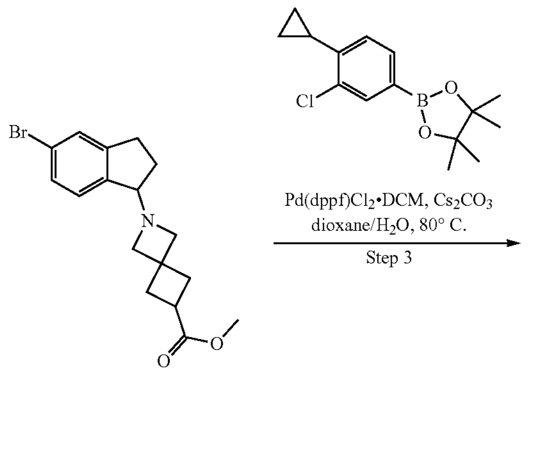

-continued

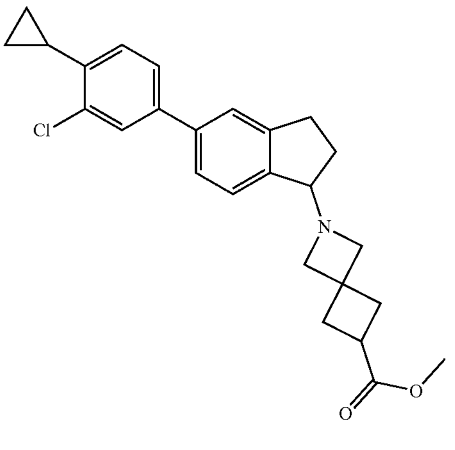

To a solution of methyl 2-(5-bromo-2,3-dihydro-1H-inden-1-yl)-2-azaspiro[3.3]heptane-6-carboxylate (189 mg, 0.540 mmol, 1.00 equiv.), $Cs_2CO_3$ (527 mg, 1.620 mmol, 3.00 equiv.) and 2-(3-chloro-4-cyclopropyl-phenyl)-4,4,5,5-tetramethyl-1,3,2-dioxaborolane (150 mg, 0.540 mmol, 1.00 equiv.) in 1,4-dioxane (3.0 mL) and water (0.3 mL) was added Pd(dppf)$Cl_2$-DCM (44 mg, 0.054 mmol, 0.10 equiv.). The reaction mixture was stirred at 80° C. overnight under a nitrogen atmosphere. LCMS showed the reaction was complete. The reaction mixture was diluted with EtOAc. The solid was filtered out. The filtrate was concentrated under reduce pressure and the residue was purified by flash column chromatography on silica gel (eluted with DCM/MeOH, 15/1) to give methyl 2-(5-(3-chloro-4-cyclopropylphenyl)-2,3-dihydro-1H-inden-1-yl)-2-azaspiro[3.3]heptane-6-carboxylate (110 mg, 48.3%) as a solid. LCMS (ESI, m/z): 422 $[M+H]^+$.

Synthesis of 2-(5-(3-chloro-4-cyclopropylphenyl)-2,3-dihydro-1H-inden-1-yl)-2-azaspiro[3.3]heptane-6-carboxylic acid

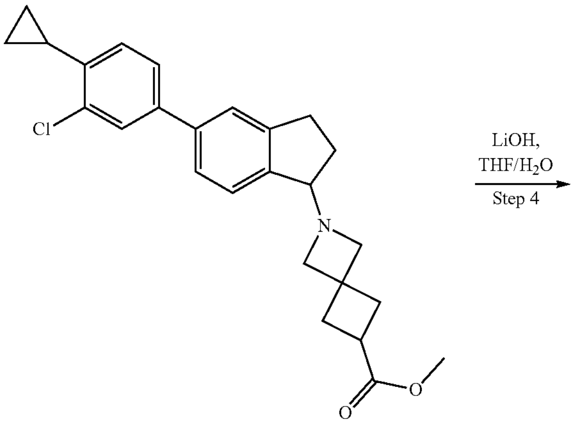

-continued

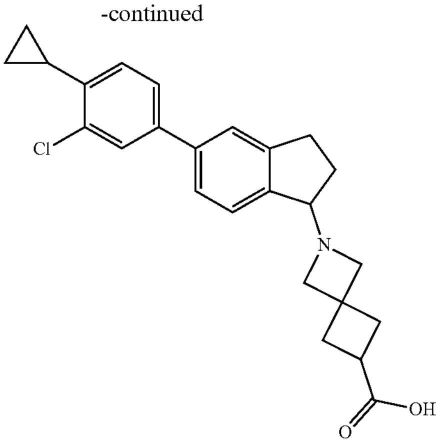

To a solution of methyl 2-(5-(3-chloro-4-cyclopropylphenyl)-2,3-dihydro-1H-inden-1-yl)-2-azaspiro[3.3]heptane-6-carboxylate (100 mg, 0.240 mmol, 1.00 equiv.) in THF (2.0 mL) and water (2.0 mL) was added LiOH·$H_2O$ (50 mg, 1.180 mmol, 5.00 equiv.). The resulting solution was stirred overnight at room temperature. LCMS showed the reaction was complete. The reaction mixture was acidified to pH 4-5 by adding 1N HCl, and then was concentrated under reduced pressure. The residue was purified by Prep-HPLC (column: Xselect CSH OBD Column 30*150 mm 5 μm; mobile phase A: water (0.05% HCl), mobile phase B: ACN; flow rate: 60 mL/min; gradient: 23% B to 47% B in 7 min; 254/210 nm; RT: 5.93 min) to afford 2-(5-(3-chloro-4-cyclopropylphenyl)-2,3-dihydro-1H-inden-1-yl)-2-azaspiro[3.3]heptane-6-carboxylic acid (39, 27.2 mg, 28%) as a solid.

$^1$H NMR (400 MHz, methanol-$d_4$) δ 7.65-7.64 (m, 2H), 7.62-7.56 (m, 2H), 7.49 (dd, J=8.0, 2.0 Hz, 1H), 7.09 (d, J=8.0 Hz, 1H), 4.50-4.47 (m, 1H), 4.31-4.26 (m, 2H), 4.21-4.15 (m, 1H), 3.33-3.31 (m, 1H), 3.27-3.19 (m, 1H), 3.11-3.04 (m, 2H), 2.68-2.64 (m, 1H), 2.60-2.48 (m, 4H), 2.28-2.15 (m, 2H), 1.10-1.05 (m, 2H), 0.77-0.73 (m, 2H).

LCMS (ESI, m/z): 408 $[M+H]^+$. Analytic Conditions: column: Shim-pack XR-ODS C18 100A Column 3.0*50 mm, 2.2 μm; mobile phase A: Water/0.05% TFA, mobile phase B: acetonitrile/0.05% TFA; flow rate: 1.20 mL/min; gradient: 20% B to 65% B in 2.5 min, 65% B to 95% B in 0.5 min, hold at 95% B for 0.6 min; 254 nm; RT: 2.248 min.

Example S40. 1-(5-(3,5-dimethoxyphenyl)-2,3-dihydro-1H-inden-1-yl)piperidine-4-carboxylic acid (40)

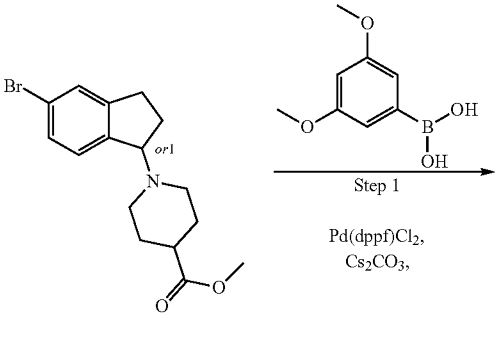

-continued

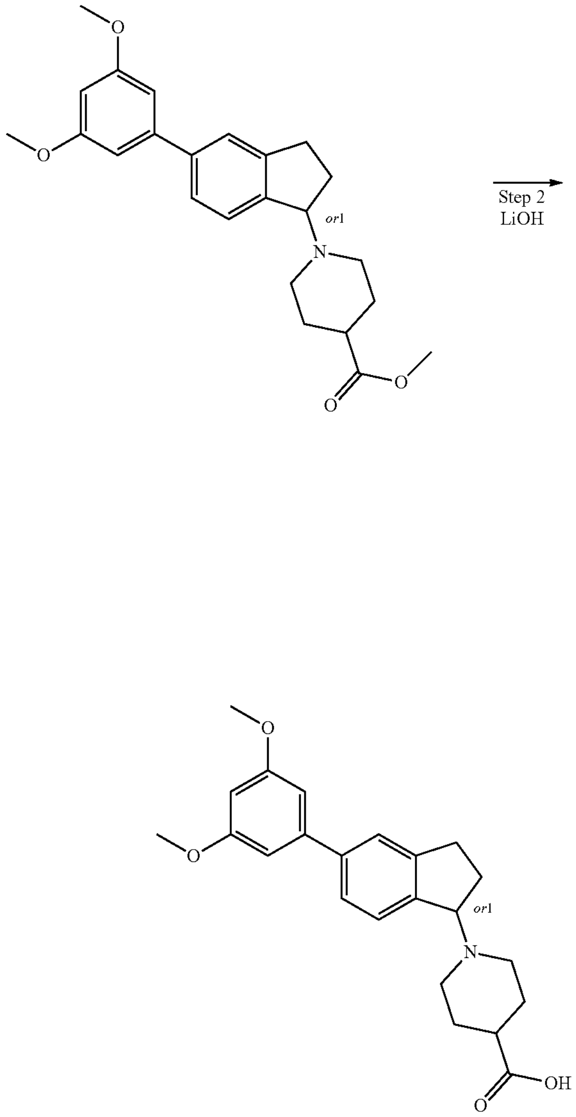

Synthesis of methyl 1-(5-(3,5-dimethoxyphenyl)-2,3-dihydro-1H-inden-1-yl)piperidine-4-carboxylate

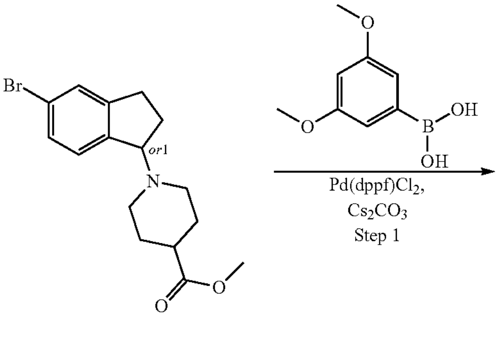

-continued

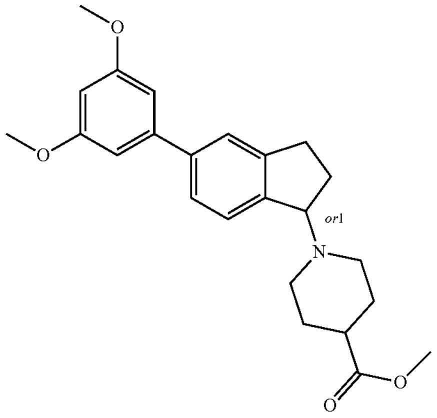

To a stirred solution of a single enantiomer of methyl 1-(5-bromo-2,3-dihydro-1H-inden-1-yl)piperidine-4-carboxylate (92 mg, 0.270 mmol, 1.00 equiv) in 1,4-dioxane (3.0 mL) and water (0.3 mL) were added (3,5-dimethoxyphenyl)boronic acid (100 mg, 0.550 mmol, 2.00 equiv), $Pd(dppf)Cl_2$ (22 mg, 0.030 mmol, 0.10 equiv) and $Cs_2CO_3$ (268 mg, 0.820 mmol, 3.00 equiv). The reaction was stirred at 80° C. for 3 h. LCMS showed the reaction was complete. The residue was purified by flash column chromatography on C18 silica (Mobile Phase A: Water (10 mmol/L $NH_4HCO_3$), Mobile Phase B: ACN; Flow rate: 25 mL/min; Gradient: 47% B to 67% B in 7 min; 254/210 nm) to afford a single enantiomer of methyl 1-(5-(3,5-dimethoxyphenyl)-2,3-dihydro-1H-inden-1-yl)piperidine-4-carboxylate (150 mg, 69% yield) as an oil. LCMS (ESI, m/z): 396 $[M+H]^+$.

Synthesis of 1-(5-(3,5-dimethoxyphenyl)-2,3-dihydro-1H-inden-1-yl)piperidine-4-carboxylic acid

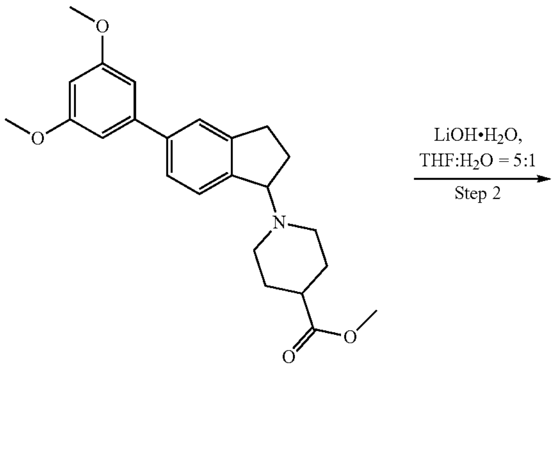

-continued

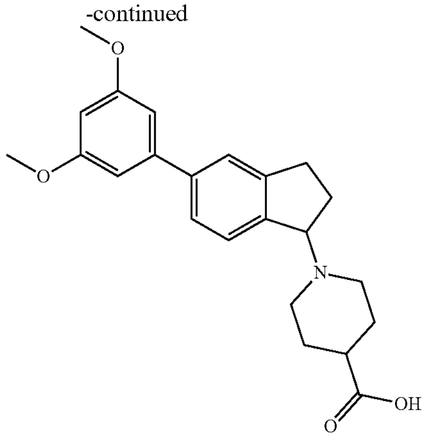

To a stirred solution of a single enantiomer of methyl 1-(5-(3,5-dimethoxyphenyl)-2,3-dihydro-1H-inden-1-yl)piperidine-4-carboxylate (150 mg, 0.380 mmol, 1.00 equiv) in THF (3.0 mL) and water (0.6 mL) were added $LiOH{\cdot}H_2O$ (47 mg, 1.140 mmol, 3.00 equiv). The reaction was stirred at room temperature for 5 h. LCMS showed the reaction was complete. The residue was purified by Prep-HPLC (Column: YMC-Actus Triart C18, 30*250 mm, 5 μm; Mobile Phase A: Water (10 MMOL/L $NH_4HCO_3$+0.10% $NH_3{\cdot}H_2O$), Mobile Phase B: ACN; Flow rate: 60 mL/min; Gradient: 16% B to 46% B in 7 min; 254/210 nm; RT: 5.95 min to afford a single enantiomer of 1-(5-(3,5-dimethoxyphenyl)-2,3-dihydro-1H-inden-1-yl)piperidine-4-carboxylic acid (40, 35.6 mg, 23% yield) as a solid.

$^1H$ NMR (400 MHz, DMSO-$d_6$) δ 12.06 (s, 1H), 7.52-7.43 (m, 2H), 7.31 (d, J=7.6 Hz, 1H), 6.76 (d, J=2.0 Hz, 2H), 6.48 (m, 1H), 4.31 (t, J=7.2 Hz, 1H), 3.8 (s, 6H), 2.98-2.72 (m, 3H), 2.54-2.53 (m, 1H), 2.32-2.27 (m, 1H), 2.22-2.13 (m, 2H), 2.07-1.98 (m, 2H), 1.88-1.71 (m, 2H), 1.65-1.42 (m, 2H).

LCMS (ESI, m/z): 382 $[M+H]^+$. Analytic Conditions: column: Titank C18, 3.0*50 mm, 3.0 m; mobile Phase A: Water/5 mM $NH_4HCO_3$, mobile Phase B: Acetonitrile; flow rate: 1.50 mL/min; gradient: 10% B to 95% B in 1.80 min, hold at 95% for 0.8 min, 95% B to 10% B in 0.15 min; 254 nm; RT: 1.178 min.

Example S41. 1-(5-(2,3-dihydrobenzofuran-6-yl)-2,3-dihydro-1H-inden-1-yl)piperidine-4-carboxylic acid (41)

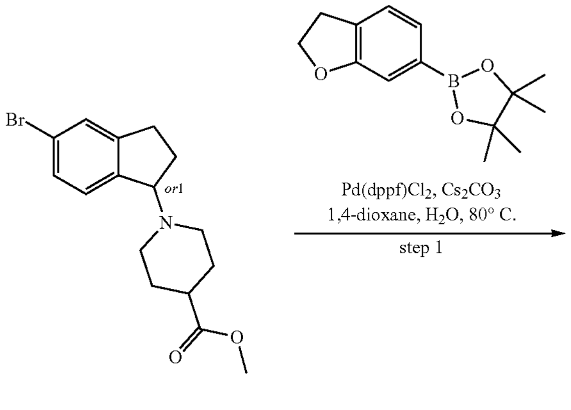

-continued

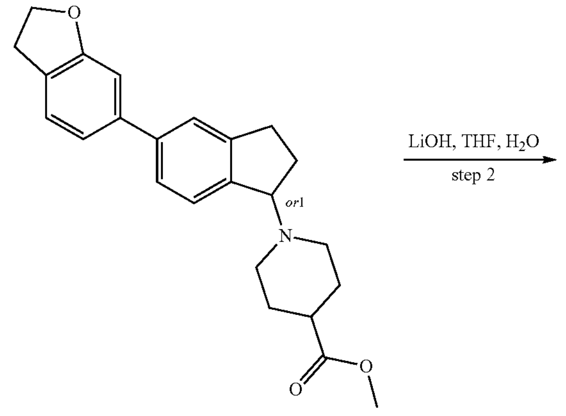

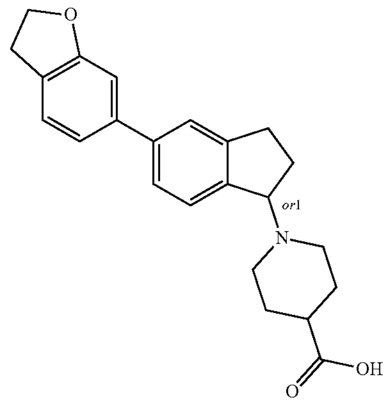

Synthesis of methyl 1-(5-(2,3-dihydrobenzofuran-6-yl)-2,3-dihydro-1H-inden-1-yl)piperidine-4-carboxylate

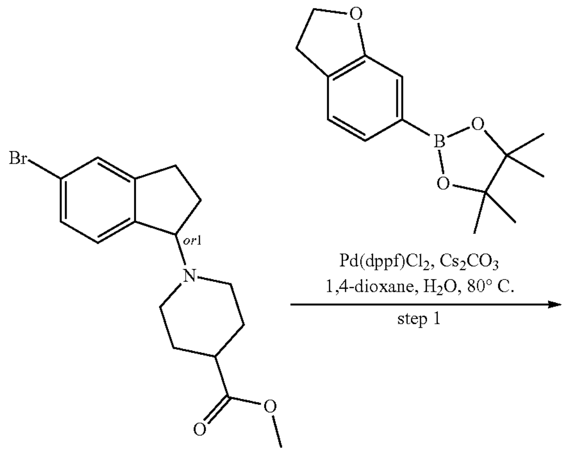

-continued

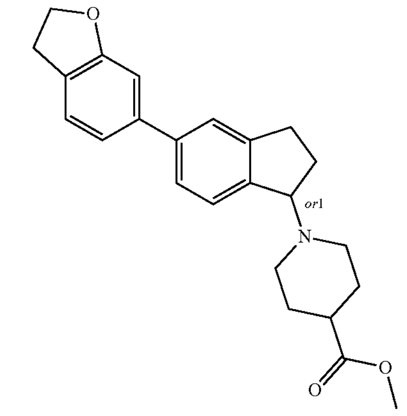

A mixture of 2-(2,3-dihydrobenzofuran-6-yl)-4,4,5,5-tetramethyl-1,3,2-dioxaborolane (200 mg, 0.820 mmol, 1.00 equiv.), a single enantiomer of methyl 1-(5-bromo-2,3-dihydro-1H-inden-1-yl)piperidine-4-carboxylate (274 mg, 0.820 mmol, 1.00 equiv.), Pd(dppf)$Cl_2$ (60 mg, 0.080 mmol, 0.10 equiv.) and $Cs_2CO_3$ (794 mg, 2.440 mmol, 3.00 equiv.) in 1,4-dioxane (5.0 mL) and water (0.5 mL) was stirred at 90° C. for 15 h under $N_2$ atmosphere. LCMS showed the reaction was complete. The reaction mixture was diluted with 20 mL of water, then extracted with ethyl acetate (3*10 mL). The combined organic layers were washed with aqueous $Na_2CO_3$ and brine, and dried over anhydrous $Na_2SO_4$ and concentrated under reduced pressure. The residue was purified by flash chromatography on silica gel (EA/PE=16%) to give a single enantiomer of methyl 1-(5-(2,3-dihydrobenzofuran-6-yl)-2,3-dihydro-1H-inden-1-yl)-piperidine-4-carboxylate (120 mg, 53.6%) as an oil. LCMS (ESI, m/z): 378 $[M+H]^+$.

Synthesis of 1-(5-(2,3-dihydrobenzofuran-6-yl)-2,3-dihydro-1H-inden-1-yl)piperidine-4-carboxylic acid

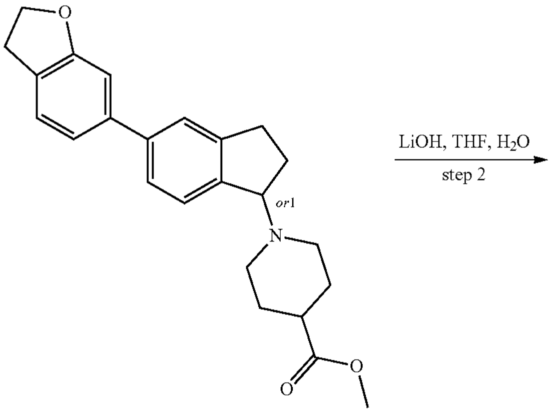

-continued

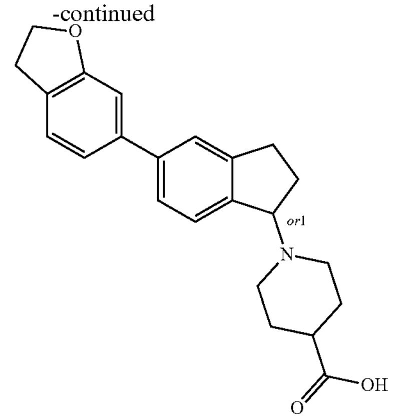

A solution of one enantiomer of methyl 1-(5-(2,3-dihydrobenzofuran-6-yl)-2,3-dihydro-1H-inden-1-yl)piperidine-4-carboxylate (110 mg, 0.290 mmol, 1.00 equiv.) and LiOH (21 mg, 0.870 mmol, 3.00 equiv.) in THF (2 mL) and water (1 mL) was stirred at room temperature for 1 h. LCMS showed the reaction was complete. The resulting solution was acidified to pH 5-6 with 2N HCl and concentrated under reduced pressure. The residue was purified by prep-HPLC (Column: YMC-Actus Triart C18, 30*250 mm, 5 μm; Mobile Phase A: water (10 mM $NH_4HCO_3$+0.1% $NH_3 \cdot H_2O$), Mobile Phase B: ACN; Flow rate: 60 mL/min; Gradient: 2% B to 22% B in 8 min; 254/210 nm; RT: 7.53 min) to give the desired product, one enantiomer of 1-(5-(2,3-dihydrobenzofuran-6-yl)-2,3-dihydro-1H-inden-1-yl) piperidine-4-carboxylic acid (41, 24.6 mg, 23.4%) as a solid.

LCMS (ESI, m/z): 364 $[M+H]^+$; Analytic Conditions: Poroshell HPH-C18, 3.0*50 mm, 2.7 μm; Mobile Phase A: water/5 mM $NH_4HCO_3$. Mobile Phase B: ACN; Flow rate: 1.20 mL/min; Gradient: 10% B to 45% B in 1.7 min, 45% B to 95% B in 0.3 min, hold at 95% B for 0.7 min, 95% B to 10% B in 0.1 min; 254 nm; RT: 1.513 min.

$^1H$ NMR (400 MHz, DMSO-$d_6$) δ 7.44-7.41 (m, 2H), 7.29 (dd, J=7.6, 6.0 Hz, 2H), 7.09 (dd, J=7.6, 1.6 Hz, 1H), 7.00 (d, J=1.6 Hz, 1H), 4.56 (t, J=8.4 Hz, 2H), 4.30 (t, J=7.6 Hz, 1H), 3.20 (t, J=8.4 Hz, 3H), 2.95-2.75 (m, 3H), 2.32-2.25 (m, 1H), 2.20-2.14 (m, 2H), 2.03 (q, J=3.6 Hz, 2H), 1.84-1.75 (m, 2H), 1.65-1.55 (m, 1H), 1.52-1.43 (m, 1H).

Example S42. 1-(5-(benzo[d]oxazol-5-yl)-2,3-dihydro-1H-inden-1-yl)piperidine-4-carboxylic acid (42)

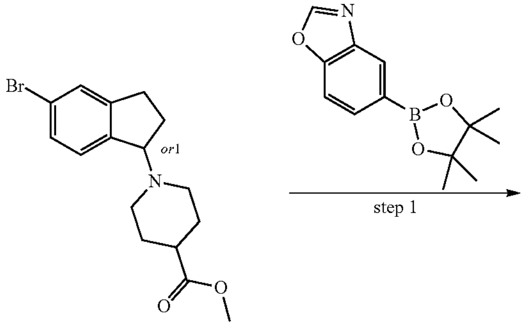

-continued

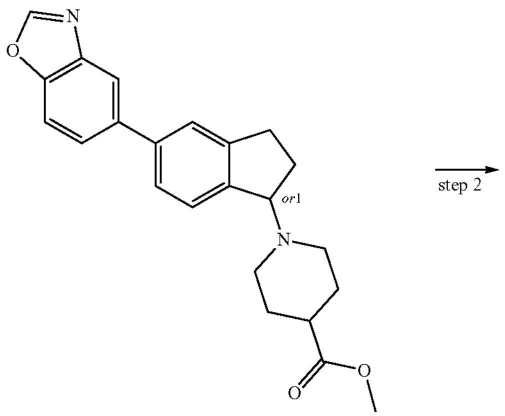

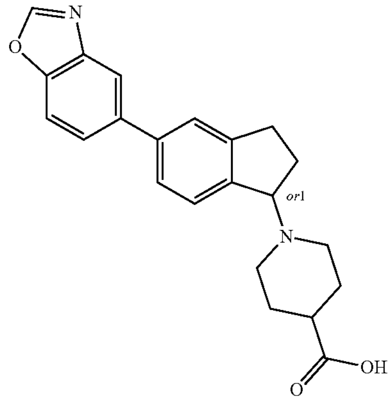

Synthesis of methyl 1-(5-(benzo[d]oxazol-5-yl)-2,3-dihydro-1H-inden-1-yl)piperidine-4-carboxylate

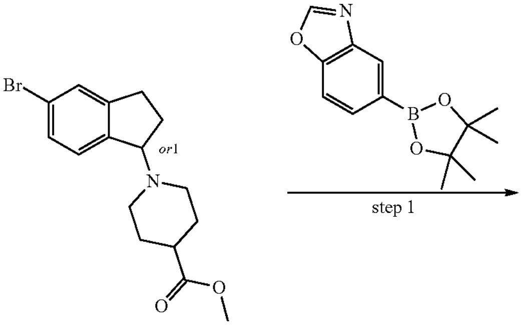

-continued

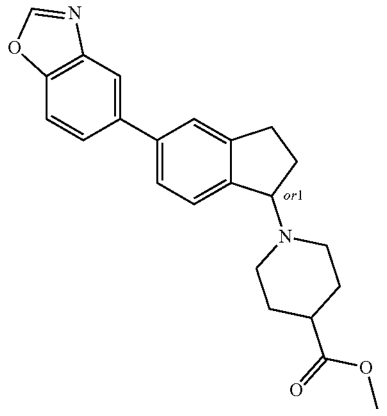

To a stirred solution of one enantiomer of methyl 1-(5-bromo-2,3-dihydro-1H-inden-1-yl)piperidine-4-carboxylate (100 mg, 0.300 mmol, 1.00 equiv.) in DME (1 mL)/water (0.3 mL) were added 5-(4,4,5,5-tetramethyl-1,3,2-dioxaborolan-2-yl)-1,3-benzoxazole (79.7 mg, 0.330 mmol, 1.10 equiv.), $Pd(PPh_3)_4$ (34.2 mg, 0.030 mmol, 0.10 equiv.). The resulting mixture was stirred at 90° C. overnight. LCMS showed the reaction was complete. The mixture was concentrated under reduced pressure. The residue was purified by flash chromatography on silica gel with DCM/MEOH (10:1) to give one enantiomer of methyl 1-(5-(benzo[d]oxazol-5-yl)-2,3-dihydro-1H-inden-1-yl)piperidine-4-carboxylate (89 mg, 79.9%) as an oil. LCMS (ESI, m/z): 377 $[M+H]^+$.

Synthesis of 1-(5-(benzo[d]oxazol-5-yl)-2,3-dihydro-1H-inden-1-yl)piperidine-4-carboxylic acid

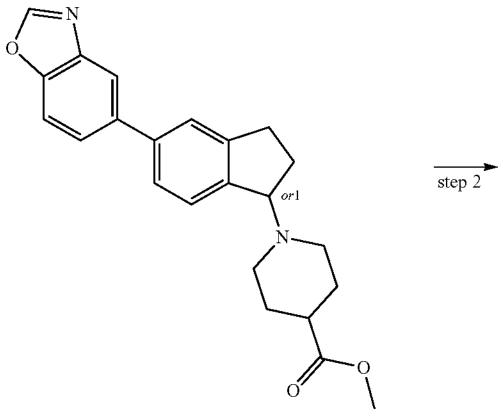

-continued

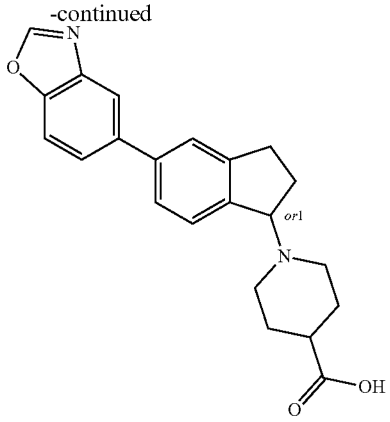

A mixture of one enantiomer of methyl 1-(5-(benzo[d]oxazol-5-yl)-2,3-dihydro-1H-inden-1-yl)piperidine-4-carboxylate (89 mg, 0.240 mmol, 1.00 equiv.) and LiOH (17 mg, 0.710 mmol, 3.00 equiv.) in THF (1 mL) and water (1 mL) was stirred at room temperature for 0.5 h. LCMS showed the reaction was complete. The pH of the solution was adjusted to 5~6 with $CH_3COOH$. The resulting mixture was concentrated under reduced pressure and the residue was purified by Prep-HPLC (Column: YMC-Actus Triart C18, 30*250 mm, 5 μm; Mobile Phase A: water (10 mM $NH_4HCO_3$+0.1% $NH_3 \cdot H_2O$), Mobile Phase B: ACN; Flow rate: 60 mL/min; Gradient: 8% B to 38% B in 7 min; 254/210 nm; RT: 5.87 min) to give one enantiomer of 1-(5-(benzo[d]oxazol-5-yl)-2,3-dihydro-1H-inden-1-yl)piperidine-4-carboxylic acid (42, 9.1 mg, 0.024 mmol, 10.1% yield) as a solid.

$^1H$ NMR (400 MHz, DMSO-$d_6$) δ 8.78 (s, 1H), 8.03 (d, J=1.6 Hz, 1H), 7.83 (d, J=8.4 Hz, 1H), 7.71 (dd, J=8.4, 1.6 Hz, 1H), 7.56-7.53 (m, 2H), 7.35 (d, J=8.0 Hz, 1H), 4.33 (t, J=7.2 Hz, 1H), 2.98-2.91 (m, 1H), 2.87-2.79 (m, 2H), 2.56-2.53 (m, 1H), 2.33-2.27 (m, 1H), 2.22-2.15 (m, 2H), 2.07-2.02 (m, 2H), 1.85-1.76 (m, 2H), 1.66-1.54 (m, 1H), 1.53-1.40 (m, 1H).

LCMS (ESI, m/z): 363 $[M+H]^+$. Analytic Conditions: Shim-pack XR-ODS C18, 3.0*50 mm, 2.2 μm; Mobile Phase A: Water/0.05% TFA, Mobile Phase B: Acetonitrile/0.05% TFA; Flow rate: 1.20 mL/min; Gradient: 5% B to 100% B in 2.0 min, hold at 100% B for 0.7 min, 100% B to 5% B in 0.2 min; 254 nm; RT: 1.316 min.

Example S43. 1-(5-(2,3-dihydrobenzofuran-5-yl)-2,3-dihydro-1H-inden-1-yl)piperidine-4-carboxylic acid (43)

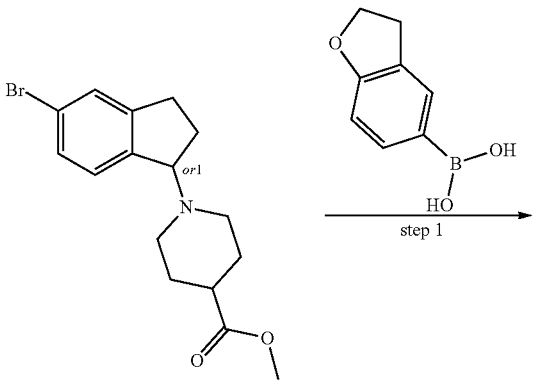

-continued

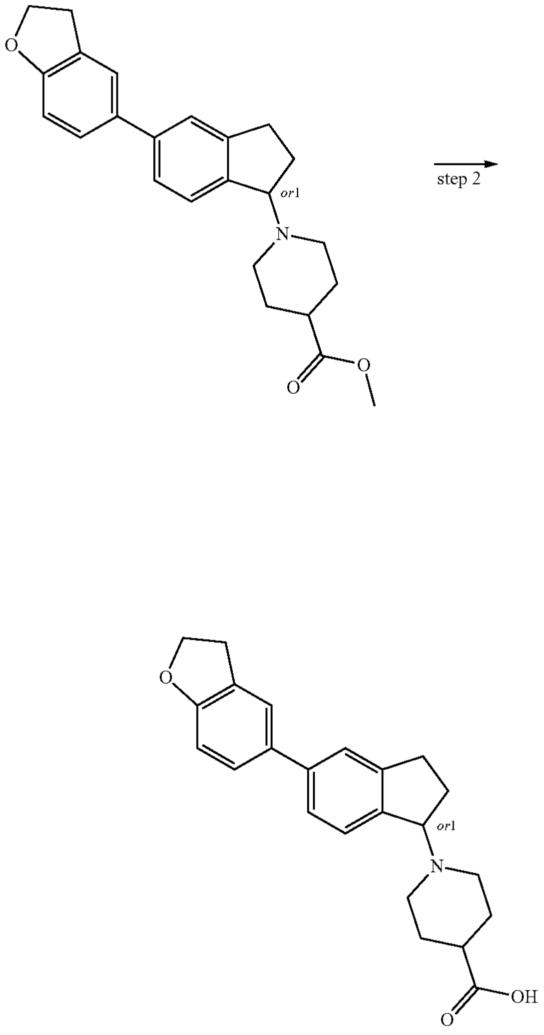

Synthesis of methyl 1-(5-(2,3-dihydrobenzofuran-5-yl)-2,3-dihydro-1H-inden-1-yl)piperidine-4-carboxylate

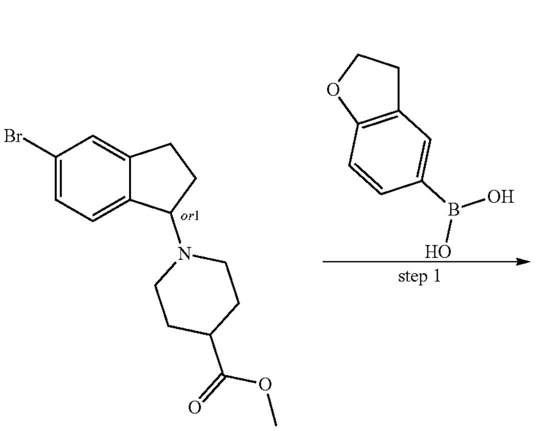

-continued

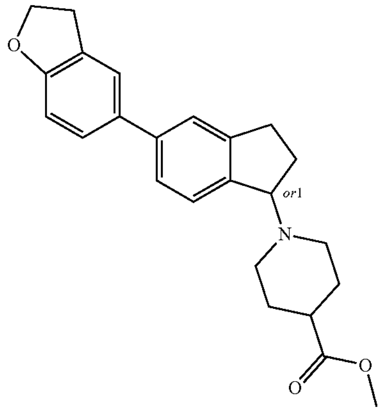

To a stirred solution of one enantiomer of methyl 1-(5-bromo-2,3-dihydro-1H-inden-1-yl)piperidine-4-carboxylate (100 mg, 0.300 mmol, 1.00 equiv.) in DME (2 mL)/water (0.2 mL) was added 2,3-dihydrobenzofuran-5-ylboronic acid (53 mg, 0.330 mmol, 1.10 equiv.), $Pd(PPh_3)_4$ (34 mg, 0.030 mmol, 0.100 equiv.), $Na_2CO_3$ (94 mg, 0.890 mmol, 3.00 equiv.). The resulting mixture was stirred at 90° C. overnight. LCMS showed the reaction was complete. The mixture was concentrated under reduced pressure. The residue was purified by flash chromatography on silica gel (eluted with DCM/MEOH, 10/1) to afford one enantiomer of methyl 1-(5-(2,3-dihydrobenzofuran-5-yl)-2,3-dihydro-1H-inden-1-yl)piperidine-4-carboxylate (94 mg, 84.2%) as an oil. LCMS (ESI, m/z): 378 $[M+H]^+$.

Synthesis of 1-(5-(2,3-dihydrobenzofuran-5-yl)-2,3-dihydro-1H-inden-1-yl)piperidine-4-carboxylic acid

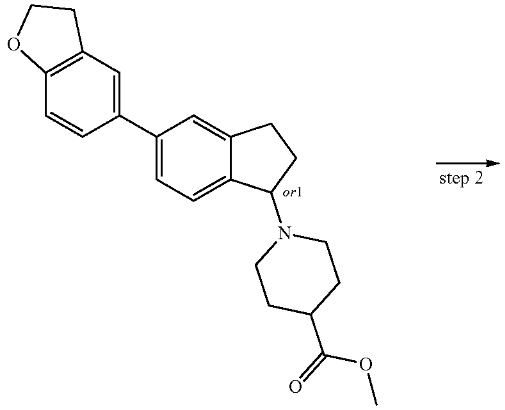

-continued

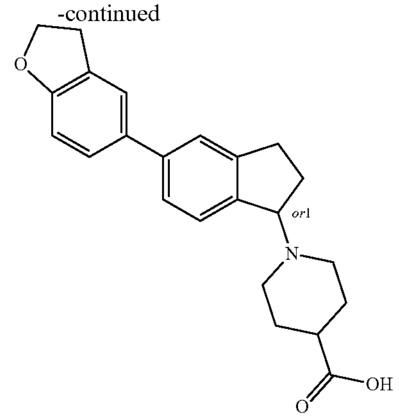

A mixture of one enantiomer of methyl 1-(5-(2,3-dihydrobenzofuran-5-yl)-2,3-dihydro-1H-inden-1-yl)piperidine-4-carboxylate (94 mg, 0.250 mmol, 1.00 equiv.) and LiOH (32 mg, 0.750 mmol, 3.00 equiv.) in THF (1 mL) and water (1 mL) was stirred at room temperature for 0.5 h. LCMS showed the reaction was complete. The pH value of the solution was adjusted to 3~4 with 2N HCl. The resulting mixture was concentrated under reduced pressure and the residue was purified by Prep-HPLC (Column: YMC-Actus Triart C18, 30*250 mm, 5 μm; Mobile Phase A: water (10 mM $NH_4HCO_3$+0.1% $NH_3 \cdot H_2O$), Mobile Phase B: ACN; Flow rate: 60 mL/min; Gradient: 12% B to 40% B in 8 min; 254/210 nm; RT: 7.45 min) to give one enantiomer of 1-(5-(2,3-dihydrobenzofuran-5-yl)-2,3-dihydro-1H-inden-1-yl)piperidine-4-carboxylic acid (43, 38.5 mg, 42.3%) as a solid.

$^1$H NMR (400 MHz, DMSO-$d_6$) δ 12.03 (br, 1H), 7.50 (s, 1H), 7.41-7.34 (m, 3H), 7.28 (d, J=7.6 Hz, 1H), 6.82 (d, J=8.4 Hz, 1H), 4.56 (t, J=8.4 Hz, 2H), 4.29 (t, J=7.2 Hz, 1H), 3.25-3.21 (m, 2H), 2.94-2.75 (m, 3H), 2.59-2.51 (m, 1H), 2.31-2.25 (m, 1H), 2.21-2.14 (m, 2H), 2.02 (q, J=7.6 Hz, 2H), 1.84-1.75 (m, 2H), 1.65-1.55 (m, 1H), 1.52-1.43 (m, 1H).

LCMS (ESI, m/z): 364 $[M+H]^+$. Analytic Conditions: Shim-pack XR-ODS C18, 3.0*50 mm, 2.2 m; Mobile Phase A: Water/0.05% TFA, Mobile Phase B: Acetonitrile/0.05% TFA; Flow rate: 1.20 mL/min; Gradient: 5% B to 100% B in 2.0 min, hold at 100% B for 0.7 min, 100% B to 5% B in 0.2 min; 254 nm; RT: 1.391 min.

Example S44. 1-(2,2',3,3'-tetrahydro-1H,1'H-[5,5'-biinden]-1-yl)piperidine-4-carboxylic acid (44)

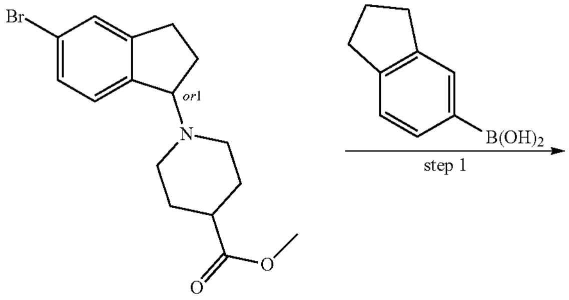

-continued

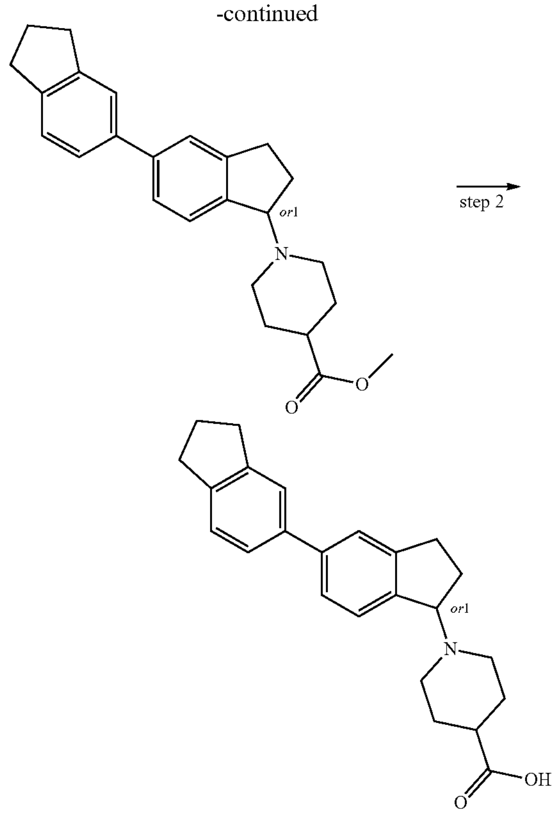

Synthesis of methyl 1-(2,2',3,3'-tetrahydro-1H,1'H-[5,5'-biinden]-1-yl)piperidine-4-carboxylate

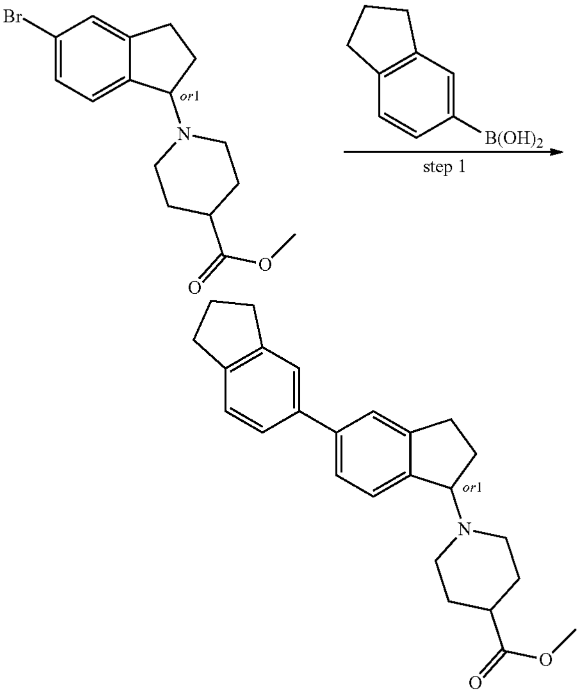

Into a solution of one enantiomer of methyl 1-(5-bromo-2,3-dihydro-1H-inden-1-yl)piperidine-4-carboxylate (150 mg, 0.440 mmol, 1.00 equiv.), indan-5-ylboronic acid (86 mg, 0.530 mmol, 1.20 equiv.) in 1,4-dioxane (2.0 mL), water (0.2 mL) were added $Cs_2CO_3$ (433 mg, 1.330 mmol, 3.00 equiv.) and Pd(dppf)$Cl_2$ (72 mg, 0.090 mmol, 0.20 equiv.). The resulting solution was stirred at 80° C. for 3 h under nitrogen atmosphere. LCMS showed the reaction was complete. The reaction mixture was filtered and the filtration was concentrated under reduced pressure. The residue was purified by flash chromatography on silica gel (PE/EA=9/1) to afford one enantiomer of methyl 1-(2,2',3,3'-tetrahydro-1H, 1'H-[5,5'-biinden]-1-yl)piperidine-4-carboxylate (140 mg, 84%) as an oil. LCMS (ESI, m/z): 376 $[M+H]^+$.

Synthesis of 1-(2,2',3,3'-tetrahydro-1H,1'H-[5,5'-biinden]-1-yl)piperidine-4-carboxylic acid

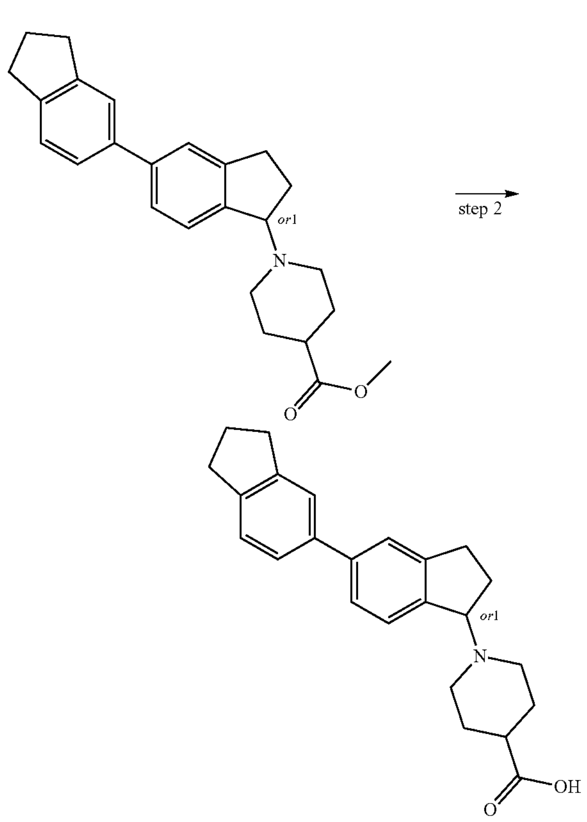

A mixture of one enantiomer of methyl 1-(2,2',3,3'-tetrahydro-1H,1'H-[5,5'-biinden]-1-yl)piperidine-4-carboxylate (100 mg, 0.270 mmol, 1.00 equiv.) and LiOH·$H_2O$ (33 mg, 0.800 mmol, 3.00 equiv) in THF (1.0 mL) and water (1.0 mL) was stirred at room temperature for 12 h. LCMS showed the reaction was complete. The solution was adjusted to pH 4-5 with 1N HCl, and then was concentrated under vacuum. The residue was purified by Prep-HPLC (Column: YMC-Actus Triart C18, 30*250 mm, 5 μm; Mobile Phase A: water (10 mmol/L $NH_4HCO_3$+0.1% $NH_3 \cdot H_2O$), Mobile Phase B: ACN; Flow rate: 60 mL/min; Gradient: 20% B to 50% B in 8 min; 254/210 nm; RT: 6.32 min) to give one enantiomer of 1-(2,2',3,3'-tetrahydro-1H, 1'H-[5,5'-biinden]-1-yl)piperidine-4-carboxylic acid (44, 29.7 mg, 30%) as a solid.

$^1H$ NMR (400 MHz, Methanol-$d_4$) δ 7.58-7.52 (m, 3H), 7.46 (s, 1H), 7.37-7.35 (m, 1H), 7.27 (d, J=8.0 Hz, 1H), 3.38-3.34 (m, 3H), 3.20-3.14 (m, 2H), 3.06-2.89 (m, 6H), 2.85-2.81 (m, 1H), 2.48-2.38 (m, 2H), 2.35-2.27 (m, 1H), 2.15-2.03 (m, 4H), 1.97-1.83 (m, 1H).

LCMS (ESI, m/z): 362 $[M+H]^+$. Analytic Conditions: column: Poroshell HPH-C18 Column 3.0*50 mm, 2.7 μm; mobile Phase A: water/5 mM $NH_4HCO_3$, mobile Phase B: acetonitrile; flow rate: 1.20 mL/min; gradient: 10% B to 50% B in 2.0 min, 50% B to 95% B in 0.25 min, hold at 95% for 0.45 min, 95% B to 10% B in 0.1 min; 254 nm; RT: 1.916 min.

Example S45. 1-(2,2',3,3'-tetrahydro-1H,1'H-[4,5'-biinden]-1'-yl)piperidine-4-carboxylic acid (45)

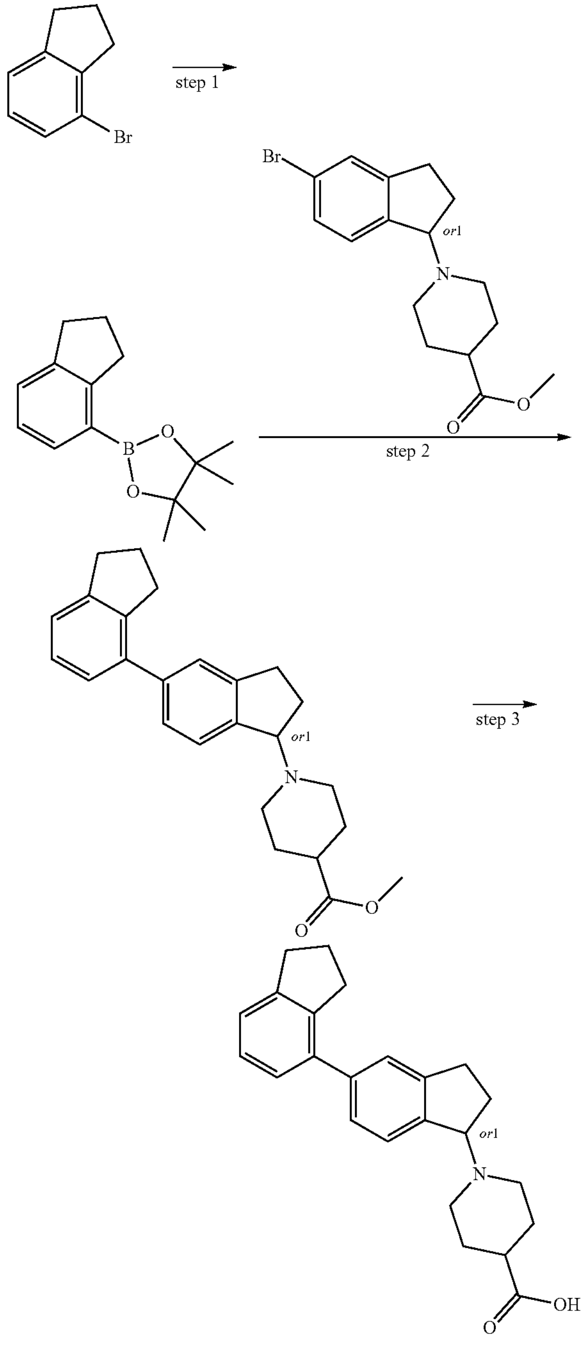

Synthesis of 2-(2,3-dihydro-1H-inden-4-yl)-4,4,5,5-tetramethyl-1,3,2-dioxaborolane

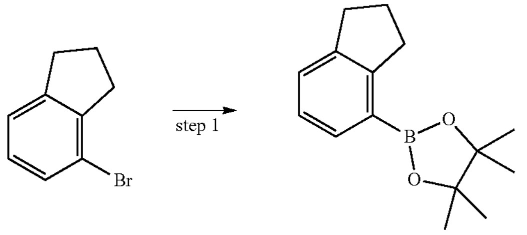 [SMILES: Brc1cccc2c1CCC2 ; CC1(C)OB(c2cccc3c2CCC3)OC1(C)C]

Into a solution of 4-bromoindane (300 mg, 1.520 mmol, 1.00 equiv.), bis (pinacolato)diboron (580 mg, 2.280 mmol, 1.50 equiv.) in 1,4-dioxane (4.0 mL) were added AcOK (447 mg, 4.570 mmol, 3.00 equiv.) and Pd(dppf)$Cl_2$ (124 mg, 0.150 mmol, 0.10 equiv.) at room temperature. The resulting solution was stirred at 80° C. for 3 h under nitrogen atmosphere. LCMS showed the reaction was complete. The reaction mixture was filtered and the filtration was concentrated under reduced pressure. The residue was purified by flash chromatography on silica gel (PE/EA=10/1) to afford 2-(2,3-dihydro-1H-inden-4-yl)-4,4,5,5-tetramethyl-1,3,2-dioxaborolane (260 mg, 69%) as an oil. LCMS (ESI, m/z): 245 $[M+H]^+$.

Synthesis of methyl 1-(2,2',3,3'-tetrahydro-1H,1'H-[4,5'-biinden]-1'-yl)piperidine-4-carboxylate

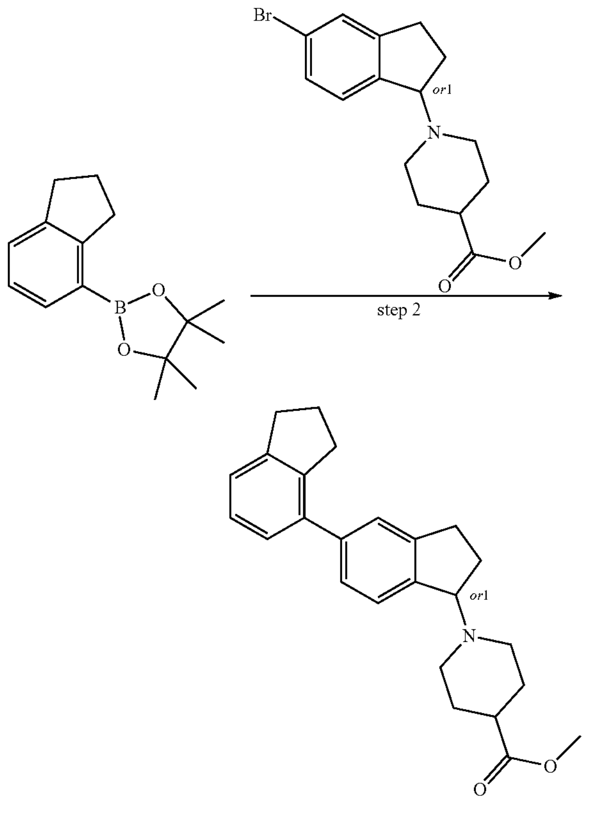

Into a solution of one enantiomer of methyl 1-(5-bromo-2,3-dihydro-1H-inden-1-yl)piperidine-4-carboxylate (270 mg, 0.800 mmol, 1.00 equiv.), 2-(2,3-dihydro-1H-inden-4-yl)-4,4,5,5-tetramethyl-1,3,2-dioxaborolane (234 mg, 0.960 mmol, 1.20 equiv) in 1,4-dioxane (5.0 mL) and water (0.5 mL) were added $Cs_2CO_3$ (781 mg, 2.390 mmol, 3.00 equiv.) and Pd(dppf) $Cl_2$·DCM (130 mg, 0.160 mmol, 0.20 equiv.) at room temperature. The resulting mixture was stirred at 80° C. for 3 h under nitrogen atmosphere. LCMS showed the reaction was complete. The reaction mixture was filtered and the filtration was concentrated under reduced pressure. The residue was purified by flash chromatography on silica gel (PE/EA=2/1) to afford one enantiomer of methyl 1-(2,2',3,3'-tetrahydro-1H,1'H-[4,5'-biinden]-1'-yl)piperidine-4-carboxylate (200 mg, 66%) as an oil. LCMS (ESI, m/z): 376 $[M+H]^+$.

Synthesis of 1-(2,2',3,3'-tetrahydro-1H,1'H-[4,5'-biinden]-1'-yl)piperidine-4-carboxylic acid

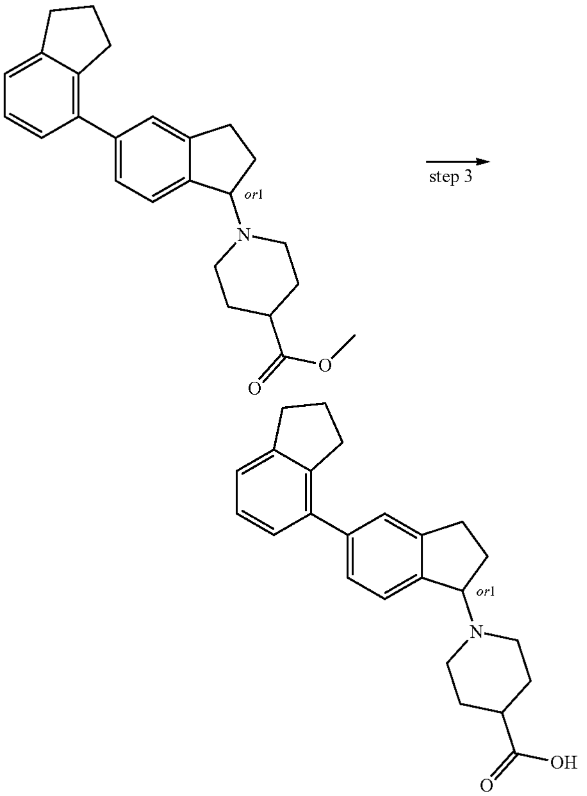

A mixture of one enantiomer of methyl 1-(2,2',3,3'-tetrahydro-1H,1'H-[4,5'-biinden]-1'-yl)piperidine-4-carboxylate (100 mg, 0.270 mmol, 1.00 equiv.) and LiOH·$H_2O$ (34 mg, 0.810 mmol, 3.00 equiv.) in THF (1.0 mL) and water (1.0 mL) was stirred at room temperature for 12 h. LCMS showed the reaction was complete. The solution was adjusted to pH 4-5 with 1N HCl, and then was concentrated under vacuum. The residue was purified by Prep-HPLC (Column: YMC-Actus Triart C18, 30*250 mm, 5 μm; Mobile Phase A: water (10 mmol/L $NH_4HCO_3$+0.1% $NH_3$·$H_2O$), Mobile Phase B: ACN; Flow rate: 60 mL/min; Gradient: 20% B to 50% B in 8 min; 254/210 nm; RT: 6.32 min) to give one enantiomer of 1-(2,2',3,3'-tetrahydro-1H, 1'H-[4,5'-biinden]-1'-yl)piperidine-4-carboxylic acid (45, 47.8 mg, 49%) as a solid.

$^1$H NMR (300 MHz, DMSO-$d_6$) δ 11.99 (s, 1H), 7.32-7.23 (m, 3H), 7.22-7.19 (m, 2H), 7.16-7.11 (m, 1H), 4.30 (t, J=7.2 Hz, 1H), 2.93-2.75 (m, 7H), 2.56-2.52 (m, 1H), 2.33-2.26 (m, 1H), 2.21-2.13 (m, 2H), 2.05-1.91 (m, 4H), 1.84-1.74 (m, 2H), 1.67-1.58 (m, 1H), 1.54-1.42 (m, 1H).

LCMS (ESI, m/z): 362 $[M+H]^+$. Analytic Conditions: column: Titank C18 Column 3.0*50 mm, 3.0 μm; mobile Phase A: Water/5 mM $NH_4HCO_3$, mobile Phase B: acetonitrile; flow rate: 1.50 mL/min; gradient: 10% B to 95% B in 1.8 min, hold at 95% for 0.8 min, 95% B to 10% B in 0.15 min; 254 nm; RT: 1.316 min.

BIOLOGICAL EXAMPLES

Example B1. Cell Membrane Preparations

CHO cells expressing recombinant S1P5 receptors were cultured in 500 $cm^2$ culture trays and, once confluent, rinsed and detached with cell-lifting buffer (10 mM HEPES, 154 mM NaCl, 6.85 mM EDTA, pH 7.4). Cells were then pelleted by centrifugation, resuspended, and homogenized in membrane preparation buffer (10 mM HEPES and 10 mM EDTA, pH 7.4) using a Polytron PT 1200E homogenizer (Kinematica, Luzern, Switzerland). Cellular proteins were pelleted by centrifugation at 48,000×g at 4° C. for 30 minutes. The resulting supernatant was discarded, and the pellet was re-suspended again in membrane preparation buffer, homogenized for a second time, and then centrifuged again as described above. The final cellular protein pellet was suspended in ice cold resuspension buffer (10 mM HEPES and 0.1 mM EDTA, pH 7.4), divided into aliquots, and stored at −80° C. until use.

Example B2. GTPγS Binding Assay

Functional binding assays for $[^{35}S]$-GTPγS were performed in 96-well non-binding surface plates with a final volume of 200 μL. The test compounds were serially diluted in DMSO and added to assay plates using a Tecan D300E digital printer with a total volume of 0.4 μL. The control sphingosine-1-phosphate (S1P) was prepared separately by preparing a 400 μM stock solution from a 100 nmol pellet of SIP in 10 mM $Na_2CO_3$ with 2% s-cyclodextrin. The serial dilution of S1P was done using complete assay buffer (20 mM HEPES, 10 mM $MgCl_2$, 100 mM NaCl, 1 mM EDTA, 0.1% fatty acid free bovine serum albumin (BSA), and 30 μg/mL saponin, pH 7.4) and transferred to wells already containing 0.4 μL DMSO. All the wells were then loaded to a total volume of 40 μL of complete assay buffer, except the non-specific binding (NSB) wells. For NSB wells, 40 μL/well of 50 μM GTPγS (Sigma Aldrich, cat #G8634, St. Louis, MO) was added to wells containing 0.4 μL of DMSO. The assay was started by the addition of 120 μL/well of CHO-S1P receptor membrane solution containing 40 μg/mL of membrane protein, 16.67 μM guanosine diphosphate (GDP; Sigma Aldrich, cat #G7127, St. Louis, MO), and 2.5 mg/mL of WGA PVT SPA beads in complete buffer. Assay plates were then sealed and incubated at room temperature with gentle agitation for 30 minutes. Next, 40 μL/well of 1 nM of $[^{35}S]$-GTPγS (PerkinElmer, cat #NEG030X250UC, Waltham, MA) in basic assay buffer (20 mM HEPES, 10 mM $MgCl_2$, 100 mM NaCl, and 1 mM EDTA, pH 7.4) was added to the assay plates to yield a final concentration of 200 μM and the plates were further incubated for 40 minutes at room temperature with gentle agitation. The assay was terminated by centrifugation of the plates at 1000 rpm for 3 minutes using an Eppendorf 5810R centrifuge (Eppendorf, Hamburg, Germany) and G protein bound radioactivity was quantitated using a MicroBeta2 microplate scintillation counter (PerkinElmer, Waltham, MA). As G protein bound radioactivity directly correlates to receptor activation and coupling to the G protein, this assay is a measure of S1P5 agonism. Results are shown in Table 2.

TABLE 2

S1P5 GTPγS Binding of Exemplary Compounds.

| Compound No. | S1P5 GTPγS binding |
|---|---|
| 1 | ++++ |
| 2 | ++++ |
| 3a | ++++ |
| 3b | ++++ |
| 4a | ++ |
| 4b | ++++ |
| 5 | ++ |
| 6a | +++ |
| 6b | ++++ |
| 7a | +++ |
| 7b | ++ |
| 8a | ++ |
| 8b | + |
| 9a | + |
| 9b | + |
| 10 | ++ |
| 11 | +++ |
| 12 | +++ |
| 13a | +++ |
| 13b | +++ |
| 14a | ++++ |
| 14b | ++++ |
| 15 | ++++ |
| 16 | ++ |
| 17 | +++ |
| 18 | ++++ |
| 19 | ++++ |
| 20 | ++++ |
| 21 | +++ |
| 22a | ++++ |
| 22b | ++++ |
| 23 | +++ |
| 24 | +++ |
| 25a | +++ |
| 25b | ++ |
| 26a | ++ |
| 26b | +++ |
| 27a | ++++ |
| 27b | ++ |
| 28a | ++ |
| 28b | +++ |
| 29 | +++ |
| 30a | ++++ |
| 30b | ++++ |
| 31a | ++++ |
| 31b | ++++ |
| 32a | ++ |
| 32b | ++++ |
| 33 | ++++ |
| 34a | ++++ |
| 34b | ++++ |
| 35a | +++ |
| 35b | +++ |
| 36a | ++++ |
| 36b | ++++ |
| 37a | ++ |
| 37b | +++ |
| 38 | +++ |
| 39 | +++ |
| 40 | ++ |
| 41 | ++ |
| 42 | + |
| 43 | ++ |
| 44 | +++ |
| 45 | ++ |

++++ indicates binding ≤10 nM
+++ indicates binding between greater than 10 nM and ≤100 nM
++ indicates binding between greater than 100 nM and ≤1,000 nM
+ indicates binding between greater than 1,000 nM and ≤10,000 nM Although the present invention has been described in some detail by way of illustration and example for purposes of clarity of understanding, the descriptions and examples should not be construed as limiting the scope of the invention. The disclosures of all patent and scientific literature cited herein are expressly incorporated herein in their entirety by reference.

The invention claimed is:

1. A compound of Formula (I):

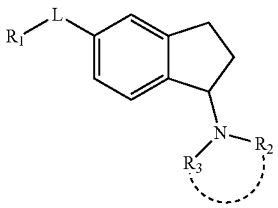

(I)

or a pharmaceutically acceptable salt thereof, wherein:

L is —C(Y)⩶C(X)— or a bond;

X and Y are independently H, O, $H_2$, or absent;

⩶ is a single, double, or triple bond;

$R_1$ is $C_6$-$C_{10}$ aryl, fused bicyclic 8- to 10-membered heteroaryl, or fused bicyclic 8- to 10-membered heterocyclyl, each of which is optionally substituted by 1-5 R' groups, wherein the heterocyclyl and heteroaryl contain 1-3 heteroatoms selected from nitrogen and oxygen;

each R' is independently halo, $C_1$-$C_6$ alkyl, $C_1$-$C_6$ haloalkyl, $C_1$-$C_6$ alkoxy, or $C_3$-$C_6$ cycloalkyl;

$R_2$ is H or $C_1$-$C_6$ alkyl;

$R_3$ is $—(CH_2)_x—CO_2H$ or

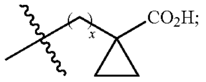

or the dashed line between $R_2$ and $R_3$ represents a ring structure where $R_2$ and $R_3$ are taken together with the nitrogen atom to which they are attached to form a 4- to 6-membered heterocyclyl substituted by 1-5 $R_4$ groups, wherein at least one $R_4$ group is $—CO_2H$ or contains a $—CO_2H$ moiety;

x is 1-5; and each $R_4$ is independently $—CO_2H$, halo, or $C_1$-$C_6$ alkyl, or two $R_4$ groups are taken together with the carbon atoms to which they are attached to form a fused, bridged, or spiro $C_3$-$C_5$ cycloalkyl optionally substituted by $—CO_2H$.

2. The compound of claim 1, or a pharmaceutically acceptable salt thereof, wherein:

L is —C≡C—, —HC═CH—, $—CH_2CH_2—$, —C(O)—$CH_2$—, or $—CH_2—C(O)—$.

3. The compound of claim 1, or a pharmaceutically acceptable salt thereof, wherein:

L is a bond.

4. The compound of claim 1, or a pharmaceutically acceptable salt thereof, wherein:

$R_1$ is phenyl, phenyl fused to a cycloalkyl, fused bicyclic 9-membered heteroaryl, or fused bicyclic 9-membered heterocyclyl, each of which is optionally substituted by 1-3 R' groups, wherein the heterocyclyl and heteroaryl contain 1-2 heteroatoms selected from nitrogen and oxygen.

5. The compound of claim 1, or a pharmaceutically acceptable salt thereof, wherein:

each R' is independently halo, $C_1$-$C_3$ alkyl, $C_1$-$C_3$ haloalkyl, $C_1$-$C_3$ alkoxy, or $C_3$-$C_6$ cycloalkyl.

6. The compound of claim 5, or a pharmaceutically acceptable salt thereof, wherein:

each R' is independently Cl, F, methyl, ethyl, isopropyl, $—CF_3$, $—OCH_3$, or cyclopropyl.

7. The compound of claim 4, or a pharmaceutically acceptable salt thereof, wherein:

$R_1$ is

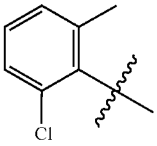
,
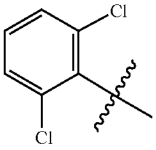
,
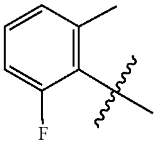
,
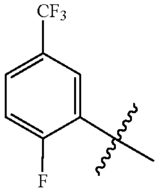
,
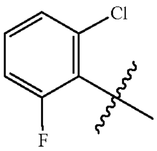
,
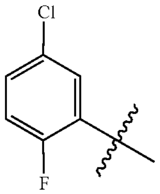
,
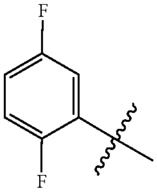
,
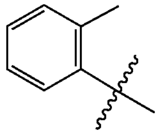
,
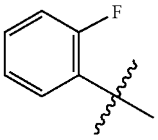
,
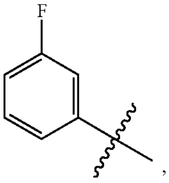
,
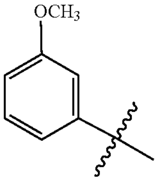
,
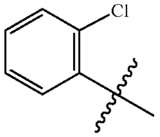
,
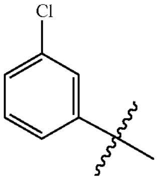
,
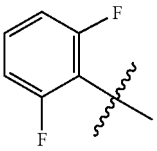
, -continued

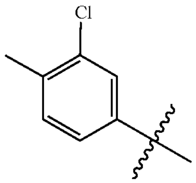,
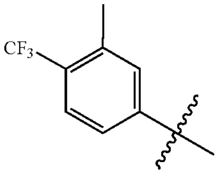,
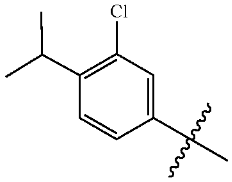,
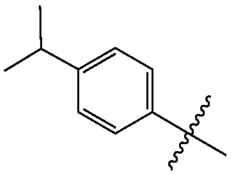,
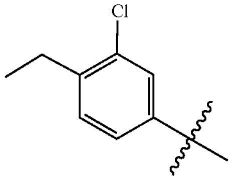,
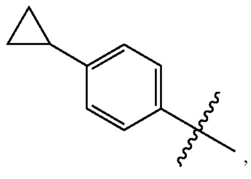,
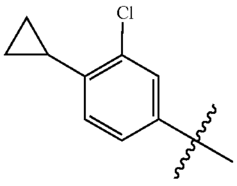,
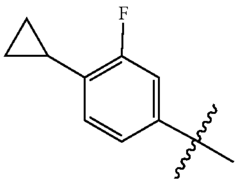,
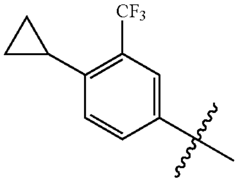,
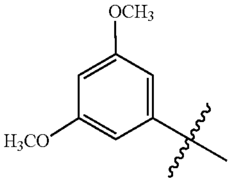,
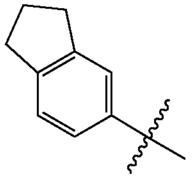,
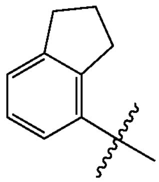,
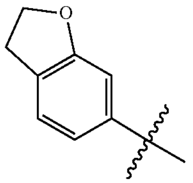,
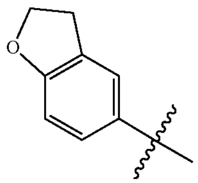, or
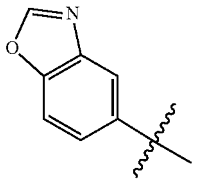.

8. The compound of claim 1, or a pharmaceutically acceptable salt thereof, wherein:

$R_2$ is H or $C_1$-$C_3$ alkyl;

$R_3$ is —$(CH_2)_x$—$CO_2H$ or

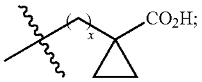

and x is 1-3.

9. The compound of claim 8, or a pharmaceutically acceptable salt thereof, wherein:

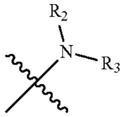 is 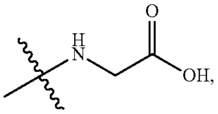,
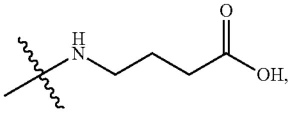,
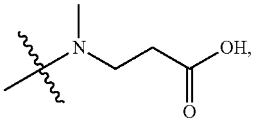, 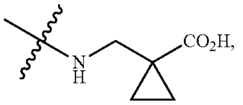, or
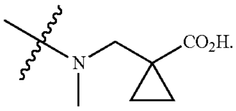.

10. The compound of claim 1, or a pharmaceutically acceptable salt thereof, wherein:

$R_2$ and $R_3$ are taken together with the nitrogen atom to which they are attached to form a 4- to 6-membered heterocyclyl substituted by 1-3 $R_4$ groups, wherein at least one $R_4$ group is —$CO_2H$ or contains a —$CO_2H$ moiety.

11. The compound of claim 10, or a pharmaceutically acceptable salt thereof, wherein:

$R_2$ and $R_3$ are taken together with the nitrogen atom to which they are attached to form azetidinyl, pyrrolidinyl, or piperidinyl, each of which is substituted by 1-3 $R_4$ groups, wherein at least one $R_4$ group is —$CO_2H$ or contains a —$CO_2H$ moiety.

12. The compound of claim 1, or a pharmaceutically acceptable salt thereof, wherein:

each $R_4$ is independently —$CO_2H$, halo, or $C_1$-$C_3$ alkyl, or two $R_4$ groups are taken together with the carbon atoms to which they are attached to form a fused, bridged, or spiro $C_3$-$C_5$ cycloalkyl optionally substituted by —$CO_2H$, wherein at least one $R_4$ group is —$CO_2H$ or contains a —$CO_2H$ moiety.

13. The compound of claim 12, or a pharmaceutically acceptable salt thereof, wherein:

each $R_4$ is independently —$CO_2H$, F, or methyl, or two $R_4$ groups are taken together with the carbon atoms to which they are attached to form a fused cyclopropyl, a spiro cyclopropyl, a spiro cyclobutyl, or a bridged cyclopentyl, each of which is optionally substituted by —$CO_2H$, wherein at least one $R_4$ group is —$CO_2H$ or contains a —$CO_2H$ moiety.

14. The compound of claim 1, or a pharmaceutically acceptable salt thereof, wherein:

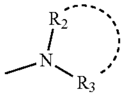 is 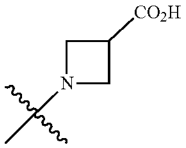,
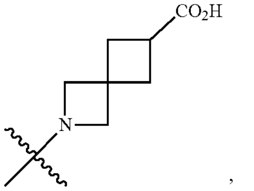, 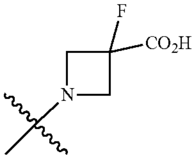,
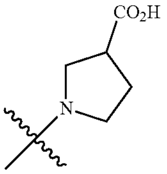, 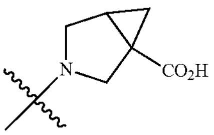,
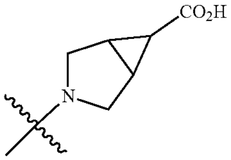, 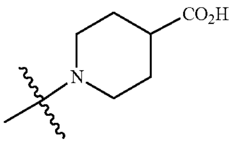,
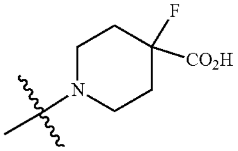, 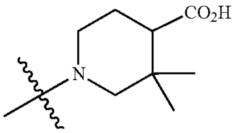,
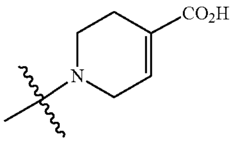, 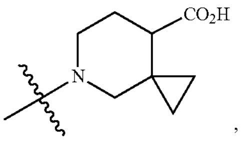,
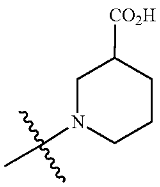, 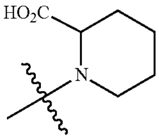, or
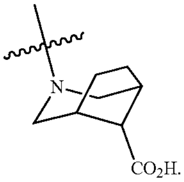
15. The compound of claim 1, or a pharmaceutically acceptable salt thereof, wherein the compound is of Formula (II):
(II)
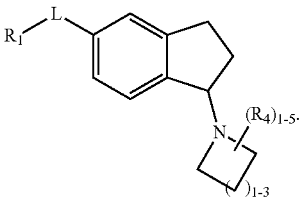
16. The compound of claim 1, or a pharmaceutically acceptable salt thereof, wherein the compound is of Formula (IIIa) or (IIIb):
(IIIa)
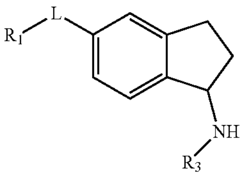
(IIIb)
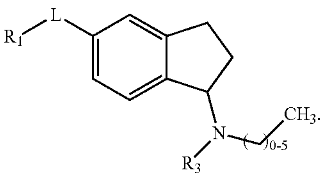
17. A compound selected from:
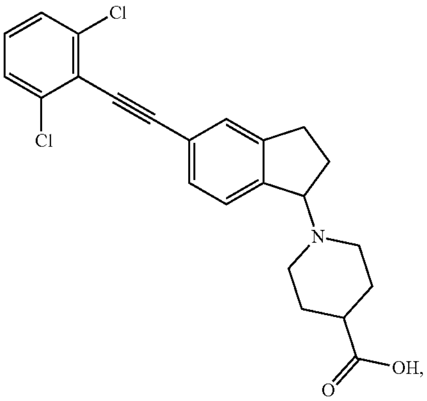
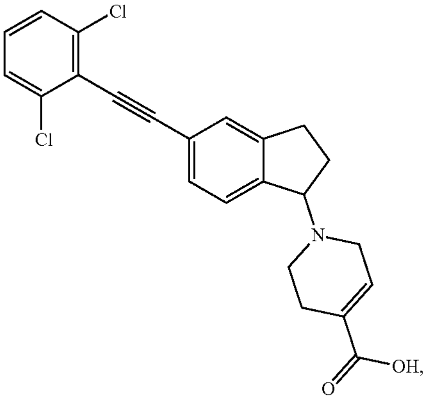

-continued
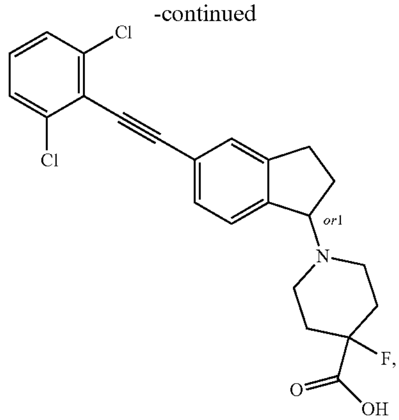
Enantiomer 1
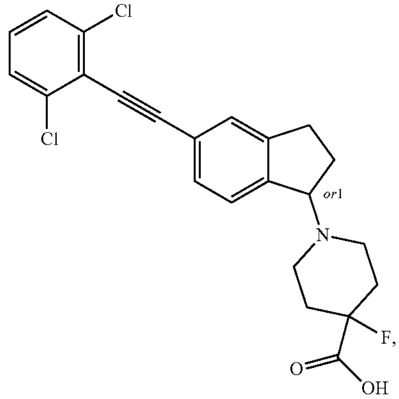
Enantiomer 2
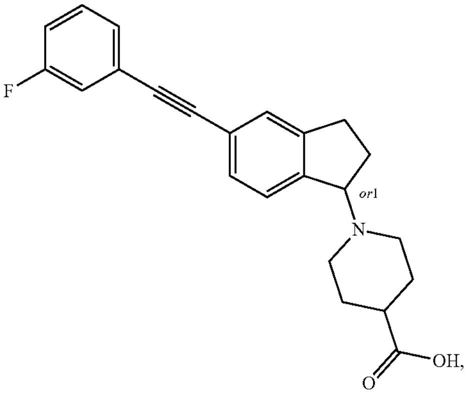
Enantiomer 1
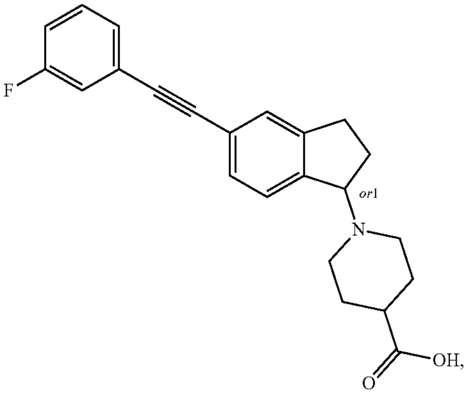
Enantiomer 2
-continued
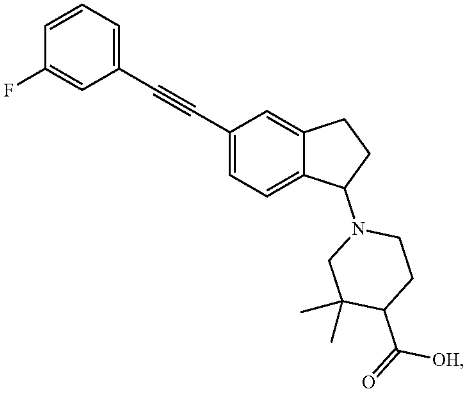
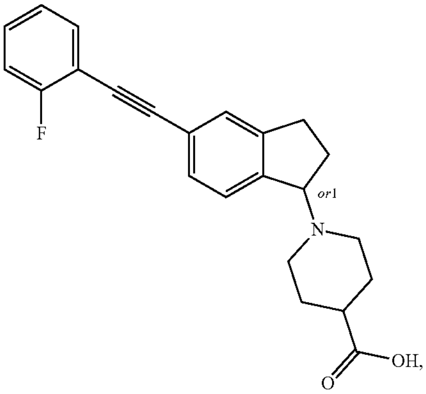
Enantiomer 1
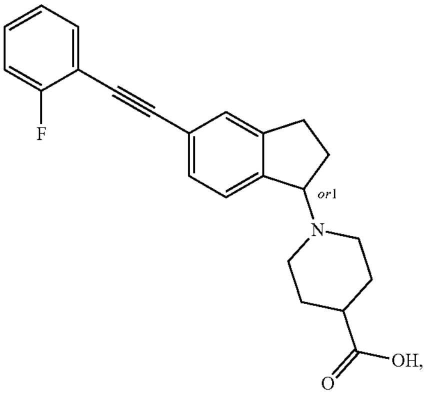
Enantiomer 2
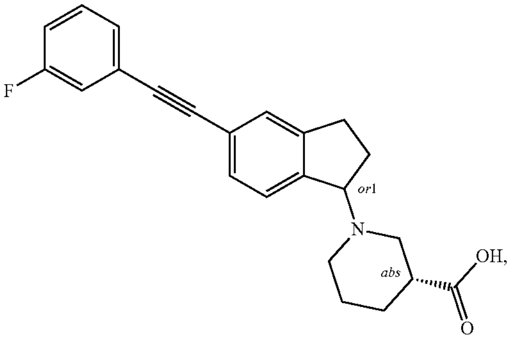
Enantiomer 1

-continued
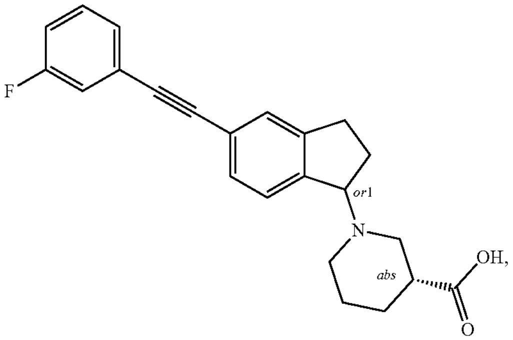
Enantiomer 2
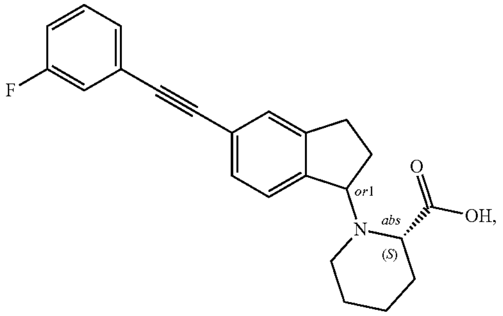
Enantiomer 1
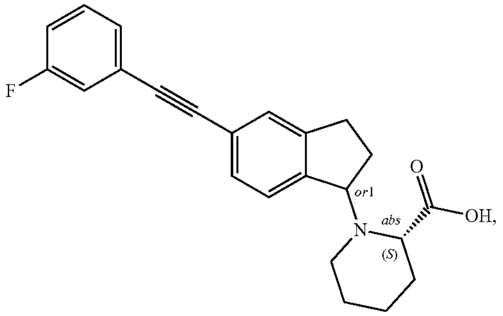
Enantiomer 2
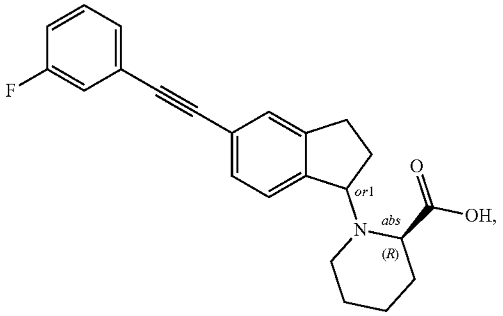
Enantiomer 1
-continued
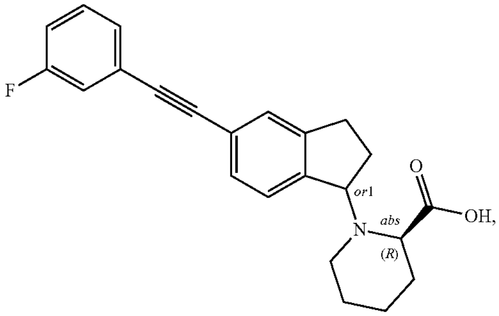
Enantiomer 2
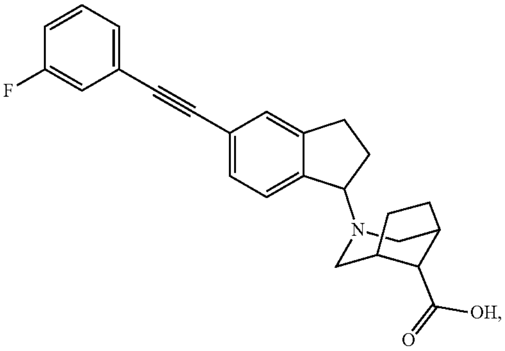
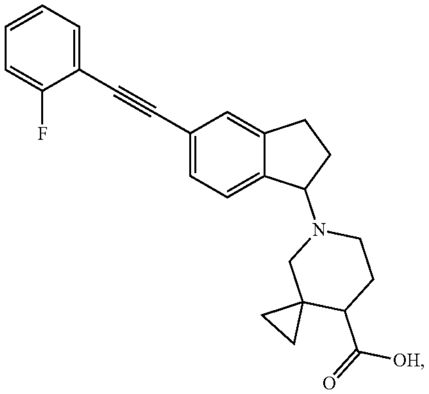
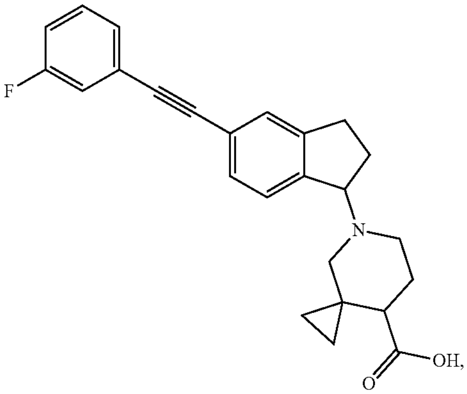

-continued
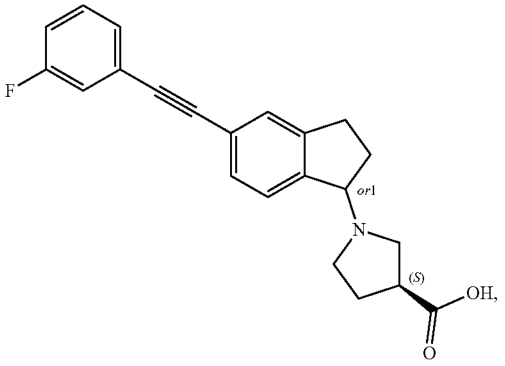
Enantiomer 1
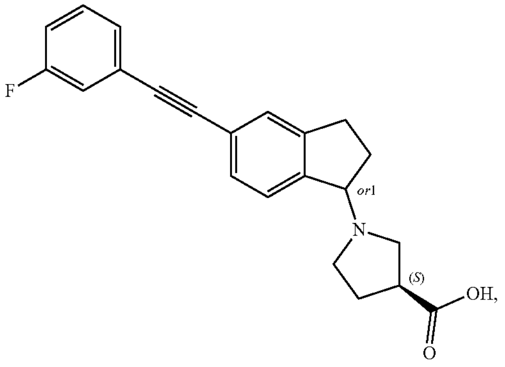
Enantiomer 2
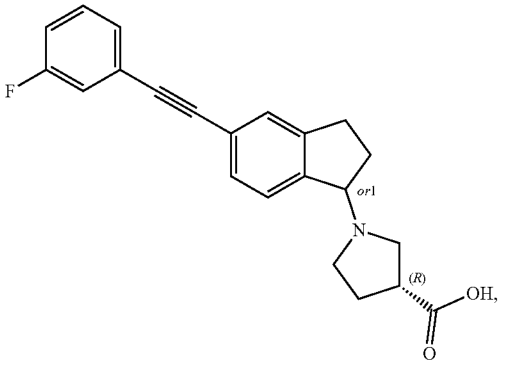
Enantiomer 1
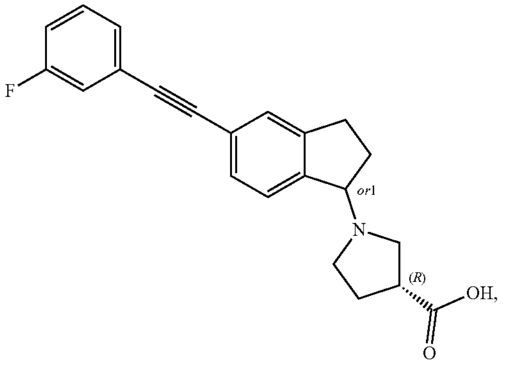
Enantiomer 2
-continued
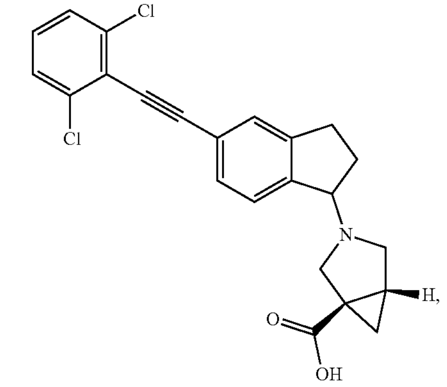
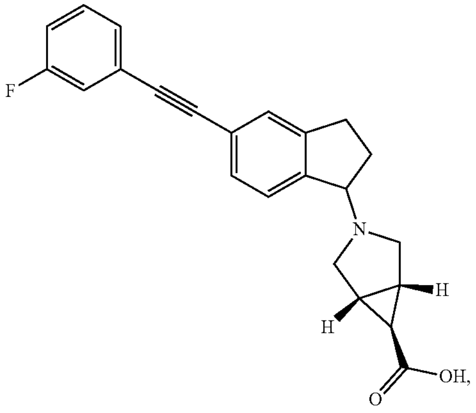
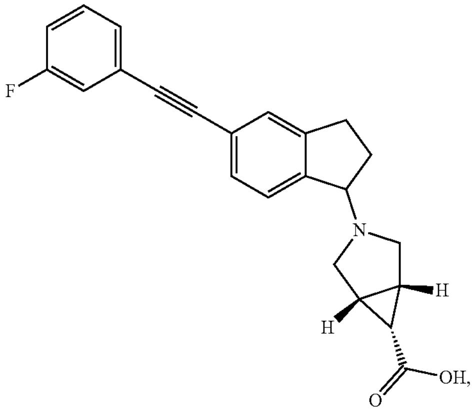
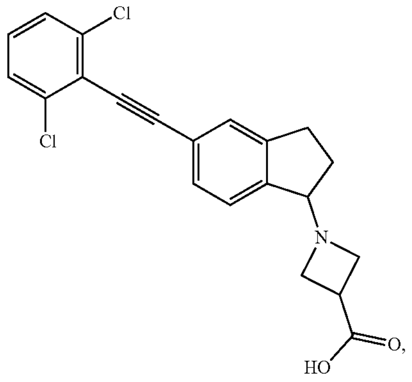

-continued
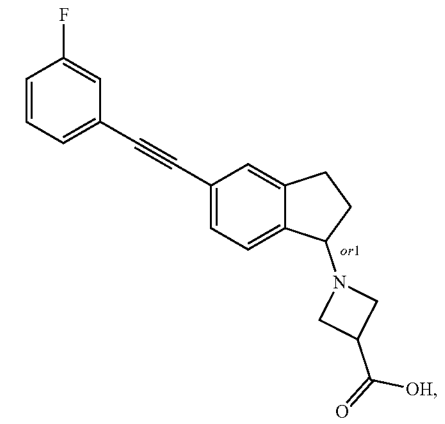
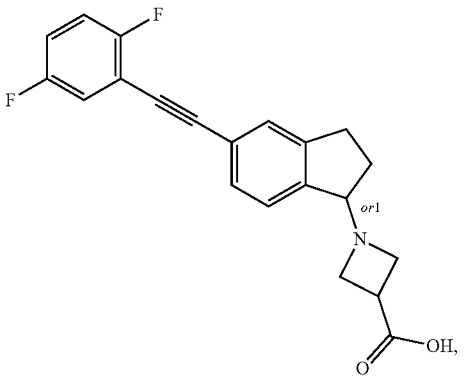
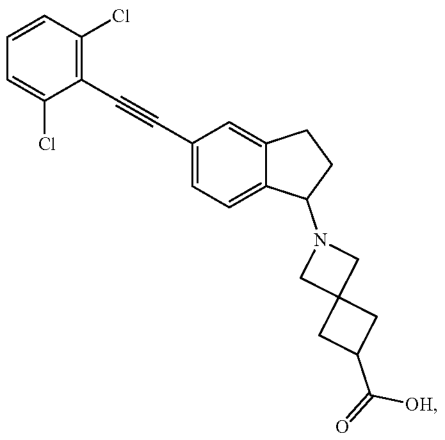
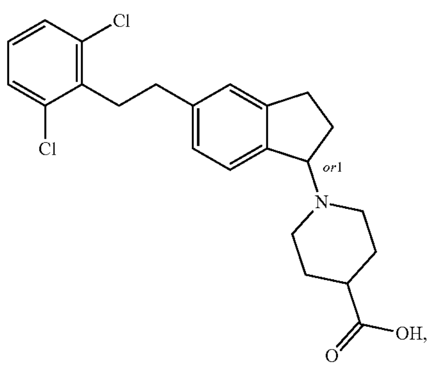
Enantiomer 1
-continued
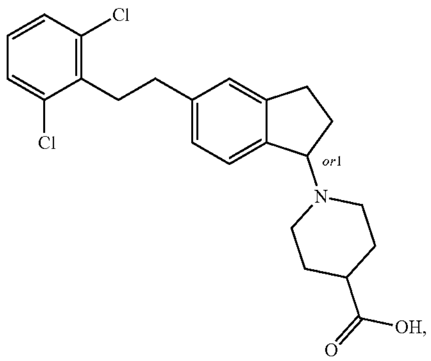
Enantiomer 2
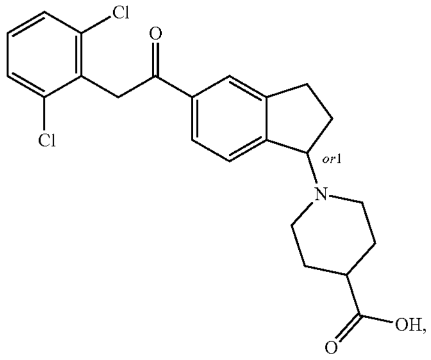
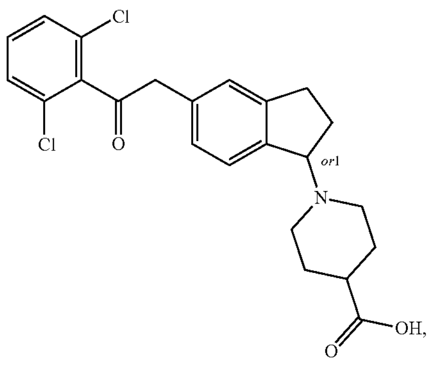
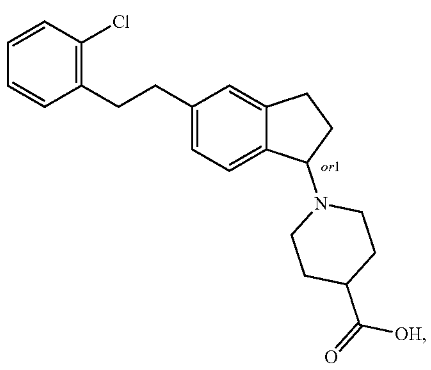
Enantiomer 1

-continued
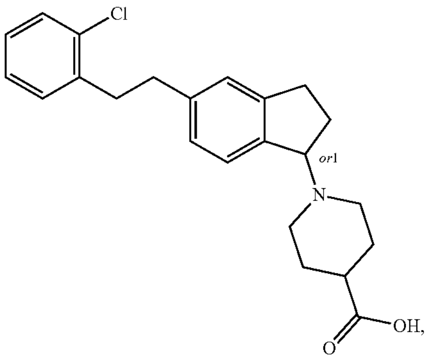
Enantiomer 2
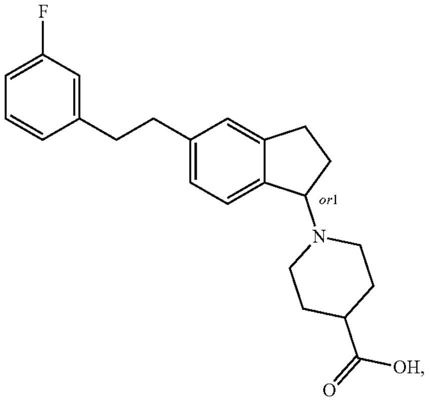
Enantiomer 1
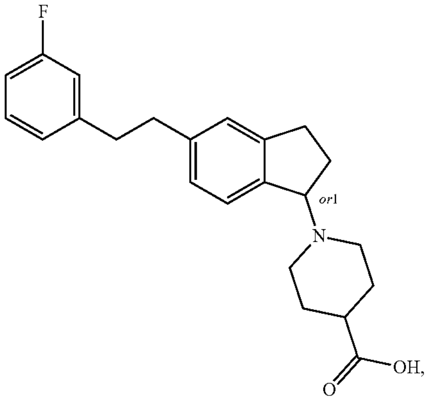
Enantiomer 2
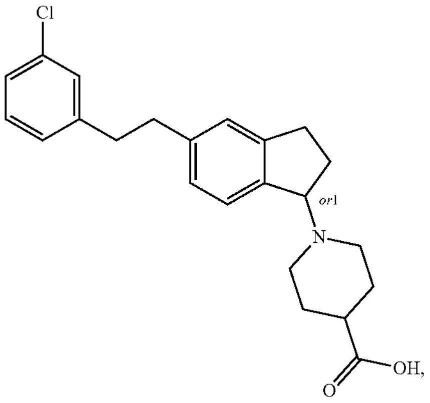
Enantiomer 1
-continued
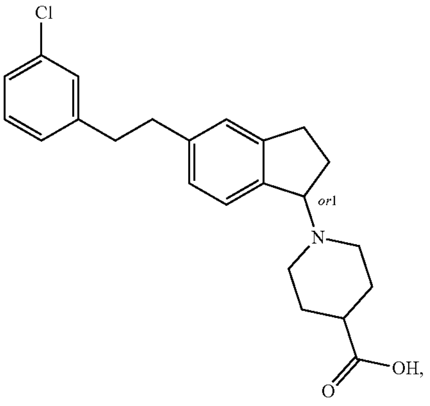
Enantiomer 2
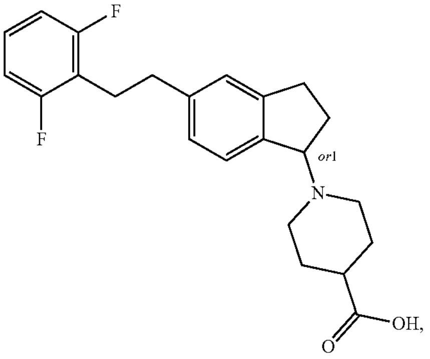
Enantiomer 1
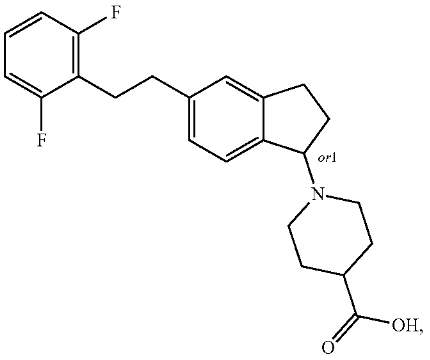
Enantiomer 2
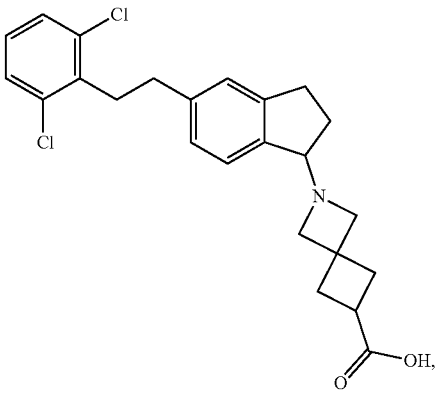

-continued
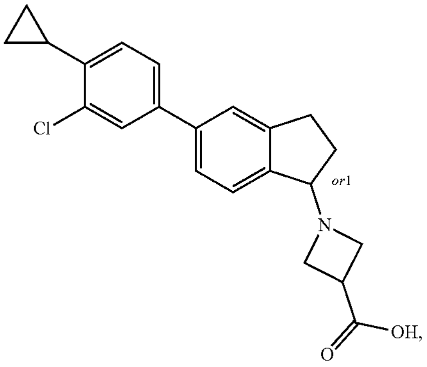
Enantiomer 1
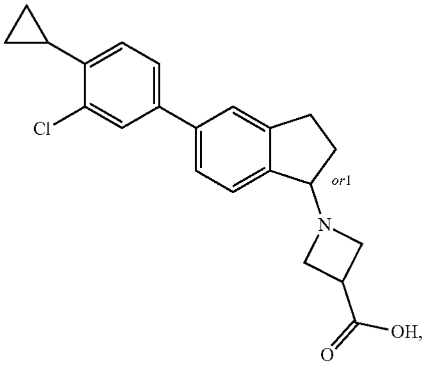
Enantiomer 2
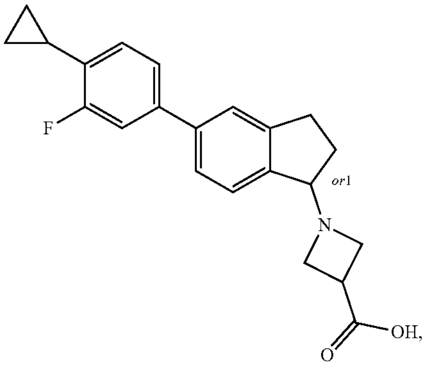
Enantiomer 1
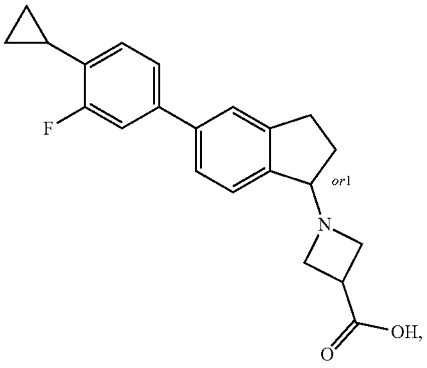
Enantiomer 2
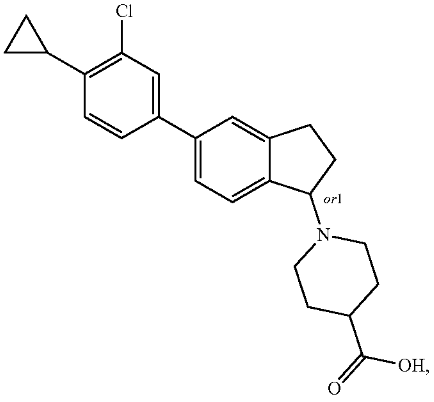
Enantiomer 1
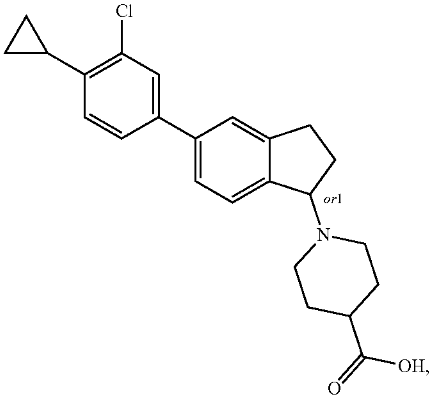
Enantiomer 2
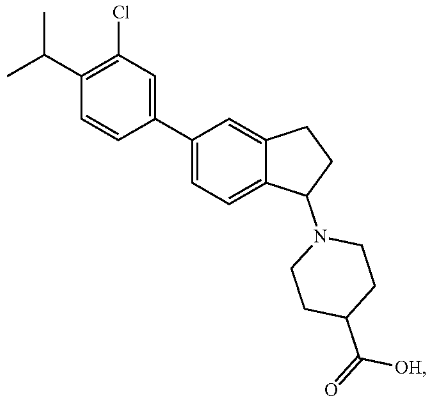
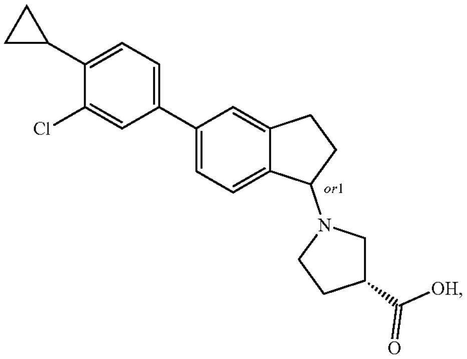
Enantiomer 1

-continued
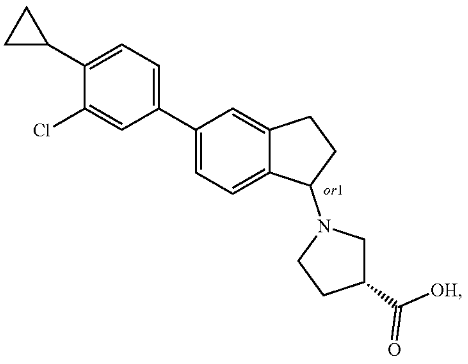
Enantiomer 2
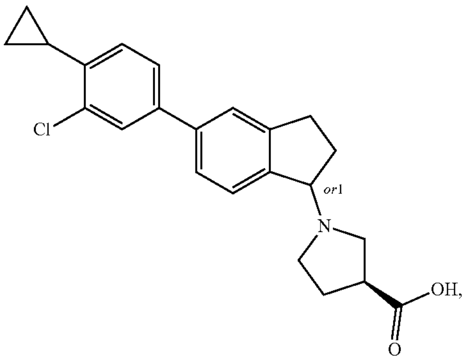
Enantiomer 1
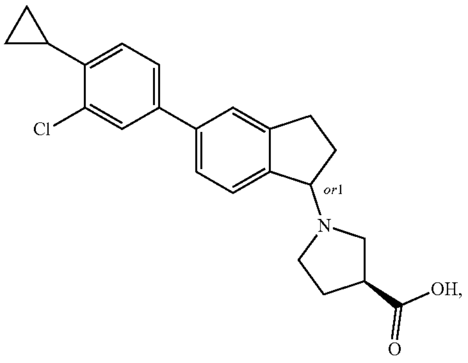
Enantiomer 2
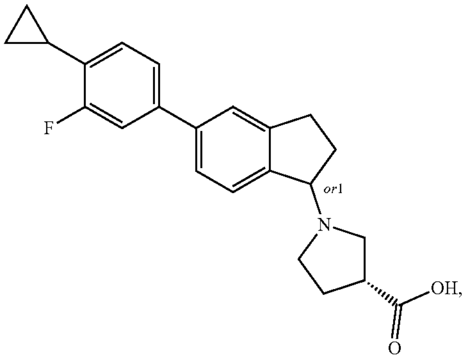
Enantiomer 1
-continued
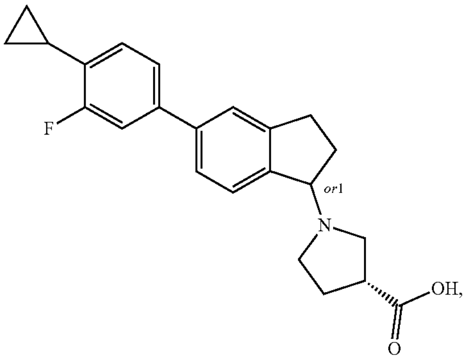
Enantiomer 2
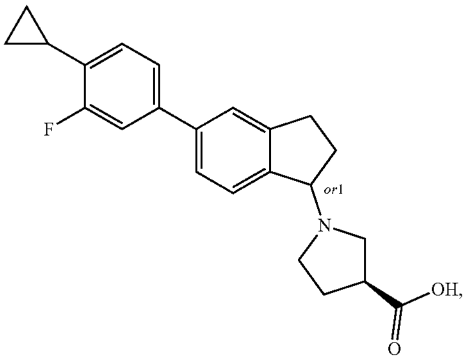
Enantiomer 1
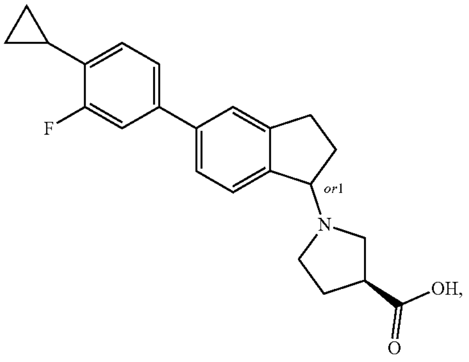
Enantiomer 2
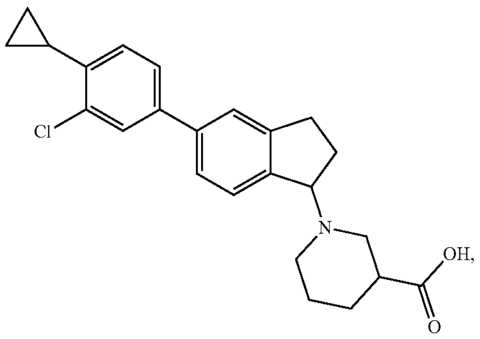

-continued

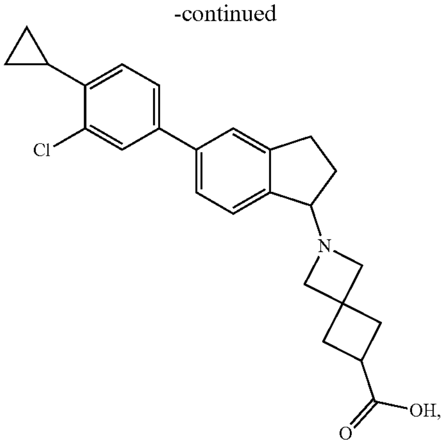

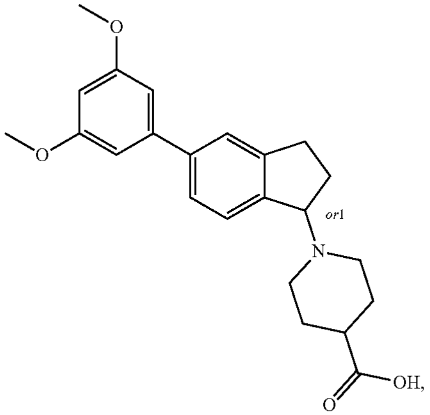

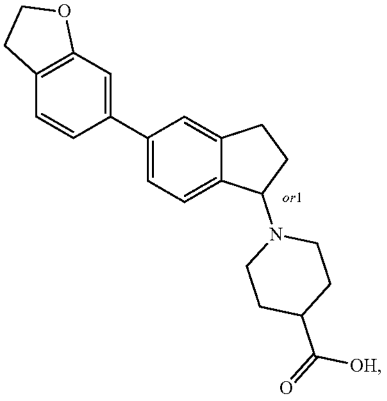

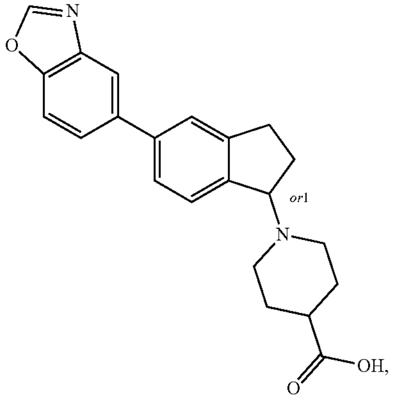

-continued

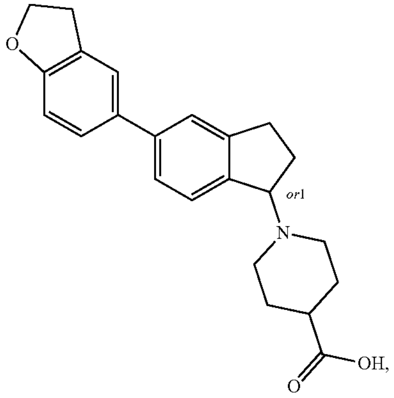

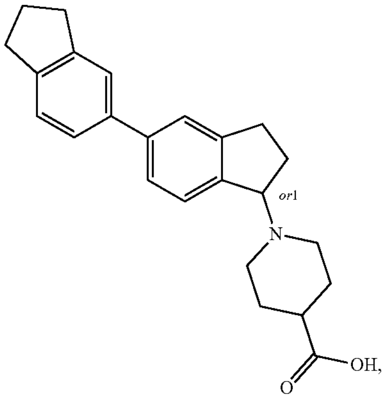

or

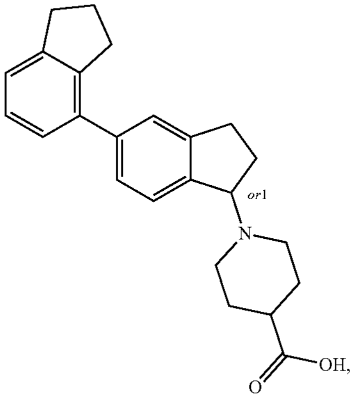

or a pharmaceutically acceptable salt thereof.

18. A pharmaceutical composition comprising the compound of claim 1, or a pharmaceutically acceptable salt thereof, and a pharmaceutically acceptable excipient.

19. A method of modulating sphingosine 1-phosphate receptor 5 (S1P5) comprising contacting S1P5 with an effective amount of the compound of claim 1, or a pharmaceutically acceptable salt thereof.

* * * * *